United States Patent
Sampson et al.

(10) Patent No.: US 11,147,792 B2
(45) Date of Patent: Oct. 19, 2021

(54) INHIBITORS OF MICROBIALLY INDUCED AMYLOID

(71) Applicants: Axial Therapeutics, Inc, Woburn, MA (US); California Institute of Technology, Pasadena, CA (US)

(72) Inventors: Timothy Sampson, Los Angeles, CA (US); Sarkis Mazmanian, Glendale, CA (US); Anthony Stewart Campbell, Framingham, MA (US)

(73) Assignees: AXIAL THERAPEUTICS, INC., Woburn, MA (US); CALIFORNIA INSTITUTE OF TECHNOLOGY, Pasadena, CA (US)

( * ) Notice: Subject to any disclaimer, the term of this patent is extended or adjusted under 35 U.S.C. 154(b) by 31 days.

(21) Appl. No.: 16/611,406

(22) PCT Filed: May 14, 2018

(86) PCT No.: PCT/US2018/032605
§ 371 (c)(1),
(2) Date: Nov. 6, 2019

(87) PCT Pub. No.: WO2018/213204
PCT Pub. Date: Nov. 22, 2018

(65) Prior Publication Data
US 2020/0163933 A1 May 28, 2020

Related U.S. Application Data

(60) Provisional application No. 62/506,457, filed on May 15, 2017, provisional application No. 62/506,433, filed on May 15, 2017.

(51) Int. Cl.
*A61K 31/353* (2006.01)
*A61P 25/28* (2006.01)
(Continued)

(52) U.S. Cl.
CPC ............ *A61K 31/353* (2013.01); *A61K 31/05* (2013.01); *A61K 31/192* (2013.01);
(Continued)

(58) Field of Classification Search
CPC .... A61K 31/353; A61K 31/05; A61K 31/192; A61K 31/216; A61K 31/235;
(Continued)

(56) References Cited

U.S. PATENT DOCUMENTS 5,443,826 A    8/1995 Borody
5,951,977 A    9/1999 Nisbet et al.
(Continued)

FOREIGN PATENT DOCUMENTS

EP    2624863 B1    4/2016
EP    3072524 A1    9/2016
(Continued)

OTHER PUBLICATIONS

Adams et al. (2011). Gastrointestinal flora and gastrointestinal status in children with autism-comparisons to typical children and correlation with autism severity. BMC Gastroenterol 11, 22.
(Continued)

*Primary Examiner* — Taylor V Oh
(74) *Attorney, Agent, or Firm* — Knobbe, Martens, Olson & Bear LLP

(57) ABSTRACT

The present disclosure provides methods and compositions for the prevention, amelioration, or alleviation of one or more neurological disorders associated with microbially-induced amyloid formation. Methods of inhibiting, ameliorating, reducing the likelihood, delaying the onset of, treating, or preventing an amyloid disorder are disclosed. Methods of identifying compounds capable of inhibiting the formation of microbially-induced amyloid fibrils are disclosed.

25 Claims, 32 Drawing Sheets

(51) Int. Cl.
| | |
|---|---|
| A61P 25/16 | (2006.01) |
| A61K 31/05 | (2006.01) |
| A61K 31/192 | (2006.01) |
| A61K 31/216 | (2006.01) |
| A61K 31/235 | (2006.01) |
| A61K 31/465 | (2006.01) |
| A61K 31/522 | (2006.01) |
| A61K 45/06 | (2006.01) |

(52) U.S. Cl.
CPC .......... *A61K 31/216* (2013.01); *A61K 31/235* (2013.01); *A61K 31/465* (2013.01); *A61K 31/522* (2013.01); *A61K 45/06* (2013.01); *A61P 25/16* (2018.01); *A61P 25/28* (2018.01)

(58) Field of Classification Search
CPC .... A61K 31/465; A61K 31/522; A61K 45/06; A61K 31/12; A61K 31/352; A61P 25/28; A61P 25/16; A61P 39/06
USPC ...................................................... 514/263.3
See application file for complete search history.

(56) References Cited

U.S. PATENT DOCUMENTS

| | | |
|---|---|---|
| 9,452,189 B2 | 9/2016 | Mazmanian et al. |
| 2002/0013270 A1 | 1/2002 | Bolte |
| 2002/0151506 A1* | 10/2002 | Castillo ............... A61K 31/215 514/27 |
| 2004/0005304 A1 | 1/2004 | Brudnak |
| 2004/0028689 A1 | 2/2004 | Borody |
| 2004/0137092 A1 | 7/2004 | Castillo et al. |
| 2004/0170617 A1 | 9/2004 | Finegold |
| 2006/0167057 A1 | 7/2006 | Kong et al. |
| 2007/0116779 A1 | 5/2007 | Mazzio |
| 2008/0015247 A1 | 1/2008 | Lines |
| 2008/0153114 A1 | 6/2008 | Fleming et al. |
| 2009/0118257 A1 | 5/2009 | Jankowski et al. |
| 2009/0156471 A1 | 6/2009 | Gazit et al. |
| 2010/0040558 A1 | 2/2010 | Shytle et al. |
| 2011/0081320 A1 | 4/2011 | Westall et al. |
| 2011/0118135 A1 | 5/2011 | State et al. |
| 2012/0087895 A1 | 4/2012 | Mazmanian et al. |
| 2012/0088841 A1 | 4/2012 | Majeed et al. |
| 2012/0190055 A1 | 7/2012 | Cezar et al. |
| 2012/0207726 A1 | 8/2012 | Lipkin et al. |
| 2012/0237482 A1 | 9/2012 | Rodriguez |
| 2012/0252775 A1 | 10/2012 | Finegold |
| 2012/0309701 A1 | 12/2012 | Janetka et al. |
| 2013/0115257 A1 | 5/2013 | Gysemans et al. |
| 2013/0303397 A1 | 11/2013 | Vebø et al. |
| 2014/0065132 A1 | 3/2014 | Hsiao et al. |
| 2015/0152484 A1 | 6/2015 | Krajmalnik-Brown et al. |
| 2015/0259728 A1 | 9/2015 | Cutliffe et al. |
| 2016/0040215 A1 | 2/2016 | Henn et al. |
| 2016/0120916 A1 | 5/2016 | Hsaio et al. |
| 2016/0120917 A1 | 5/2016 | Bailey et al. |
| 2016/0120920 A1 | 5/2016 | Hsiao et al. |
| 2016/0339065 A1 | 11/2016 | Adams et al. |
| 2017/0024527 A1 | 1/2017 | Apte et al. |

FOREIGN PATENT DOCUMENTS

| | | |
|---|---|---|
| JP | 2008-532033 A | 8/2008 |
| JP | 2008-535520 A | 9/2008 |
| WO | WO 1992/018529 A1 | 10/1992 |
| WO | WO 1996/011014 A1 | 4/1996 |
| WO | WO 2001/49281 | 7/2001 |
| WO | WO 2002/007741 | 1/2002 |
| WO | WO 2006/8090185 A1 | 8/2006 |
| WO | WO 2006/110406 A1 | 10/2006 |
| WO | WO 2007/080721 | 7/2007 |
| WO | WO 2009/055362 A1 | 4/2008 |
| WO | WO 2009/003147 | 12/2008 |
| WO | WO 2010/056985 A2 | 5/2010 |
| WO | WO 2010/082205 | 7/2010 |
| WO | WO 2011/0139914 A1 | 11/2011 |
| WO | WO 2012/048152 A1 | 4/2012 |
| WO | WO 2012/159052 A2 | 11/2012 |
| WO | WO 2014/076655 A1 | 5/2014 |
| WO | WO 2014/121301 A1 | 8/2014 |
| WO | WO 2015/181449 A1 | 12/2015 |
| WO | WO 2016/069792 A1 | 5/2016 |
| WO | WO 2016/069801 A1 | 5/2016 |
| WO | WO 2016/110768 A1 | 7/2016 |
| WO | WO 2017/205302 A1 | 11/2017 |

OTHER PUBLICATIONS

Agarwal et al (Front Mol Biase 2: 1-10, 2015).
Al-Asmakh et al. (2012). Gut microbial communities modulating brain development and function. Gut Microbes 3, 366-373.
Altieri et al. (2011). Urinary p-cresol is elevated in small children with severe autism spectrum disorder. Biomarkers 16, 252-260.
Amaral et al. (2008). Commensal microbiota is fundamental for the development of inflammatory pain. Proc Natl Acad Sci USA 105, 2193-2197.
Amasheh et al. (2009). Na+ absorption defends from paracellular back-leakage by claudin-8 upregulation. Biochem Biophys Res Commun 378, 45-50.
American Psychiatric Association: Diagnostic and Statistical Manual of Mental Disorders, Fourth Edition, Text Revision. Washington, DC, pp. 69-84, American Psychiatric Association, 2000.
Atladottir, et al. (2010). Maternal infection requiring hospitalization during pregnancy and autism spectrum disorders. J Autism Dev Disord 40, 1423-1430.
Bailey, K.R., and Crawley, J.N. (2009). Anxiety-Related Behaviors in Mice. In Methods of Behavior Analysis in Neuroscience, J.J. Buccafusco, ed. (Boca Raton (FL)).
Barbara, et al. (2005) "Interactions between commensal bacteria and gut sensorimotor function in health and disease" The American journal of gastroenterology 100, 2560-2568.
Bercik et al. (2011). The anxiolytic effect of Bifidobacterium longum NCC3001 involves vagal pathways for gut-brain communication. Neurogastroenterol Motil 23, 1132-1139.
Blumberg, R., and Powrie, F. (2012). Microbiota, disease, and back to health: a metastable journey. Sci Transl Med 4, 137rv137.
Boksa, P. (2010). Effects of prenatal infection on brain development and behavior: a review of findings from animal models. Brain Behav Immun 24, 881-897.
Bourin et al. (2007). Animal models of anxiety in mice. Fundamental & clinical pharmacology 21, 567-574.
Bravo et al. (2011). Ingestion of Lactobacillus strain regulates emotional behavior and central GABA receptor expression in a mouse via the vagus nerve. Proc Natl Acad Sci U S A 108, 16050-16055.
Breiman, L. (2001). Random forests. Mach Learn 45, 5-32.
Brown, et al. (2000). Stress produced by gavage administration in the rat. Contemporary topics in laboratory animal science—American Association for Laboratory Animal Science 39, 17-21.
Buie, et al. (2010). Evaluation, diagnosis, and treatment of gastrointestinal disorders in individuals with ASDs: a consensus report. Pediatrics 125 Suppl 1, S1-18.
Bull et al. (2003). Indolyl-3-acryloylglycine (IAG) is a putative diagnostic urinary marker for autism spectrum disorders. Med Sci Monit 9, CR422-425.
Burlingham et al. (2003). 34S isotope effect on sulfate ester hydrolysis: mechanistic implications. J Am Chem Soc 125, 13036-13037.
Campbell et al., Bacterial diversity, community structure and potential growth rates along an estuarine salinity gradient, Isme J, (2012).
Canitano, R., and Scandurra, V. (2008). Risperidone in the treatment of behavioral disorders associated with autism in children and adolescents. Neuropsychiatr Dis Treat 4, 723-730.
Caporaso et al. (2010). PyNAST: a flexible tool for aligning sequences to a template alignment. Bioinformatics 26, 266-267.
Caporaso et al. (2010). QIIME allows analysis of high-throughput community sequencing data. Nat Methods 7, 335-336.

(56) References Cited

OTHER PUBLICATIONS

CDC (2012). Prevalence of autism spectrum disorders—autism and developmental disabilities monitoring network, 14 sites, United States, 2008. MMWR Surveill Summ 61, 1-19.
Chen et al. (Scientific Reports, 6: 1-10, 2016).
Chi, "Clinical, animal studies probe DISC1's role in autism" Spectrum, Mar. 1, 2010, https:-spectrumnews.org-news-clinical-animal-studies-probe-disc1s-role-in-autism-.
Chorell et al. "Bacterial Chaperones CsgE and CsgC Differentially Modulate Human α-Synuclein Amyloid Formation via Transient Contacts", (2015). PLoS ONE 10(10).
Clemente et al. (2012). The impact of the gut microbiota on human health: an integrative view. Cell 148, 1258-1270.
Cohen-Poradosu et al. (2011). Bacteroides fragilis-stimulated interleukin-10 contains expanding disease. The Journal of infectious diseases 204, 363-371.
Collins et al. (2012). The interplay between the intestinal microbiota and the brain. Nat Rev Microbiol 10, 735-742.
Collinson et al., "Purification and characterization of thin, aggregative fimbriae from *Salmonella enteritidis*", (1991), *Journal of Bacteriology*. 173(15).
Coury, et al. (2012). Gastrointestinal conditions in children with autism spectrum disorder: developing a research agenda. Pediatrics 130 Suppl 2, S160-168.
Critchfield, et al. (2011). The potential role of probiotics in the management of childhood autism spectrum disorders. Gastroenterology research and practice 2011, 161358.
Cryan, J.F., and Dinan, T.G. (2012). Mind-altering microorganisms: the impact of the gut microbiota on brain and behaviour. Nat Rev Neurosci 13, 701-712.
De Angelis et al., "Fecal Microbiota and Metabolome of Children with Autism and Pervasive Developmental Disorder Not Otherwise Specified", PLOS ONE, vol. 8, No. 10, e76993, pp. 1-18, Oct. 2013.
De Hoon et al. (2004). Open source clustering software. Bioinformatics 20, 1453-1454.
De Magistris et al. (2010). Alterations of the intestinal barrier in patients with autism spectrum disorders and in their first-degree relatives. J Pediatr Gastroenterol Nutr 51, 418-424.
Desbonnet, et al. (2013). Microbiota is essential for social development in the mouse. Molecular psychiatry.
D'Eufemia, et al. (1996). Abnormal intestinal permeability in children with autism. Acta Paediatr 85, 1076-1079.
Edgar, et al. (2011). UCHIME improves sensitivity and speed of chimera detection. Bioinformatics 27, 2194-2200.
Edgar, R.C. (2010). Search and clustering orders of magnitude faster than BLAST. Bioinformatics 26, 2460-2461.
Evans et al, (Mol Cell 57: 1-23, 2015).
Ewaschuk, et al. (2008). Secreted bioactive factors from Bifidobacterium infantis enhance epithelial cell barrier function. Am J Physiol Gastrointest Liver Physiol 295, G1025-1034.
Faith, D.P. (1992). Conservation Evaluation and Phylogenetic Diversity. Biol Conserv 61, 1-10.
Finegold, et al. (2002). Gastrointestinal microflora studies in late-onset autism. Clin Infect Dis 35, S6-S16.
Finegold, et al. (2010). Pyrosequencing study of fecal microflora of autistic and control children. Anaerobe 16, 444-453.
Finegold, et al. (2012). Microbiology of regressive autism. Anaerobe 18, 260-262.
Finegold, S.M. (2011). Desulfovibrio species are potentially important in regressive autism. Medical hypotheses 77, 270-274.
Fleming et al. "Early and Progressive Sensorimotor Anomalies in Mice Overexpressing Wild-Type Human ☐—Synuclein", J. Neurosci. 24, 9434-9440 (2004).
Frye, et al. (2013). Unique acyl-carnitine profiles are potential biomarkers for acquired mitochondrial disease in autism spectrum disorder. Translational psychiatry 3, e220.
Ganapathy et al., "Endogenous Elevation of Homocysteine Induces Retinal Neuron Death in the Cystathionine-Beta-Synthenase Mutant Mouse," Invest. Opthamol. Vis. Sci., 50(9):4460-4470 (2009).

Geyer, M.A., and Swerdlow, N.R. (2001). Measurement of startle response, prepulse inhibition, and habituation. Curr Protoc Neurosci Chapter 8, Unit 8 7.
Gondalia, et al. (2012). Molecular characterisation of gastrointestinal microbiota of children with autism (with and without gastrointestinal dysfunction) and their neurotypical siblings. Autism Res 5, 419-427.
Gorrindo, et al. (2012). Gastrointestinal dysfunction in autism: parental report, clinical evaluation, and associated factors. Autism Res 5, 101-108.
Gorrindo, et al. (2013). Enrichment of elevated plasma f2t-isoprostane levels in individuals with autism who are stratified by presence of gastrointestinal dysfunction. PLoS One 8, e68444.
Grenham, G. Clarke, J. F. Cryan, T. G. Dinan, Brain-gut-microbe communication in health and disease. Front Physiol 2, 94 (Dec. 7, 2011).
Grimes, A.J. (1959). Synthesis of 35S-labelled arylsulphates by intact animals and by tissue preparations, with particular reference to l-tyrosine O-sulphate. Biochem J 73, 723.
Grimsley, et al. (2011). Development of social vocalizations in mice. PloS one 6, e17460.
Gulati et al., Mouse Background Strain Profoundly Influences Paneth Cell Function and Intestinal Microbial Composition, PLoS One 7, e32403 (2012).
Gupta, "The phylogeny of proteobacteria: relationships to other eubacterial phyla and eukaryotes.", FEMS Microbiology Reviews 24 (4):367-402, 2000.
Hallmayer, et al. (2011). Genetic heritability and shared environmental factors among twin pairs with autism. Arch Gen Psychiatry 68, 1095-1102.
Hammock et al., "2003 Progress Report: Environmental Factors in the Etiology of Autism: Analytic Biomarkers (xenobiotic) Core," Extramural Research, United States Environmental Protection Agency (2003), retrieved online from EPA. <http:--cfpub.epa.gov-ncer_abstracts-index.cfm-fuseaction-display.abstractDetail-abstract-7872-report-2003>.
Han, et al. (2012). Autistic-like behaviour in Scn1a+-- mice and rescue by enhanced GABA-mediated neurotransmission. Nature 489, 385-390.
Hansen et al. The colitis-associated transcriptional profile of commensal Bacteroides thetaiotaomicron enhances adaptive immune responses to a bacterial antigen. PLoS One. 2012;7(8):e42645. doi: 10.1371 -journal.pone.0042645. Epub Aug. 3, 2012.
Heijtz, et al. (2011). Normal gut microbiota modulates brain development and behavior. Proc Natl Acad Sci U S A 108, 3047-3052.
Hering, et al. (2012). Determinants of colonic barrier function in inflammatory bowel disease and potential therapeutics. The Journal of physiology 590, 1035-1044.
Holmes, et al. (2006). Claudin profiling in the mouse during postnatal intestinal development and along the gastrointestinal tract reveals complex expression patterns. Gene Expr Patterns 6, 581-588.
Hooper, et al. (2012). Interactions between the microbiota and the immune system. Science 336, 1268-1273.
Horvath, K., and Perman, J.A. (2002). Autism and gastrointestinal symptoms. Curr Gastroenterol Rep 4, 251-258.
Hsiao et al., "Microbiota modulate behavioral and physiological abnormalities associated with neurodevelopmental disorders," Cell, vol. 155, No. 7, pp. 1451-1463 Dec. 1, 2013.
Hsiao, E.Y., and Patterson, P.H. (2011). Activation of the maternal immune system induces endocrine changes in the placenta via IL-6. Brain Behav Immun 25, 604-615.
Hsiao, Elaine, "Gastrointestinal Issues in Autism spectrum disorder", Harvard Review of Psychiatry, Mar.-Apr. 2014, vol. 22(2), pp. 104-111.
Hsiao, et al. (2012). Modeling an autism risk factor in mice leads to permanent immune dysregulation. Proc Natl Acad Sci U S A 109, 12776-12781.
Huang, et al. (2011). The human commensal Bacteroides fragilis binds intestinal mucin. Anaerobe 17, 137-141.
Ibrahim, et al. (2009). Incidence of gastrointestinal symptoms in children with autism: a population based study. Pediatrics 124, 680-686.

(56) References Cited

OTHER PUBLICATIONS

Jandhyala et al., "Role of the normal gut microbiota", World Journal of Gastroenterology 21(9): 8787-8803,2015.
Kang, et al. (2013). Reduced Incidence of and Other Fermenters in Intestinal Microflora of Autistic Children. PLoS One 8, e68322.
Kau, et al. (2011). Human nutrition, the gut microbiome and the immune system. Nature 474, 327-336.
Keszthelyi, et al. (2009). Understanding the role of tryptophan and serotonin metabolism in gastrointestinal function. Neurogastroenterol Motil 21,1239-1249.
Kidd, Autism, an extreme challege to integrative medicine. Part 2: medical management. Altem. Med. Rev. Vol. 7, No. 6, pp. 472-499 (2002).
Kilpinen, et al., Association of *DISC1* with autism and Asperger syndrome Molecular Psychiatry (2008) 13, 187-196.
Klein etal (Mol Cell Previews 57: 391-393, 2015).
Knights, et al. (2011). Supervised classification of human microbiota. FEMS microbiology reviews 35, 343-359.
Koenig, et al. (2011). Succession of microbial consortia in the developing infant gut microbiome. Proc Natl Acad Sci U S A 108 Suppl 1, 4578-4585.
Kohane, et al. (2012). The co-morbidity burden of children and young adults with autism spectrum disorders. PLoS One 7, e33224.
Korosi, et al. (2012). Early-life stress mediated modulation of adult neurogenesis and behavior. Behav Brain Res 227, 400-409.
Kursa, M.B., and Rudnicki, W.R. (2010). Feature Selection with the Boruta Package. J Stat Softw 36, 1-13.
Lafaye, et al. (2004). Profiling of sulfoconjugates in urine by using precursor ion and neutral loss scans in tandem mass spectrometry. Application to the investigation of heavy metal toxicity in rats. J Mass Spectrom 39, 655-664.
Lazic, S.E. (2013). Comment on "Stress in puberty unmasks latent neuropathological consequences of prenatal immune activation in mice". Science 340, 811; discussion 811.
Leatham, et al. (2009). Precolonized human commensal *Escherichia coli* strains serve as a barrier to *E. coli* O157:H7 growth in the streptomycin-treated mouse intestine. Infect Immun 77, 2876-2886.
Lee et al., in International Meeting for Autism Research (Toronto, Canada, May 17-19, 2012).
Lee, A., and Gemmell, E. (1972). Changes in the mouse intestinal microflora during weaning: role of volatile fatty acids. Infect Immun 5, 1-7.
Li et al (The Faseb J express art, pp. 1-22, 2004).
Lionnet et al (Acta Neuropathol 135: 1-12, published online Oct. 16, 2017).
Lopetuso et al., "Commensal Clostridia: leading players in the maintenance of gut homeostasis", Gut Pathogents 5(1): 23, 2013.
Lozupone, C., and Knight, R. (2005). UniFrac: a new phylogenetic method for comparing microbial communities. Appl Environ Microbiol 71, 8228-8235.
Ludwig, et al. (2004). ARB: a software environment for sequence data. Nucleic Acids Res 32, 1363-1371.
Macfabe, D.F. (2012). Short-chain fatty acid fermentation products of the gut microbiome: implications in autism spectrum disorders. Microbial Ecology in Health & Disease 23, 19260.
Malkova, et al. (2012). Maternal immune activation yields offspring displaying mouse versions of the three core symptoms of autism. Brain Behav Immun 26, 607-616.
Mandal, et al. (2011). Maternal immune stimulation during pregnancy affects adaptive immunity in offspring to promote development of TH17 cells. Brain Behav Immun 25, 863-871.
Maslowski, et al., "Diet, gut microbiota and immune responses" Nature Immunology vol. 12 No. 1, pp. 5-9, Jan. 2011.
Matsumoto, et al. (2012). Impact of intestinal microbiota on intestinal luminal metabolome. Sci Rep 2, 233.
Mayer, E.A. (2011). Gut feelings: the emerging biology of gut-brain communication. Nat Rev Neurosci 12, 453-466.
Mazmanian, et al. (2008). A microbial symbiosis factor prevents intestinal inflammatory disease. Nature 453, 620-625.

Mazurek, et al. (2013). Anxiety, sensory over-responsivity, and gastrointestinal problems in children with autism spectrum disorders. J Abnorm Child Psychol 41, 165-176.
McCarthy et al. (2015), STC-1 Cells. In: Verhoeckx K. et al. (eds) *The Impact of Food Bioactives on Health*. Springer, Cham.
Ming, et al. (2012). Metabolic perturbance in autism spectrum disorders: a metabolomics study. Journal of proteome research 11, 5856-5862.
Mulder, et al. (2004). Platelet serotonin levels in pervasive developmental disorders and mental retardation: diagnostic group differences, within-group distribution, and behavioral correlates. J Am Acad Child Adolesc Psychiatry 43, 491-499.
Mulle et al., "The Gut Microbiome: A New Frontier in Autism Research", Curr Psychiatry Rep., vol. 15, No. 2, pp. 1-13, Feb. 2013.
Nemeroff et al., "Are platelets the link between depression and ischemic heart disease?", American Heat Journal 140(4): S57-S62, 2000.
Nicholson, et al. (2012) "Host-gut microbiota metabolic interactions" Science 336, 1262-1267.
Nieswandt, et al. (2004) "Flow-cytometric analysis of mouse platelet function" Methods Mol Biol 272, 255-268.
Nikolov, et al. (2009). Gastrointestinal symptoms in a sample of children with pervasive developmental disorders. J Autism Dev Disord 39, 405-413.
Novarino, et al. (2012). Mutations in BCKD-kinase lead to a potentially treatable form of autism with epilepsy. Science 338, 394-397.
Ochoa-Reparaz, et al. (2010). Central nervous system demyelinating disease protection by the human commensal Bacteroides fragilis depends on polysaccharide A expression. J Immunol 185, 4101-4108.
Odamaki, et al. (2008). Distribution of different species of the Bacteroides fragilis group in individuals with Japanese cedar pollinosis. Appl Environ Microbiol 74, 6814-6817.
O'Mahony, et al. (2009). Early life stress alters behavior, immunity, and microbiota in rats: implications for irritable bowel syndrome and psychiatric illnesses. Biological psychiatry 65, 263-267.
Ono et al., "Antioxidant compounds have potent anti-fibrillogenic and fibril0destabilizing effects for α-synuclein fibrils in vitro", Journal of Neurochemistry, 2006, 97, 105-115.
Onore, et al. (2012). The role of immune dysfunction in the pathophysiology of autism. Brain Behav Immun 26, 383-392.
Parracho, et al. (2005b). Differences between the gut microflora of children with autistic spectrum disorders and that of healthy children. Journal of medical microbiology 54, 987-991.
Patterson, Maternal Infection and Immune Involvement in Autism, Trends Mol Med 17, 389 (Jul. 2011).
Patterson, P. H. 2011. Modeling features of autism in animals. Pediatric Res 69:34R-40R.
Penagarikano et al., "What does *CNTNAP2* reveal about autism spectrum disorder?" Trends in Molecular Medicine, 2012, vol. 18, pp. 156-163.
Penagarikano, et al. (2011). Absence of CNTNAP2 leads to epilepsy, neuronal migration abnormalities, and core autism-related deficits. Cell 147, 235-246.
Perry, et al. (2007). Sensorimotor gating deficits in adults with autism. Biological psychiatry 61, 482-486.
Persico, A.M., and Napolioni, V. (2012). Urinary p-cresol in autism spectrum disorder. Neurotoxicology and teratology 36, 82-90.
Petra, Louis, "Does the human gut mircrobiota contribute to the etiology of autism spectrum disorders?", Digestive diseases and sciences, vol. 57, No. 8, Jun. 27, 2012, pp. 1987-1989.
Portfors, C.V. (2007). Types and functions of ultrasonic vocalizations in laboratory rats and mice. J Am Assoc Lab Anim Sci 46, 28-34.
Price, et al. (2009). FastTree: Computing Large Minimum Evolution Trees with Profiles instead of a Distance Matrix. Mol Biol Evol 26, 1641-1650.
Pruesse, et al. (2012). SINA: Accurate high-throughput multiple sequence alignment of ribosomal RNA genes. Bioinformatics 28, 1823-1829.

(56) References Cited

OTHER PUBLICATIONS

Quast, et al. (2013). The SILVA ribosomal RNA gene database project: improved data processing and web-based tools. Nucleic Acids Res 41, D590-D596.
Rao, et al. (2009). A randomized, double-blind, placebo-controlled pilot study of a probiotic in emotional symptoms of chronic fatigue syndrome. Gut Pathog 1,6.
Resta-Lenert, S.C., and Barrett, K.E. (2009). Modulation of intestinal barrier properties by probiotics: role in reversing colitis. Ann N Y Acad Sci 1165, 175-182.
Riehle, et al. (2012). The Genboree Microbiome Toolset and the analysis of 16S rRNA microbial sequences. Bmc Bioinformatics 13.
Rietdijk et al., "Exploring Braak's Hypothesis of Parkinson's Disease", Front. Neurol., Feb. 13, 2017.
Robinson, et al. "From Structure to Function: the Ecology of Host-Associated Microbial Communities" Microbiology and Molecular Biology Reviews, Sep. 2010, pp. 456-476.
Rong et al., "Cystathionine Beta Synthase Participates in Murine Oocyte Maturation Mediated by Homocysteine," Reprod. Toxicol., 24(1):89-96 (2007).
Rossignol, D.A., and Frye, R.E. (2012). Mitochondrial dysfunction in autism spectrum disorders: a systematic review and meta-analysis. Mol Psychiatry 17, 290-314.
Round et al.: "Coordination of tolerogenic immune responses by the commensal microbiota." J. Autoimmun., 34:J220-225 (2010).
Round, J.L., and Mazmanian, S.K. (2009). The gut microbiota shapes intestinal immune responses during health and disease. Nat Rev Immunol 9, 313-323.
Round, J.L., and Mazmanian, S.K. (2010). Inducible Foxp3+ regulatory T-cell development by a commensal bacterium of the intestinal microbiota. Proc Natl Acad Sci U S A 107, 12204-12209.
Saldanha, A.J. (2004). Java Treeview-extensible visualization of microarray data. Bioinformatics 20, 3246-3248.
Sampson et al., "Gut Microbiota Regulate Motor Deficits and Neuroinflammation in a Model of Parkinson's Disease", Cell 167(6):1469-1480 (2016).
Sandler, et al. (2000). Short-term benefit from oral vancomycin treatment of regressive-onset autism. J Child Neurol 15, 429-435.
Sankoorikal, et al. (2006). A mouse model system for genetic analysis of sociability: C57BL-6J versus BALB-cJ inbred mouse strains. Biological psychiatry 59, 415-423.
Scattoni, et al. (2011). Unusual repertoire of vocalizations in adult BTBR T+tf—J mice during three types of social encounters. Genes, brain, and behavior 10, 44-56.
Schmeisser, et al. (2012). Autistic-like behaviours and hyperactivity in mice lacking ProSAP1-Shank2. Nature 486, 256-260.
Schwartzer, et al. (2013). Maternal immune activation and strain specific interactions in the development of autism-like behaviors in mice. Translational psychiatry 3, e240.
Segata, et al. (2011). Metagenomic biomarker discovery and explanation. Genome biology 12, R60.
Seltzer, et al., "The Symptoms of Autism Spectrum Disorders in Adolescence and Adulthood" Journal of Autism and Developmental Disorders, vol. 33, No. 6, pp. 565-581, Dec. 2003.
Sharma, et al. (2010) "Molecular modulation of intestinal epithelial barrier: contribution of microbiota" Journal of biomedicine & biotechnology 2010, 305879.
Shi, et al. (2009). Activation of the maternal immune system alters cerebellar development in the offspring. Brain Behav Immun 23, 116-123.
Silverman, et al. (2010). Behavioural phenotyping assays for mouse models of autism. Nature Reviews Neuroscience 11, 490-502.
Smith et al., Host Genetics and Environmental Factors Regulate Ecological Succession of the Mouse Colon Tissue-Associated Microbiota, PLoS One 7, e30273 (Jan. 2012).
Smith, E.A., and Macfarlane, G.T. (1997). Formation of Phenolic and Indolic Compounds by Anaerobic Bacteria in the Human Large Intestine. Microb Ecol 33, 180-188.
Smith, et al. (2007). Maternal immune activation alters fetal brain development through interleukin-6. J Neurosci 27, 10695-10702.
Sommese, et al. (2012). Evidence of Bacteroides fragilis protection from Bartonella henselae-induced damage. PLoS One 7, e49653.
Song, et al. (2004). Real-time PCR quantitation of Clostridia in feces of autistic children. Appl Environ Microbiol 70, 6459-6465.
Suzuki, et al. (2011). Interleukin-6 (IL-6) regulates claudin-2 expression and tight junction permeability in intestinal epithelium. J Biol Chem 286, 31263-31271.
Tabuchi, et al. (2007). A neuroligin-3 mutation implicated in autism increases inhibitory synaptic transmission in mice. Science 318, 71-76.
Tamura, et al. (2011). Loss of claudin-15, but not claudin-2, causes Na+ deficiency and glucose malabsorption in mouse small intestine. Gastroenterology 140, 913-923.
Thomas, et al. (2009). Marble burying reflects a repetitive and perseverative behavior more than novelty-induced anxiety. Psychopharmacology 204, 361-373.
Tillisch, et al. (2013). Consumption of fermented milk product with probiotic modulates brain activity. Gastroenterology 144, 1394-1401 e1394.
Tsai, et al. (2012). Autistic-like behaviour and cerebellar dysfunction in Purkinje cell Tsc1 mutant mice. Nature 488, 647-651.
Turner, J.R. (2009). Intestinal mucosal barrier function in health and disease. Nat Rev Immunol 9, 799-809.
Wang et al., "Is Urinary Indolyl-3-Acryloylglycine A Biomarkerfor Autism with Gastrointestinal Symptoms?" Biomarkers, 14(8):596-603 (2009).
Wang, et al. (2011). The prevalence of gastrointestinal problems in children across the United States with autism spectrum disorders from families with multiple affected members. Journal of developmental and behavioral pediatrics, JDBP 32, 351-360.
Wang, et al. (2012). Elevated fecal short chain fatty acid and ammonia concentrations in children with autism spectrum disorder. Dig Dis Sci 57, 2096-2102.
White, et al. (2009). Statistical Methods for Detecting Differentially Abundant Features in Clinical Metagenomic Samples. Plos Comput Biol 5.
White, J.F. (2003). Intestinal pathophysiology in autism. Exp Biol Med (Maywood) 228, 639-649.
Wikoff, et al. (2009) "Metabolomics analysis reveals large effects of gut microflora on mammalian blood metabolites", Proc Natl Acad Sci USA 106, 3698-3703.
Williams, et al. (2011). Impaired carbohydrate digestion and transport and mucosal dysbiosis in the intestines of children with autism and gastrointestinal disturbances. PLoS One 6, e24585.
Williams, et al. (2012). Application of novel PCR-based methods for detection, quantitation, and phylogenetic characterization of Sutterella species in intestinal biopsy samples from children with autism and gastrointestinal disturbances. MBio 3.
Winek et al., "The Gut Microbiome as Therapeutic Target | Central Nervous System Diseases: Implications for Stroke", Neurotherapeutics 13(4): 762-774, 2016.
Wirtz, et al. (2007). Chemically induced mouse models of intestinal inflammation. Nature protocols 2, 541-546.
Wittebolle, et al. (2009). Initial community evenness favours functionality under selective stress. Nature 458, 623-626.
Won, et al. (2012). Autistic-like social behaviour in Shank2-mutant mice improved by restoring NMDA receptor function. Nature 486, 261-265.
Yadav, et al., "Pharmacological inhibition of gut-derived serotonin synthesis is a potential bone anabolic treatment for osteoporosis", Nature Medicine 16(3):308-312, 2010.
Yang, et al. (2011). Automated three-chambered social approach task for mice. Curr Protoc Neurosci Chapter 8, Unit 8 26.
Yap, et al. (2010). Urinary metabolic phenotyping differentiates children with autism from their unaffected siblings and age-matched controls. Journal of proteome research 9, 2996-3004.
Zhou et al., "Promiscuous Cross-seeding between Bacterial Amyloids Promotes Interspecies Biofilms", (2012). Journal of Biological Chemistry 287(42).
Extended Search Report issued in European application No. EP16164727.6, dated Jun. 24, 2016.
Extended Search Report issued in European Application No. 11831629.8, dated Mar. 3, 2014.

(56) References Cited

OTHER PUBLICATIONS

Extended Search Report issued in European application No. EP13832132.8, dated Aug. 25, 2016.
Final Office Action issued in U.S. Appl. No. 14/925,240, dated Jan. 24, 2018.
Final Office Action issued in U.S. Appl. No. 14/925,510, dated Jan. 26, 2018.
International Preliminary Report on Patentability issued in application No. PCT/US2015/057897, dated May 2, 2017.
International Preliminary Report on Patentability issued in application No. PCT/US2015/057888, dated May 11, 2017.
International Preliminary Report on Patentability issued in application No. PCT/US2015/057891, dated May 2, 2017.
International Search Report and Written Opinion issued in Application No. PCT/US2018/032605, dated Aug. 3, 2018.
International Search Report and Written Opinion issued in Application PCT/US2011/055159, dated Feb. 27, 2012.
International Search Report and Written Opinion issued in application No. PCT/US2015/057888, dated Jan. 12, 2016.
International Search Report and Written Opinion issued in application No. PCT/US2015/057897, dated Jan. 12, 2016.
International Search Report and Written Opinion issued in application No. PCT/US2015/057891, dated Jun. 30, 2016.
International Search Report and Written Opinion issued in application No. PCT/US2018/044433, dated Nov. 26, 2018.
International Search Report and Written Opinion issued in application No. PCT/US2017/033881, dated Oct. 30, 2017.
International Search Report issued in application No. PCT/US2017/063108, dated Jan. 30, 2018.
International Search Report issued in application No. PCT/US2013/057148, dated Feb. 28, 2014.
Notice of Allowance issued in U.S. Appl. No. 13/267,748, dated Jul. 6, 2016.
Office Action issued in EP Application No. EP11831629.8, dated Apr. 1, 2015.
Office Action issued in U.S. Appl. No. 14/925,510, dated Aug. 12, 2016.
Office Action issued in JP Application No. 2013-532955, dated Aug. 18, 2015.
Office Action issued in U.S. Appl. No. 14/925,510, dated Aug. 22, 2017.
Office Action issued in JP Application No. 2016-088694, dated Feb. 7, 2017.
Office Action issued in EP Application No. 13832132.8, dated Jan. 11, 2018.
Office Action issued in U.S. Appl. No. 14/925,510, dated Jan. 25, 2017.
Office Action issued in CA Application No. 2,813,606, dated Jul. 20, 2017.
Office Action issued in JP Application No. 2015-530008, dated Jun. 13, 2017.
Office Action issued in U.S. Appl. No. 14/012,769, dated Mar. 29, 2017.
Office Action issued in U.S. Appl. No. 14/839,041, dated May 25, 2017.
Office Action issued in U.S. Appl. No. 14/925,240, dated May 5, 2017.
Office Action issued in EP Application No. 11831629.8, dated Nov. 10, 2014.
Office Action issued in U.S. Appl. No. 13/267,748, dated Nov. 18, 2015.
Office Action dated Nov. 21, 2013 for U.S. Appl. No. 13/267,748, filed Oct. 6, 2013.
Office Action issued in U.S. Appl. No. 14/839,041, dated Oct. 5, 2016.
Office Action issued in U.S. Appl. No. 14/925,240, dated Oct. 7, 2016.
Partial Supplementary Search Report issued in EP application No. 13832132.8, dated May 2, 2016.
Search Report and Written Opinion issued in application No. PCT-US2018-032605, dated Aug. 3, 2018.
Search Report and Written Opinion issued in application No. PCT-US2017-063108, dated Jan. 30, 2018.
Alkasir et al., Nov. 19, 2016, Human gut microbiota: the links with dementia development, Protein & Cell, 8(2):90-102.
Pistollato et al., Sep. 15, 2016, Role of gut microbiota and nutrients in amyloid formation and pathogenesis of Alzheimer disease, Nutrition Reviews, 74(10):624-634.
Supplementary European Search Report dated Apr. 28, 2021 in patent application No. 18802357.6.

* cited by examiner

Veh.

ECGC

Str

Mid.

Str.

Str.

Mid.

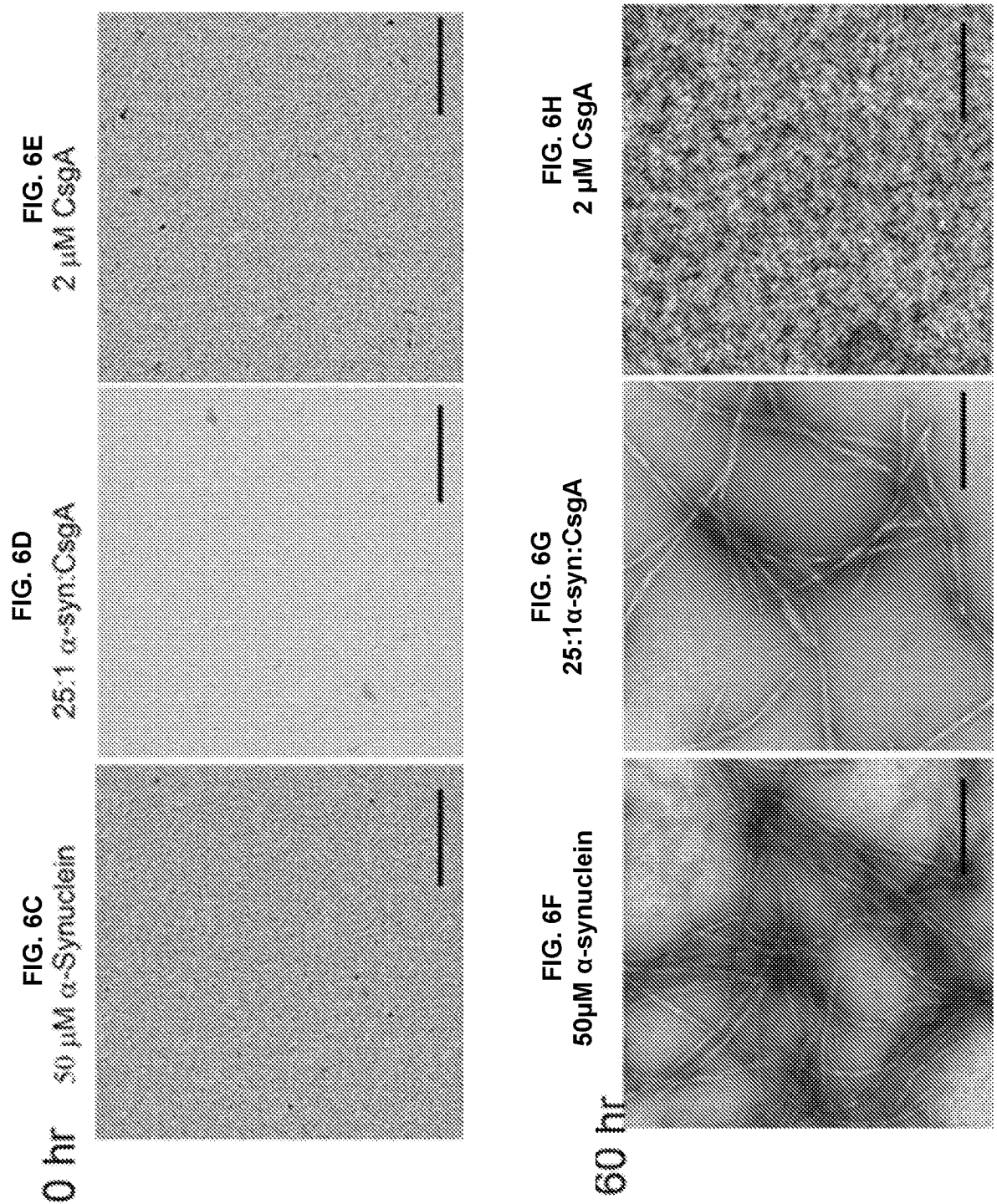

60 hr  50µM α-synuclein

+5% CsgA seeds

+5% α-synuclein seeds

5% α-Synuclein seeds

5% CsgA seeds

INHIBITORS OF MICROBIALLY INDUCED AMYLOID

INCORPORATION BY REFERENCE TO ANY PRIORITY APPLICATIONS

Any and all applications for which a foreign or domestic priority claim is identified in the Application Data Sheet (including any PCT Request) as filed with the present application are hereby incorporated by reference under 37 CFR 1.57. This Application is a U.S. National Phase application of PCT Application No. PCT/US2018/032605, filed on May 14, 2018, designating the United States of America and published in the English language, which claims the benefit of U.S. Provisional Application No. 62/506,457, filed May 15, 2017, and U.S. Provisional Application No. 62/506,433 filed May 15, 2017, each of which is hereby incorporated by reference in its entirety.

STATEMENT REGARDING FEDERALLY SPONSORED R&D

This invention was made with government support under Grant No. R01NS085910 awarded by the U.S. National Institutes of Health. The government has certain rights in the invention.

FIELD

The present disclosure relates to inhibitors of amyloid formation, and especially inhibitors of microbially-induced amyloid formation, as well as the use of such inhibitors to treat or inhibit neurological disorders and other disorders that present amyloid accumulation. Methods of identifying compositions that inhibit or promote amyloid formation are also provided.

BACKGROUND

Many neurodegenerative diseases are associated with atypical aggregation of proteins in the brain, which leads to cell death and a resulting manifestation of many neuropathies. It is believed that disease specificity is a consequence of (i) the specific proteins involved in aggregation, (ii) the specific regions of the brain affected, and (iii) the specific neuronal cell types affected. In the case of the natural human protein α-synuclein, aberrant aggregation of this protein leads to any of over 50 "α-synucleinopathies," of which Parkinson's Disease is the most common and most widely studied. In Parkinson's Disease, α-synuclein aggregation leads to the accumulation of large precipitated aggregates, called Lewy bodies, within certain neuronal cell types, most typically those that produce the neurotransmitter dopamine. When enough α-synuclein aggregate is present, neuronal death occurs and dopamine production declines. Dopamine is required for proper control of movement, and once dopaminergic neurons are killed they are not replaced. Over time the dopamine pool declines irreversibly to a point where motor symptoms progress and become debilitating.

The most pathogenic form of α-synuclein is still unclear, e.g., whether full intact Lewy bodies or smaller oligomeric α-synuclein fibrils are most relevant to disease progression and pathology. Traditional pharmaceutical and biotech approaches to inhibiting α-synuclein aggregation have focused on attacking the aggregation process in the neurons and brain regions most associated with disease symptoms. Small molecule approaches, antibody approaches and a vaccine approach all have been attempted and continue to be evaluated as interventions for Parkinson's Disease and other α-synucleinopathies. Importantly, all of these strategies presently rely on the therapeutic entity crossing the blood-brain barrier and reaching the target neuronal tissue. Traversing the blood-brain barrier remains one of the most significant pharmacokinetic challenges that hinders drug development for neurodegenerative diseases. Accordingly, there is a need for inhibitors of amyloid formation, and especially α-synuclein aggregation inhibitors, that have the potential for providing therapeutic effects without having to cross the blood-brain barrier.

SUMMARY

Without being limited by any particular theory, some embodiments of the present disclosure relate to the discovery of compositions which inhibit the aggregation of bacterial amyloid (e.g., aggregates of the CsgA protein), human amyloid (e.g., aggregates of the α-synuclein protein), and/or co-aggregates of bacterial and human amyloid (e.g., co-aggregates of the bacterial CsgA protein and the human α-synuclein protein, including aggregates in which the bacterial CsgA protein initiates or "seeds" aggregation of the human α-synuclein protein). Surprisingly, the inventors have found that certain compounds that, in the absence of this disclosure may have been considered to be potential inhibitors of amyloid formation, were found herein to be weak inhibitors (e.g., Anle 138b) or even to promote aggregation (e.g., thymol), as evaluated under one or more of the assay conditions described in the present disclosure. Additionally, identified herein are specific inhibitors and classes of inhibitors useful in reducing, inhibiting, and/or preventing the production of amyloid aggregates in accordance with compositions and methods of some embodiments herein.

In some embodiments, the compositions include an inhibitor of amyloid formation selected from:

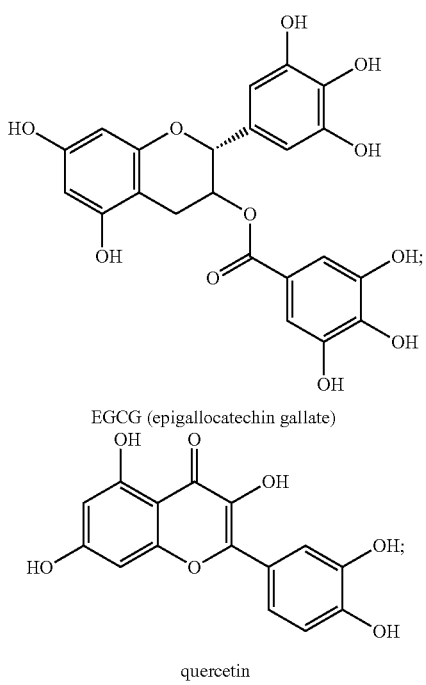

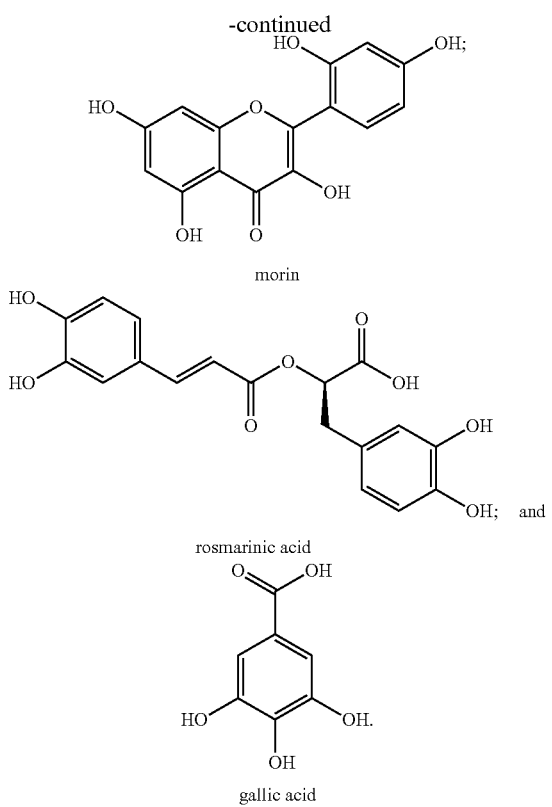

morin rosmarinic acid gallic acid

More generally, in some embodiments, the present disclosure provides compositions that include an inhibitor of amyloid formation according to Formula I:

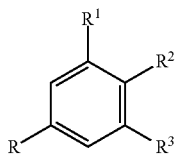

where
R$^1$ is selected from —H, —OH, or —OCH$_3$;
R$^2$ is selected from —H, —OH, or —OCH$_3$;
R$^3$ is selected from —H, —OH, or —OCH$_3$;
provided that at least one of R$^1$, R$^2$ and R$^3$ is not —H; and
wherein
R is selected from —OH, —C(O)OH, —C(O)OR$^4$ or R$^4$;
wherein
R$^4$ is selected from a C2-C20 branched or unbranched alkyl, alkenyl, carbocyclyl, aryl, heteroalkyl, heteroalkenyl, heterocyclyl or heteroaryl.

In some embodiments, the present disclosure provides compositions that include an inhibitor of amyloid formation according to Formula II:

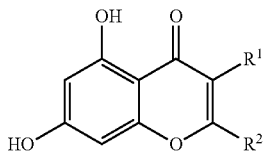

where
R$^1$ is selected from —H, —CH$_3$, —OH, —OCH$_3$, 3-hydroxyphenyl, 4-hydroxyphenyl, 2,4-dihydroxyphenyl, 3,4-dihydroxyphenyl, 3,5-dihydroxyphenyl, 3,4,5-trihydroxyphenyl, 3-methoxyphenyl, 4-methoxyphenyl, 2,4-methoxyphenyl, 3,4-dimethoxyphenyl, 3,5-dimethoxyphenyl, 3,4,5-trimethoxyphenyl, 2-hydroxy-4-methoxyphenyl, 3-hydroxy-4-methoxyphenyl, 2-methoxy-4-hydroxyphenyl, 3-methoxy-4-hydroxyphenyl, 3,4-dihydroxy-5-methoxyphenyl, 3,5-dihydroxy-4-methoxyphenyl, 3,4-methoxy-5-hydroxyphenyl, and 3,5-dimethoxy-4-hydroxyphenyl; and
R$^2$ is selected from —H, —CH$_3$, —OH, —OCH$_3$, 3-hydroxyphenyl, 4-hydroxyphenyl, 2,4-dihydroxyphenyl, 3,4-dihydroxyphenyl, 3,5-dihydroxyphenyl, 3,4,5-trihydroxyphenyl, 3-methoxyphenyl, 4-methoxyphenyl, 2,4-methoxyphenyl, 3,4-dimethoxyphenyl, 3,5-dimethoxyphenyl, 3,4,5-trimethoxyphenyl, 2-hydroxy-4-methoxyphenyl, 3-hydroxy-4-methoxyphenyl, 2-methoxy-4-hydroxyphenyl, 3-methoxy-4-hydroxyphenyl, 3,4-dihydroxy-5-methoxyphenyl, 3,5-dihydroxy-4-methoxyphenyl, 3,4-methoxy-5-hydroxyphenyl, and 3,5-dimethoxy-4-hydroxyphenyl; provided that at least one of R$^1$ and R$^2$ is —H, —CH$_3$, —OH, or —OCH$_3$.

As used herein, "alkyl" has its customary and ordinary meaning as understood by one of skill in the art in view of this disclosure. It refers to a branched, or straight chain saturated chemical group containing only carbon and hydrogen, such as methyl, isopropyl, isobutyl, sec-butyl and pentyl. In various embodiments, alkyl groups can either be unsubstituted or substituted with one or more substituents, e.g., halogen, hydroxyl, substituted hydroxyl, acyloxy, amino, substituted amino, amido, cyano, nitro, guanidino, amidino, mercapto, substituted mercapto, carboxy, sulfonyloxy, carbonyl, benzyloxy, aryl, heteroaryl, carbocyclyl, heterocyclyl, or other functionality that may be suitably blocked with a protecting group. Alkyl groups can have, for example, 1 to 20 carbon atoms, 1 to 9 carbon atoms, 1 to 6, or 1 to 5 carbon atoms.

As used herein. "alkenyl" has its customary and ordinary meaning as understood by one of skill in the art in view of this disclosure. It refers to a straight or branched chain chemical group containing only carbon and hydrogen and containing at least one carbon-carbon double bond, such as 1-propenyl, 2-propenyl, 2-methyl-1-propenyl, 1-butenyl, 2-butenyl, and the like. In various embodiments, alkenyls can either be unsubstituted or substituted with one or more substituents, e.g., halogen, hydroxyl, substituted hydroxyl, acyloxy, amino, substituted amino, amido, cyano, nitro, guanidino, amidino, mercapto, substituted mercapto, carboxy, sulfonyloxy, carbonyl, benzyloxy, aryl, heteroaryl, carbocyclyl, heterocyclyl, or other functionality that may be suitably blocked with a protecting group. Alkenyl groups can have, for example, 2 to 20 carbon atoms, 2 to 9 carbon atoms, 2 to 6, or 2 to 5 carbon atoms.

As used herein, "heteroalkenyl," has its customary and ordinary meaning as understood by one of skill in the art in view of this disclosure. It refers to an alkenyl group, as described herein, in which one or more of the constituent carbon atoms have been replaced by nitrogen, oxygen, or sulfur. In some embodiments, the heteroalkenyl group can be further substituted with 1, 2, 3, or 4 substituent groups as described herein for alkenyl groups. Examples of heteroalkenyl groups are an "alkenoxy" which, as used herein, refers alkenyl-O—. A heteroalkenylene is a divalent heteroalkenyl group.

As used herein, "carbocyclyl" has its customary and ordinary meaning as understood by one of skill in the art in view of this disclosure. It refers to a non-aromatic cyclic ring system containing only carbon atoms in the ring system backbone, such as cyclopropyl, cyclobutyl, cyclopentyl, cyclohexyl, and cyclohexenyl. Carbocyclyls may include multiple fused rings. Carbocyclyls may have any degree of saturation provided that at least one ring in the ring system is not aromatic. In various embodiments, carbocyclyl groups can either be unsubstituted or substituted with one or more substituents, e.g., halogen, alkoxy, acyloxy, amino, amido, cyano, nitro, hydroxyl, mercapto, carboxy, carbonyl, benzyloxy, aryl, heteroaryl, or other functionality that may be suitably blocked with a protecting group. Carbocyclyl groups can have, for example, 3 to 10 carbon atoms, or 3 to 6.

As used herein, "cycloalkyl" has its customary and ordinary meaning as understood by one of skill in the art in view of this disclosure. It refers to a fully saturated carbocyclyl ring system. Examples include cyclopropyl, cyclobutyl, cyclopentyl, and cyclohexyl.

As used herein, "aryl" has its customary and ordinary meaning as understood by one of skill in the art in view of this disclosure. It refers to an aromatic radical having a single-ring (e.g., phenyl) or multiple condensed rings (e.g., naphthyl or anthryl) with only carbon atoms present in the ring backbone. In various embodiments, aryl groups can either be unsubstituted or substituted with one or more substituents, e.g., amino, cyano, hydroxyl, lower alkyl, haloalkyl, alkoxy, nitro, halo, mercapto, carboxy, carbonyl, benzyloxy, aryl, heteroaryl, and other substituents. Some embodiments include substitution with an alkoxy group, which may be further substituted with one or more substituents, e.g., amino, cyano, hydroxyl, lower alkyl, haloalkyl, alkoxy, nitro, halo, mercapto, and other substituents.

As used herein, the term "heteroaryl" has its customary and ordinary meaning as understood by one of skill in the art in view of this disclosure. It refers to an aromatic radical having one or more heteroatom(s) (e.g., N, O, or S) in the ring backbone and may include a single ring (e.g., pyridine) or multiple condensed rings (e.g., quinoline). In various embodiments, heteroaryl groups can either be unsubstituted or substituted with one or more substituents, e.g., amino, cyano, hydroxyl, lower alkyl, haloalkyl, alkoxy, nitro, halo, mercapto, carboxy, carbonyl, benzyloxy, aryl, heteroaryl, and other substituents. Examples of heteroaryl include thienyl, pyrridyl, furyl, oxazolyl, oxadiazolyl, pyrollyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl, quinolinyl, quinazolinyl and others.

As used herein. "heterocyclyl" has its customary and ordinary meaning as understood by one of skill in the art in view of this disclosure. It refers to a non-aromatic cyclic ring system comprising at least one heteroatom in the ring system backbone. Heterocyclyls may include multiple fused rings. Heterocyclyls may have any degree of saturation provided that at least one ring in the ring system is not aromatic. The heteroatom(s) may be present in either a non-aromatic or aromatic ring in the ring system. In various embodiments, heterocyclyls may be substituted or unsubstituted with one or more substituents, e.g., halogen, alkoxy, acyloxy, amino, amido, cyano, nitro, hydroxyl, mercapto, carboxy, carbonyl, benzyloxy, aryl, heteroaryl, and other substituents, and are attached to other groups via any available valence, preferably any available carbon or nitrogen. Heterocycles can be, for example, 5-7 membered. In six membered monocyclic heterocycles, the heteroatom(s) are selected from one up to three of O, N or S, and when the heterocycle is five membered, it can have one or two heteroatoms selected from O, N, or S. Examples of heterocyclyl include pyrrolidinyl, piperidinyl, azepanyl, tetrahydrofuranyl, tetrahydropyranyl, oxepanyl, tetrahydrothiophenyl, tetrahydrothiopyranyl, thiepanyl, indolinyl and dihydrobenzofuranyl.

As used herein, "heteroalkyl" has its customary and ordinary meaning as understood by one of skill in the art in view of this disclosure. It refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —OCH$_3$, etc.), an amine (e.g., —NHCH$_3$, —N(CH$_3$)$_2$, etc.), or a thioalkyl group (e.g., —SCH$_3$). If a non-terminal carbon atom of the alkyl group which is not attached to the parent molecule is replaced with a heteroatom (e.g., O, N, or S) the resulting heteroalkyl groups are, respectively, an alkyl ether (e.g., —CH$_2$CH$_2$—O—CH$_3$, etc.), an alkyl amine (e.g., —CH$_2$NHCH$_3$, —CH$_2$N(CH$_3$)$_2$, etc.), or a thioalkyl ether (e.g., —CH$_2$—S—CH$_3$). If a terminal carbon atom of the alkyl group is replaced with a heteroatom (e.g., O. N, or S), the resulting heteroalkyl groups are, respectively, a hydroxyalkyl group (e.g., —CH$_2$CH$_2$—OH), an aminoalkyl group (e.g., —CH$_2$NH$_2$), or an alkyl thiol group (e.g., —CH$_2$CH$_2$—SH). A heteroalkyl group can have, for example, 1 to 20 carbon atoms, 1 to 10 carbon atoms, or 1 to 6 carbon atoms. A $C_1$-$C_6$ heteroalkyl group means a heteroalkyl group having 1 to 6 carbon atoms.

In some embodiments, the present disclosure provides compositions that include an inhibitor of amyloid formation according to Formula III:

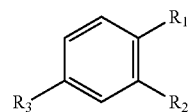

where $R_1$ may comprise —H, —OH, —OCH$_3$, —CH$_3$, —CH(CH$_3$)$_2$, —C(CH$_3$)$_3$, —CH$_2$CH$_3$, —C$_6$H$_5$, —C$_6$H$_4$CH$_3$, —C$_6$H$_4$OH, —C$_6$H$_4$C(O)H, —C$_6$H$_4$C(O)CH$_3$, —C$_6$H$_4$C(O)CH$_3$, —C$_6$H$_4$OC(O)CH$_3$, —C(O)H, —C(O)CH$_3$, —OC(O)H, or —OC(O)CH$_3$;

$R_2$ may comprise —H, —OH, —OCH$_3$, —CH$_3$, —CH(CH$_3$)$_2$, —C(CH$_3$)$_3$, —CH$_2$CH$_3$, —C$_6$H$_5$, —C$_6$H$_4$CH$_3$, —C$_6$H$_4$OH, —C$_6$H$_4$C(O)H, —C$_6$H$_4$C(O)CH$_3$, —C$_6$H$_4$C(O)CH$_3$, —C$_6$H$_4$OC(O)CH$_3$, —C(O)H, —C(O)CH$_3$, —OC(O)H, or —OC(O)CH$_3$; and $R_3$ may comprise —H, —OH, —OCH$_3$, —OCH$_2$CH$_3$, —OCH$_2$CH$_2$CH$_3$, —CH$_3$, —CH(CH$_3$)$_2$, —C(CH$_3$)$_3$, —CH$_2$CH$_3$, —CH$_2$CH$_2$CH$_3$, —CH$_2$CHCH$_2$, —CHCHCH$_3$, —C$_6$H$_5$, —C$_6$H$_4$CH$_3$, —C$_6$H$_4$OH, —C$_6$H$_4$C(O)H, —C$_6$H$_4$C(O)CH$_3$, —C$_6$H$_4$C(O)CH$_3$, —C$_6$H$_4$OC(O)CH$_3$, C(O)H, —C(O)CH$_3$, —C(O)CH$_2$CH$_3$, —C(O)CH$_2$CH$_2$CH$_3$, —OC(O)H, —OC(O)CH$_3$, —OC(O)CH$_2$CH$_3$—OC(O)CH$_2$CH$_3$, —CH$_2$CH$_2$CH$_3$, —CHCHCH$_2$CH$_3$, —CH$_2$CHCHCH$_3$, or —CH$_2$CH$_2$CHCH$_2$. In some embodiments, $R_1$ is —H, —OH, —OCH$_3$, —CH$_3$, —CH(CH$_3$)$_2$, —C(CH$_3$)$_3$, —CH$_2$CH$_3$, —C$_6$H$_5$, —C$_6$H$_4$CH$_3$, —C$_6$H$_4$OH, —C$_6$H$_4$C(O)H, —C$_6$H$_4$C(O)CH$_3$, —C$_6$H$_4$C(O)CH$_3$, —C$_6$H$_4$OC(O)CH$_3$, —C(O)H, —C(O)CH$_3$, —OC(O)H, or —OC(O)CH$_3$; R$_2$ is —H, —OH, —OCH$_3$, —CH$_3$, —CH(CH$_3$)$_2$, —C(CH$_3$)$_3$, —CH$_2$CH$_3$, —C$_6$H$_5$, —C$_6$H$_4$CH$_3$, —C$_6$H$_4$OH, —C$_6$H$_4$C(O)H, —C$_6$H$_4$C(O)CH$_3$, —C$_6$H$_4$C(O)CH$_3$, —C$_6$H$_4$OC(O)CH$_3$, —C(O)H, —C(O)CH$_3$, —OC(O)H, or —OC(O)CH$_3$; and R$_3$ is —H, —OH, —OCH$_3$, —OCH$_2$CH$_3$, —OCH$_2$CH$_2$CH$_3$, —CH$_3$, —CH(CH$_3$)$_2$, —C(CH$_3$)$_3$, —CH$_2$CH$_3$, —CH$_2$CH$_2$CH$_3$, —CH$_2$CHCH$_2$, —CHCHCH$_3$, —C$_6$H$_5$, —C$_6$H$_4$CH$_3$, —C$_6$H$_4$OH, —C$_6$H$_4$C(O)H, —C$_6$H$_4$C(O)CH$_3$, —C$_6$H$_4$C(O)CH$_3$, —C$_6$H$_4$OC(O)CH$_3$, C(O)H, —C(O)CH$_3$, —C(O)CH$_2$CH$_3$, —C(O)CH$_2$CH$_2$CH$_3$, —OC(O)H, —OC(O)CH$_3$, —OC(O)CH$_2$CH$_3$—OC(O)CH$_2$CH$_2$CH$_3$, —CH$_2$CH$_2$CH$_2$CH$_3$, —CHCHCH$_2$CH$_3$, —CH$_2$CHCHCH$_3$, or —CH$_2$CH$_2$CHCH$_2$.

In some embodiments, the present disclosure provides compositions that include an inhibitor of amyloid formation selected from the group consisting of: EGCG (epigallocatechin gallate), quercetin (2-(3,4-dihydroxyphenyl)-3,5,7-trihydroxychromen-4-one), morin (2-(2,4-dihydroxyphenyl)-3,5,7-trihydroxychromen-4-one), rosmarinic acid ((2R)-2-[[(2"E")-3-(3,4-dihydroxyphenyl)-1-oxo-2-propenyl]]oxy]-3-(3,4-dihydroxyphenyl) propanoic acid), gallic acid (3,4,5-trihydroxybenzoic acid), lauryl gallate (dodecyl 3,4,5-trihydroxybenzoate), methoxyhydroquinone (2-methoxybenzene-1,4-diol), curcumin ((1E,6E)-1,7-Bis(4-hydroxy-3-methoxyphenyl)hepta-1,6-diene-3,5-dione), resveratrol ((E)-5-(4-hydroxystyryl)benzene-1,3-diol), apigenin (5,7-dihydroxy-2-(4-hydroxyphenyl)-4H-1-benzopyran-4-one), NDGA (nordihydroguaiaretic acid or 4,4'-(2,3-dimethylbutane-1,4-diyl)dibenzene-1,2-diol), phloretin (3-(4-hydroxyphenyl)-1-(2,4,6-trihydroxyphenyl) propan-1-one), genistein (5,7-dihydroxy-3-(4-hydroxyphenyl)chromen-4-one), isoeugenol (2-methoxy-4-(prop-1-en-1-yl)phenol), 4-allyl-1,2-dimethoxybenzene, eugenol (2-methoxy-4-(prop-2-en-1-yl)phenol), 4-ethylguaiacol (4-ethyl-2-methoxyphenol), guaiacol (2-methoxyphenol), thymol (5-methyl-2-(propan-2-yl)phenol), carvacrol (2-methyl-5-(propan-2-yl)phenol), and Anle 138b, or a subgroup consisting of two or more of any of the listed compounds, for example, the group consisting of one or more of the following molecules: EGCG, quercetin, morin, rosmarinic acid, gallic acid and lauryl gallate; the group consisting of one or more of the following molecules: EGCG, quercetin, genistein, apigenein, resveratrol, rosmarinic acid, and NDGA; the group consisting of one or more of the following molecules: quercetin, genistein, apigenein, resveratrol, rosmarinic acid, and NDGA; or the group consisting of one or more of the following molecules: quercetin, EGCG, resveratrol, rosmarinic acid, and NDGA; or the group consisting of one or more of the following molecules: EGCG, quercetin, morin, rosmarinic acid, gallic acid; or the group consisting of one or more of the following molecules: quercetin, resveratrol, rosmarinic acid, and NDGA; or the group consisting of: one or more of the following molecules: resveratrol, rosmarinic acid, and quercetin; or the group consisting of one or more of the following molecules: quercetin, morin, rosmarinic acid, and gallic acid; or the group consisting of one or more of the following molecules: quercetin, morin, rosmarinic acid, gallic acid and lauryl gallate; or the group consisting of one or more of the following molecules: quercetin, genistein, apigenein, resveratrol, rosmarinic acid, and NDGA; or the group consisting of one or more of the following molecules: quercetin, genistein, apigenein, resveratrol, rosmarinic acid, and NDGA; or the group consisting of one or more of EGCG, quercertin, morin, rosmarinic acid, gallic acid, methoxyhydroquinone, curcumin, resveratrol, apigenin, NDGA, phloretin, genistein, and lauryl gallate; or the group consisting of one or more of EGCG, morin, gallic acid, methoxyhydroquinone, curcumin, NDGA, phloretin, lauryl gallate, isoeugenol, 4-allyl-1,2-dimethoxy-benzene, eugenol, and guaiacol; or the group consisting of one or more of: EGCG, quercetin, morin, rosmarinic acid, gallic acid, methoxyhydroquinone, resveratrol, NDGA, and phloretin; or the group consisting of one or more of: EGCG, quercetin, morin, rosmarinic acid, and gallic acid; or the group consisting of one or more of quercertin, morin, rosmarinic acid, gallic acid, methoxy-hydroquinone, curcumin, resveratrol, apigenin, NDGA, phloretin, genistein, and lauryl gallate; or the group consisting of one or more of morin, gallic acid, methoxy-hydroquinone, curcumin, NDGA, phloretin, lauryl gallate, isoeugenol, 4-allyl-1,2-dimethoxy-benzene, eugenol, and guaiacol; or the group consisting of one or more of: quercetin, morin, rosmarinic acid, gallic acid, methoxy-hydroquinone, resveratrol, NDGA, and phloretin; or the group consisting of one or more of: quercetin, morin, rosmarinic acid, and gallic acid.

In some embodiments, the composition is formulated for delivery outside of the systemic circulation of a subject. Said composition may be formulated for enteric or intranasal delivery, for example, and/or said compositions may further be formulated for controlled release within the lower intestine or colon. The aforementioned compositions may comprise an enteric-coated capsule, tablet, soft-gel, spray dried powder, polymer matrix, hydrogel, enteric-coated solid, crystalline solid, amorphous solid, glassy solid, coated micronized particle, liquid, nebulized liquid, aerosol, or microcapsule.

The present disclosure further provides a method of disrupting the formation of amyloid aggregates, comprising contacting an amyloid or a precursor of an amyloid with a composition comprising one or more polyphenols or polyphenol-like compounds, such as a composition comprising a compound having the structure of Formula I, Formula II or Formula III, and/or one or more of the molecules provided in Table 2 or Table 3 (below), and/or a derivative thereof.

The present disclosure further provides a method of disrupting the formation of amyloid aggregates in a subject, comprising administering to said subject a composition comprising one or more polyphenols or polyphenol-like compounds, such as a composition comprising a compound having the structure of Formula I, Formula II or Formula III and/or one or more of the molecules provided in Table 2 or Table 3 (below), and/or a derivative thereof. Optionally, said subject is additionally selected or identified as one that would receive the benefit of a molecule that disrupts the formation of amyloid aggregates prior to administration of said composition. Such selection or identification can be made by clinical or diagnostic evaluation, prior to administering said composition. Such selected subjects may have been diagnosed or evaluated for Parkinson's Disease, Lewy Body Dementia, incidental Lewy body disease, Lewy body variant of Alzheimer's disease, multiple system atrophy, or pure autonomic failure, or any combination thereof. Optionally, prior to, during or after administration of the composition, the disruption or inhibition of the formation of amyloid aggregates in said subject is measured or evaluated.

The present disclosure further provides a method of inhibiting, ameliorating, reducing the likelihood, delaying the onset of, treating, or preventing an amyloid disorder in a subject. The method can comprise administering to the subject a composition comprising one or more polyphenols or polyphenol-like compounds, such as a composition comprising a compound having the structure of Formula I, Formula II or Formula III, and/or one or more of the molecules provided in Table 2 or Table 3 (below), and/or a derivative thereof. Optionally, the subject is additionally selected or identified as one that would receive the benefit of a molecule that inhibits or disrupts the formation of amyloid aggregates prior to administration of said composition, for example by detecting a presence or level of a bacterial protein (such as CsgA), or a presence or level of a microbial organism that makes the bacterial protein in an intestinal sample of the subject. Such selection or identification can be made by clinical or diagnostic evaluation, prior to administering said composition. Such selected subjects may have been diagnosed or evaluated for Parkinson's Disease, Lewy Body Dementia, incidental Lewy body disease, Lewy body variant of Alzheimer's disease, multiple system atrophy, or pure autonomic failure, or any combination thereof. Optionally, prior to, during or after administration of the composition, the disruption or inhibition of the formation of amyloid aggregates in said subject is measured or evaluated.

In some embodiments according to the methods and compositions as described herein, said amyloid aggregates may comprise one or more mammalian amyloid or mammalian amyloid precursors such as proteins, and/or one or more bacterial or fungal proteins (e.g., a composition comprising CsgA). In some embodiments according to the methods and compositions disclosed herein, said amyloid aggregates may be present within the gastrointestinal tract, the enteric nervous tissue, cranial sinus, or nasal cavity (e.g., the olfactory bulb).

In some embodiments according to the methods and compositions of the present disclosure, said composition may be administered to said subject daily, multiple times per day, or less frequently than daily. In some embodiments, said administration may be repeated. In some embodiments, said composition may be administered every second day, every third day, every fourth day, every fifth day, every sixth day, or every seventh day. In some embodiments, the composition administered in a given administration is different from a composition previously administered. In some embodiments, the dose administered in a given administration is different from a dose previously administered. In some embodiments according to the methods and compositions of the present disclosure, enteric amyloid levels and/or amyloid aggregation are monitored during or following the course of administration.

In some embodiments, the methods of the present disclosure further comprise measuring or evaluating a change in the subject's nervous system, such as a neurological symptom, motor behavior, or other behavior of the subject, which may comprise, e.g., one or more of anosmia, hyposmia, bradykinesia, ataxia, tremor, muscle rigidity, impaired posture and balance, loss of automatic movements, dysarthria or other speech changes, handwriting changes, orthostatic hypotension, memory deficit, dysphagia, incontinence, sleep disruption, cardiac arrhythmia, visual disturbance, psychiatric problems including depression and/or visual, auditory, olfactory, and/or tactile hallucinations, vertigo, cognitive dysfunction, altered dopamine levels, altered serotonin levels, altered kynurenine levels, or any combination thereof. In some embodiments, the methods of the present disclosure further comprise measuring or evaluating a change in the gastrointestinal system, such as a gastrointestinal symptom or behavior of the subject, which may comprise, e.g., one or more of dysphagia, reduced gut motility, gastroparesis, constipation (including chronic constipation and chronic idiopathic constipation), small intestine bacterial overgrowth (SIBO), diarrhea, abdominal pain and/or cramping, bloating, flatulence, nausea, or any other symptoms of irritable bowel syndrome (IBS), inflammatory bowel disease (IBD), ulcerative colitis, Crohn's disease, intestinal hyperpermeability, leaky gut, intestinal dysbiosis, or any combinations thereof. As used herein, the terms IBS and IBD have their customary and ordinary meaning as understood by one of skill in the art in view of this disclosure. The term "intestinal hyperpermeability" means abnormal increased permeability of the barrier formed by the intestinal epithelial lining between the intestinal lumen and the surrounding issues. Such hyperpermeability may result from inflammation of the intestinal lining and/or failure of the tight junctions between cells of the intestinal epithelium, which allows the passage of substances from the lumen into the surrounding tissues where some may enter the peritoneal cavity and/or systemic circulation. Because of this leakage of substances from the gut or intestinal lumen, intestinal hyperpermeability may be referred to as "leaky gut" or "leaky gut syndrome."

In some embodiments, the compositions of the present disclosure may be administered to a subject prior to, or following, the appearance of a neurological symptom or condition. In some embodiments, the compositions of the present disclosure may be administered to a subject prior to, or following, the appearance of a gastrointestinal symptom or condition associated with an amyloid disorder. In some embodiments, said subject is selected as one that has been identified as being at risk for developing or already having Lewy Body Dementia, incidental Lewy body disease, Lewy body variant of Alzheimer's disease, multiple system atrophy, pure autonomic failure, or any combination thereof, such as by clinical or diagnostic evaluation. In some embodiments, said subject is under the age of 18, 18-30, 30-50, 50-60, 60-70, or over the age of 70. In some embodiments, said subject is one that has been identified or selected as being at risk for developing or already having Parkinson's disease, such as by clinical or diagnostic evaluation or family history analysis.

In some embodiments according to the compositions and methods disclosed herein said composition may be coadministered with caffeine, nicotine, theophylline, theobromine, xanthine, methylxanthine, or derivatives thereof. In some embodiments, the methods as disclosed herein further comprise administering to said subject an inhibitor of α-synuclein aggregation. In some embodiments, the methods as disclosed herein further comprise administering to said subject L-DOPA, carbodopa, levodopa, Droxidopa, rasagiline, apomorphine hydrochloride, Bromocriptine, Rotigotine, Pramipexole, Ropinirole, Benzotropine, Trihexyphenidyl, Selegiline, Entacapone, Tolcapone, Amantadine, Pimavanersin, Rivastigmine or the like, or any combination thereof. In some embodiments, the methods as disclosed herein comprise administering to said subject an inhibitor of α-synuclein aggregation, and further comprise administering to said subject L-DOPA, carbodopa, levodopa, Droxidopa, rasagiline, apomorphine hydrochloride, Bromocriptine, Rotigotine, Pramipexole, Ropinirole, Benzotropine, Trihexyphenidyl, Selegiline, Entacapone, Tolcapone, Amantadine, Pimavanersin, Rivastigmine or the like, or any combination thereof. In some embodiments, the inhibitor of α-synuclein aggregation and the L-DOPA, carbodopa, levodopa, Droxidopa, rasagiline, apomorphine hydrochloride, Bromocriptine, Rotigotine, Pramipexole, Ropinirole, Benzotropine, Trihexyphenidyl, Selegiline, Entacapone, Tolcapone, Amantadine, Pimavanersin, Rivastigmine or the like are administered in the same composition. In some embodiments, the inhibitor of α-synuclein aggregation and the L-DOPA, carbodopa, levodopa, Droxidopa, rasagiline, apomorphine hydrochloride, Bromocriptine, Rotigotine, Pramipexole, Ropinirole, Benzotropine, Trihexyphenidyl, Selegiline, Entacapone, Tolcapone, Amantadine, Pimavanersin, Rivastigmine or the like are administered in separate compositions. In some embodiments, the separate compositions are administered at the same time. In some embodiments, the separate compositions are administered at the different times.

In some embodiments, the composition according to any of the compositions and methods disclosed herein is for medical use. In some embodiments, the composition according to any of the compositions and methods disclosed herein is for use in treating an amyloid disorder as described herein (such as an amyloid disorder of Table 1). In some embodiments, the amyloid disorder is selected from the group consisting of Parkinson's Disease, Lewy Body Dementia, incidental Lewy body disease, Lewy body variant of Alzheimer's disease, multiple system atrophy, or pure autonomic failure, or any combination of two or more of these. In some embodiments the composition according to the compositions and methods disclosed herein is for use in preparing a medicament for the treatment for an amyloid disorder as described herein (such as an amyloid disorder of Table 1). In some embodiments, the amyloid disorder is selected from the group consisting of Parkinson's Disease, Lewy Body Dementia, incidental Lewy body disease, Lewy body variant of Alzheimer's disease, multiple system atrophy, or pure autonomic failure, or any combination of two or more of these. In some embodiments, the composition comprises one or more polyphenols or polyphenol-like compounds, such as a compound having the structure of Formula I, Formula II or Formula III, and/or one or more of the molecules provided in Table 2 or Table 3 (below). In some embodiments, the composition is formulated for delivery to the gastrointestinal tract, for example via oral or rectal delivery, or formulated with an enteric coating. In some embodiments, the composition is formulated for delivery to the central nervous system, for example via intraspinal or intracranial, or formulated to cross the blood-brain barrier.

The present disclosure provides methods of identifying compositions that affect the formation of microbially-induced amyloid. In some approaches, the methods comprise contacting a plurality of concentrations of a microbial amyloid or a microbial amyloid precursor with a plurality of concentrations of α-synuclein and/or other mammalian amyloid or mammalian amyloid precursor in the presence of a composition, analyzing or measuring the formation of amyloid after the reaction set forth above; and comparing said analysis or measurement to an analysis or measurement of a control, wherein said control comprises analyzing or measuring the formation of amyloid after the reaction set forth above in the absence of said composition. In some methods and compositions disclosed herein, said microbial amyloid or microbial amyloid precursor comprises CsgA. In some embodiments, the methods according to the present disclosure also comprise agitation during the contacting step and/or prior to measurement.

In certain embodiments, said contacting of a plurality of concentrations of a microbial amyloid or a microbial amyloid precursor (e.g., a composition comprising CsgA) with a plurality of concentrations of α-synuclein and/or other mammalian amyloid or mammalian amyloid precursor is conducted in the presence of an indicator of amyloid formation. In some further embodiments, said indicator is a fluorescent indicator, a spin-labeled indicator, an enzyme, an antibody, or a colorimetric indicator. In some further embodiments, said indicator is Thioflavin T (ThT). Where said indicator of amyloid formation is an antibody, the methods of the present disclosure provide that said antibody may have specificity for aggregated α-synuclein and/or another mammalian amyloid or mammalian amyloid precursor, and optionally may be conjugated to a fluorescent label, an enzyme, a colorimetric label, a spin label, a metal ion binding moiety, a nucleic acid, a polysaccharide, or a polypeptide. In some embodiments according to the methods of the present disclosure, CsgA and said α-synuclein and/or other such bacterial amyloid precursor and/or mammalian amyloid/mammalian amyloid precursor are each separately labeled.

In some embodiments according to the methods of the present disclosure, formation of amyloid is analyzed or measured by internal fluorescence, by fluorescence of a dye or label, by fluorescence resonance energy transfer, by fluorescence polarization, by fluorescence polarization transfer, by UV/Vis Spectroscopy, by magnetic resonance, by Raman scattering, by electron paramagnetic spin resonance, by light microscopy, by electron microscopy, by scanning tunneling microscopy, or by atomic force microscopy.

As noted above, the methods of the present disclosure contemplate identifying a composition that affects the formation of microbially-induced amyloid, comprising contacting a plurality of concentrations of a microbial amyloid or a microbial amyloid precursor in the presence of a composition, analyzing or measuring the formation or disaggregation of amyloid after the reaction set forth above; and comparing said analysis or measurement to an analysis or measurement of a control, wherein said control comprises analyzing or measuring the formation of amyloid after the reaction set forth in above in the absence of said composition. In some embodiments according to the methods of the present disclosure, said composition comprises a mixture of compounds. Said composition may comprise tissue, bodily fluid or an extract thereof. In some embodiments, said composition comprises feces, urine, blood, spinal fluid, or saliva, or a component thereof. In some embodiments, said composition comprises an extract from a natural product. In some embodiments, said natural product is an herb, a botanical substance, or foodstuff. In some further embodiments, said natural product is a fungal tissue, legume, seed, berry, leaf, fruit, flower, plant root, plant stem, or plant bark. In some embodiments, said composition may comprise one or more bacteria, bacterial extracts, lysates, conditioned culture media, lyophilized bacteria, lyophilized lysates, lyophilized culture media, or any combination thereof.

In some embodiments according to the methods of the present disclosure, said contacting a plurality of concentrations of a microbial amyloid or a microbial amyloid precursor (e.g., a composition comprising CsgA) with a plurality of concentrations of α-Synuclein and/or other mammalian amyloid or mammalian amyloid precursor in the presence of a composition, analyzing or measuring the formation of amyloid after the reaction set forth above; and comparing said analysis or measurement to an analysis or measurement of a control, further comprises identifying or selecting a composition that alters or modulates or is suspected of altering or modulating amyloid formation. In some embodiments, the methods described herein further comprise identifying or selecting compositions that reduce or enhance amyloid formation. In some embodiments, the methods described herein further comprise identifying or selecting compositions that reduce or enhance amyloid formation that also do not cross the blood brain barrier. The compounds identified by these methods, can be administered to subjects identified or selected as a population that would benefit from receiving a compound that alters amyloid formation (e.g., a compound that reduces amyloid formation, preferably without crossing the blood brain barrier). Such selected subjects may have been diagnosed or evaluated for Parkinson's Disease, Lewy Body Dementia, incidental Lewy body disease, Lewy body variant of Alzheimer's disease, multiple system atrophy, or pure autonomic failure, or any combination thereof.

The methods according to the present disclosure further contemplate a method of making microbially-induced amyloid, comprising contacting a plurality of concentrations of a microbial amyloid or a microbial amyloid precursor with a plurality of concentrations of α-Synuclein and/or other mammalian amyloid or mammalian amyloid precursor in the presence or absence of a composition; generating microbially-induced amyloid; and analyzing or quantifying the microbially-induced amyloid. In some further embodiments, said microbial amyloid or microbial amyloid precursor comprises CsgA. In some further embodiments, the methods according to the present disclosure further comprise agitation during said contacting or prior to measurement. In some further embodiments, said method is conducted in the presence of an indicator of amyloid formation. In some further embodiments, said indicator of amyloid formation may comprise a fluorescent indicator, a spin-labeled indicator, or a colorimetric indicator. In some embodiments, said indicator said indicator is Thioflavin T (ThT). In some embodiments, CsgA and α-Synuclein, or other such bacterial amyloid/bacterial amyloid precursor and mammalian amyloid/mammalian amyloid precursor are each separately labeled. In some embodiments, said amyloid formation is analyzed or measured by internal fluorescence, by fluorescence of a dye or label, by fluorescence resonance energy transfer, by fluorescence polarization, by fluorescence polarization transfer, by UV/Vis Spectroscopy, by magnetic resonance, by Raman scattering, by electron paramagnetic spin resonance, by light microscopy, by electron microscopy, by scanning tunneling microscopy, or by atomic force microscopy.

In some embodiments according to the methods of the present disclosure, said composition to be present during said contacting of a plurality of concentrations of a microbial amyloid or a microbial amyloid precursor (e.g., a composition comprising CsgA) with a plurality of concentrations of α-Synuclein and/or other mammalian amyloid or mammalian amyloid precursor comprises a mixture of compounds. The composition may comprise tissue, bodily fluid or an extract thereof. In some embodiments, said composition comprises feces, urine, blood, spinal fluid, or saliva, or a component thereof. In some embodiments, the composition comprises an extract from a natural product. In some further embodiments, the natural product is an herb, a botanical substance, or foodstuff. In some embodiments, said natural product is a fungal tissue, legume, seed, berry, leaf, fruit, flower, plant root, plant stem, or plant bark. In some embodiments, the composition may comprise one or more bacteria, bacterial extracts, lysates, conditioned culture media, lyophilized bacteria, lyophilized lysates, lyophilized culture media, or any combination thereof. In some embodiments, the methods above further comprise identifying or selecting compositions that increase or reduce amyloid formation, preferably compounds that also do not cross the blood brain barrier. The compounds identified by these methods, can be administered to subjects identified or selected as a population that would benefit from receiving a compound that alters amyloid formation (e.g., a compound that reduces amyloid formation, preferably without crossing the blood brain barrier). Such selected subjects may have been diagnosed or evaluated for Parkinson's Disease, Lewy Body Dementia, incidental Lewy body disease, Lewy body variant of Alzheimer's disease, multiple system atrophy, or pure autonomic failure, or any combination thereof.

In some embodiments, the inhibitors of amyloid formation may be intended for administration systemically or locally to the enteric of central nervous system. For example, inhibitors which are effective against mammalian amyloid or mammalian amyloid precursor protein aggregation may be useful in treatment of one or more of the amyloid disorders described herein (e.g., one or more of the disorders of Table 1). Therefore, for such embodiments, the compositions comprising the inhibitors of amyloid formation may be formulated for parenteral administration, including systemic administration (e.g., intravenous, subcutaneous, intramuscular, intraperitoneal) or local administration (e.g., local injection near the vagus nerve, intraspinal injection, or intracranial injection). For delivery into the CNS, it is necessary for the inhibitors to pass through the blood brain barrier. Therefore, in such embodiments, the inhibitors are preferably lipid soluble molecules, or may be modified to increase lipid solubility, or may be co-administered with compounds that enhance passage through the blood brain barrier (see, e.g., WO2014076655A1, WO2012159052A2, WO01992018529A1).

The present disclosure also contemplates a kit comprising a microbial amyloid or a microbial amyloid precursor and α-Synuclein and/or other mammalian amyloid or mammalian amyloid precursor, being present in one or more containers within said kit whereby the methods of the present disclosure may be practiced. In some embodiments, said microbial amyloid or microbial amyloid precursor comprises CsgA.

The methods of the present disclosure further provide a method of treating or inhibiting an amyloid disorder (e.g., Parkinson's Disease, Lewy Body Dementia, incidental Lewy body disease, Lewy body variant of Alzheimer's disease, multiple system atrophy, or pure autonomic failure, or any combination thereof) in a tested subject comprising contacting a plurality of concentrations of a microbial amyloid or a microbial amyloid precursor with a plurality of concentrations of α-Synuclein and/or other mammalian amyloid or mammalian amyloid precursor, which may be obtained from a biological sample from said tested subject, in the presence or absence of a composition; analyzing or measuring the formation of amyloid; and comparing the analysis or measurement made with an analysis or measurement of a control, wherein said control may comprise analyzing or measuring the formation of amyloid in the absence of said composition or comparison to a standard such as the amount or rate or formation of amyloid from a healthy subject or a subject having amyloidosis (e.g., a subject suffering from Parkinson's Disease, Lewy Body Dementia, incidental Lewy body disease, Lewy body variant of Alzheimer's disease, multiple system atrophy, or pure autonomic failure, or any combination thereof); and if the formation of amyloid in the presence of said composition is increased relative to the formation of amyloid in the absence of said composition or if the amount or rate or formation of amyloid is the same or greater in the sample from the tested subject, for example, than the amount, rate, or formation of amyloid from the healthy subject control or the control subject having amyloidosis, administering to said tested subject an effective amount of a pharmaceutical composition suitable for inhibiting or treating said amyloid disorder. In some further embodiments of these methods, said microbial amyloid or microbial amyloid precursor comprises, consists essentially of, or consists of CsgA. In some embodiments, said pharmaceutical composition comprises one or more probiotic bacteria. In some further embodiments, said pharmaceutical composition comprises one or more bacteria selected from the group consisting of *Bacteroides, Prevotella, Parabacteroides, Faecalibacterium, Clostridium, Eubacterium, Roseburia, Blautia, Coprococcus, Ruminococcus, Lactobacillus, Akkermansia* and *Bifiobacterium*, or any combination thereof. In some further embodiments, the pharmaceutical composition comprises one or more bacteria selected from the group consisting of *B. fragilis, B. vulgatus, B. thetaiotaomicron, B. ovatus, B. cellulosilyticus, B. caccae, B. uniformis, P. copri, P. distasonis, F. prausnitzii, C. nexile, C. scindens, E. hallii, E. rectale, R. hominis, R. intestinalis, B. hansenii, B. producta, B. hydrogenotrophica, C. catus, C. eutactus, R. obeum, R. bromii, R. inulinovorans, L. reuteri, L. rhamnosus, L. casei, A. muciniphila, B. longum, B. infantis, B. bifidum, B. breve* and *B. adolescentis*; or any combination thereof. In some embodiments, the pharmaceutical composition further comprises a compound as described herein. In some embodiments, the methods as described herein further comprise identifying or selecting said tested subject as one that would benefit from a treatment or inhibition of an amyloid disorder, and may further comprise identifying or selecting said subject as one at risk of or showing symptoms of one or more of Parkinson's Disease, Lewy Body Dementia, incidental Lewy body disease, Lewy body variant of Alzheimer's disease, multiple system atrophy, pure autonomic failure, or any combination thereof.

BRIEF DESCRIPTION OF THE DRAWINGS

FIG. 1A is a graph showing Crystal violet staining of biofilm growth by wild-type *E. coli* following 4 days in static culture, with indicated concentrations of epigallocatechin gallate (EGCG); data assessed by optical density (OD). FIG. 1C is a graph showing RNA was extracted from fecal pellets and csgA expression quantified by qRT-PCR, relative to the *E. coli* reference gene rrsA. FIGS. 1D-H show assessment of motor function was assessed at 15-16 weeks of age by quantifying beam traversal time (FIG. 1D), pole descent time (FIG. 1E), nasal adhesive removal time (FIG. 1F), hindlimb clasping score (FIG. 1G), and wirehang tests (FIG. 1H). FIG. 1I is a graph showing principal component analysis of compiled motor scores from tests in (FIGS. 1D-H). FIGS. 1J-K are a series of graphs showing Proteinase K resistant αSyn aggregates (annotated with white arrows) in the substantia nigra imaged via immunofluorescence microscopy. Shown are vehicle-treated (FIG. 1J) and EGCG-treated mice (FIG. 1K). Fewer proteinase K resistant αSyn aggregates were observed in the mouse treated with EGCG (FIG. 1K) than in the vehicle-treated control (FIG. 1J). FIGS. 1L-M show quantification of insoluble αSyn fibrils in the striatum (FIG. 1L) and ventral midbrain (FIG. 1M) by dot blot assay. FIGS. 1N-O are a series of graphs showing thin sections of brain were stained for Iba1 (microglia), 3D cellular reconstructions generated, and morphological characteristics quantified from microglia resident in the striatum (FIG. 1N) and substantia nigra (FIG. 1O). n=3 (FIGS. 1A, 1B, 1N, 1O), n=8 (FIG. 1C), n=10-11 (FIGS. 1D-I), n=4 (FIGS. 1L-M). Points represent individuals, bars represent the mean and standard error. Data analyzed by one-way ANOVA with Tukey post-hoc test for FIG. 1A, two-tailed Mann-Whitney for FIGs. C-K, or two-tailed t-test for FIG. 1L. For FIGS. 1A-1L $*p \leq 0.05$; $p \leq 0.01$; $*p \leq 0.001$. Motor data are compiled from 2 independent cohorts.

FIG. 2A is a graph showing total αSyn in whole brain lysates quantified by ELISA. FIG. 2B is a graph showing quantification of insoluble αSyn fibrils in the striatum by dot blot assay. FIGS. 2C-D show quantification of TNFα (FIG. 2C) and IL-6 (FIG. 2D) by ELISA from the striatum. FIGS. 2E-G show the results of staining thin sections of brains derived from ASO mice. Sections were stained for Iba1 (microglia), 3D cellular reconstructions generated, and morphological characteristics quantified of microglia resident in the striatum. n=3 (FIGS. 2A-B), n=6-7 (FIG. 2C, 2D), n=4 (FIGS. 2E-G) (averaged from 20-40 cells for diameters, or 5-7 cells for branching). Points represent individuals, bars represent the mean and standard error. Data analyzed by one-way ANOVA with Tukey post-hoc test for FIGS. 2A-D, or two-tailed t-test for FIGS. 2E and 2F. $*p \leq 0.05$; $p \leq 0.01$; $*p \leq 0.001$; $****p \leq 0.0001$. Consistent with these data, csgA is predicted to be enriched in microbes derived from persons with PD.

FIG. 3G is a graph depicting principal component analysis of compiled motor scores of FIGS. 3A-F. FIGS. 3H-I depict quantification of insoluble αSyn fibrils in the striatum (FIG. 3H) and ventral midbrain (FIG. 3I) by dot blot assay. n=8 (FIGS. 3A-G), n=4 (FIG. 3H). Points represent individuals, bars represent the mean and standard error. Time courses analyzed by two-way ANOVA, with Sidak post-hoc test for between group comparisons indicated above individual time points, and brackets indicating significance between treatments. Data in (FIG. 3H) analyzed by two-tailed Mann-Whitney test. For FIGS. 3A-I, $*p \leq 0.05$; $p \leq 0.01$; $*p \leq 0.001$; $****p \leq 0.0001$.

FIG. 5F depicts principal component analysis of compiled motor scores from FIGS. 5A-D. Thin sections of brain were stained for Iba1 (microglia) and morphological characteristics quantified of microglia resident in the striatum (FIGS. 5G-H) and substantia nigra (FIGS. 5I-J). N=10-11 (FIGS. 5A-F), n=3 (FIGS. 5G-J) (averaged from 5-7 cells for branching). Bars represent the mean and standard error. Time courses analyzed by two-way ANOVA, with Sidak post-hoc test for between group comparisons indicated above individual time points, and brackets indicating significance between treatments. Data in (FIGS. 5G-J) analyzed by two-tailed t-test. *$p \leq 0.05$; $p \leq 0.01$; **$p \leq 0.0001$.

FIGS. 6A-6K are a series of graphs illustrating that the bacterial amyloid protein, CsgA, in accordance with some embodiments herein seeds aSyn fibrilization. In vitro biophysical analysis was conducted with purified αSyn and CsgA proteins. FIG. 6A shows aggregation as measured by Thioflavin T fluorescence over time during αSyn amyloid formation alone or in the presence of CsgA monomers (25:1 molar ratio, yellow). FIG. 6B shows time to reach exponential fibrilization, lag phase. FIGS. 6C-H are a series of representative transmission electron micrographs of αSyn alone (FIGS. 6C, 6F) or CsgA alone (FIGS. 6E, 6H), or in combination (FIGS. 6D, 6G), at 0 hours (FIGS. 6C-E) and 60 hours (FIGS. 6F-H) post-aggregation. FIGS. 6I-K are a series of graphs illustrating circular dichroism spectroscopic analysis of αSyn fibrilization alone or in the presence of CsgA at 0, 12.5, and 60 hours post-aggregation. For FIG. 6A and FIG. 6B, n=3. Bars represent the mean and standard error. Data are analyzed by two-tailed, t-test. **$p \leq 0.01$. Data are representative of 2 independent trials.

FIG. 7A is a graph showing thioflavin T fluorescence during αSyn amyloid formation alone or in the presence of 5% seeds previously generated by addition of CsgA monomer to αSyn (as in FIG. 6A) or αSyn alone. FIGS. 7B-F are a series of transmission electron micrograph of fibril structures generated by the addition of above seeds and of seeds themselves.

DETAILED DESCRIPTION

Figure 1A:
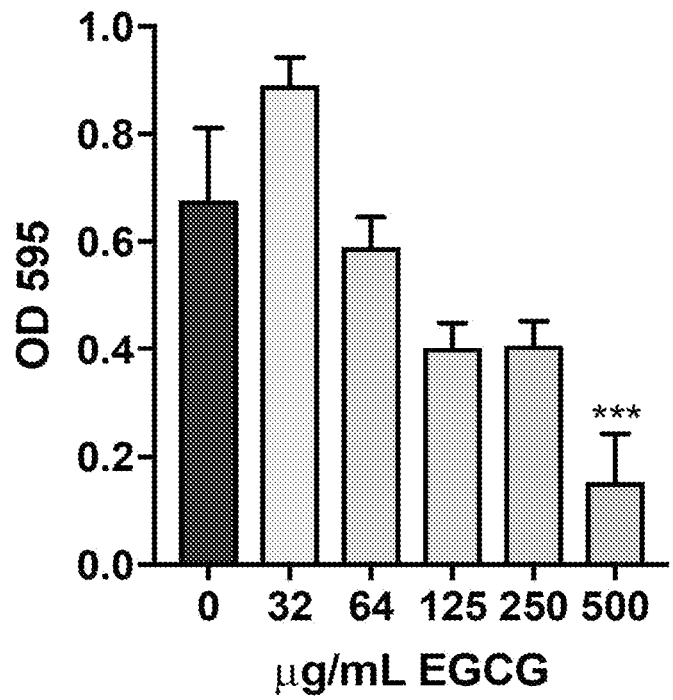
FIGS. 1A-O are a series of graphs and images depicting that curli-driven pathophysiology in mice requires functional amyloid formation.

The majority of cases of neurodegenerative diseases are idiopathic, which, conventionally, has made it difficult to identify the etiology of most such diseases. An emerging theory is that many neurodegenerative diseases start not in the brain or central nervous system (CNS), but in the periphery and gradually migrate to the brain over the course of many years in a slow, progressive process. Still, the molecular etiology in the periphery has been the subject of study. In the case of Parkinson's Disease, it is known that constipation and hyposmia occur in many patients often decades before the emergence of the stereotypical motor symptoms that currently define Parkinson's Disease. Without being limited by theory, it is therefore contemplated that α-synuclein aggregation begins in the gastrointestinal (GI) tract and in the olfactory bulb, and that aggregated α-synuclein gradually progresses to the brain in a prion-like propagative process. In this scenario, known more generally as Braak's Hypothesis, it is contemplated that analysis of the molecular mechanisms involved in these peripheral tissues can lead to non-intuitive, non-conventional approaches for preventing and/or treating amyloid disorders, such as α-synucleinopathies, such as Parkinson's Disease.

Without being limited by theory, one molecular mechanism contemplated herein implicates bacterial amyloid as the seeding factor that nucleates or otherwise leads to α-synuclein aggregation thereby initiating the pathological process that leads ultimately to Lewy body deposition and clinical manifestation of Parkinson's Disease and other α-synucleinopathies. Bacterial amyloids are aggregated forms of secreted bacterial proteins and are thought to play a role in both bacterial adhesion to host cells and biofilm formation. In the right environment and in the presence of host proteins prone to aggregation, it is believed, without being limited by theory, that bacterial amyloids themselves serve as a direct structural template for host protein aggregation in a prion-like fashion. The bacterial chaperone machinery responsible for driving bacterial amyloid aggregation may also use the host protein as a substrate and thereby facilitate host protein aggregation into amyloid structures. Once aggregated, the host protein aggregation is perpetuated in a prion-like fashion through the enteric nervous system over the course of many years. Ultimately, these aggregates spread into brain tissue and result in the stereotypical clinical symptoms of Parkinson's Disease. This effect may also result in the development of other amyloid-driven diseases such as Alzheimer's disease, in which aggregation of the host proteins A-beta and/or tau are implicated. Consistent with this, analysis of current publicly-available human microbiome datasets reveals increased representation of the curli-associated csgA gene from E. coli in persons with Parkinson's Disease, and transplantation of fecal microbes from PD patients into germ-free (GF) wild-type or ASO mice results in greater csgA abundance compared to microbiomes from healthy controls, based on PICRUSt imputed analysis of 16s rRNA sequences (See Example 7). It is shown herein that intestinal amyloid aggregates can lead to symptoms associated with Parkinson's Disease and other amyloid disorders (See Examples 6-8), and that treating these animals with compounds that inhibit and/or disrupt amyloid aggregates can ameliorate these symptoms associated with Parkinson's Disease and other amyloid disorders (See Example 10). Accordingly, it is contemplated that methods and compositions as described herein can be useful in inhibiting, ameliorating, reducing the likelihood, delaying the onset of, treating, and/or preventing an amyloid disorders for example, any of the amyloid disorders of Table 1, such as an α-synucleinopathy, Parkinson's Disease, Lewy Body Dementia, incidental Lewy body disease, Lewy body variant of Alzheimer's disease, multiple system atrophy, pure autonomic failure, or a combination of two or more of the listed items. In some embodiments, a composition as described herein is for medical use, for example use in inhibiting, ameliorating, reducing the likelihood, delaying the onset of, treating, and/or preventing the amyloid disorder (for example one or more of the amyloid disorders listed in Table 1). In some embodiments, a method for inhibiting, ameliorating, reducing the likelihood, delaying the onset of, treating, and/or preventing the amyloid disorder comprising administering a composition comprising a compound as described herein, one or more polyphenols or derivatives thereof, for example any of the compounds of Table 2 or Table 3. In some embodiments, the composition comprises or consists essentially of one or more compounds selected from the group consisting of the compounds identified by a compound activity range of "+++" in any column of Table 3. In some embodiments, the composition comprises or consists essentially of one or more compounds selected from the group consisting of the set of compounds identified by a compound activity range of "++" or "+++" in any column of Table 3 In some embodiments, the composition comprises or consists essentially of one or more compounds selected from the group consisting of the set of compounds identified by a compound activity range of "+", "++," or "+++" in any column of Table 3. In some embodiments, the composition comprises or consists essentially of one or more compounds selected from the group consisting of the compounds identified by a compound activity range of "+++" in the "αSyn" column of Table 3. In some embodiments, the composition comprises or consists essentially of one or more compounds selected from the group consisting of the set of compounds identified by a compound activity range of "++" or "+++" in the "αSyn" column of Table 3 In some embodiments, the composition comprises or consists essentially of one or more compounds selected from the group consisting of the set of compounds identified by a compound activity range of "+", "++," or "+++" in the "αSyn" column of Table 3. In some embodiments, the composition comprises or consists essentially of one or more compounds selected from the group consisting of the compounds identified by a compound activity range of "+++" in the "CsgA-seeded αSyn" column of Table 3. In some embodiments, the composition comprises or consists essentially of one or more compounds selected from the group consisting of the set of compounds identified by a compound activity range of "++" or "+++" in the "CsgA-seeded αSyn" column of Table 3 In some embodiments, the composition comprises or consists essentially of one or more compounds selected from the group consisting of the set of compounds identified by a compound activity range of "+", "++," or "+++" in the "CsgA-seeded αSyn" column of Table 3. In some embodiments, the composition comprises or consists essentially of one or more compounds selected from the group consisting of the compounds identified by a compound activity range of "+++" in the "CsgA" column of Table 3. In some embodiments, the composition comprises or consists essentially of one or more compounds selected from the group consisting of the set of compounds identified by a compound activity range of "++" or "+++" in the "CsgA" column of Table 3 In some embodiments, the composition comprises or consists essentially of one or more compounds selected from the group consisting of the set of compounds identified by a compound activity range of "+", "++" or "+++" in the "CsgA" column of Table 3. In some embodiments, the composition comprises or consists essentially of at least one of: EGCG, quercetin, morin, rosmarinic acid, gallic acid, lauryl gallate, methoxyhydroquinone, curcumin, resveratrol, apigenin, NDGA, phloretin, and genistein. In some embodiments, the subject is selected as in need of the composition by detecting a presence and/or level of aggregates in an intestinal sample of the subject, such as a fecal sample. A presence or level of intestinal aggregates greater than a negative control (for example, fecal sample of a healthy control subject, or control subject known not to have an amyloid disorder) can indicate that the subject is in need of the composition. In some embodiments, detecting the presence and/or level of intestinal aggregates in a sample of the subject comprises detecting a presence and/or level of a bacterial protein in the sample, for example a curli-associated protein, such as CsgA. In some embodiments, detecting the presence and/or level of intestinal aggregates in a sample of the subject comprises detecting a level of a bacteria that produces an amyloid in the sample, for example a curli-associated protein, such as CsgA. For example, a bacterial amyloid can be detected directly, or a nucleic acid encoding the amyloid can be detected in the sample, thus indicating a presence of amyloid-producing bacteria in the subject's gastrointestinal tract. Examples of amyloid-producing bacteria can include CsgA-producing Enterobacteraceae such as *E. coli.*

Amyloids are produced in the gastrointestinal tract by members of the gastrointestinal microbiota, such as *E. coli* and some other Proteobacteria. These microbial amyloids may interact with cells with which they are in contact in the gastrointestinal tract and affect α-synuclein expression and/or α-synuclein aggregation. The STC-1 cell line was derived from tumors of the mouse small intestine and possesses many features of native gastrointestinal enteroendocrine cells (McCarthy et al. (2015). STC-1 Cells. In: Verhoeckx K. et al. (eds) *The Impact of Food Bioactives on Health.* Springer, Chain.). In an in vitro assay wherein α-synuclein expression by STC-1 cells was determined by Western blot, exposure to an *E. coli* strain expressing wild-type CsgA resulted in a notable increase in α-synuclein expression, while exposure to an isogenic mutant in which csgA was deleted had little effect on α-synuclein levels (See FIG. 9 and Example 33). Thus, while the exact mechanisms by which CsgA affected α-synuclein expression are unclear, CsgA can interact with enteroendocrine-like cells of the gastrointestinal tract and cause α-synuclein over-expression in vitro, suggesting that similar effects may take place in vivo when pathogenic microbial amyloids contact enteroendocrine cells or other cells in the gastrointestinal tract. While mouse α-synuclein is generally not observed to aggregate, over-expression of human α-synuclein may lead to aggregation that in turn impairs cell function, propagates in a prion-like fashion to adjacent cells in the gastrointestinal tract and enteric nervous system, and has detrimental effects on gastrointestinal function. These negative effects can include one or more of intestinal dysbiosis, intestinal hyperpermeability, irritable bowel syndrome (IBS), inflammatory bowel disease (IBD), ulcerative colitis and/or Crohn's disease. These disorders can be associated with one or more symptoms, including dysphagia, reduced gut motility, gastroparesis, constipation (including chronic constipation and chronic idiopathic constipation), small intestinal bacterial overgrowth (SIBO), diarrhea (including chronic diarrhea), abdominal pain and/or cramping, bloating, flatulence, and nausea. In some cases, neurological and gastrointestinal symptoms of amyloid disorders can be linked. For example, in Parkinson's Disease and Parkinsonism (a clinical syndrome characterized by tremor, bradykinesia, rigidity, and postural instability) decreased levels of L-dopamine can lead to the neurological symptom of dyskinesia and the gastrointestinal symptom of chronic idiopathic constipation. Thus, treatments which improve gut motility, including the methods of the invention, can improve L-dopamine absorption in the gut and, thereby, reduce dyskinesia. Therefore, treatments that manage constipation (or, more generally, intestinal dysbiosis or intestinal hyperpermeability) can slow the progression of motor symptoms of Parkinson's Disease as well as increasing "on-time" periods of adequate control of Parkinson's Disease symptoms.

Consistent with the ability of STC-1 cells to respond to *E. coli* CsgA in vitro, gastrointestinal cells have been observed to sense and respond to microbial amyloids. For example, *Salmonella enterica* CsgA has been shown to modulate gastrointestinal permeability in mice via activation of the TLR2/PI3K pathway. Additionally, Tukel discloses in U.S. Pat. No. 9,814,756 a method for modulating gastrointestinal permeability via administration of variants of CsgA and/or CsgB. Tukel discloses in U.S. Pat. No. 9,814,756 decreasing permeability of epithelium of the small intestine or large intestine by administering a composition comprising, inter alia, an isolated curli fibril having epithelium permeability-reducing activity such as (i) a CsgA polypeptide variant which differs from a naturally occurring CsgA polypeptide in that from 1 to 5 amino acids have been substituted, deleted or added; (ii) a CsgB polypeptide variant which differs from a naturally occurring CsgB polypeptide in that from 1 to 5 amino acids have been substituted, deleted or added; or (iii) a combination of said CsgA polypeptide variant and said CsgB polypeptide variant. Thus, while there may be additional mechanisms by which microbial amyloids interact with gastrointestinal cells, at least one such mechanism is contemplated herein.

The present disclosure relates to methods and compositions for the treatment, amelioration, or prevention of amyloid disorders. Disclosed herein are compositions and methods, which alter the ability of bacterial amyloid to promote aggregation and amyloid formation of the eukaryotic protein α-synuclein. Said alterations may include alterations in the extent, rate of formation, stability, and/or rate of disaggregation of microbially induced amyloid, or any combination thereof. Further disclosed herein are compositions and methods useful for the treatment or inhibition of neurodegenerative diseases, as well as, compositions and methods useful for the prevention or amelioration of the progression of neurodegenerative diseases. Further disclosed herein are compositions and methods useful for the treatment or inhibition of gastrointestinal dysfunction related to neurodegenerative diseases. Additionally disclosed herein are methods for studying the molecular etiology of mammalian amyloid diseases and the molecular link between bacterial amyloid production and mammalian amyloid production. According to the methods of the present disclosure, said neurodegenerative diseases and/or mammalian amyloid diseases may comprise one or more of Parkinson's disease (PD), Lewy body dementia, multiple system atrophy, and all other α-synucleinopathies, PD-associated constipation, PD-associated hyposmia, Huntington's Disease, Alexander's Disease, amyotrophic lateral sclerosis (ALS), Alzheimer's Disease and other diseases in which amyloids are implicated. In some embodiments, the composition comprises, consists essentially of, or consists of a compound selected from the group consisting of: EGCG, quercetin, morin, rosmarinic acid, gallic acid, lauryl gallate, methoxyhydroquinone, curcumin, resveratrol, apigenin, NDGA, phloretin and genistein. The present disclosure further relates to methods that facilitate the evaluation of aggregation and dis-aggregation of both host and bacterial amyloid proteins. Methods of the present disclosure are also useful for identifying drug candidates that affect these processes.

It is contemplated that in some embodiments, a composition comprising, consisting essentially of, or consisting of one or more of gallic acid, morin, EGCG, methoxyhydroquinone, NDGA and phloretin is useful in preventing α-synuclein aggregation, the seeding of α-synuclein aggregation by CsgA or other microbial amyloids, and the formation of microbial amyloids that may seed α-synuclein aggregation in vivo, and these compounds may thus be useful in preventing or treating Parkinson's Disease and/or other α-synucleinopathies (See, e.g., Example 32 and Table 3).

It is contemplated that in some embodiments, a composition comprising, consisting essentially of, or consisting of lauryl gallate may be useful in preventing α-synuclein aggregation with or without seeding by microbial amyloids and thereby may have benefit in preventing or treating α-synucleinopathies independent of microbial amyloids (See, e.g., Example 32 and Table 3).

It is contemplated that in some embodiments, a composition comprising, consisting essentially of, or consisting of guaiacol, 4-allyl-1,2-dimethoxybenzene, isoeugenol and/or eugenol may be useful in preventing α-synuclein aggregation seeded by microbial amyloids and thereby have therapeutic benefit, for example if dosed at sites where microbial amyloids may be abundant, such as the gastrointestinal tract (See, e.g., Example 32 and Table 3).

It is contemplated that in some embodiments, a composition comprising, consisting essentially of, or consisting of resveratrol, rosmarinic acid and/or quercetin may have therapeutic benefit in Parkinson's Disease and other α-synucleinopathies. Without being limited by theory, this benefit may be due to these compounds' inhibition of aggregation of α-synuclein and/or microbial amyloids. It is further contemplated that for compounds in which more than one type of aggregation is inhibited, these inhibitory effects may be additive or synergistic. (See, e.g., Example 32 and Table 3).

Some embodiments include methods of ameliorating or inhibiting a gastrointestinal symptom in a subject in need thereof. The method can comprising administering to the subject one or more of the compositions as described herein, for example, a composition comprising, consisting essentially of, or consisting of any one or more of the following molecules: EGCG, quercetin, morin, rosmarinic acid, gallic acid and lauryl gallate, or any of the molecules of Table 2 or Table 3. Example gastrointestinal symptoms can include one or more of dysphagia, reduced gut motility, gastroparesis, constipation (including chronic constipation and chronic idiopathic constipation), small intestine bacterial overgrowth (SIBO), diarrhea, abdominal pain and/or cramping, bloating, flatulence and nausea. In some embodiments, the method further comprises detecting a change in the gastrointestinal symptom following the administration of the compound.

Methods of Inhibiting or Disrupting Aggregation

The methods as disclosed herein comprise compositions and methods that inhibit or disrupt one or more of the following (1) bacterial amyloid aggregation on the bacterial surface or in the proximal extracellular space; (2) the interaction between bacterial amyloid and α-synuclein in the GI tract or olfactory system; and/or (3) aggregation of α-synuclein in the GI tract (including the enteric neuronal cells). According to the methods of the present disclosure, α-synuclein should be viewed as a representative amyloid protein of the wider range of known host amyloid proteins, including one or more of Beta amyloid from Amyloid precursor protein, Medin, tau, Apolipoprotein AI, Atrial natriuretic factor, Beta amyloid, Cystatin, IAPP (Amylin), Beta-2 microglobulin, Transthyretin, PrP, Gelsolin, Lysozyme, Huntingtin, Keratoepithelin, Calcitonin, Prolactin, Serum amyloid A, and/or Immunoglobulin light chain AL, and the compositions and methods as disclosed herein may be adapted by one of skill in the art to disrupt the aggregation of any amyloid protein in which one amyloid protein (bacterial or human) prompts aggregation of another amyloid protein.

Representative disorders that present amyloid formation and the proteins involved in these disorders, which may be inhibited or disrupted using the methods of the present disclosure, include but are not limited to those disclosed in Table 1.

TABLE 1

Amyloid Disorders

| Disease | Protein featured | Abbreviation |
|---|---|---|
| Alzheimer's disease (AD) | Beta amyloid from Amyloid precursor protein | Aβ, APP |
| Aortic medial amyloid | Medin | AMed |
| Atherosclerosis | Apolipoprotein AI | A ApoA1 |
| Cardiac arrhythmias, isolated atrial amyloidosis | Atrial natriuretic factor | AANF |
| Cerebral amyloid angiopathy | Beta amyloid | Aβ |
| Cerebral amyloid angiopathy (Icelandic type) | Cystatin | ACys |
| Diabetes mellitus type 2 | IAPP (Amylin) | AIAPP |
| Dialysis related amyloidosis | Beta-2 microglobulin | Aβ2M |
| Familial amyloid polyneuropathy | Transthyretin | ATTR |
| Fatal familial insomnia | PrP$^{Sc}$ | APrP |
| Finnish amyloidosis | Gelsolin | AGel |
| Hereditary non-neuropathic systemic amyloidosis | Lysozyme | ALys |
| Huntington's disease (HD) | Huntingtin | HTT |
| Lattice corneal dystrophy | Keratoepithelin | AKer |
| Medullary carcinoma of the thyroid | Calcitonin | ACal |
| Parkinson's disease (PD) | α-synuclein | a-Syn |
| Prolactinomas | Prolactin | APro |
| Rheumatoid arthritis (RA) | Serum amyloid A | AA |
| Sporadic Inclusion body myositis (S-IBM) | various, including beta-amyloid | |
| Systemic AL amyloidosis | Immunoglobulin light chain AL | AL |
| Transmissible spongiform encephalopathy (e.g., bovine spongiform encephalopathy) | PrP$^{Sc}$ | APrP |

The methods of the compositions and methods of the invention can also be used to treat amyloid-mediated disorders of the gastrointestinal tract including intestinal dysbiosis, intestinal hyperpermeability, irritable bowel syndrome (IBS), inflammatory bowel disease (IBD), ulcerative colitis and/or Crohn's disease. These disorders can be associated with one or more symptoms, including dysphagia, reduced gut motility, gastroparesis, constipation (including chronic constipation and chronic idiopathic constipation), small intestinal bacterial overgrowth (SIBO), diarrhea (including chronic diarrhea), abdominal pain and/or cramping, bloating, flatulence, and nausea.

As used herein, the term "intestinal dysbiosis" has its customary and ordinary meaning as understood by one of skill in the art in view of this disclosure and refers to an imbalance and/or maladaptation of the flora or microbiota within the gut or intestines, and particularly the small intestine. Such dysbiosis is characterized by a change in the composition of the intestinal or gut microbiome, in terms of the species/strains which are present and/or the relative abundance or proportion of the species/strains which are present, in which the change has a deleterious effect on the host organism. The deleterious effect on the host organism can result from microbiome-mediated changes in electrolyte balance, biofilm formation, integrity of the barrier formed by the intestinal epithelial lining, or the release from the microbiome of metabolites which are directly (e.g., as toxicity or effectors) or indirectly (e.g., as pre-cursors to toxins or effector) injurious to the health of the host.

As used herein, the term "intestinal hyperpermeability" has its customary and ordinary meaning as understood by one of skill in the art in view of this disclosure. It refers to abnormal increased permeability of the barrier formed by the intestinal epithelial lining between the intestinal lumen and the surrounding issues. Such hyperpermeability may result from inflammation of the intestinal lining and/or failure of the tight junctions between cells of the intestinal epithelium, which allows the passage of substances from the lumen into the surrounding tissues where some may enter the peritoneal cavity and/or systemic circulation. Because of this leakage of substances from the gut or intestinal lumen, intestinal hyperpermeability may be referred to as "leaky gut" or "leaky gut syndrome."

As used herein, the term "amyloid disorders," including variations of this root term, includes, but is not limited to any or all of the disorders of Table 1 as well as amyloid-mediated disorders of the gastrointestinal tract.

As used herein, the term "mammalian amyloid or mammalian amyloid precursor" includes, but is not limited to, one or more of tau, Beta amyloid from Amyloid precursor protein, Medin, Apolipoprotein AI, Atrial natriuretic factor, Beta amyloid, Cystatin, IAPP (Amylin), Beta-2 microglobulin, Transthyretin, PrP, Gelsolin, Lysozyme, Huntingtin, Keratoepithelin, Calcitonin, Prolactin, Serum amyloid A, and/or Immunoglobulin light chain AL. In certain methods and compositions disclosed herein, said microbial amyloid or microbial amyloid precursor comprises CsgA.

Some embodiments include a method of inhibiting, ameliorating, reducing the likelihood, delaying the onset of, treating, or preventing an amyloid disorder, the method comprising administering a composition as described herein to a subject in need thereof. The amyloid disorder can be selected from the group consisting of: α-synucleinopathy, Parkinson's Disease, Lewy Body Dementia, incidental Lewy body disease, Lewy body variant of Alzheimer's disease, multiple system atrophy, and pure autonomic failure, or any combination of any of these. The amyloid disorder can also be selected from the group consisting of: intestinal dysbiosis, intestinal hyperpermeability, irritable bowel syndrome (IBS), inflammatory bowel disease (IBD), ulcerative colitis and/or Crohn's disease. In some embodiments, the composition administered in the method comprises, consists essentially of, or consists of any of the molecules of Table 2 or Table 3. In some embodiments, the composition administered in the method comprises, consists essentially of, or consists of one or more of: EGCG, quercetin, morin, rosmarinic acid, gallic acid, lauryl gallate, methoxyhydroquinone, curcumin, resveratrol, apigenin, NDGA, phloretin and genistein. In some embodiments of the method, the amyloid disorder comprises intestinal amyloid aggregates. For example, the aggregates can comprise a bacterial protein, for example a curli-associated protein such as CsgA. Accordingly, in some embodiments, the method further comprises detecting a presence or level of such a bacterial protein in an intestinal sample of the subject, or a presence of level of a microbial organism that produces the bacterial protein (e.g., a curli-associated protein such as CsgA) in the intestinal sample of the subject, for example a fecal sample. For example, the protein can be detected by an immunoassay such as an ELISA, Western Blot, lateral flow assay, no-wash assay or the like. For example, the microbial organism that produces the bacterial protein can be detected by nucleic acid analysis (such as qualitative or quantitative PCR, microarray analysis, or sequencing). An intestinal presence of the bacterial protein or microbial organism that produces the protein, or a level of the bacterial protein (or microbial organism that produces the protein) greater than a control can identify the subject as being in need of the composition. By way of example, suitable controls can include subjects that are negative for the bacterial protein (or microbial organisms that make the bacterial protein), for example healthy individuals, or an individual identified as not having the bacterial protein (or microbial organisms that make the bacterial protein) in their intestines. In some embodiments, the method comprises detecting a presence or level of intestinal curli (or a curli-associated protein such as CsgA), or an intestinal level of a microorganism that produces intestinal curli-associated protein (such as CsgA) in a sample of the subject. In some embodiments, the subject is identified as a member of a subpopulation of subject having the amyloid disorder, and in need of the composition. In some embodiments, the method further comprises determining a decrease or absence of the intestinal amyloid aggregates following the administration.

The compositions of the present disclosure may, in some embodiments, inhibit the formation of α-synuclein aggregates (e.g., fibrils, Lewy bodies, or other aggregates) or other host amyloid at its point of initiation in the gut, thus depriving microbially induced amyloid aggregation thought to serve as a template or seed for α-synuclein or other host amyloid aggregation and doing so without having to cross the blood brain barrier. Targeting α-synuclein or other host amyloid aggregation in the gut obviates the need for the drug to cross the blood-brain barrier, providing efficacy at a lower dose, with fewer side-effects due to reduction in systemic exposure. Further, targeting α-synuclein or other host amyloid aggregation at its point of initiation allows intervention at an earlier stage in the pathogenic process, preventing or inhibiting disease progression before motor symptoms or other neurodegenerative symptoms develop. Targeting α-synuclein aggregation in the gut may also address gastrointestinal dysfunction and/or ameliorate gastrointestinal symptoms or behaviors of the subject, which may comprise, e.g., one or more of dysphagia, reduced gut motility, gastroparesis, constipation (including chronic constipation and chronic idiopathic constipation), small intestine bacterial overgrowth (SIBO), diarrhea, abdominal pain and/or cramping, bloating, flatulence, nausea, or any other symptoms of irritable bowel syndrome (IBS), inflammatory bowel disease (IBD, e.g., ulcerative colitis and Crohn's disease), intestinal hyperpermeability, or any combinations thereof, for example in accordance with compositions and methods of some embodiments herein.

In addition to targeting host amyloid aggregation in the brain as an approach to treating or inhibiting neurodegenerative diseases, targeting bacterial amyloid aggregation provides new therapies for infectious diseases, such as urinary tract infections (UTIs). In both cases, certain classes of compounds have been identified, largely represented as "polyphenols" or polyphenol equivalents, as having the ability to inhibit amyloid aggregation process in tissues of interest, such as in the brain for α-synuclein and the urinary mucosae for UTIs.

In some embodiments, the compositions and methods of the present disclosure contemplate the use of polyphenols and/or polyphenol equivalents as inhibitors of the interaction between a host amyloid, such as α-synuclein and a bacterial amyloid, such as curli or adhesive pili. In some embodiments, the compositions and methods of the present disclosure, contemplate the use of polyphenols and/or polyphenol equivalents as inhibitors of host amyloid aggregation and/or promoters of amyloid dis-aggregation in peripheral tissue, such as the gut or nasopharynx, rather than in the brain. The compositions and methods of the present disclosure further contemplate modified polyphenols or polyphenol equivalents, that act locally in the gut and are essentially not absorbed into peripheral tissues, such as, for example, non-orally bioavailable analogs of polyphenols that retain amyloid inhibiting activity, but do not traverse the gut epithelium or enter the primary circulation.

In some embodiments, the compositions and methods of the present disclosure contemplate formulations that enable delivery of said compositions to the site of action in the lower small intestine, the large intestine, and/or the colon. Said formulations may comprise enteric coated tablets, capsules, liquid-gels or powders, and the like, such that the formulation inhibits the release of the drug in the stomach or upper GI tract. Alternatively, said compositions may comprise intrinsically enteric capsules or similar solid dosage forms wherein the capsule composition comprises a polymer or material that dissolves at or near the site of action, such as, for example, EnTrinsic® intrinsically enteric capsules, preferably in the lower GI tract, and more especially the lower small intestine, the large intestine, or the colon. In some embodiments, said compositions are not absorbed and remain in the GI tract.

The compositions and methods of the present disclosure contemplate gut-restricted small molecule inhibitors that target one or more elements of amyloid formation. Exemplary compositions include polyphenol and polyphenol-like inhibitors, many of which are orally bioavailable, and may further comprise the compounds EGCG, eugenol and derivatives, Anle138b, D-519, D-520, CLR01. The compositions and methods of the present disclosure also contemplate gut-selective or gut-restricted, non-orally absorbed derivatives of non-polyphenol classes that are known to have the ability to inhibit amyloid formation. The compositions and methods according to the present disclosure further contemplate non-orally absorbed, gut-selective derivatives or formulations of said polyphenol or non-polyphenol compounds.

"Subject" as used herein, has its customary and ordinary meaning as understood by one of skill in the art in view of this disclosure. It refers to a human or a non-human mammal including but not limited to a dog, cat, horse, donkey, mule, cow, domestic buffalo, camel, llama, alpaca, bison, yak, goat, sheep, pig, elk, deer, domestic antelope, or a non-human primate selected or identified for a diagnosis, treatment, inhibition, amelioration of a neurological disease or neurological disorder associated with microbially induced amyloid, such as Parkinson's Disease, Lewy Body Dementia, incidental Lewy body disease, Lewy body variant of Alzheimer's disease, multiple system atrophy, pure autonomic failure, intestinal dysbiosis, intestinal hyperpermeability, irritable bowel syndrome (IBS), inflammatory bowel disease (IBD), ulcerative colitis, Crohn's disease, or any combination thereof.

"Diagnosing" has its customary and ordinary meaning as understood by one of skill in the art in view of this disclosure. It can refer to the act or process of determining whether a subject exhibits any symptom or indicator of a neurological disease or neurological disorder associated with microbially induced amyloid such as Parkinson's Disease, Lewy Body Dementia, incidental Lewy body disease, Lewy body variant of Alzheimer's disease, multiple system atrophy, pure autonomic failure, or any combination thereof. It can also refer to the act or process of determining whether a subject exhibits any symptom or indicator of a gastrointestinal disorder associated with microbially induced amyloid such as intestinal dysbiosis, intestinal hyperpermeability, irritable bowel syndrome (IBS), inflammatory bowel disease (IBD), ulcerative colitis and/or Crohn's disease. Diagnosing may further comprise the determination of whether the body of a subject or any tissue, fluid, component, organ, or compartment thereof contains microbially induced amyloid. Diagnosing may further comprise the determination of whether the body of a subject or any tissue, fluid, component, organ, or compartment thereof contains any factor capable of affecting the rate of aggregation or disaggregation of microbially induced amyloid.

"Subject suspected of having" has its customary and ordinary meaning as understood by one of skill in the art in view of this disclosure. It refers to a subject exhibiting one or more clinical indicators of a disease or condition. In certain embodiments, the disease or condition may comprise one or more of Parkinson's Disease, Lewy Body Dementia, incidental Lewy body disease, Lewy body variant of Alzheimer's disease, multiple system atrophy, pure autonomic failure, or any combination thereof. In some embodiments, the disorder can be selected from the group consisting of: intestinal dysbiosis, intestinal hyperpermeability, irritable bowel syndrome (IBS), inflammatory bowel disease (IBD), ulcerative colitis and/or Crohn's disease.

"Subject in need thereof" has its customary and ordinary meaning as understood by one of skill in the art in view of this disclosure. It refers to a subject selected or identified as one being in need of diagnosis of a disorder implicating amyloid formation, or one in need of a treatment, inhibition, amelioration of a neurological disease or neurological disorder associated with microbially induced amyloid such as Parkinson's Disease, Lewy Body Dementia, incidental Lewy body disease, Lewy body variant of Alzheimer's disease, multiple system atrophy, pure autonomic failure, or any combination thereof. In other embodiments, the disorder can be selected from the group consisting of: intestinal dysbiosis, intestinal hyperpermeability, irritable bowel syndrome (IBS), inflammatory bowel disease (IBD), ulcerative colitis and/or Crohn's disease.

"Microbially induced amyloid" as used herein has its customary and ordinary meaning as understood by one of skill in the art in view of this disclosure. It refers to amyloid fibrils or aggregates that are produced through the contact of a mammalian or microbial protein with one or more microbial proteins. Said microbial protein may comprise one or more proteins of bacterial or fungal origin, although the present disclosure contemplates amyloid produced by the interaction of proteins, whatever their origin, with proteins originating from bacteriophages, viruses, bacteria, archaea, fungi, and other eukaryotes.

A "therapeutic effect" has its customary and ordinary meaning as understood by one of skill in the art in view of this disclosure. It relieves, to some extent, one or more of the symptoms of a disease or disorder, and includes curing the disease or disorder. "Curing" means that the symptoms of active disease are eliminated. However, certain long-term or permanent effects of the disease may exist even after a cure is obtained (such as tissue damage).

"Amelioration" has its customary and ordinary meaning as understood by one of skill in the art in view of this disclosure. It refers to a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

"Modulation" has its customary and ordinary meaning as understood by one of skill in the art in view of this disclosure. It refers to an alteration in the presence, absolute level, relative level, function or activity of any factor within the body of a subject or any tissue, fluid, component, organ, or compartment thereof. In certain embodiments, modulation refers to an increase in gene expression. In certain embodiments, modulation refers to a decrease in gene expression. In certain embodiments, modulation refers to an increase or decrease in total serum levels of a specific protein. In certain embodiments, modulation refers to an increase or decrease in free serum levels of a specific protein. In certain embodiments, modulation refers to an increase or decrease in the aggregation state of a protein. In certain embodiments, modulation refers to increasing or decreasing the stability of amyloid fibrils. In certain embodiments modulation refers to increasing or decreasing the length, width, spacing, or density of amyloid fibrils. In certain embodiments, modulation refers to an increase or decrease in total serum levels of a specific non-protein factor, e.g., a metabolite. In certain embodiments, modulation refers to an increase or decrease in free serum levels of a specific non-protein factor. In certain embodiments, modulation refers to an increase or decrease in total bioavailability of a specific protein. In certain embodiments, modulation refers to an increase or decrease in total bioavailability of a specific non-protein factor. In certain embodiments, modulation refers to alterations in the aggregation state of a protein. In certain embodiments modulation refers to alterations in the rate or extent of aggregation or disaggregation of microbially induced amyloid.

In some embodiments, the compositions and methods of the present disclosure comprise, consist, or consist essentially of a composition comprising a compound having Formula I:

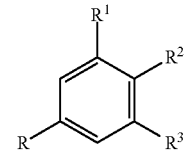

where:
R1 is selected from —H, —OH, or —OCH$_3$;
R2 is selected from —H, —OH, or —OCH$_3$;
R3 is selected from —H, —OH, or —OCH$_3$;
provided that at least one of R$^1$, R$^2$ and R$^3$ is not —H; and wherein
R is selected from —OH, —C(O)OH, —C(O)OR$^4$ or R$^4$; wherein R$^4$ is selected from a C$_2$-C$_{20}$ branched or unbranched alkyl, alkenyl, cyclyl, aryl, heteroalkyl, heteroalkenyl, heterocyclyl or heteroaryl.

In some embodiments, the compositions and methods of the present disclosure comprise, consist, or consist essentially of a composition comprising a compound having Formula II:

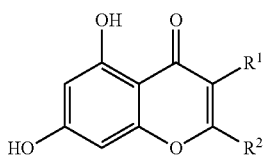

where
R1 is selected from —H, —CH₃, —OH, —OCH₃, 3-hydroxyphenyl, 4-hydroxyphenyl, 2,4-dihydroxyphenyl, 3,4-dihydroxyphenyl, 3,5-dihydroxyphenyl, 3,4,5-trihydroxyphenyl, 3-methoxyphenyl, 4-methoxyphenyl, 2,4-methoxyphenyl, 3,4-dimethoxyphenyl, 3,5-dimethoxyphenyl, 3,4,5-trimethoxyphenyl, 2-hydroxy-4-methoxyphenyl, 3-hydroxy-4-methoxyphenyl, 2-methoxy-4-hydroxyphenyl, 3-methoxy-4-hydroxyphenyl, 3,4-dihydroxy-5-methoxyphenyl, 3,5-dihydroxy-4-methoxyphenyl, 3,4-methoxy-5-hydroxyphenyl, and 3,5-dimethoxy-4-hydroxyphenyl; and R2 is selected from —H, —CH₃, —OH, —OCH₃, 3-hydroxyphenyl, 4-hydroxyphenyl, 2,4-dihydroxyphenyl, 3,4-dihydroxyphenyl, 3,5-dihydroxyphenyl, 3,4,5-trihydroxyphenyl, 3-methoxyphenyl, 4-methoxyphenyl, 2,4-methoxyphenyl, 3,4-dimethoxyphenyl, 3,5-dimethoxyphenyl, 3,4,5-trimethoxyphenyl, 2-hydroxy-4-methoxyphenyl, 3-hydroxy-4-methoxyphenyl, 2-methoxy-4-hydroxyphenyl, 3-methoxy-4-hydroxyphenyl, 3,4-dihydroxy-5-methoxyphenyl, 3,5-dihydroxy-4-methoxyphenyl, 3,4-methoxy-5-hydroxyphenyl, and 3,5-dimethoxy-4-hydroxyphenyl; provided that at least one of R1 and R2 is —H, —CH₃, —OH, or —OCH₃.

In some embodiments, the compositions and methods of the present disclosure comprise, consist, or consist essentially of a composition comprising a compound having Formula III:

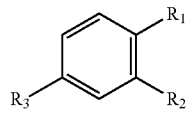

where:
R1 may comprise: —H, —OH, —OCH₃, —CH₃, —CH(CH₃)₂, —C(CH₃)₃, —CH₂CH₃, —C₆H₅, —C₆H₄CH₃, —C₆H₄OH, —C₆H₄C(O)H, —C₆H₄C(O)CH₃, —C₆H₄C(O)CH₃, —C₆H₄OC(O)CH₃, —C(O)H, —C(O)CH₃, —OC(O)H, or —OC(O)CH₃;

R2 may comprise: —H, —OH, —OCH₃, —CH₃, —CH(CH₃)₂, —C(CH₃)₃, —CH₂CH₃, —C₆H₅, —C₆H₄CH₃, —C₆H₄OH, —C₆H₄C(O)H, —C₆H₄C(O)CH₃, —C₆H₄C(O)CH₃, —C₆H₄OC(O)CH₃, —C(O)H, —C(O)CH₃, —OC(O)H, or —OC(O)CH₃; and R3 may comprise: —H, —OH, —OCH₃, —OCH₂CH₃, —OCH₂CH₂CH₃, —CH₃, —CH(CH₃)₂, —C(CH₃)₃, —CH₂CH₃, —CH₂CH₂CH₃, —CH₂CHCH₂, —CHCHCH₃, —C₆H₅, —C₆H₄CH₃, —C₆H₄OH, —C₆H₄C(O)H, —C₆H₄C(O)CH₃, —C₆H₄C(O)CH₃, —C₆H₄OC(O)CH₃, —C(O)H, —C(O)CH₃, —C(O)CH₂CH₃, —C(O)CH₂CH₂CH₃, —OC(O)H, —OC(O)CH₃, —OC(O)CH₂CH₃—OC(O)CH₂CH₂CH₃, —CH₂CH₂CH₂CH₃, —CHCHCH₂CH₃, —CH₂CHCHCH₃, or —CH₂CH₂CHCH₂. In some embodiments, R¹ is —H, —OH, —OCH₃, —CH₃, —CH(CH₃)₂, —C(CH₃)₃, —CH₂CH₃, —C₆H₅, —C₆H₄CH₃, —C₆H₄OH, —C₆H₄C(O)H, —C₆H₄C(O)CH₃, —C₆H₄C(O)CH₃, —C₆H₄OC(O)CH₃, —C(O)H, —C(O)CH₃, —OC(O)H, or —OC(O)CH₃; R² is —H, —OH, —OCH₃, —CH₃, —CH(CH₃)₂, —C(CH₃)₃, —CH₂CH₃, —C₆H₅, —C₆H₄CH₃, —C₆H₄OH, —C₆H₄C(O)H, —C₆H₄C(O)CH₃, —C₆H₄C(O)CH₃, —C₆H₄OC(O)CH₃, —C(O)H, —C(O)CH₃, —OC(O)H, or —OC(O)CH₃; and R3 is —H, —OH, —OCH₃, —OCH₂CH₃, —OCH₂CH₂CH₃, —CH₃, —CH(CH₃)₂, —C(CH₃)₃, —CH₂CH₃, —CH₂CH₂CH₃, —CH₂CHCH₂, —CHCHCH₃, —C₆H₅, —C₆H₄CH₃, —C₆H₄OH, —C₆H₄C(O)H, —C₆H₄C(O)CH₃, —C₆H₄C(O)CH₃, —C₆H₄OC(O)CH₃, —C(O)H, —C(O)CH₃, —C(O)CH₂CH₃, —C(O)CH₂CH₂CH₃, —OC(O)H, —OC(O)CH₃, —OC(O)CH₂CH₃—OC(O)CH₂CH₂CH₃, —CH₂CH₂CH₂CH₃, —CHCHCH₂CH₃, —CH₂CHCHCH₃, or —CH₂CH₂CHCH₂.

In some embodiments according to the present disclosure, any of the compositions as described herein is formulated for delivery outside of the systemic circulation of a subject. Such formulations may be made by methods as are known to one of skill in the art of drug formulation and delivery, and may include enteric-coated capsules, tablets, soft-gels, spray dried powders, polymer matrices, hydrogels, enteric-coated solids, crystalline solids, amorphous solids, glassy solids, coated micronized particles, liquids, nebulized liquids, aerosols, or microcapsules.

The methods of the present disclosure further contemplate the administration of a composition comprising, consisting of, or consisting essentially of a composition comprising one or more compounds having the structures shown in Table 2, Table 3, or Tables 2 and 3.

TABLE 2

Amyloid Formation Inhibitors

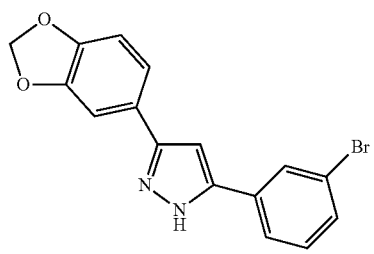 [SMILES: Brc1cccc(-c2cc(-c3ccc4c(c3)OCO4)n[nH]2)c1]

TABLE 2-continued
Amyloid Formation Inhibitors
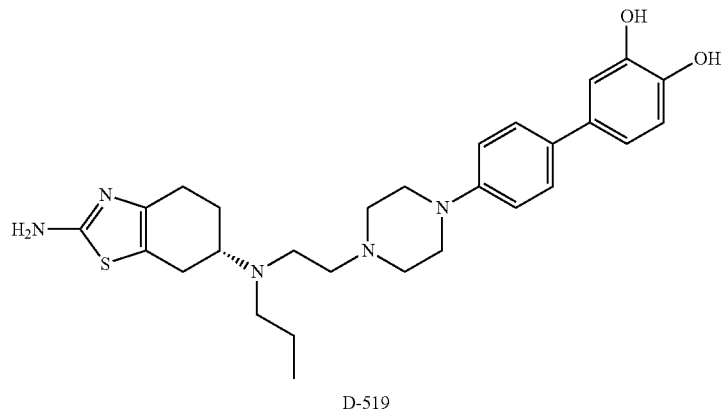 [SMILES: CCCN(CCN1CCN(c2ccc(-c3ccc(O)c(O)c3)cc2)CC1)[C@H]1CCc2nc(N)sc2C1]
D-519
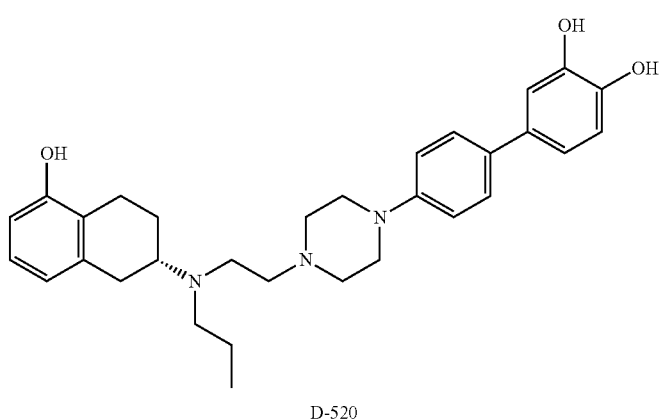 [SMILES: CCCN(CCN1CCN(c2ccc(-c3ccc(O)c(O)c3)cc2)CC1)[C@H]1CCc2c(O)cccc2C1]
D-520
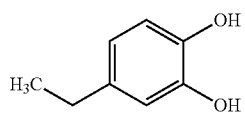
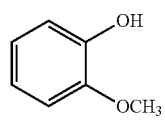
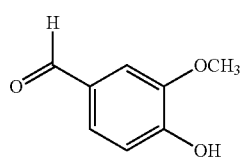 [SMILES: COc1cc(C=O)ccc1O]
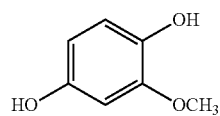
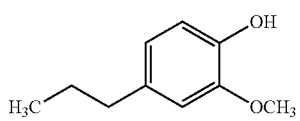

TABLE 2-continued
Amyloid Formation Inhibitors
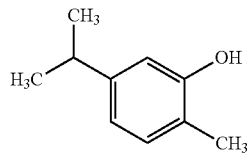
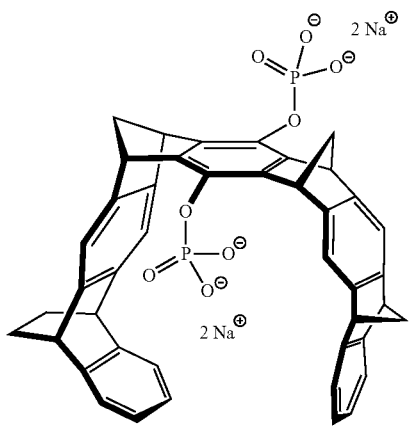
CLR01
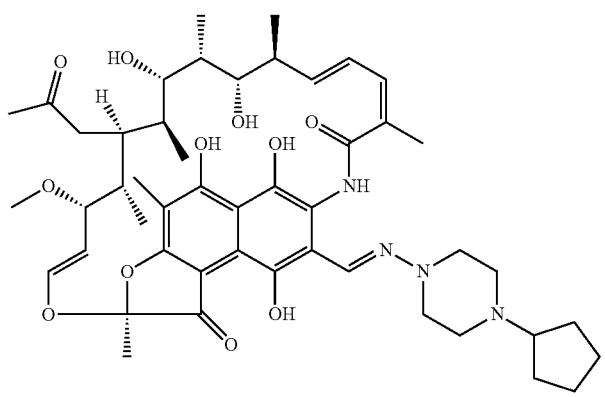 [SMILES: CO[C@H]1/C=C/O[C@@]2(C)Oc3c(C)c(O)c4c(O)c(c(/C=N/N5CCN(C6CCCC6)CC5)c(O)c4c3C2=O)NC(=O)/C(C)=C\C=C\[C@H](C)[C@H](O)[C@@H](C)[C@@H](O)[C@@H](C)[C@H](CC(C)=O)[C@@H]1C]
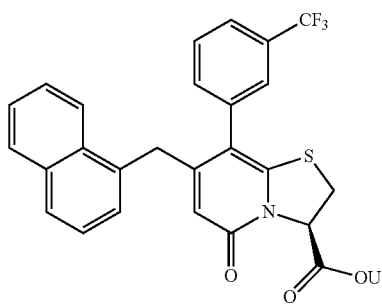
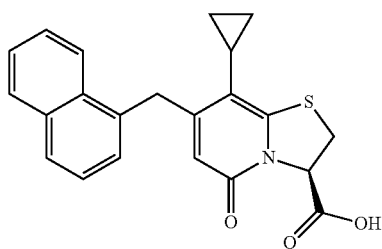 [SMILES: O=C(O)[C@@H]1CSc2c(C3CC3)c(Cc3cccc4ccccc34)cc(=O)n21]

TABLE 2-continued
Amyloid Formation Inhibitors
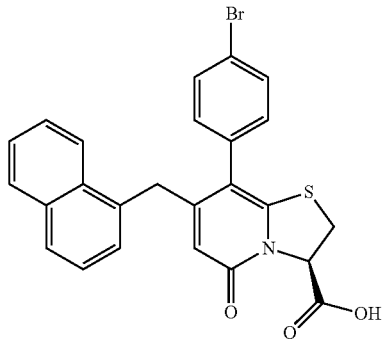 [SMILES: O=C(O)[C@@H]1CSc2c(-c3ccc(Br)cc3)c(Cc3cccc4ccccc34)cc(=O)n21]
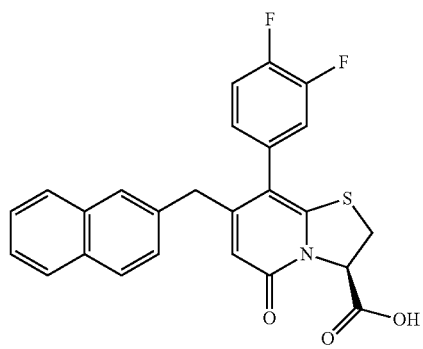 [SMILES: O=C(O)[C@@H]1CSc2c(-c3ccc(F)c(F)c3)c(Cc3ccc4ccccc4c3)cc(=O)n21]
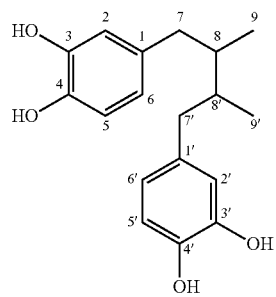 [SMILES: CC(Cc1ccc(O)c(O)c1)C(C)Cc1ccc(O)c(O)c1]
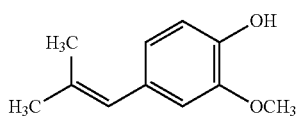
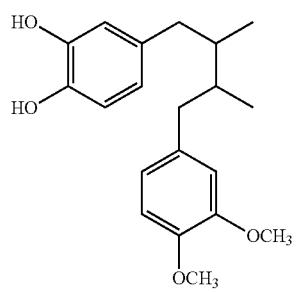 [SMILES: COc1ccc(CC(C)C(C)Cc2ccc(O)c(O)c2)cc1OC]

TABLE 2-continued
Amyloid Formation Inhibitors
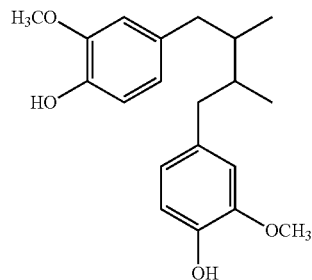 [SMILES: COc1cc(CC(C)C(C)Cc2ccc(O)c(OC)c2)ccc1O]
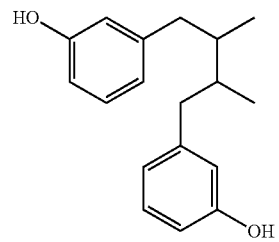 [SMILES: CC(Cc1cccc(O)c1)C(C)Cc1cccc(O)c1]
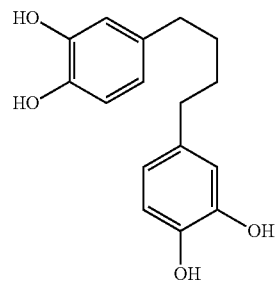 [SMILES: Oc1ccc(CCCCc2ccc(O)c(O)c2)cc1O]
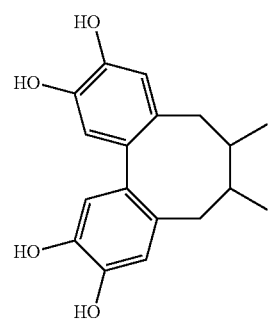 [SMILES: CC1Cc2cc(O)c(O)cc2-c2cc(O)c(O)cc2CC1C]
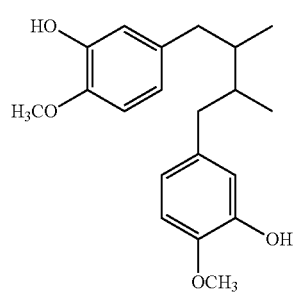 [SMILES: COc1ccc(CC(C)C(C)Cc2ccc(OC)c(O)c2)cc1O]

The methods of the present disclosure further contemplate the administration of a composition comprising, consisting of, or consisting essentially of a compound selected from the group consisting of: EGCG (epigallocatechin gallate), quercetin (2-(3,4-dihydroxyphenyl)-3,5,7-trihydroxychromen-4-one), morin (2-(2,4-dihydroxyphenyl)-3,5,7-trihydroxychromen-4-one), rosmarinic acid ((2R)-2-[[(2"E")-3-(3,4-dihydroxyphenyl)-1-oxo-2-propenyl]]oxy]-3-(3,4-dihydroxyphenyl) propanoic acid), gallic acid (3,4,5-trihydroxybenzoic acid), lauryl gallate (dodecyl 3,4,5-trihydroxybenzoate), methoxyhydroquinone (2-methoxybenzene-1,4-diol), curcumin ((1E,6E)-1,7-Bis(4-hydroxy-3-methoxyphenyl)hepta-1,6-diene-3,5-dione), resveratrol ((E)-5-(4-hydroxystyryl)benzene-1,3-diol), apigenin (5,7-dihydroxy-2-(4-hydroxyphenyl)-4H-1-benzopyran-4-one), NDGA (nordihydroguaiaretic acid or 4,4'-(2,3-dimethylbutane-1,4-diyl)dibenzene-1,2-diol), phloretin (3-(4-hydroxyphenyl)-1-(2,4,6-trihydroxyphenyl)propan-1-one), genistein (5,7-dihydroxy-3-(4-hydroxyphenyl)chromen-4-one), isoeugenol (2-methoxy-4-(prop-1-en-1-yl)phenol), 4-allyl-1,2-dimethoxybenzene, eugenol (2-methoxy-4-(prop-2-en-1-yl)phenol), 4-ethylguaiacol (4-ethyl-2-methoxyphenol), guaiacol (2-methoxyphenol), thymol (5-methyl-2-(propan-2-yl)phenol), carvacrol (2-methyl-5-(propan-2-yl)phenol), and Anle 138b, or a subgroup consisting of two or more of any of the listed compounds, for example, the group consisting of one or more of the following molecules: EGCG, quercetin, morin, rosmarinic acid, gallic acid and lauryl gallate; the group consisting of one or more of the following molecules: EGCG, quercetin, genistein, apigenein, resveratrol, rosmarinic acid, and NDGA; the group consisting of one or more of the following molecules: quercetin, genistein, apigenein, resveratrol, rosmarinic acid, and NDGA; or the group consisting of one or more of the following molecules: quercetin, EGCG, resveratrol, rosmarinic acid, and NDGA; or the group consisting of one or more of the following molecules: EGCG, quercetin, morin, rosmarinic acid, gallic acid; or the group consisting of one or more of the following molecules: quercetin, resveratrol, rosmarinic acid, and NDGA; or the group consisting of: one or more of the following molecules: resveratrol, rosmarinic acid, and quercetin; or the group consisting of one or more of the following molecules: quercetin, morin, rosmarinic acid, and gallic acid.

Said compounds in accordance with methods and compositions of some embodiments may also be incorporated into formulations for delivery outside the systemic circulation. Such formulations may include enteric-coated capsules, tablets, soft-gels, spray dried powders, polymer matrices, hydrogels, enteric-coated solids, crystalline solids, amorphous solids, glassy solids, coated micronized particles, liquids, nebulized liquids, aerosols, or microcapsules.

The methods of the present disclosure further contemplate the administration of one or more polyphenols or derivatives thereof. Exemplary polyphenols for use in these methods include but are not limited to flavonoids, stilbenoids, or phenolic acids or any combination thereof. Further exemplary polyphenols useful in these methods may be selected from the subclasses of flavones, isoflavones, isoflavanes, flavanones, flavanols, catechins, lignans, proanthocyanidins, tannins, theaflavins, thearubigins, anthocyanidins, chalcones, dihydrochalcones, stilbenes, polyhydroxylated stilbenes, resveratrol analogs, cinnamic acid derivatives, benzoic acid derivatives, chlorogenic acid derivatives, and/or derivatives of caffeic acid, ferulic acid, p-coumarinic acid, gentisic acid, or gallic acid or any combination thereof.

Further exemplary polyphenols include but are not limited to Aminogenistein, Apigenin, Baicalein, Chrysin, Nobiletin, Diosmin, Tangeretin, Wogonin, Luteolin, 4'-Bromoflavone, Daidzein, Daidzein, Daidzein, Daidzein, 4'-Bromoflavone, Daidzein, Daidzein, Daidzein, Daidzein, Genistein, Genistin, Bavachin, Isoxanthohumol, (+)-Taxifolin, (±)-Taxifolin, Silybin, (±)-Naringenin, 8-Isopentenylnaringenin, (±)-Hesperetin, Neobavaisoflavone, Puerarin, Isorhamnetin, Myricetin, Tiliroside, Kaempferol, Quercetin.2H2O, Trihydroxyethylrutin, Morin, Rutin.3H2O, (±)-Catechin, (−)-Epigallocatechin gallate, Cinnamtannin B-1, (+)-Catechin monohydrate, Cyanidin chloride, Delphinidin chloride, Malvidin chloride, Pelargonidin chloride, Peonidin chloride, Butein, Curcumin, Isobavachalcone, Xanthohumol, Resveratrol, Piceatannol, Polydatin, trans-3,4',5-Trimethoxystilbene, Sirtinol, 6-Chloro-2,3,4,9-tetrahydro-1Hcarbazole-1-carboxamide, Aristoforin, Caffeic acid, Caffeic acid n-octyl ester, Chlorogenic acid, Caffeic acid ethyl ester, Caffeic acid phenylethyl ester, Gallotannin, Caffeic acid methyl ester, 3,5-Di-O-caffeoylquinic acid, and derivatives and/or combinations thereof. Said polyphenols may also be incorporated into formulations for delivery outside the systemic circulation. Such formulations may include enteric-coated capsules, tablets, soft-gels, spray dried powders, polymer matrices, hydrogels, enteric-coated solids, crystalline solids, amorphous solids, glassy solids, coated micronized particles, liquids, nebulized liquids, aerosols, or microcapsules.

In some embodiments, the compositions and methods according to the present disclosure contemplate administration of one or more derivatives of the compositions and/or compounds disclosed herein. Exemplary derivatives may be produced by, for example, alkylation, methylation, ethylation, acetylation, phosphorylation, sulfoxylation, hydroxylation, amination, amidation, imination, imidation, and/or halogenation and may lead to the production of an adduct incorporating one or more additional chemical moieties. Some such additional chemical moieties may include, but are not limited to, fluoryl, chloryl, bromyl, iodyl, alkyl, alkenyl, alkynyl, cycloalkyl, cycloalkenyl, cycloaryl, benzyl, imidazolyl, amino, amido, sulfyl, sulfhydryl, phosphoryl, carboxyl, carbonyl, ester, thioester, acid ester, and/or acetyl derivatives. Such additional chemical moieties may further include the conjugation of any amino acid, polypeptide, nucleoside, nucleotide, ribonucleic acid, deoxyribonucleic acid, peptide nucleic acid, or polysaccharide.

In some compositions and methods of some embodiments in accordance with the present disclosure, a subject is selected or identified to receive the administration of the compositions described herein. In some embodiments, said subject is selected or identified as one having elevated levels of curli in the gut. Such a selection can be made by clinical or diagnostic evaluation. In some embodiments, said subject is selected or identified as one having elevated levels of microbially induced amyloid in the gut. Such a selection can also be made by clinical or diagnostic evaluation. In some embodiments, said subject is selected or identified as one having elevated levels of α-synuclein in the gut. Again, such a selection can be made by clinical or diagnostic evaluation. In some further embodiments, said subject is one showing one or more symptoms of a neurodegenerative disorder, such as a demonstration of anosmia, hyposmia, bradykinesia, ataxia, tremor, muscle rigidity, impaired posture and balance, loss of automatic movements, dysarthria or other speech changes, handwriting changes, orthostatic hypotension, memory deficit, dysphagia, incontinence, sleep disruption, cardiac arrhythmia, visual disturbance, psychiatric problems including depression and visual, auditory, olfactory, or tactile hallucinations, vertigo, cognitive dysfunction, altered dopamine levels, altered serotonin levels, and/or altered kynurenine levels, or any combination thereof. In some embodiments, said subject has been diagnosed according to methods known in the art of diagnosis of neurological and amyloid disorders, as having an amyloid disorder. In some further embodiments, said subject has been diagnosed as having or as being at risk of having Lewy Body Dementia, incidental Lewy body disease, Lewy body variant of Alzheimer's disease, multiple system atrophy, pure autonomic failure, or any combination thereof. In some embodiments, said subject further displays gastrointestinal symptoms. In some further embodiments, said gastrointestinal symptoms may comprise one or more of constipation, diarrhea, abdominal pain and/or cramping, bloating, flatulence, nausea, or any other symptoms of irritable bowel syndrome (IBS), inflammatory bowel disease (IBD), ulcerative colitis, Crohn's disease, intestinal hyperpermeability, or any combinations thereof.

In compositions and methods according to some embodiments of the present disclosure, a subject selected for treatment may be under the age of 18 years. In some embodiments, a subject selected for treatment may be between 17 and 30 years of age. In some embodiments, a subject selected for treatment may be between 29 and 50 years of age. In some embodiments, a subject selected for treatment may be between 49 and 60 years of age. In some embodiments, a subject selected for treatment may be between 59 and 70 years of age. In some embodiments, a subject selected for treatment according to the compositions and methods described herein may be greater than 69 years of age.

In compositions and methods according to some embodiments of the present disclosure, administration of one or more of the compositions as described herein provides the effect of preventing the formation of, or promoting the disaggregation of, amyloid or microbially induced amyloid in the gut, nasal cavity, olfactory bulb, or enteric nervous tissue, e.g., without having to pass the blood brain barrier. In some embodiments, administration of one or more of the compositions as described herein provides the effect of inhibiting the further aggregation of amyloid or microbially induced amyloid in the gut, nasal cavity, olfactory bulb, or enteric nervous tissue, e.g., without having to pass the blood brain barrier. In some embodiments, administration of one or more of the compositions as described herein provides the effect of causing or enhancing the disaggregation of amyloid or microbially induced amyloid in the gut, nasal cavity, olfactory bulb, or enteric nervous tissue, e.g., without having to pass the blood brain barrier. In some embodiments, administration of one or more of the compositions as described herein provides the effect of causing or enhancing the disaggregation of preexisting amyloid or microbially induced amyloid in the gut, nasal cavity, olfactory bulb, or enteric nervous tissue, e.g., without having to pass the blood brain barrier. In some embodiments, administration of one or more of the compositions as described herein provides the effect of preventing the development of one or more symptoms of one or more neurological or neurodegenerative disorders. In some embodiments, administration of one or more of the compositions as described herein provides the effect of ameliorating one or more symptoms of one or more neurological or neurodegenerative disorders. In some embodiments, administration of one or more of the compositions as described herein provides the effect of reversing one or more symptoms of one or more neurological or neurodegenerative disorders. In some embodiments, said one or more symptoms of one or more neurological disorders may comprise one or more of anosmia, hyposmia, bradykinesia, ataxia, tremor, muscle rigidity, impaired posture and balance, loss of automatic movements, dysarthria or other speech changes, handwriting changes, orthostatic hypotension, memory deficit, dysphagia, incontinence, sleep disruption, cardiac arrhythmia, visual disturbance, psychiatric problems including depression and visual, auditory, olfactory, or tactile hallucinations, vertigo, cognitive dysfunction, altered dopamine levels, altered serotonin levels, and/or altered kynurenine levels, or any combination thereof. In some embodiments, said one or more neurological disorders may comprise an amyloid disorder. In some further embodiments, said one or more neurological disorders may comprise one or more of Lewy Body Dementia, incidental Lewy body disease, Lewy body variant of Alzheimer's disease, multiple system atrophy, and/or pure autonomic failure, or any combination thereof.

In other embodiments, the inhibitors of amyloid formation may be intended for administration systemically or locally to the enteric of central nervous system. For example, inhibitors which are effective against mammalian amyloid or mammalian amyloid precursor protein aggregation may be useful in treatment of one or more of the amyloid disorders described herein (Table 1). Therefore, for such embodiments, the compositions comprising the inhibitors of amyloid formation may be formulated for parenteral administration, including systemic administration (e.g., intravenous, subcutaneous, intramuscular, intraperitoneal) or local administration (e.g., local injection near the vagus nerve, intraspinal injection, or intracranial injection). For delivery into the CNS, it is necessary for the inhibitors to pass through the blood brain barrier. Therefore, in such embodiments, the inhibitors are preferably lipid soluble molecules, or may be modified to increase lipid solubility, or may be co-administered with compounds that enhance passage through the blood brain barrier (see, e.g., WO20-14076655A1, WO2012159052A2, WO1992018529A1).

In compositions and methods according to some embodiments of the present disclosure, levels of amyloid and/or microbially induced amyloid in the tissues, fluids, or feces of the subject are monitored or evaluated during the course of therapy. In some further embodiments, levels of amyloid and/or microbially induced amyloid are monitored before and/or after the course of therapy. In some embodiments, levels of α-synuclein in the tissues, fluids, or feces of the subject are monitored during the course of therapy. In some embodiments, levels of α-synuclein are monitored before and/or after the course of therapy. In some embodiments, measurement of amyloid, microbially induced amyloid, and/or α-synuclein are measured in a fecal sample from the subject. In some embodiments, measurement of amyloid, microbially induced amyloid, and/or α-synuclein are measured in a tissue sample from the subject. In some embodiments, said tissue sample comprises gut epithelium, peritoneum, enteric nervous tissue, olfactory tissue, nasal endothelium, sinus endothelium, brain, and/or nervous tissue. In some embodiments, said tissue sample comprises cerebrospinal fluid or synovial fluid. In some embodiments, said tissue sample comprises blood, lymph, or plasma.

Methods to Identify Compounds

Disclosed herein are methods to identify compounds, which alter the ability of bacterial amyloid to promote aggregation and amyloid formation of the eukaryotic protein α-synuclein. Further disclosed herein are methods of screening for entities useful for the treatment or inhibition of neurodegenerative diseases and screening for entities useful for the prevention or amelioration of the progression of neurodegenerative diseases. Further disclosed herein are methods of screening for entities useful for the treatment or inhibition of gastrointestinal dysfunction related to neurodegenerative diseases. Additionally disclosed herein are methods for studying the molecular etiology of mammalian amyloid diseases and the molecular link between bacterial amyloid production and mammalian amyloid production. According to the methods of the present disclosure, said neurodegenerative diseases and/or mammalian amyloid diseases may comprise one or more of Parkinson's disease (PD), Lewy body dementia, multiple system atrophy, and all other α-synucleinopathies, PD-associated constipation, PD-associated hyposmia, Huntington's Disease, Alexander's Disease, amyotrophic lateral sclerosis (ALS), Alzheimer's Disease and other diseases in which amyloids are implicated.

The methods as disclosed herein comprise a suite of in vitro assays that measure one or more of the following (1) bacterial amyloid aggregation on the bacterial surface or in the proximal extracellular space; (2) the interaction between bacterial amyloid and α-synuclein in the GI tract or olfactory system; or (3) aggregation of α-synuclein in the GI tract (including the enteric neuronal cells). According to the methods of the present disclosure, α-synuclein should be viewed as a representative amyloid protein of the wider range of known mammalian amyloid or mammalian amyloid precursor proteins, and the methods as disclosed herein may be adapted by one of skill in the art to evaluate the aggregation of any amyloid protein in which a one amyloid protein (bacterial or human) prompts aggregation of another amyloid protein. Representative disorders that present amyloid formation and the proteins involved in these disorders, which may be evaluated using the methods of the present disclosure, include but are not limited to those disclosed in Table 1. Accordingly, in some embodiments, the methods comprise contacting a plurality of concentrations of a microbial amyloid or a microbial amyloid precursor with a plurality of concentrations of α-Synuclein and/or other mammalian amyloid or mammalian amyloid precursor in the presence of a composition, analyzing or measuring the formation or disaggregation of amyloid after the reaction set forth above; and comparing said analysis or measurement to an analysis or measurement of a control, wherein said control comprises analyzing or measuring the formation of amyloid after the reaction set forth above in the absence of said composition. In certain methods and compositions disclosed herein, said microbial amyloid or microbial amyloid precursor comprises CsgA.

In some embodiments, the methods according to the present disclosure contemplate contacting a microbial amyloid or a microbial amyloid precursor (e.g., a composition comprising CsgA) with varying concentrations of a mammalian amyloid or mammalian amyloid precursor in the presence of a composition, said composition comprising a compound or mixture to be tested for its ability to inhibit amyloid formation or enhance amyloid disaggregation. In some further embodiments, said combination of microbial amyloid or microbial amyloid precursor, mammalian amyloid or mammalian amyloid precursor, and test composition are analyzed or measured for changes in the amount of amyloid present. In some further embodiments, the rate and/or extent of amyloid formation within said combination of microbial amyloid or microbial amyloid precursor, mammalian amyloid or mammalian amyloid precursor, and test composition is compared to the rate of amyloid formation within a control sample lacking said composition. In some embodiments, the rate of formation of amyloid is measured. In some further embodiments, the total amount of amyloid formation is measured. In some further embodiments, the temperature of the assay is varied, whereby the stability of the newly-formed amyloid fibrils is measured relative to those formed under native conditions. In some embodiments, the methods are carried out by placing said composition within the wells of a multi-well assay plate. In some further embodiments, the methods according to the present disclosure are carried out in the presence of a physical agitator. In some further embodiments, said physical agitator comprises glass, teflon, or polymer beads. In some further embodiments, said polymer beads may comprise polystyrene, polylactic acid, poly lactic-co-glycolic acid, polycarbonate, or polytetrafluoroethylene (Teflon®) beads. In some embodiments, the beads or objects used for agitation will be from 10-1000 µm in their longest dimension. In some embodiments, the beads or objects used for agitation are from 10-100 µm, from 80-200, from 180-300 µm, from 280-400 µm, from 380-500 µm, from 480-600 µm, from 580-700 µm, from 680-800 µm, from 780-900 µm, or from 880-1000 µm in their longest dimension. In some embodiments, the beads or objects used for agitation will be greater than 1 mm in their longest dimension. In some embodiments, the beads or objects used for agitation will be less than 10 mm in their longest dimension.

In some embodiments, the microbial amyloid or microbial amyloid precursor comprises CsgA, the major protein constituent of curli, also known as adhesive pili, or any analogue or homologue thereof. In some embodiments, the microbial amyloid or microbial amyloid precursor comprises CsgB, which nucleates the conversion of CsgA to its amyloid form, or polypeptides derived therefrom. In some embodiments, said mammalian amyloid or mammalian amyloid precursor comprises α-synuclein.

In some embodiments, contacting microbial amyloid or a microbial amyloid precursor (e.g., a composition comprising CsgA) with varying concentrations of mammalian amyloid or mammalian amyloid precursor with a composition occurs in the presence of an indicator of amyloid formation. In some further embodiments, said indicator may comprise a fluorescent indicator, in which the fluorescence intensity of the indicator varies in a manner correlated with the amount of amyloid present in the sample. Said variation may occur due to changes in fluorescence related to changes in the molecular environment associated with interposition of the label into the assembling amyloid fibril. In some further embodiments, said indicator may comprise thioflavin T (ThT). In some embodiments, labels that are bound to amyloid precursor molecules may show changes in intensity or wavelength of emission due to intermolecular fluorescence quenching or fluorescence resonance energy transfer that is correlated with the formation of amyloid fibrils. Exemplary fluorescent labels are disclosed in The Molecular Probes Handbook (Invitrogen, Inc., 2010), which is hereby incorporated by reference for its teachings regarding FRET pairs, fluorescence quenching, and fluorescent probes conjugatable to proteins. Other exemplary fluorescent labels may comprise fluorescence proteins, including but not limited to the Green fluorescent protein (GFP), the Yellow Fluorescent Protein (YFP), AmCyan1, AsREd2, mBanana, mCherry, Dendra2, DsRed2, DsRed-express, DsRed-monomer, DsRed, E2-Crimson, GFP-UV, the Blue Fluorescent Protein (BFP), HcRed1, mOrange, PAmCherry, mPlum, mRaspberry, mStrawberry, tdTomato, ZsGreen1, ZsYellow1, or AcGFP1, or their derivatives, or others fluorescent proteins as are known in the art. In some further embodiments, the label attached to the mammalian amyloid precursor is different from the label that is attached to the bacterial amyloid or bacterial amyloid precursor. In some embodiments, the bacterial amyloid or bacterial amyloid precursor is unlabeled. In some embodiments, the mammalian amyloid, mammalian amyloid precursor, bacterial amyloid precursor, or bacterial amyloid contain more than one label. In some further embodiments, said indicator may comprise a colorimetric indicator, a spin label (such as, for example, 3H, 15N or 13C), a metal ion binding compound (such as, for example, a porphyrin, chelator, polyhistidine, or other metal binding polypeptide), an enzyme, or an amyloid-specific antibody. In some embodiments, the development of amyloid fibrils is observed directly by optical microscopy. In some embodiments, amyloid formation is observed by direct light transmission, or by reflectivity. In some embodiments, amyloid formation is observed by total internal reflection FTIR. In some embodiments, amyloid formation is observed by NMR, FTIR, SPIR, or SPR spectroscopy. In some embodiments, amyloid formation is observed and/or confirmed by optical birefringence. In some embodiments, samples are stained with congo red dye prior to visualization. In some embodiments, amyloid formation is observed by Raman scattering. In some embodiments, amyloid formation is observed by monitoring changes in the internal fluorescence of the sample, such as that due to internal tryptophan, tyrosine, phenylalanine, histidine, and arginine residues. In some embodiments, amyloid formation is observed by monitoring the binding of an amyloid-specific antibody, by means as are known in the art such as by conjugation of said antibody to a fluorescent label, a colorimetric label, a spin label, a radioisotope, and enzyme, a fluorescent protein, a metal binding domain or other methods known to those of ordinary skill in the art for the detection or visualization of antibodies. According to the methods as described herein, said antibody may comprise an antibody with binding activity that is selective for either amyloid, or amyloid precursor.

In some embodiments, the methods of the present disclosure may be carried out by monitoring the kinetics of fluorescence intensity of an amyloid specific dye in the presence of a mammalian amyloid precursor, and one or more bacterial amyloid precursors or aggregates. In some embodiments, said mammalian amyloid precursor is α-synuclein. In some embodiments, said bacterial amyloid precursor or aggregate is CsgA. In some embodiments, said amyloid specific dye is Thioflavin T.

In some embodiments, the present disclosure contemplates a kit for the practice of the methods described herein. In some embodiments, said kit comprises at least a mammalian amyloid or mammalian amyloid precursor, a bacterial amyloid or bacterial amyloid precursor, an indicator of amyloid formation as described herein, wherein such indicator may or may not be conjugated to said mammalian amyloid or mammalian amyloid precursor, a bacterial amyloid or bacterial amyloid precursor, and one or more reaction vessels. Said kit may comprise a multi-well plate. Said kit may further comprise instructions for the carrying out of the methods described herein.

The methods of the present disclosure provide methods of screening candidate compounds in order to identify compounds that modulate the aggregation and/or disaggregation of amyloid, especially microbially induced amyloid. In some embodiments, the methods of the present disclosure comprise the screening of a library of candidate compounds. In some further embodiments, the compositions contacted with mammalian amyloid or mammalian amyloid precursor, and bacterial amyloid precursor or bacterial amyloid, according to the methods disclosed herein, comprise one or more compounds, or combinations thereof, suspected in the art to inhibit amyloid formation or to destabilize or disaggregate existing amyloid. In certain embodiments the compositions contacted with mammalian amyloid or mammalian amyloid precursor, and bacterial amyloid precursor or bacterial amyloid, according to the methods disclosed herein, comprise a natural product or an extract from a natural product. In some embodiments the compositions contacted with mammalian amyloid or mammalian amyloid precursor, and bacterial amyloid precursor or bacterial amyloid, according to the methods disclosed herein, comprise an herb, herbal extract, or botanical substance. In some embodiments, said compositions may comprise tissue or fluid from an animal, plant, or fungus. In some further embodiments, said compositions may comprise tissue, fluid, or extracts of tissue or fluid, from a seed, fruit, flower, leaf, stem, cambium, or root of a plant, or combinations thereof. In some further embodiments, said compositions may comprise tissue, fluid, or extracts of a tissue or fluid, from the feces, urine, blood, lymphatic fluid, synovial fluid, cerebrospinal fluid, saliva, or any internal organ of an animal. In some embodiments, said composition may comprise one or more bacteria, or lysates, extracts, conditioned culture media, lyophilized bacteria, lyophilized lysates, lyophilized culture media thereof, or any combination thereof. In some embodiments said bacteria comprise one or more of *Bacteroides, Prevotella, Parabacteroides, Faecalibacterium, Eubacterium, Roseburia, Blautia, Coprococcus*, and *Bifiobacterium*, or any combination thereof.

In some embodiments, the methods of the present disclosure can be used to diagnose or assess the risk for developing an amyloid disorder in a subject. The methods of the present disclosure may be used in the treatment, prevention, and/or amelioration of one or more neurological disorders including Parkinson's Disease, Lewy Body Dementia, incidental Lewy body disease, Lewy body variant of Alzheimer's disease, multiple system atrophy, pure autonomic failure, or any combination thereof. The disorders may include behavioral symptoms as are known in the art of clinical diagnosis and treatment of neurological disorders such as communicative symptoms, stereotyped behaviors, sensorimotor issues, and/or anxiety-like behaviors in addition to physical symptoms as are known in the art of diagnosis and treatment of neurological disorders such as tremors, paralysis, dyskinesia, and/or gastrointestinal symptoms such one or more of constipation, diarrhea, abdominal pain and/or cramping, bloating, flatulence, nausea, or any other symptoms of irritable bowel syndrome (IBS), inflammatory bowel disease (IBD), ulcerative colitis, Crohn's disease, intestinal hyperpermeability, or any combinations thereof. Accordingly, such clinical and/or diagnostic evaluations and determinations can be used to identify and/or select one or more subjects for receiving one or more compounds described herein in accordance with the one or more methods provided in this disclosure. The methods of the present disclosure may, in some embodiments, include monitoring of the behavioral, physical, and/or gastrointestinal symptoms as are known in the art of diagnosis and treatment of neurological disorders. In some embodiments, the methods according to the present disclosure incorporate monitoring changes in the behavior of a subject. In some further embodiments, the methods according to the present disclosure incorporate monitoring the subject for behavioral symptoms as are known to be related to Parkinson's Disease, Lewy Body Dementia, incidental Lewy body disease, Lewy body variant of Alzheimer's disease, multiple system atrophy, pure autonomic failure, or any combination thereof. In some further embodiments, the methods according to the present disclosure incorporate monitoring the subject for bradykinesia, ataxia, tremor, muscle rigidity, impaired posture and balance, loss of automatic movements, dysarthria or other speech changes, handwriting changes, orthostatic hypotension, memory deficit, dysphagia, incontinence, sleep disruption, cardiac arrhythmia, visual disturbance, psychiatric problems including depression and visual, auditory, olfactory, or tactile hallucinations, vertigo, cognitive dysfunction, or any combination thereof or any other symptom known to those in the art of neurological diagnosis or treatment to be useful in the diagnosis of amyloid disorders, and especially α-synucleinopathies. Again, such clinical and/or diagnostic evaluations and determinations can be used to identify and/or select one or more subjects for diagnosis and/or treatment according to the methods described herein. In some embodiments, the methods of the present disclosure may include monitoring of levels of bacterial, host-derived, and microbially-induced amyloid as disclosed herein in addition to the aforementioned clinical monitoring. According to the methods of the present disclosure, said amyloid may be monitored in the gut, feces, urine, blood, saliva, cerebrospinal fluid, and/or synovial fluid of a subject. The methods of the present disclosure contemplate the monitoring of said amyloid in any tissue or fluid obtainable from a subject during the course of treatment, and thereby identifying whether said sample contains factors which enhance or inhibit amyloid formation. In some embodiments, a subject from whom a tissue, fluid, or other sample is derived, for which sample the assays described herein indicate the presence of factors, which enhance or accelerate amyloid formation, may be considered to be at elevated risk of developing an amyloid disorder. In some embodiments, said subject may be administered a drug or treatment to ameliorate or prevent said amyloid disorder. In some further embodiments, said treatment may comprise administering to said subject one or more bacteria from the genera comprising *Bacteroides, Prevotella, Parabacteroides, Faecalibacterium, Clostridium, Eubacterium, Roseburia, Blautia, Coprococcus, Ruminococcus, Lactobacillus, Akkermansia* and *Bifiobacterium*, or any combination thereof. In some further embodiments, said treatment may comprise administering to said subject one or more bacteria selected from the group comprising *B. fragilis, B. vulgatus, B. thetaiotaomicron, B. ovatus, B. cellulosilyticus, B. caccae, B. uniformis, P. copri, P. distasonis, F. prausnitzii, C. nexile, C. scindens, E. hallii, E. rectale, R. hominis, R. intestinalis, B. hansenii, B. producta, B. hydrogenotrophica, C. catus, C. eutactus, R. obeum, R. bromii, R. inulinovorans, L. reuteri, L. rhamnosus, L. casei, A. muciniphila, B. longum, B. infantis, B. bifidum, B. breve* and *B. adolescentis* or any combination thereof. Again, such clinical and/or diagnostic evaluations and determinations can be used to identify and/or select one or more subjects for receiving one or more compounds described herein in accordance with the one or more methods provided in this disclosure.

According to the methods disclosed herein, a treatment or inhibition of a disorder implicating amyloid formation may be achieved by modulating the dosing schedule for the administration of a composition such that subjects experience periodic partial or full reductions in dosing for fixed amounts of time, followed by a resumption of dosing. In some embodiments, dosages are administered daily for between one and thirty days, followed by a dosing holiday lasting for between one and thirty days. In some embodiments, during the dosing holiday, no dose is administered. In some further embodiments, the composition of the present disclosure is allowed to clear completely from the subject's body prior to administration of the next dose. In some other embodiments, during the dosing holiday, a dose less than the usual daily dose is administered. In some further embodiments, an amount of the administered composition less than the therapeutically effective amount is allowed to remain within the subject during the dosing holiday. In some further embodiments, an amount of the administered composition sufficient to maintain therapeutic levels in the affected tissues is allowed to remain within the subject. In some embodiments, a composition is administered at any time following the onset of one or more of the aforementioned symptoms of a neurological disorder associated with amyloid formation. In some embodiments, a composition according to the methods described herein is administered prior to the onset of symptoms of said disorder or disorders. In some embodiments, a composition according to the methods described herein is administered concurrently with or after the onset of symptoms of said disorder or disorders.

Additional Options and Items

The following options are set forth in accordance with some embodiments herein.

1. A method of identifying a composition that affects the formation of microbially-induced amyloid, comprising:
    (a) contacting a plurality of concentrations of a microbial amyloid or a microbial amyloid precursor (e.g., CsgA) with a plurality of concentrations of α-Synuclein in the presence of a composition;
    (b) analyzing or measuring the formation of amyloid produced by the reaction set forth in (a); and
    (c) comparing the analysis or measurement made in (b) with an analysis or measurement of a control, wherein said control comprises analyzing or measuring the formation of amyloid after the reaction set forth in (a) in the absence of said composition.

2. The method of Option 1, wherein said microbial amyloid or microbial amyloid precursor comprises CsgA.

3. The method of Options 1 or 2, further comprising agitation during (a).

4. The method of Options 1-3, wherein the contacting performed in (a) is conducted in the presence of an indicator of amyloid formation.

5. The method of Option 4, wherein said indicator is a fluorescent indicator, a spin-labeled indicator, an enzyme, an antibody, or a colorimetric indicator.

6. The method of Option 4, wherein said indicator is Thioflavin T.

7. The method of Option 4 wherein said antibody has specificity for aggregated α-Synuclein, and wherein said antibody optionally is conjugated to a fluorescent label, an enzyme, a colorimetric label, a spin label, a metal ion binding moiety, a nucleic acid, a polysaccharide, or a polypeptide.

8. The method of any of Options 1-7, wherein said CsgA and said α-Synuclein are each separately labeled.

9. The method of any of Options 1-8, wherein the formation is analyzed or measured by internal fluorescence, by fluorescence of a dye or label, by fluorescence resonance energy transfer, by fluorescence polarization, by fluorescence polarization transfer, by UV/Vis Spectroscopy, by magnetic resonance, by Raman scattering, by electron paramagnetic spin resonance, by light microscopy, by electron microscopy, by scanning tunneling microscopy, or by atomic force microscopy.

10. The method of any of Options 1-9, wherein said composition comprises a mixture of compounds.

11. The method of any of Options 1-10, wherein said composition comprises tissue, bodily fluid or an extract thereof.

12. The method of any of Options 1-11, wherein said composition comprises feces, urine, blood, spinal fluid, or saliva, or a component thereof.

13. The method of any of Options 1-10 wherein said composition comprises an extract from a natural product.

14. The method of Option 13 wherein said natural product is an herb, a botanical substance, or foodstuff.

15. The method of any of Options 13-14 wherein said natural product is a fungal tissue, legume, seed, berry, leaf, fruit, flower, plant root, plant stem, or plant bark.

16. The method of any of Options 1-10 wherein said composition comprises one or more bacteria, bacterial extracts, lysates, conditioned culture media, lyophilized bacteria, lyophilized lysates, lyophilized culture media, or any combination thereof.

17. The method of any of Options 1-16, further comprising identifying or selecting compositions that alter amyloid formation.

18. The method of any of Options 1-17, further comprising identifying or selecting compositions that reduce amyloid formation.

19. The method of any of Options 1-18, wherein the rate of formation of amyloid is analyzed or measured in (b).

20. A method of making microbially-induced amyloid, comprising:
 (a) contacting a plurality of concentrations of a microbial amyloid or a microbial amyloid precursor (e.g., CsgA) with a plurality of concentrations of α-Synuclein in the presence of a composition;
 (b) providing conditions that allow for the formation of new microbially-induced amyloid; and
 (c) analyzing or quantifying the microbially-induced amyloid formed in (b).

21. The method of Option 20, wherein said microbial amyloid or microbial amyloid precursor comprises CsgA.

22. The method of Options 20 or 21, further comprising agitation during (a).

23. The method of any of Options 20-22, wherein the contacting performed in (a) is conducted in the presence of an indicator of amyloid formation.

24. The method of Option 23, wherein said indicator is a fluorescent indicator, a spin-labeled indicator, or a colorimetric indicator.

25. The method of Options 23 or 24, wherein said indicator is Thioflavin T.

26. The method of any of Options 20-25, wherein said CsgA and said α-Synuclein are each separately labeled.

27. The method of any of Options 20-26, wherein the formation is analyzed or measured by internal fluorescence, by fluorescence of a dye or label, by fluorescence resonance energy transfer, by fluorescence polarization, by fluorescence polarization transfer, by UV/Vis Spectroscopy, by magnetic resonance, by Raman scattering, by electron paramagnetic spin resonance, by light microscopy, by electron microscopy, by scanning tunneling microscopy, or by atomic force microscopy.

28. The method of any of Options 20-27, wherein said composition comprises a mixture of compounds.

29. The method of any of Options 20-28, wherein said composition comprises tissue, bodily fluid or an extract thereof.

30. The method of any of Options 20-29, wherein said composition comprises feces, urine, blood, spinal fluid, or saliva, or a component thereof.

31. The method of any of Options 20-30 wherein said composition comprises a natural product or an extract from a natural product.

32. The method of Option 31 wherein said natural product is an herb, a botanical substance, or foodstuff.

33. The method of any of Options 28-32 wherein said natural product is a fungal tissue, legume, seed, berry, leaf, fruit, flower, plant root, plant stem, or plant bark.

34. The method of any of Options 28-33 wherein said composition comprises one or more bacteria, bacterial extracts, lysates, conditioned culture media, lyophilized bacteria, lyophilized lysates, lyophilized culture media, or any combination thereof.

35. The method of any of Options 20-34, further comprising identifying or selecting compositions that reduce amyloid formation.

36. The method of any of Options 20-35, wherein the rate of formation of amyloid is analyzed or quantified in (c).

37. A kit comprising a microbial amyloid or a microbial amyloid precursor and α-Synuclein, being present in one or more containers within said kit.

38. The kit of Option 37, wherein said microbial amyloid or microbial amyloid precursor comprises CsgA.

39. A method of treating or inhibiting an amyloid disorder in a subject comprising:
 (a) contacting a plurality of concentrations of a microbial amyloid or a microbial amyloid precursor with a plurality of concentrations of α-Synuclein in the presence of a composition;
 (b) analyzing or measuring the formation of new amyloid after the reaction set forth in (a);
 (c) comparing the analysis or measurement made in (b) with an analysis or measurement of a control, wherein said control comprises analyzing or measuring the formation of amyloid after the reaction set forth in (a) in the absence of said composition; and
 (d) if the formation of amyloid in the presence of said composition is increased relative to the formation of amyloid in the absence of said composition, administering to said subject an effective amount of a pharmaceutical composition suitable for inhibiting or treating said amyloid disorder.

40. The method of Option 39, wherein said microbial amyloid or microbial amyloid precursor comprises CsgA.

41. The method of any of Options 39-40, wherein said composition comprises tissue, bodily fluid or an extract thereof.

42. The method of any of Options 39-41, wherein said composition comprises feces, urine, blood, spinal fluid, or saliva, or a component thereof.

43. The method of Options 39-42, wherein said pharmaceutical composition comprises one or more probiotic bacteria.

44. The method of Options 39-43, wherein said pharmaceutical composition comprises one or more bacteria selected from the group consisting of *Bacteroides, Prevotella, Parabacteroides, Faecalibacterium, Eubacterium, Roseburia, Blautia, Coprococcus*, and *Bifiobacterium*, or any combination thereof.

45. The method of Options 39-44, wherein said pharmaceutical composition comprises one or more bacteria selected from the group consisting of *B. fragilis, B. vulgatus*, and *B. thetaiotaomicron*; or any combination thereof.

46. The method of any of Options 39-45, wherein the rate of formation of amyloid is analyzed or quantified in (b).

47. The method of any of Options 39-46, further comprising identifying or selecting said subject as one that would benefit from a treatment or inhibition of an amyloid disorder.

48. The method of any of Options 39-47, further comprising identifying or selecting said subject as one at risk of or showing symptoms of one or more of Parkinson's Disease, Lewy Body Dementia, incidental Lewy body disease, Lewy body variant of Alzheimer's disease, multiple system atrophy, pure autonomic failure, or any combination thereof.

The following items are set forth in accordance with some embodiments herein.

1. A pharmaceutical composition for inhibiting amyloid formation, the composition comprising a compound selected from the group consisting of: EGCG (epigallocatechin gallate), quercetin (2-(3,4-dihydroxyphenyl)-3,5,7-trihydroxychromen-4-one), morin (2-(2,4-dihydroxyphenyl)-3,5,7-trihydroxychromen-4-one), rosmarinic acid ((2R)-2-[[(2"E")-3-(3,4-dihydroxyphenyl)-1-oxo-2-propenyl]]oxy]-3-(3,4-dihydroxyphenyl)propanoic acid), gallic acid (3,4,5-trihydroxybenzoic acid), lauryl gallate (dodecyl 3,4,5-trihydroxybenzoate), methoxyhydroquinone (2-methoxybenzene-1,4-diol), curcumin ((1E,6E)-1,7-Bis(4-hydroxy-3-methoxyphenyl)hepta-1,6-diene-3,5-dione), resveratrol ((E)-5-(4-hydroxystyryl)benzene-1,3-diol), apigenin (5,7-dihydroxy-2-(4-hydroxyphenyl)-4H-1-benzopyran-4-one), NDGA (nordihydroguaiaretic acid or 4,4'-(2,3-dimethylbutane-1,4-diyl)dibenzene-1,2-diol), phloretin (3-(4-hydroxyphenyl)-1-(2,4,6-trihydroxyphenyl)propan-1-one), genistein (5,7-dihydroxy-3-(4-hydroxyphenyl)chromen-4-one), isoeugenol (2-methoxy-4-(prop-1-en-1-yl)phenol), 4-allyl-1,2-dimethoxybenzene, eugenol (2-methoxy-4-(prop-2-en-1-yl)phenol), 4-ethylguaiacol (4-ethyl-2-methoxyphenol), guaiacol (2-methoxyphenol), thymol (5-methyl-2-(propan-2-yl)phenol), carvacrol (2-methyl-5-(propan-2-yl)phenol), and Anle 138b.

2. A pharmaceutical composition for inhibiting amyloid formation, the composition comprising a compound having a structure of Formula I:

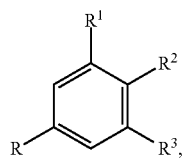

wherein
$R^1$ is selected from —H, —OH, or —OCH$_3$;
$R^2$ is selected from —H, —OH, or —OCH$_3$;
$R^3$ is selected from —H, —OH, or —OCH$_3$;
provided that at least one of $R^1$, $R^2$ and $R^3$ is not —H; and
wherein
R is selected from —OH, —C(O)OH, —C(O)OR$^4$ or R$^4$;
wherein
$R^4$ is selected from a $C_2$-$C_{20}$ branched or unbranched alkyl, alkenyl, carbocyclyl, aryl, heteroalkyl, heteroalkenyl, heterocyclyl or heteroaryl group.

3. A pharmaceutical composition for inhibiting amyloid formation comprising a compound having a structure of Formula II:

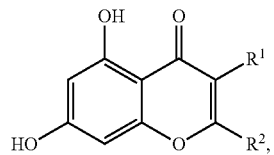

wherein $R^1$ is selected from —H, —CH$_3$, —OH, —OCH$_3$, 3-hydroxyphenyl, 4-hydroxyphenyl, 2,4-dihydroxyphenyl, 3,4-dihydroxyphenyl, 3,5-dihydroxyphenyl, 3,4,5-trihydroxyphenyl, 3-methoxyphenyl, 4-methoxyphenyl, 2,4-methoxyphenyl, 3,4-dimethoxyphenyl, 3,5-dimethoxyphenyl, 3,4,5-trimethoxyphenyl, 2-hydroxy-4-methoxyphenyl, 3-hydroxy-4-methoxyphenyl, 2-methoxy-4-hydroxyphenyl, 3-methoxy-4-hydroxyphenyl, 3,4-dihydroxy-5-methoxyphenyl, 3,5-dihydroxy-4-methoxyphenyl, 3,4-methoxy-5-hydroxyphenyl, and 3,5-dimethoxy-4-hydroxyphenyl, and wherein $R^2$ is selected from —H, —CH$_3$, —OH, —OCH$_3$, 3-hydroxyphenyl, 4-hydroxyphenyl, 2,4-dihydroxyphenyl, 3,4-dihydroxyphenyl, 3,5-dihydroxyphenyl, 3,4,5-trihydroxyphenyl, 3-methoxyphenyl, 4-methoxyphenyl, 2,4-methoxyphenyl, 3,4-dimethoxyphenyl, 3,5-dimethoxyphenyl, 3,4,5-trimethoxyphenyl, 2-hydroxy-4-methoxyphenyl, 3-hydroxy-4-methoxyphenyl, 2-methoxy-4-hydroxyphenyl, 3-methoxy-4-hydroxyphenyl, 3,4-dihydroxy-5-methoxyphenyl, 3,5-dihydroxy-4-methoxyphenyl, 3,4-methoxy-5-hydroxyphenyl, and 3,5-dimethoxy-4-hydroxyphenyl, provided that at least one of $R^1$ and $R^2$ is —H, —CH$_3$, —OH, or —OCH$_3$.

4. A pharmaceutical composition for inhibiting amyloid formation comprising a compound having a structure of Formula III:

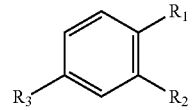

wherein $R_1$ is: —H, —OH, —OCH$_3$, —CH$_3$, —CH(CH$_3$)$_2$, —C(CH$_3$)$_3$, —CH$_2$CH$_3$, —C$_6$H$_5$, —C$_6$H$_4$CH$_3$, —C$_6$H$_4$OH, —C$_6$H$_4$C(O)H, —C$_6$H$_4$C(O)CH$_3$, —C$_6$H$_4$C(O)CH$_3$, —C$_6$H$_4$OC(O)CH$_3$, —C(O)H, —C(O)CH$_3$, —OC(O)H, or —OC(O)CH$_3$;

wherein $R_2$ is: —H, —OH, —OCH$_3$, —CH$_3$, —CH(CH$_3$)$_2$, —C(CH$_3$)$_3$, —CH$_2$CH$_3$, —C$_6$H$_5$, —C$_6$H$_4$CH$_3$, —C$_6$H$_4$OH, —C$_6$H$_4$C(O)H, —C$_6$H$_4$C(O)CH$_3$, —C$_6$H$_4$C(O)CH$_3$, —C$_6$H$_4$OC(O)CH$_3$, —C(O)H, —C(O)CH$_3$, —OC(O)H, or —OC(O)CH$_3$; and wherein $R^3$ is: —H, —OH, —OCH$_3$, —OCH$_2$CH$_3$, —OCH$_2$CH$_2$CH$_3$, —CH$_3$, —CH(CH$_3$)$_2$, —C(CH$_3$)$_3$, —CH$_2$CH$_3$, —CH$_2$CH$_2$CH$_3$, —CH$_2$CHCH$_2$, —CHCHCH$_3$, —C$_6$H$_5$, —C$_6$H$_4$CH$_3$, —C$_6$H$_4$OH, —C$_6$H$_4$C(O)H, —C$_6$H$_4$C(O)CH$_3$, —C$_6$H$_4$C(O)CH$_3$, —C$_6$H$_4$OC(O)CH$_3$, —C(O)H, —C(O)CH$_3$, —C(O)CH$_2$CH$_3$, —C(O)CH$_2$CH$_2$CH$_3$, —OC(O)H, —OC(O)CH$_3$, —OC(O)CH$_2$CH$_3$—OC(O)CH$_2$CH$_2$CH$_3$, —CH$_2$CH$_2$CH$_2$CH$_3$, —CHCHCH$_2$CH$_3$, —CH$_2$CHCHCH$_3$, or —CH$_2$CH$_2$CHCH$_2$.

5. A pharmaceutical composition for inhibiting amyloid formation comprising a compound having the structure of Formula III:

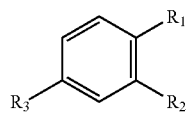

wherein $R_1$ is selected from: —H, —OH, —OCH$_3$, —CH$_3$, —CH(CH$_3$)$_2$, —C(CH$_3$)$_3$, —CH$_2$CH$_3$, —C$_6$H$_5$, —C$_6$H$_4$CH$_3$, —C$_6$H$_4$OH, —C$_6$H$_4$C(O)H, —C$_6$H$_4$C(O)CH$_3$, —C$_6$H$_4$C(O)CH$_3$, —C$_6$H$_4$OC(O)CH$_3$, —C(O)H, —C(O)CH$_3$, —OC(O)H, or —OC(O)CH$_3$;

wherein $R_2$ is selected from: —H, —OH, —OCH$_3$, —CH$_3$, —CH(CH$_3$)$_2$, —C(CH$_3$)$_3$, —CH$_2$CH$_3$, —C$_6$H$_5$, —C$_6$H$_4$CH$_3$, —C$_6$H$_4$OH, —C$_6$H$_4$C(O)H, —C$_6$H$_4$C(O)CH$_3$, —C$_6$H$_4$C(O)CH$_3$, —C$_6$H$_4$OC(O)CH$_3$, —C(O)H, —C(O)CH$_3$, —OC(O)H, or —OC(O)CH$_3$; and wherein $R^3$ is selected from: —H, —OH, —OCH$_3$, —OCH$_2$CH$_3$, —OCH$_2$CH$_2$CH$_3$, —CH$_3$, —CH(CH$_3$)$_2$, —C(CH$_3$)$_3$, —CH$_2$CH$_3$, —CH$_2$CH$_2$CH$_3$, —CH$_2$CHCH$_2$, —CHCHCH$_3$, —C$_6$H$_5$, —C$_6$H$_4$CH$_3$, —C$_6$H$_4$OH, —C$_6$H$_4$C(O)H, —C$_6$H$_4$C(O)CH$_3$, —C$_6$H$_4$C(O)CH$_3$, —C$_6$H$_4$OC(O)CH$_3$, —C(O)H, —C(O)CH$_3$, —C(O)CH$_2$CH$_3$, —C(O)CH$_2$CH$_2$CH$_3$, —OC(O)H, —OC(O)CH$_3$, —OC(O)CH$_2$CH$_3$—OC(O)CH$_2$CH$_2$CH$_3$, —CH$_2$CH$_2$CH$_2$CH$_3$, —CHCHCH$_2$CH$_3$, —CH$_2$CHCHCH$_3$, —CH$_2$CH$_2$CHCH$_2$, or —CH$_2$CHCH$_3$CHCH$_3$CH$_2$C$_6$H$_3$(OH)$_2$.

6. The composition of item 1, wherein the compound is selected from the group consisting of Anle 138b, EGCG, Gallic acid, lauryl gallate, 4-allyl-1,2-dimethoxybenzene, isoeugenol, eugenol, 4-ethylguaiacol, Morin, Thymol, Carvacrol, curcumin, phloretin, Guiacol, Methoxyhydroquinone, and NDGA.

7. The composition of item 1, wherein the compound is selected from the group consisting of: EGCG, quercertin, morin, rosmarinic acid, gallic acid, methoxy-hydroquinone, curcumin, resveratrol, apigenin, NDGA, phloretin, genistein, and lauryl gallate.

8. The composition of item 1, wherein the compound is selected from the group consisting of: EGCG, quercetin, morin, rosmarinic acid, gallic acid and lauryl gallate 9. The composition of item 1, wherein the compound is selected from the group consisting of: EGCG quercetin, genistein, apigenein, resveratrol, rosmarinic acid, and NDGA.

10. The composition of item 1, the compound is selected from the group consisting of: quercertin, morin, rosmarinic acid, gallic acid, methoxy-hydroquinone, curcumin, resveratrol, apigenin, NDGA, phloretin, genistein, and lauryl gallate.

11. The composition of item 1, wherein the compound is selected from the group consisting of Anle 138b, Gallic acid, lauryl gallate, 4-allyl-1,2-dimethoxybenzene, isoeugenol, eugenol, 4-ethylguaiacol, Morin, Thymol, Carvacrol, curcumin, phloretin, Guiacol, Methoxyhydroquinone, and NDGA.

12. A composition comprising a compound selected from the group consisting of genistein, apigenein, resveratrol, rosmarinic acid, quercetin, EGCG, and NDGA.

13. A composition comprising a compound selected from the group consisting of resveratrol, rosmarinic acid, quercetin, EGCG, and NDGA.

14. A composition comprising a compound selected from the group consisting of resveratrol, rosmarinic acid, and quercetin.

15. The composition of any one of Items 1-14, wherein said composition is formulated for delivery outside of the systemic circulation of a subject.

16. The composition of any one of Items 1-15, wherein said composition is formulated for enteric or intranasal delivery.

17. The composition of any one of Items 1-16, wherein said composition is formulated for controlled release within the lower intestine or colon.

18. The composition of any one of Items 1-17, wherein said composition is formulated for delivery systemically or locally to the enteric or central nervous system of a subject.

19. The composition of any one of Items 1-18, wherein said composition is formulated for delivery by intravenous, subcutaneous, intramuscular, intraperitoneal, intraspinal or intracranial injection.

20. The composition of any of Items 1-19, wherein said composition is an enteric-coated capsule, tablet, soft-gel, spray dried powder, polymer matrix, hydrogel, enteric-coated solid, crystalline solid, amorphous solid, glassy solid, coated micronized particle, liquid, nebulized liquid, aerosol, or microcapsule.

21. A method of disrupting and/or inhibiting the formation of amyloid aggregates comprising contacting amyloid or a precursor of amyloid with a composition comprising a compound is selected from the group consisting of: quercetin, morin, rosmarinic acid, gallic acid, methoxy-hydroquinone, curcumin, resveratrol, apigenin, NDGA, phloretin, genistein, and lauryl gallate, or a combination of two or more of any of the listed items.

22. A method of disrupting and/or inhibiting the formation of amyloid aggregates comprising contacting amyloid or a precursor of amyloid with a composition comprising one or more polyphenols or polyphenol-like compounds, such as one or more of the compositions of any one of items 1-20 and/or a composition comprising any one or more of the following molecules:

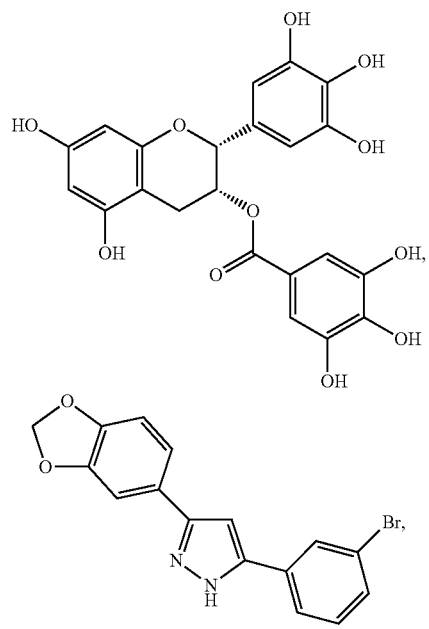

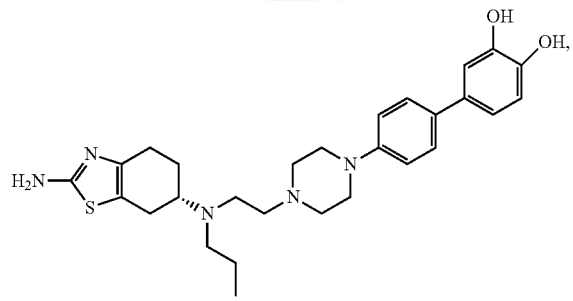
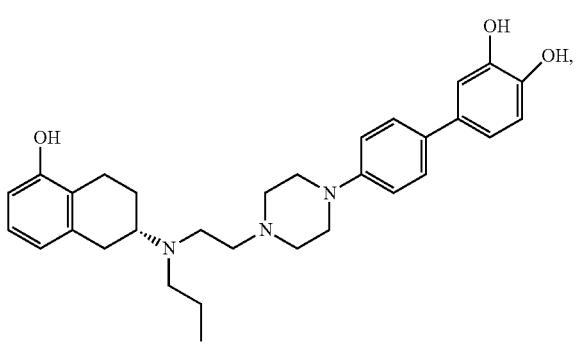
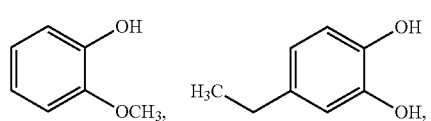
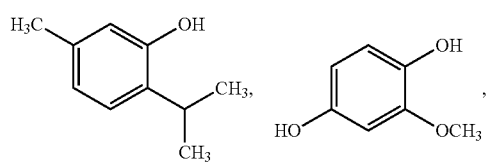
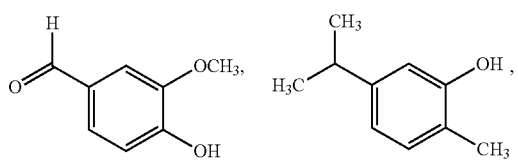
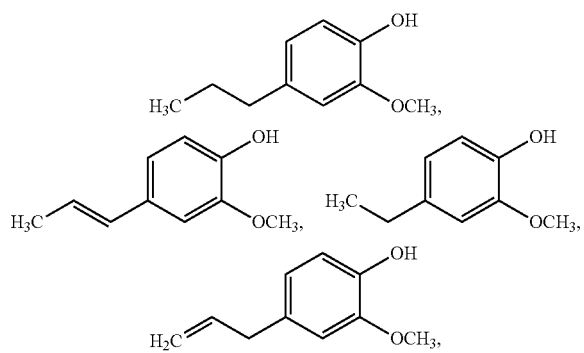
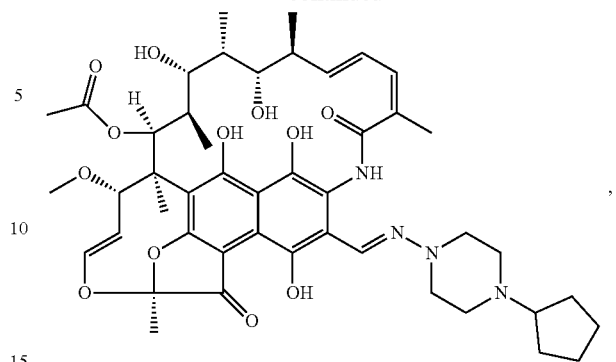
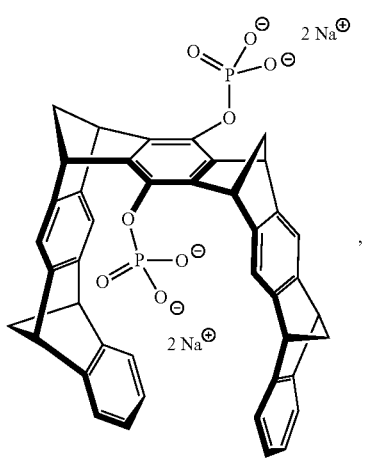
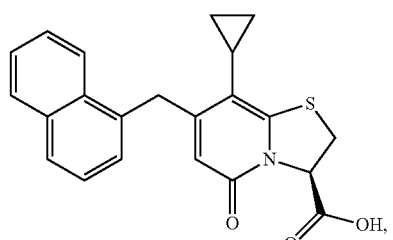
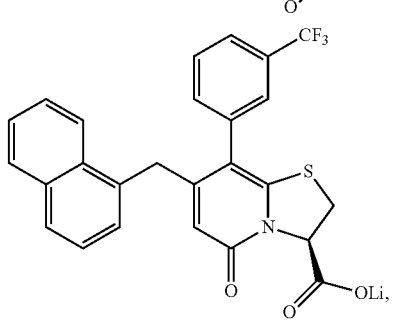
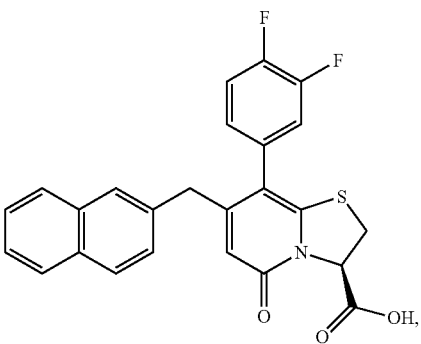

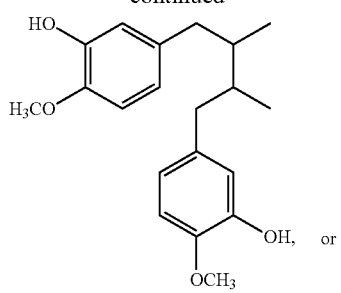
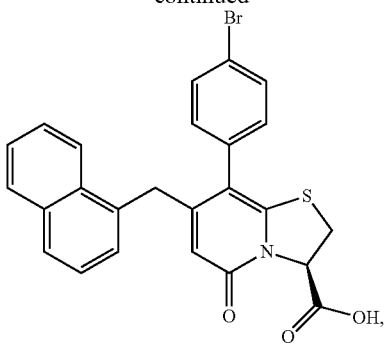
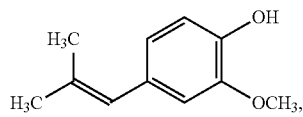
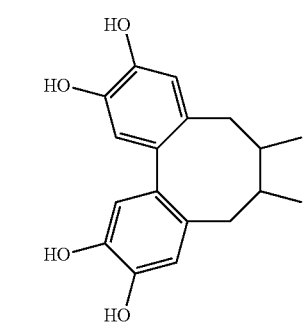 [SMILES: CC1Cc2cc(O)c(O)cc2-c2cc(O)c(O)cc2CC1C]
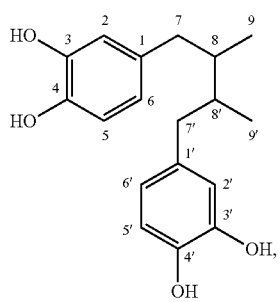
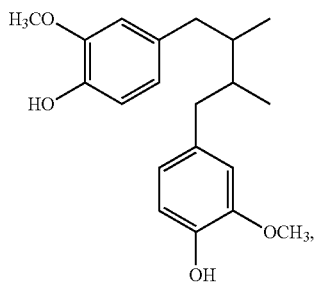

and/or any derivatives and/or any combinations thereof.

23. A method of disrupting the formation of amyloid aggregates in a subject comprising:

administering to said subject a composition comprising one or more polyphenols or polyphenol-like compounds, such as any one or more of the compositions of any one of items 1-20, and/or a composition comprising any one or more of the following molecules:

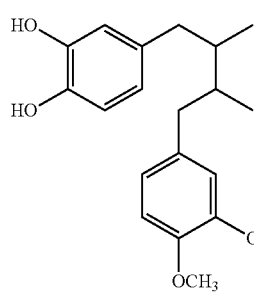
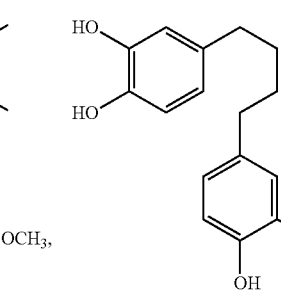
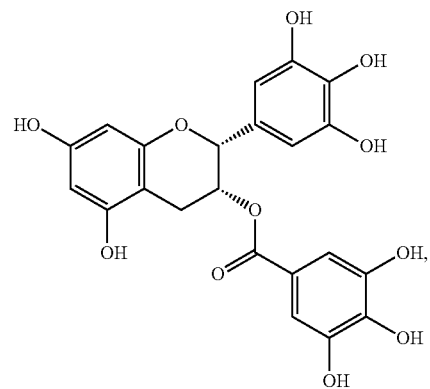
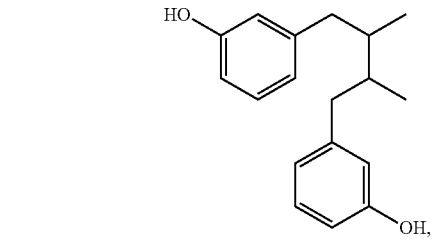
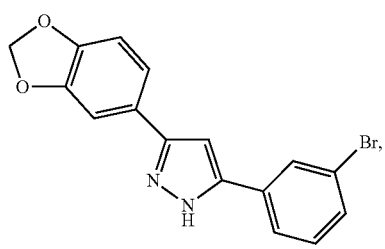

-continued
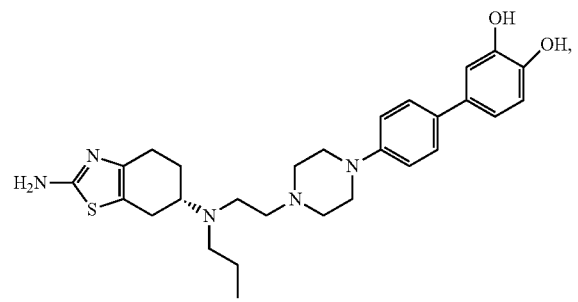
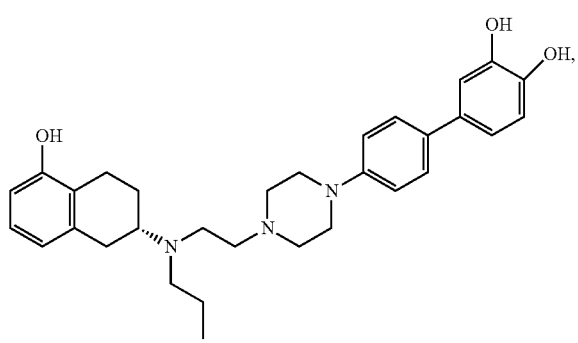
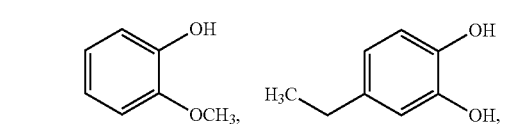
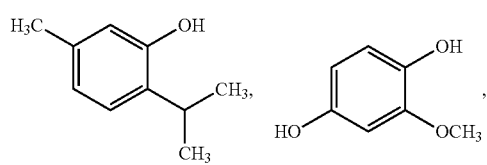
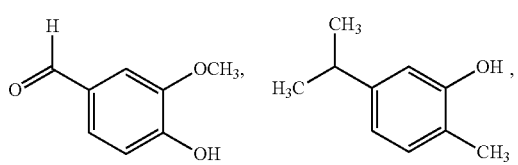
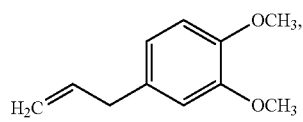
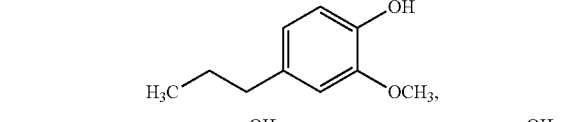
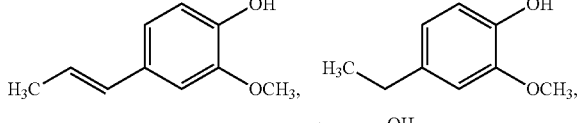
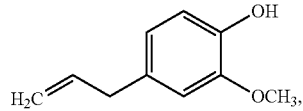
-continued
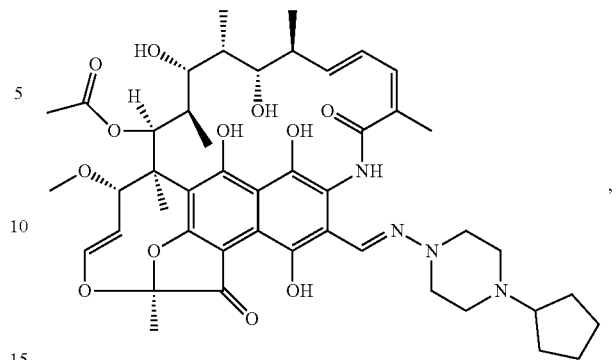
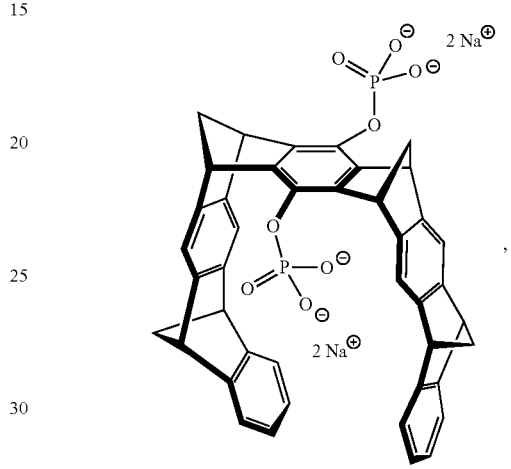
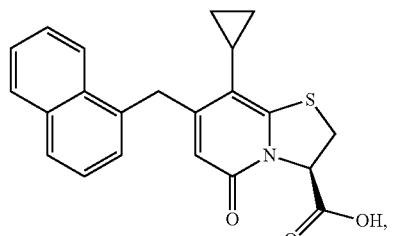
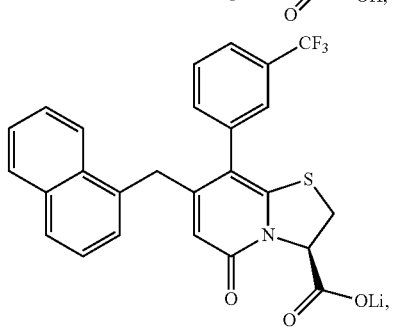
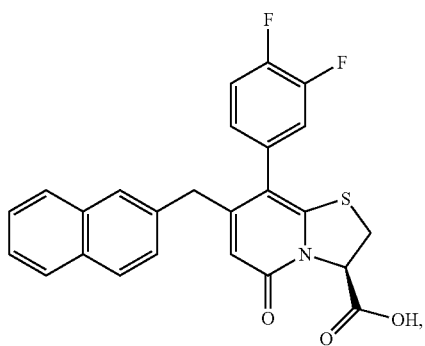

-continued

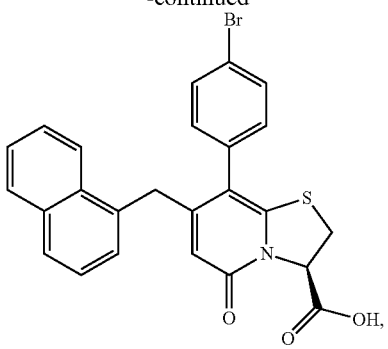

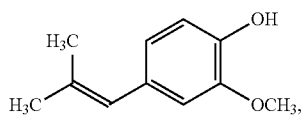

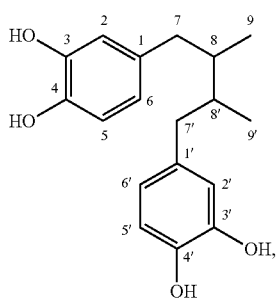

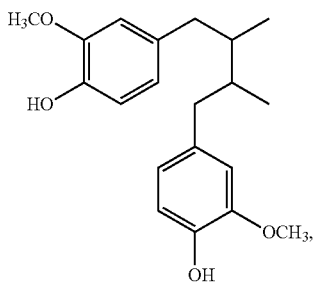

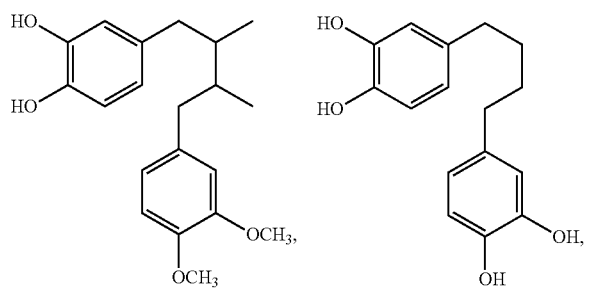

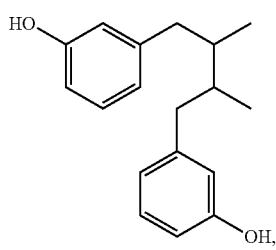

-continued

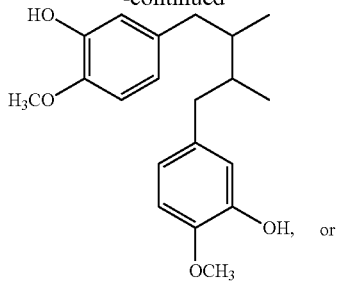

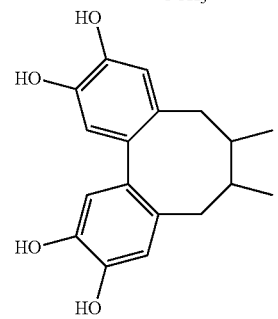

and/or any derivatives and/or any combinations thereof; and optionally, selecting said subject to receive the benefit of a molecule that disrupts the formation of amyloid aggregates, such as by clinical or diagnostic evaluation, prior to administering said composition; and/or optionally, measuring a disruption or inhibition of the formation of amyloid aggregates in said subject after administration of said composition.

24. A method of disrupting the formation of amyloid aggregates comprising contacting amyloid or a precursor of amyloid with a composition comprising one or more polyphenols or polyphenol-like compounds, such as one or more of the compositions of any one of items 1-20 and/or a composition comprising any one or more of the following molecules: EGCG, quercetin, morin, rosmarinic acid, gallic acid, and lauryl gallate.

25. A method of disrupting the formation of amyloid aggregates comprising contacting amyloid or a precursor of amyloid with a composition comprising one or more polyphenols or polyphenol-like compounds, such as one or more of the compositions of any one of items 1-20 and/or a composition comprising any one or more of the following molecules: EGCG, quercetin, genistein, apigenein, resveratrol, rosmarinic acid, and NDGA 26. A method of disrupting the formation of amyloid aggregates comprising contacting amyloid or a precursor of amyloid with a composition comprising one or more polyphenols or polyphenol-like compounds, such as one or more of the compositions of any one of items 1-20 and/or a composition comprising any one or more of the following molecules: quercetin, genistein, apigenein, resveratrol, rosmarinic acid, and NDGA.

27. A method of disrupting the formation of amyloid aggregates comprising contacting amyloid or a precursor of amyloid with a composition comprising one or more polyphenols or polyphenol-like compounds, such as one or more of the compositions of any one of items 1-20 and/or a composition comprising any one or more of the following molecules: quercetin, EGCG, resveratrol, rosmarinic acid, and NDGA.

28. A method of inhibiting, ameliorating, reducing the likelihood, delaying the onset of, treating, or preventing an amyloid disorder, the method comprising administering to a subject in need thereof one or more of the compositions of any one of items 1-20 and/or a composition comprising any one or more of the following molecules: EGCG, Anle 138b, Gallic acid, lauryl gallate, 4-allyl-1,2-dimethoxybenzene, isoeugenol, eugenol, 4-ethylguaiacol, Morin 2-(2,4-dihydroxyphenyl)-3,5,7-trihydroxychromen-4-one, Thymol, Carvacrol, curcumin, phloretin, Guiacol, Methoxyhydroquinone, or NDGA (Nordihydroguaiaretic acid), or any of the molecules of Table 2 or Table 3.

29. A method of inhibiting, ameliorating, reducing the likelihood, delaying the onset of, treating, or preventing an amyloid disorder, the method comprising administering to a subject in need thereof a composition comprising any one or more of the molecules selected from the group consisting of: EGCG, quercetin, morin, rosmarinic acid, gallic acid and lauryl gallate.

30. The method of any one of items 28-29, wherein the composition comprises any one or more of the molecules selected from the group consisting of: quercetin, morin, rosmarinic acid, gallic acid and lauryl gallate.

31. The method of any one of items 28-30, wherein the amyloid disorder is selected from the group consisting of: α-synucleinopathy, Parkinson's Disease, Lewy Body Dementia, incidental Lewy body disease, Lewy body variant of Alzheimer's disease, multiple system atrophy, or pure autonomic failure, or any combination thereof.

32. The method of any one of items 28-31, wherein the amyloid disorder comprises intestinal amyloid aggregates, for example aggregates that comprise a bacterial protein such as CsgA.

33. The method of any one of items 28-32, wherein the amyloid disorder is intestinal dysbiosis, intestinal hyperpermeability, irritable bowel syndrome (IBS), inflammatory bowel disease (IBD), ulcerative colitis and Crohn's disease.

34. The method of any one of items 28-33, further comprising detecting a presence or level of a bacterial protein, such as CsgA, or a microorganism that produces the bacterial protein in an intestinal sample of the subject.

35. The method of item 34, wherein the subject is selected as in need of the composition if a presence of the bacterial protein or the microorganism that produces the bacterial protein is detected in the intestinal sample, or if a level of the bacterial protein or the microorganism that produces the bacterial protein in the intestinal sample is greater than a predetermined level or control.

36. The method of any one of items 32-35, further comprising determining a decrease or absence of the intestinal amyloid aggregates following the administration.

37. The method of any one of items 32-36, further comprising identifying the subject as displaying a gastrointestinal symptom.

38. A method of ameliorating a gastrointestinal symptom in a subject in need thereof, the method comprising administering to the subject one or more of the compositions of any one of items 1-20 and/or a composition comprising any one or more of the following molecules: EGCG, quercetin, morin, rosmarinic acid, gallic acid and lauryl gallate, or any of the molecules of Table 2 or Table 3.

39. The method of any one of items 28-38, wherein the subject suffers from gastrointestinal symptoms comprising one or more of dysphagia, reduced gut motility, gastroparesis, constipation (including chronic constipation and chronic idiopathic constipation), small intestine bacterial overgrowth (SIBO), diarrhea, abdominal pain and/or cramping, bloating, flatulence and nausea.

40. The method of item 38, wherein the gastrointestinal symptom comprises one or more of constipation, diarrhea, abdominal pain and/or cramping, bloating, flatulence, nausea, a symptom of irritable bowel syndrome (IBS), a symptom inflammatory bowel disease (IBD), and intestinal hyperpermeability.

41. The method of any one of Items 22-40, wherein the composition comprises at least one of: EGCG, quercetin, genistein, apigenein, resveratrol, rosmarinic acid, quercetin, EGCG, and NDGA 42. The method of any one of Items 22-40, wherein the composition comprises at least one of: quercetin, genistein, apigenein, resveratrol, rosmarinic acid, and NDGA.

43. The method of any one of Items 22-40, wherein the composition comprises at least one of: quercetin, EGCG, resveratrol, rosmarinic acid, and NDGA.

44. The method of any one of Items 22-40, wherein the composition comprises at least one of: quercetin, resveratrol, rosmarinic acid, and NDGA.

45. The method of any of Items 22-44, wherein said composition is formulated for enteric or intranasal delivery.

46. The method of any of Items 22-45, wherein said composition is formulated for controlled release within the lower intestine or colon.

47. The method of any of Items 22-46, wherein said composition is an enteric-coated capsule, tablet, soft-gel, spray dried powder, polymer matrix, hydrogel, enteric-coated solid, crystalline solid, amorphous solid, glassy solid, coated micronized particle, liquid, nebulized liquid, aerosol, or microcapsule.

48. The method of any of Items 22-47, wherein said amyloid aggregates comprise one or more mammalian proteins such as, any one or more of α-synuclein, tau, Beta amyloid from Amyloid precursor protein, Medin, Apolipoprotein AI, Atrial natriuretic factor, Beta amyloid, Cystatin, IAPP (Amylin), Beta-2 microglobulin, Transthyretin, PrP, Gelsolin, Lysozyme, Huntingtin, Keratoepithelin, Calcitonin, Prolactin, Serum amyloid A, and/or Immunoglobulin light chain AL.

48. The method of any of Items 22-48, wherein said amyloid aggregates comprise one or more bacterial or fungal proteins, such as CsgA.

50. The method of any of Items 22-49, wherein said amyloid aggregates comprise a bacterial protein, such as CsgA and α-synuclein.

51. The method of any of Items 22-50, wherein said amyloid aggregates are present within the gastrointestinal tract, cranial sinus, or nasal cavity.

52. The method of any of Items 22-51, wherein said amyloid aggregates are present within enteric nervous tissue or the olfactory bulb.

53. The method of any of Items 22-52, wherein the composition is administered daily.

54. The method of any of Items 22-53, wherein the composition is administered multiple times per day.

55. The method of any of Items 22-54, wherein the composition is administered less frequently than daily.

56. The method of any of Items 22-53 or 55, wherein the composition is administered every second day, every third day, every fourth day, every fifth day, every sixth day, or every seventh day.

57. The method of any of Items 22-56, further comprising measuring or evaluating enteric amyloid levels and/or amyloid aggregation during the course of administration.

58. The method of any of Items 22-57, further comprising measuring or evaluating enteric amyloid levels and/or amyloid aggregation following the course of administration.

59. The method of any of Items 22-58, further comprising measuring or evaluating a change in the nervous system, such as a neurological symptom or behavior of the subject.

60. The method of any of Items 22-59, wherein said subject is under the age of 18, 18-30, 30-50, 50-60, 60-70, or over the age of 70.

61. The method of any of Items 22-60, further comprising measuring or evaluating a change in the gastrointestinal system, such as a gastrointestinal symptom or behavior of the subject.

62. The method of Item 61, wherein said gastrointestinal symptom comprises constipation.

63. The method of any of Items 22-62, wherein said subject suffers from gastrointestinal symptoms comprising one or more of constipation, diarrhea, abdominal pain and/or cramping, bloating, flatulence, nausea, or any other symptoms of irritable bowel syndrome (IBS), inflammatory bowel disease (IBD, such as ulcerative colitis and Crohn disease), intestinal hyperpermeability, or any combinations thereof.

64. The method of any of Items 22-63, wherein the composition is administered following the appearance of a neurological symptom or condition.

65. The method of Item 64, wherein said neurological symptom or condition comprises one or more of anosmia, hyposmia, bradykinesia, ataxia, tremor, muscle rigidity, impaired posture and balance, loss of automatic movements, dysarthria or other speech changes, handwriting changes, orthostatic hypotension, memory deficit, dysphagia, incontinence, sleep disruption, cardiac arrhythmia, visual disturbance, psychiatric problems including depression and visual, auditory, olfactory, or tactile hallucinations, vertigo, cognitive dysfunction, altered dopamine levels, altered serotonin levels, altered kynurenine levels, and/or any combination thereof.

66. The method of any of Items 22-65, wherein the composition is administered prior to the appearance of a neurological symptom or condition.

67. The method of any of Items 22-66, wherein the method is repeated.

68. The method of any of Items 22-67, wherein, for a given administration, the composition is different from a composition previously administered.

69. The method of any of Items 22-68, wherein, for a given administration, the dose administered is different from a dosage previously administered.

70. The method of any of Items 22-69, wherein the composition is coadministered with a caffeine, nicotine, theophylline, theobromine, xanthine, methylxanthine, or derivatives thereof.

71. The method of any of Items 22-70, further comprising administering to said subject an inhibitor of α-synuclein aggregation.

72. The method of any of Items 22-71, wherein said subject is one that has been identified or selected as being at risk for developing or already having Parkinson's disease, such as by clinical or diagnostic evaluation.

73. The method of any of Items 22-72, wherein said subject is one that has been identified or selected as being at risk for developing or already having Lewy Body Dementia, incidental Lewy body disease, Lewy body variant of Alzheimer's disease, multiple system atrophy, pure autonomic failure, or any combination thereof, such as by clinical or diagnostic evaluation.

74. The method of item 39, wherein the gastrointestinal symptoms are associated with Parkinson's Disease or Parkinsonism.

75. The method of any one of items 21-73, wherein the amyloid disorder can be diagnosed by detecting the presence or level of intestinal bacterial amyloid aggregates.

Pharmaceutical Formulations, Administration and Dosing

"Administering" has its customary and ordinary meaning as understood by one of skill in the art in view of this disclosure. It refers to providing a pharmaceutical agent, dietary supplement, or composition to a subject, and includes, but is not limited to, administering by a medical professional and self-administration. Administration of the compounds disclosed herein or the pharmaceutically acceptable salts thereof can be via any of the accepted modes of administration for agents that serve similar utilities including, but not limited to, orally, intraperitoneally, or rectally. Oral administrations are customary in administering the compositions that are the subject of the preferred embodiments. However, in some embodiments, the compositions to be administered according to the methods of the present disclosure are administered rectally, such as by enema or suppository. In some embodiments, administration of the compounds may occur outside the body, for example, by apheresis or dialysis.

The term "agent" has its customary and ordinary meaning as understood by one of skill in the art in view of this disclosure. It includes any substance, molecule, element, compound, entity, or a combination thereof. It includes, but is not limited to, e.g., protein, polypeptide, peptide or mimetic, small organic molecule, polysaccharide, polynucleotide, polymer, resin, organic or inorganic microparticle, organic or inorganic nanoparticle, and the like. It can be a natural product, a synthetic compound, or a chemical compound, or a combination of two or more substances.

"Solvate" has its customary and ordinary meaning as understood by one of skill in the art in view of this disclosure. It refers to the compound formed by the interaction of a solvent and an active pharmaceutical ingredient (or API), a metabolite, or salt thereof. Suitable solvates are pharmaceutically acceptable solvates including hydrates.

In some embodiments, the methods of the present disclosure contemplate the administration of one or more compositions useful for the amelioration or treatment of one or more neurological disorders associated with amyloid formation. Said compositions can be formulated into pharmaceutical compositions and/or dietary supplements for use in treating, inhibiting, or ameliorating a neurological disease or neurological disorder associated with amyloid formation such as Parkinson's disease (PD), Lewy body dementia, multiple system atrophy, and all other α-synucleinopathies, PD-associated constipation, PD-associated hyposmia, Huntington's Disease, Alexander's Disease, amyotrophic lateral sclerosis (ALS), and/or Alzheimer's Disease and/or other diseases in which amyloids are implicated. Standard pharmaceutical and/or dietary supplement formulation techniques are used, such as those disclosed in Remington's The Science and Practice of Pharmacy, 21st Ed., Lippincott Williams & Wilkins (2005), incorporated herein by reference in its entirety. Accordingly, some embodiments include pharmaceutical and/or dietary supplement compositions comprising: (a) a safe and therapeutically effective amount of one or more compounds described herein, or pharmaceutically acceptable salts thereof; and (b) a pharmaceutically acceptable carrier, diluent, excipient or combination thereof.

The term "pharmaceutically acceptable carrier" or "pharmaceutically acceptable excipient" has its customary and ordinary meaning as understood by one of skill in the art in view of this disclosure. It includes any and all solvents, diluents, emulsifiers, binders, buffers, dispersion media, coatings, antibacterial and antifungal agents, isotonic and absorption delaying agents and the like, or any other such compound as is known by those of skill in the art to be useful in preparing pharmaceutical formulations. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press.

Some examples of substances, which can serve as pharmaceutically-acceptable carriers or components thereof in accordance with methods and compositions of some embodiments herein, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of *theobroma*; polyols such as propylene glycol, glycerine, sorbitol, mannitol, and polyethylene glycol; alginic acid; emulsifiers, such as the TWEENS; wetting agents, such as sodium lauryl sulfate; coloring agents; flavoring agents; tableting agents, stabilizers; antioxidants; preservatives; pyrogen-free water; isotonic saline; and/or phosphate buffer solutions, or any combination thereof.

The choice of a pharmaceutically-acceptable carrier to be used in conjunction with the one or more compounds for administration as described herein can be determined by the way the compound is to be administered.

In addition, the present disclosure includes compositions comprising various salts, esters, hydrates, prodrugs, fluorinated analogs, or isotopically substituted analogs, including deuterated forms, of the compounds described herein.

As used herein, "systemic circulation" has its customary and ordinary meaning as understood by one of skill in the art in view of this disclosure. It refers to circulation within the blood or circulatory system of a subject.

As used herein, "enteric coating" has its customary and ordinary meaning as understood by one of skill in the art in view of this disclosure. It refers to a pharmaceutical excipient coating or placed around a particle which, by control of its solubility or timing of dissolution, increases the likelihood that said particle will be protected from solvent until its arrival in a desired portion of the gastrointestinal tract, for example, by conferring resistance to stomach acid or by having higher solubility at neutral or basic pH. Representative enteric coatings include, for example, those described in Remington's The Science and Practice of Pharmacy, 21st Ed., Lippincott Williams & Wilkins (2005). Exemplary enteric coatings include but are not limited to, shellac, sodium alginate, zein, cellulose acetate trimellitate, methyl methacrylate-methacrylic acid copolymer, polyvinyl acetate phthalate, polylactic acid, polylactic-co-glycolic acid, hypromellose acetate, hypromellose acetate succinate, Hydroxypropyl methyl cellulose phthalate, Cellulose acetate succinate, Cellulose acetate phthalate, Methyl acrylate-methacrylic acid copolymer, polyvinyl acetate phthalate, Opadry®, and others as are known in the art of drug delivery and formulation. In accordance with method and compositions of some embodiments, the composition comprising a compound as described herein further comprises an enteric coating.

In some embodiments according to the methods and compositions disclosed herein, the compositions to be administered are formulated for enteric or intranasal delivery, and may further be formulated for controlled release within the lower intestine or colon. Such formulations may be made by methods as are known to one of skill in the art of drug formulation and delivery, and may include enteric-coated capsules, tablets, soft-gels, spray dried powders, polymer matrices, hydrogels, enteric-coated solids, crystalline solids, amorphous solids, glassy solids, coated micronized particles, liquids, nebulized liquids, aerosols, or microcapsules.

The term "gut selective" as used herein has its customary and ordinary meaning as understood by one of skill in the art in view of this disclosure. It refers to a composition or formulation that is released in the gut of a subject, and preferably is not absorbed, or if absorption occurs, does not enter the systemic circulation.

The term "intrinsically enteric" as used herein has its customary and ordinary meaning as understood by one of skill in the art in view of this disclosure. With reference to a pharmaceutical formulation refers to a composition which innately has the ability to prevent disintegration or release in the gastric environment.

A composition for administration to a subject as described herein is preferably provided in a unit dosage form. As used herein, a "unit dosage form" has its customary and ordinary meaning as understood by one of skill in the art in view of this disclosure. It refers to a composition containing an amount of a compound that is suitable for administration to a subject, in a single dose, according to good medical practice. The preparation of a single or unit dosage form however, does not imply that the dosage form is administered once per day or once per course of therapy. A unit dosage form may comprise a single daily dose or a fractional sub-dose wherein several unit dosage forms are to be administered over the course of a day in order to complete a daily dose. According to the present disclosure, a unit dosage form may be given more or less often that once daily, and may be administered more than once during a course of therapy. Such dosage forms may be administered in any manner consistent with their formulation, including orally, rectally, nasally, and/or parenterally. While single administrations are specifically contemplated, the compositions administered according to the methods described herein may also be administered as a continuous infusion or via an implantable infusion pump.

The methods as described herein may utilize any of a variety of suitable forms for a variety of routes for administration, for example, for oral, nasal, rectal, or parenteral routes of administration. Depending upon the particular route of administration desired, a variety of pharmaceutically-acceptable carriers well-known in the art may be used. Pharmaceutically-acceptable carriers include, for example, solid or liquid fillers, diluents, hydrotropes, surface-active agents, and encapsulating substances. Optional pharmaceutically-active materials may be included, which do not substantially interfere with the activity of the one or more compounds in the formulation. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and/or bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and/or melting agents. Further solid dosage forms may comprise milled powders, spray-dried powders, crystalline forms, amorphous forms, and glassy forms, which may be administered as tablets or may be administered as aerosols or airborne particles, for example for nasal or pulmonary delivery. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and/or flavoring agents, or any combination thereof. Further liquid dosage forms may comprise forms for intranasal or pulmonary delivery. Such dosage forms may comprise liquids for intranasal injection, nasal lavage, pulmonary lavage, nebulization or aerosol delivery.

The pharmaceutically-acceptable carriers suitable for the preparation of unit dosage forms for peroral administration in accordance with methods and compositions of some embodiments herein are well-known in the art. Tablets typically comprise conventional pharmaceutically-compatible adjuvants as inert diluents, such as calcium carbonate, sodium carbonate, mannitol, lactose and/or cellulose; binders such as starch, gelatin and/or sucrose; disintegrants such as starch, alginic acid and/or croscarmelose; lubricants such as magnesium stearate, stearic acid, microcrystalline cellulose, carboxymethyl cellulose, and/or talc. Tablets may also comprise solubilizers or emulsifiers, such as poloxamers, cremophor/Kolliphor®/Lutrol®, or methylcellulose, hydroxypropylmethylcellulose, or others as are known in the art, or any combination thereof. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and/or fruit flavors, or any combination thereof, are useful adjuvants for chewable tablets. Capsules typically comprise one or more solid diluents disclosed above. The selection of carrier components depends on secondary considerations like taste, cost, and shelf stability, which can be readily made by a person skilled in the art.

Peroral (PO) compositions in accordance with methods and compositions of some embodiments herein also include liquid solutions, emulsions, or suspensions. The pharmaceutically-acceptable carriers suitable for preparation of such compositions are well known in the art. Typical components of carriers for syrups, elixirs, emulsions and/or suspensions include ethanol, glycerol, propylene glycol, polyethylene glycol, liquid sucrose, sorbitol and/or water. For a suspension, typical suspending agents include methyl cellulose, sodium carboxymethyl cellulose, AVICEL RC-591, tragacanth and/or sodium alginate; typical wetting agents include lecithin and/or polysorbate 80; and typical preservatives include methyl paraben and/or sodium benzoate, or any combination thereof. Peroral liquid compositions may also contain one or more components such as sweeteners, flavoring agents and/or colorants, as disclosed above.

Such compositions may also be coated by conventional methods, typically with pH or time-dependent coatings, such that the subject one or more compounds are released in the gastrointestinal tract in the vicinity of the desired application, or at various times to extend the desired action. Exemplary dosage forms for release in the gastrointestinal tract may incorporate one or more of cellulose acetate phthalate, polyvinyl acetate phthalate, hydroxypropyl methyl cellulose phthalate, ethyl cellulose, Eudragit coatings, waxes, alginate and/or shellac, or other excipients known to those of skill in the art, or any combination thereof. According to some embodiments, the compositions to be administered according to the methods described herein are formulated for release in the gastrointestinal tract. According to some embodiments, the compositions to be administered according to the methods described herein are formulated for release in the lower gastrointestinal tract. In some embodiments, the compositions are provided as enteric coated capsules, tablets, soft gels; or intrinsically enteric capsules.

The actual unit dose of the compositions in accordance with methods and compositions of some embodiments herein depends on the one or more compounds in the formulation. In some embodiments, the amount of each compound in the formulation may be from 0.01 mg/kg to 0.05 mg/kg of body weight per day, from 0.04 mg/kg to 0.1 mg/kg of body weight per day, from 0.09 mg/kg to 0.15 mg/kg of body weight per day, from 0.14 mg/kg to 0.2 mg/kg of body weight per day, from 0.2 mg/kg to 0.5 mg/kg of body weight per day, from 0.4 mg/kg to 1 mg/kg of body weight per day, from 1 mg/kg to 6 mg/kg of body weight per day, 5 mg/kg to 500 mg/kg or more of body weight per day, from 10 mg/kg or less to 70 mg/kg, from 50 mg/kg to 80 mg/kg of body weight per day, from 70 mg/kg to 120 mg/kg of body weight per day, from 100 mg/kg to 300 mg/kg of body weight per day, or from 250 mg/kg to 500 mg/kg of body weight per day. In some embodiments, the dose may be less than 100 mg/kg, 500 mg/kg, 300 mg/kg, 200 mg/kg, 150 mg/kg, 100 mg/kg, 50 mg/kg, 40 mg/kg, 30 mg/kg, 25 mg/kg, 20 mg/kg, 10 mg/kg, 7.5 mg/kg, 6 mg/kg, 5 mg/kg, 4 mg/kg, 3 mg/kg, 2.5 mg/kg, or 1 mg/kg of body weight per day or an amount that is within a range defined by any two of the aforementioned amounts. In some embodiments, the actual unit dose is 5, 10, 25, 50, 75, 100, 150, or 200 mg/kg of body weight per day or an amount that is within a range defined by any two of the aforementioned amounts. Thus, for administration to a 70 kg person, for example, the dosage range is from 0.1 mg to 1 mg, 0.9 mg to 2 mg, from 1.5 mg to 5 mg, from 4 mg to 10 mg, from 9 mg to 20 mg, from 15 mg to 50 mg, from 40 mg to 75 mg, from 50 mg to 100 mg, from 75 mg to 200 mg, from 100 mg to 300 mg, from 200 mg to 400 mg, 350 mg to 750 mg, from 500 mg to 1 g, from 750 mg to 2 g, from 1 g to 5 g, from 2.5 g to 6 g, from 4 g to 10 g, from 8 g to 20 g, from 15 g to 35 g, or from 1 g or less to 35 g or more, or an amount that is within a range defined by any two of the aforementioned amounts. In some embodiments, the actual unit dose is 6 g. In some embodiments, the actual unit dose is 10 g. In some embodiments, the actual unit dose is 35 g. In some embodiments, the actual unit dose is 1 g or less but not zero. In some embodiments, the actual unit dose is 10 g or less but not zero. In some embodiments, the actual unit dose is 35 mg or less but not zero.

"Loading dose," as used herein refers to an initial dose of a compound which is higher than subsequent doses.

"Maintenance dose," as used herein refers to a subsequent dose that follows a loading dose, and occurs later in time than a loading dose. One of ordinary skill in the art will be aware that the dosage form or mode of administration of a maintenance dose may be different from that used for the loading dose. In any of the embodiments disclosed herein, a maintenance dose may comprise administration of the unit dosage form on any dosing schedule contemplated herein, including but not limited to, monthly or multiple times per month, biweekly or multiple times each two weeks, weekly or multiple times per week, daily or multiple times per day. It is contemplated within the present disclosure that dosing holidays may be incorporated into the dosing period of the maintenance dose. Such dosing holidays may occur immediately after the administration of the loading dose or at any time during the period of administration of the maintenance dose. As used herein, the period of administration of the maintenance dose may be referred to as the "maintenance phase" of the treatment period.

"Mode of administration" as used herein refers to the avenue by which one or more compounds are administered to a subject. As used herein, "mode of administration" comprises the dosage form (for example, a tablet, powder, dissolved liquid, suspension, emulsion, etc.) and mechanism by which the dosage form is applied to the subject (for example, by injection, topically, such as by cream, lotion, or patch; orally, such as by a pill, dissolved liquid, oral suspension, buccal film, or mouth rinse). As used herein, "mode of administration" also comprises the dose, dose amount, and dosing schedule by which a compound is administered to a subject.

In some embodiments, the compositions to be administered according to the methods of the present disclosure are provided with, or mixed into, a foodstuff, beverage, or other ingestible item. In some embodiments, said beverage, foodstuff, or other ingestible item may comprise one or more of a candy, an applesauce, a yogurt, a soft pudding, a gelatin foodstuff, a juice, milk, a soy or nut beverage, a thickened beverage, or a cheese, or any combination thereof. One of ordinary skill will readily recognize that the combination of the compositions to be administered according to the methods of the disclosure can be combined with any suitable food or beverage to facilitate ingestion of the compositions.

In some embodiments in accordance with methods and compositions of some embodiments herein, the mode of administration comprises administering a loading dose followed by a maintenance dose. In some embodiments, the loading dose is 20 g or less but not zero; 15 g or less but not zero; 10 g or less but not zero, 6 g or less but not zero, 4 g or less but not zero, 2 g or less but not zero, or 1 g or less but not zero or an amount that is within a range defined by any two of the aforementioned amounts. In some embodiments, the maintenance dose is 20 g or less but not zero; 10 g or less but not zero, 6 g or less but not zero, 4 g or less but not zero, 2 g or less but not zero, 1 g or less but not zero, 500 mg or less but not zero, or 250 mg or less but not zero or an amount that is within a range defined by any two of the aforementioned amounts.

In some embodiments in accordance with methods and compositions of some embodiments herein, the loading dose is administered over a period of one day or 24-hour period. In some embodiments the loading dose is administered in a single administration. In some embodiments, the loading dose is administered in multiple administrations. In some embodiments, the loading dose is administered in multiple administrations during a single day or 24-hour period. In some embodiments the loading dose is administered over a period of 2 days. In some embodiments the loading dose is administered over a period of 3 days. In some embodiments the loading dose is administered over a period of 4 days. In some embodiments the loading dose is administered over a period of 5, 6 or 7 days. In some embodiments, the loading dose is administered over a period of 8-14 days or fewer. In some embodiments, the loading dose is administered over a period of 14 days.

The methods according to the present disclosure contemplate varying or controlling the timing of administration of a composition described herein, in order to enhance the effectiveness of any treatment that is administered. In some embodiments, a composition to be administered according to the methods of the present disclosure may be administered with food, such as concurrently with a meal or other ingestion of a foodstuff. In some further embodiments, a composition to be administered according to the methods of the present disclosure may be administered immediately before or immediately after a meal or other ingestion of a foodstuff. In some further embodiments, a composition to be administered according to the methods of the present disclosure may be administered within 1-5 minutes, within 3-10 minutes, within 6-15 minutes, within 10-20 minutes, within 15-30 minutes, within 20-45 minutes, or within one hour before or after a meal or other ingestion of a foodstuff. In some embodiments, a composition to be administered according to the methods of the present disclosure may be administered without food, such as between 1-3 hours, between 2-5 hours, between 4-8 hours, between 6-12 hours, between 9-18 hours, between 12-24 hours, or more than 24 hours before or after a meal or other ingestion of a foodstuff.

As used herein, "duration of the treatment" refers to the time commencing with administration of the first dose and concluding with the administration of the final dose, such length of time being determined by one of ordinary skill in the art of treating neurological disorders or disorders implicating intestinal hyperpermeability or "leaky gut," with reference to the symptoms and health of the subject being treated therefor. Such duration may be determined with reference to periodic, sporadic, or ongoing monitoring of the levels of amyloid as disclosed herein or as known to one of skill in the art of treating neurological disorders.

As used herein, "dosing holiday" refers to a period of 24 hours or more during which either no dose is administered to the subject, or a reduced dose is administered to the subject. As used herein, "reduced dose" refers to a dose that is less than the total daily dose to be administered to a subject.

According to the present disclosure, the dosing schedule may be varied so as to attain the desired therapeutic effect. In each of the embodiments as disclosed herein, variations in dosing schedule may be repeated throughout the duration of the therapeutic protocol being administered. In each of the embodiments as disclosed herein, the first dosage may be higher, lower, or the same as the dosages following the first dosage. In each of the embodiments disclosed herein, a loading dose may precede the disclosed dosing regimen, and a dosing holiday may or may not follow the administration of the loading dose.

In some embodiments the methods of the present disclosure comprise administration of one or more compositions as provided herein daily or less frequently than daily, such as every second day, every third day, every fourth day, every fifth day, every sixth day, or every seventh day or for a time period that is within a range defined by any two of the aforementioned times. In some embodiments, the compositions as described herein are formulated for such administration.

According to the methods disclosed herein, a treatment or inhibition of a disorder implicating amyloid formation may be achieved by modulating the dosing schedule for the administration of a composition such that subjects experience periodic partial or full reductions in dosing for fixed amounts of time, followed by a resumption of dosing. In some embodiments, dosages are administered daily for between one and thirty days, followed by a dosing holiday lasting for between one and thirty days. In some embodiments, during the dosing holiday, no dose is administered. In some further embodiments, the composition of the present disclosure is allowed to clear completely from the subject's body prior to administration of the next dose. In some other embodiments, during the dosing holiday, a dose less than the usual daily dose is administered. In some further embodiments, an amount of the administered composition less than the therapeutically effective amount is allowed to remain within the subject during the dosing holiday. In some further embodiments, an amount of the administered composition sufficient to maintain therapeutic levels in the affected tissues is allowed to remain within the subject. In some embodiments, a composition is administered at any time following the onset of one or more of the aforementioned symptoms of a neurological disorder associated with amyloid formation. In some embodiments, a composition according to the methods described herein is administered prior to the onset of symptoms of said disorder or disorders. In some embodiments, a composition according to the methods described herein is administered concurrently with or after the onset of symptoms of said disorder or disorders.

The methods and compositions described herein are further illustrated by the following examples.

Example 1

To a subject, one or more of the compounds described above (e.g., a composition comprising a compound of Formula I, Formula II or Formula III, preferably a compound set forth in Table 2 or Table 3) is administered orally or rectally on a regular basis, such as daily. Bacterial amyloid formation in the GI tract and/or α-synuclein aggregation levels within the GI tissue are monitored by fecal sampling or by biopsy. Therapy is continued to prevent bacterial amyloid (curli) formation and/or α-synuclein aggregation. Changes in the patient's GI function and motor symptoms are monitored. For subjects in which the administration of said one or more compounds results in reduced formation of microbially-induced amyloid in the gut, improvements in one or more GI symptoms, one or more motor symptoms and/or one or more neurological symptoms are observed.

Example 2

One or more of the compounds described above or a derivative thereof (e.g., a composition comprising a compound of Formula I, Formula II or Formula III, preferably a compound set forth in Table 2 or Table 3) is obtained or synthesized and incorporated into an enteric or colon-selective formulations to release material at site of action and by-pass the stomach and most of the small intestine. This provides delivery of the composition at the site of curli production and/or α-synuclein aggregation, and minimizes absorption of the composition into systemic circulation.

Example 3

One or more of the compounds described above or a derivative thereof (e.g., a composition comprising a compound of Formula I, Formula II or Formula III, preferably a compound set forth in Table 2 or Table 3) is obtained or synthesized and incorporated into a formulation for controlled release in the lower small intestine or in the colon. This provides for lower and/or less frequent dosing, and side effects are minimized. Controlled release in the lower small intestine or colon may be achieved by any of a variety of approaches known in the art and includes enteric coated capsules, tablets, soft gels, intrinsically enteric capsules, multi-layered formulations, coated micronized forms of the polymeric material, and the like.

Example 4

A subject is administered a combination of more than one of the compounds described above (e.g., a plurality of compositions that each comprise a compound of Formula I, Formula II or Formula III, preferably a plurality of compositions that each comprise a compound set forth in Table 2 or Table 3). Combining a curli inhibitor with an α-synuclein aggregation inhibitor blocks aggregation at two critical points simultaneously. For subjects in which the administration of said one or more compounds results in reduced formation of microbially-induced amyloid in the gut, improvements in one or more GI symptoms, one or more motor symptoms and/or one or more neurological symptoms are observed or measured.

Example 5

The Thy1-α-synuclein (α-synuclein-overexpressing [ASO]) mouse displays progressive deficits in fine and gross motor function, as well as, gut motility defects. Evidence has linked unregulated α-synuclein expression in humans to a higher risk of PD, providing an epidemiological foundation for the Thy1-α-synuclein mouse model. Defects in coordinated motor tasks become evident at 12 weeks of age. Motor function is measured via four tests: beam traversal, pole descent, nasal adhesive removal, and hind limb clasping reflexes, as previously validated in this model (described in Fleming et al., *J. Neurosci.* 24, 9434-9440 (2004), and Sampson et al., *Cell* 167(6):1469-1480 (2016) the content of which are hereby expressly incorporated by reference in its entirety). ASO mice require significantly more time to cross a challenging beam compared to wild-type littermates and also exhibit increased time to descend a pole, two measures of gross motor function. Removal of an adhesive from the nasal bridge, a test of fine motor control, is also impaired in SPF-ASO mice compared to SPF-WT mice, as is the hind limb clasping reflex, a measure of striatal dysfunction.

ASO neonates are divided into two groups. To one group is administered one or more compositions as described above, and the other is untreated or mock-treated. Compositions are administered daily for 12-13 weeks. At 13 weeks and thereafter, motor skills are evaluated. ASO mice treated with the compositions described above require less time to cross a challenging beam, decreased time to descend a pole, enhanced removal of an adhesive from the nasal bridge, and an enhanced hind limb clasping reflex relative to untreated ASO mice.

Fecal pellets are also obtained from test animals. Fecal pellets from treated ASO mice show lower levels of bacterial adhesive pili (curli), as well as, lower levels of aggregated α-synuclein relative to untreated ASO animals.

After 16 weeks, animals are sacrificed and their brain enteric nervous tissue is analyzed for the presence of α-synuclein aggregates. Utilizing an antibody that recognizes only conformation-specific α-synuclein aggregates and fibrils, immunofluorescence microscopy is performed to visualize α-synuclein inclusions. Notable aggregation of α-synuclein is observed in the caudoputamen (CP), substantia nigra (SN), and enteric neurons of untreated ASO animals relative to levels seen in treated animals. Western blots of brain extracts are also performed. Significantly less insoluble α-synuclein is found in brains and enteric nervous tissue of treated ASO animals.

Example 6

Figure 1B:
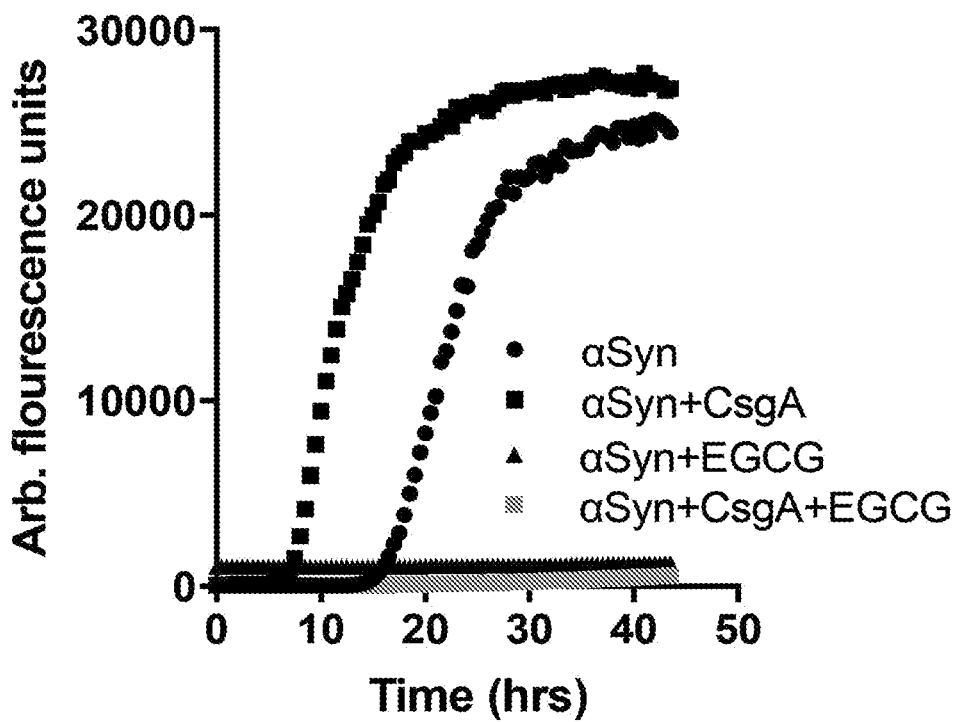
FIG. 1B is a graph showing in vitro αSyn aggregation measured by Thioflavin T fluorescence during αSyn amyloid formation alone or in the presence of CsgA (25:1 molar ratio), with and without EGCG (50 μM) treatment.

Roles of functional amyloid formation in curli-driven pathophysiology were examined in mice. As an initial matter, effects of epigallocatechin gallate (EGCG) on biofilm growth by wild-type *E. coli* were examined, along with effects of EGCG on αSyn amyloid formation in vitro. FIG. 1A is a graph showing Crystal violet staining of biofilm growth by wild-type *E. coli* following 4 days in static culture, with indicated concentrations of EGCG; data assessed by optical density (OD). FIG. 1B is a graph showing in vitro αSyn aggregation measured by Thioflavin T fluorescence during αSyn amyloid formation alone or in the presence of CsgA (25:1 molar ratio), with and without EGCG (50 µM) treatment.

Figure 1C:
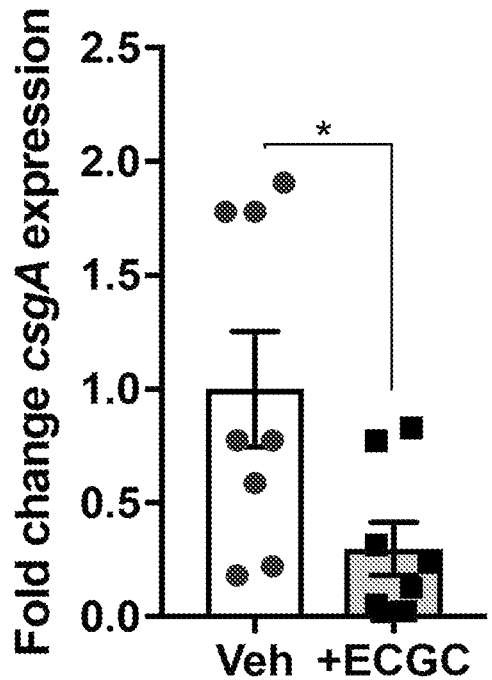
FIGS. 1C-L show results for germ-free Thy1-αSyn mice (ASO) mono-colonized with WT *E. coli* at 5-6 weeks of age, and given water alone (Vehicle: Veh) or treated with EGCG ad lib in drinking water (+EGCG).
Figure 1D:
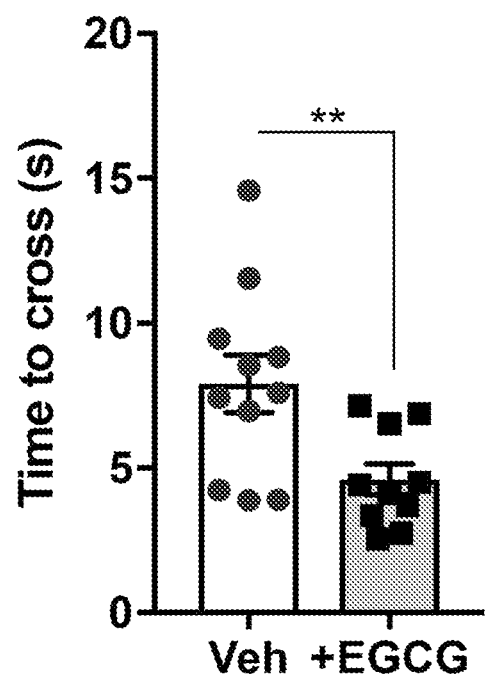
Figure 1E:
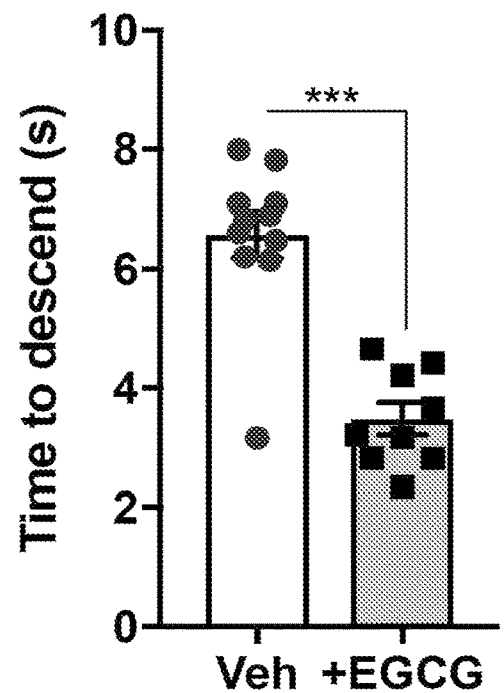
Figure 1F:
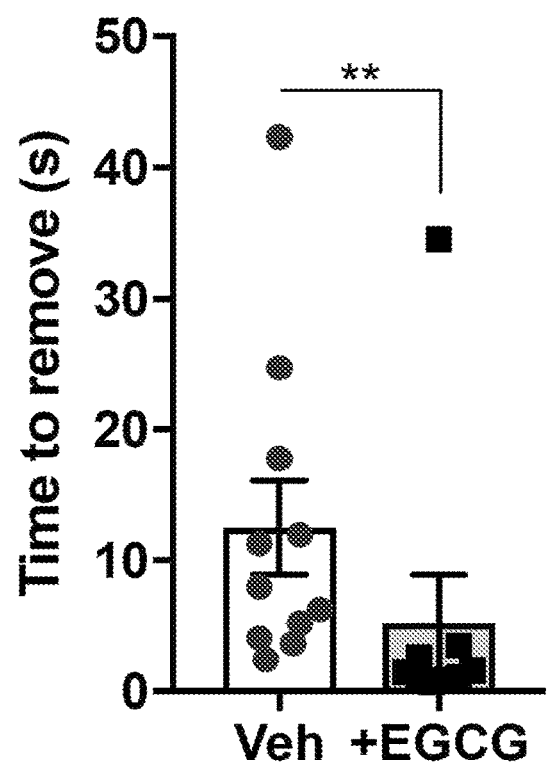
Figure 1G:
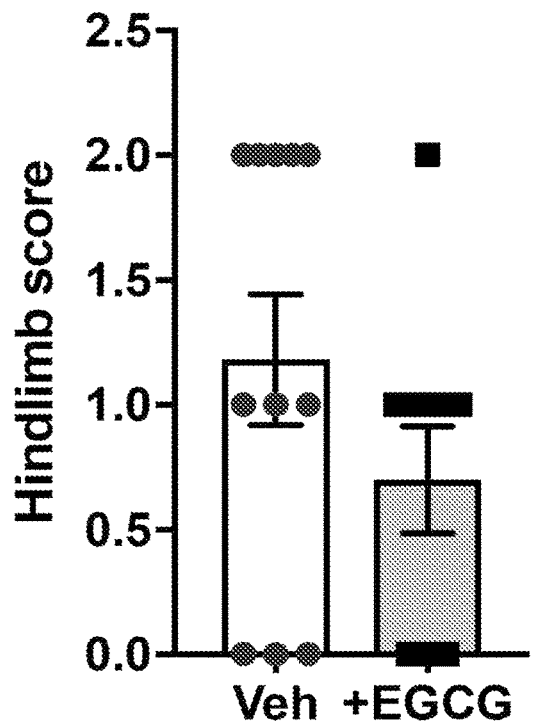
Figure 1H:
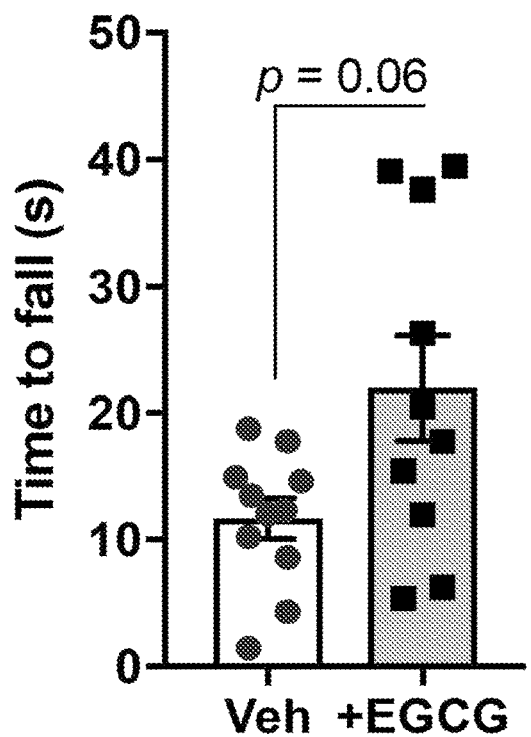

Germ-free Thy1-αSyn mice (ASO) mono-colonized with WT *E. coli* at 5-6 weeks of age, and given water alone (Vehicle: Veh) or treated with EGCG ad lib in drinking water (+EGCG). RNA was extracted from fecal pellets and csgA expression quantified by qRT-PCR, relative to rrsA. FIG. 1C is a graph showing fold-change in csgA expression. Motor function was assessed at 15-16 weeks of age by quantifying beam traversal time (FIG. 1D), pole descent time (FIG. 1E), nasal adhesive removal time (FIG. 1F), hindlimb clasping score (FIG. 1G), and wire hang tests (FIG. 1H). Time to cross, time to descent, time to remove, and hindlimb score were lower in the EGCG-treated mice, while time to fall was higher in the EGCG-treated mice compared to vehicle treated control.

Figure 1I:
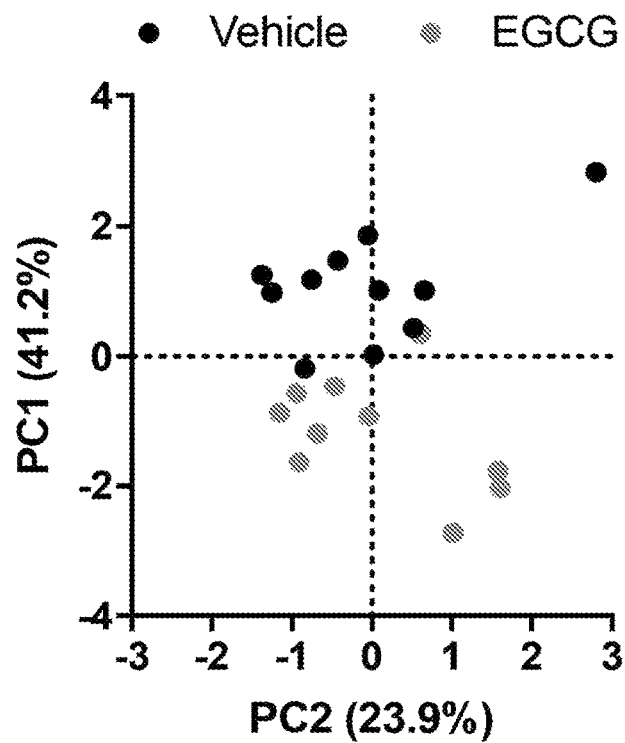
Figure 1J:
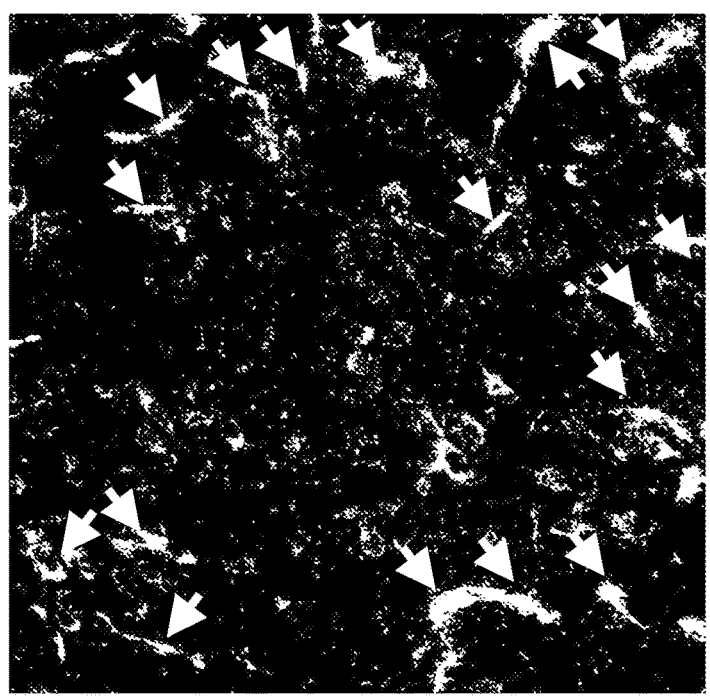
Figure 1K:
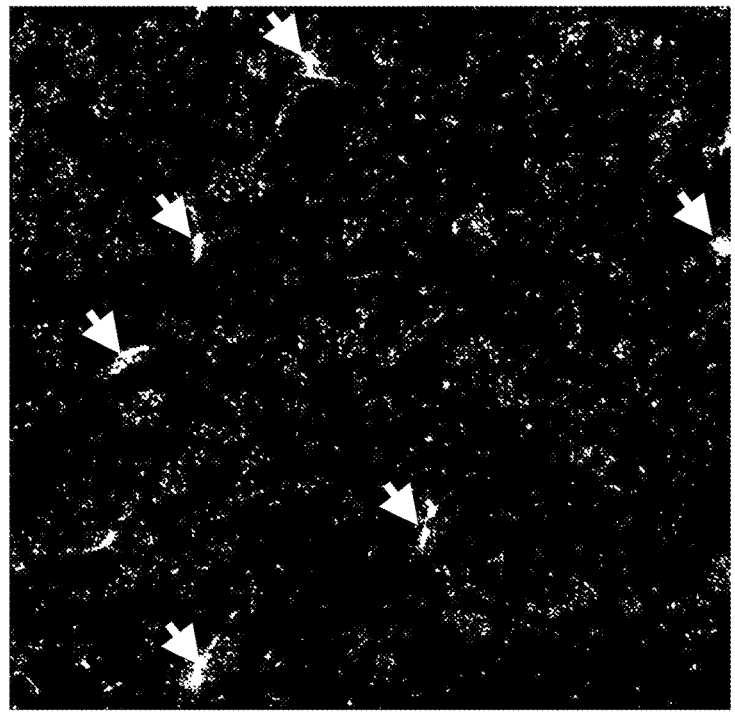

FIG. 1I is a graph showing principal component analysis of compiled motor scores from tests in (FIGS. 1D-H). FIGS. 1J-K are a series of graph showing Proteinase K resistant αSyn aggregates (indicated by white arrows) in the substantia nigra imaged via immunofluorescence microscopy. Shown are vehicle-treated (FIG. 1J) and EGCG-treated mice (FIG. 1K). Levels of Proteinase K resistant αSyn aggregates were lower in the EGCG-treated mice than in untreated controls. Thus, assessment of motor performance reveals that EGCG treatment in accordance with some embodiments herein successfully dampens progressive motor deficits exacerbated by *E. coli*, while also preventing αSyn aggregation in both the striatum and midbrain.

Figure 1L:
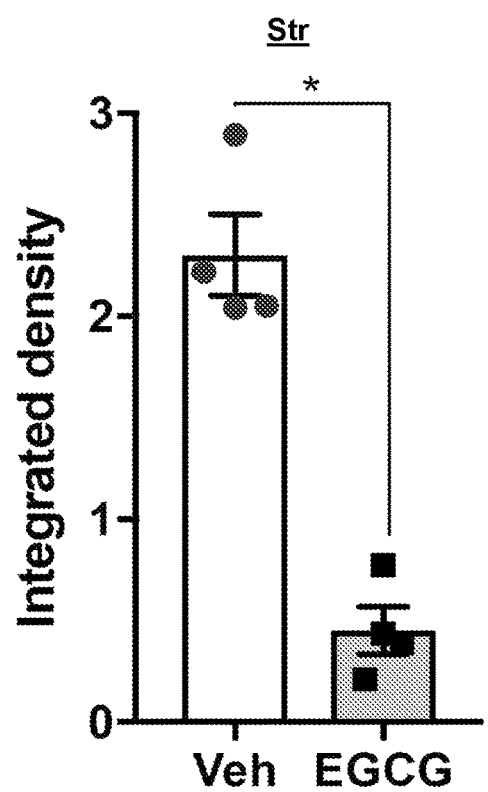
Figure 1M:
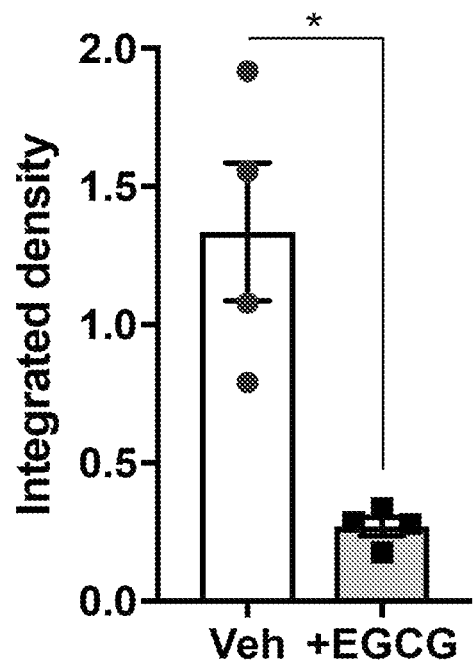
Figure 1N:
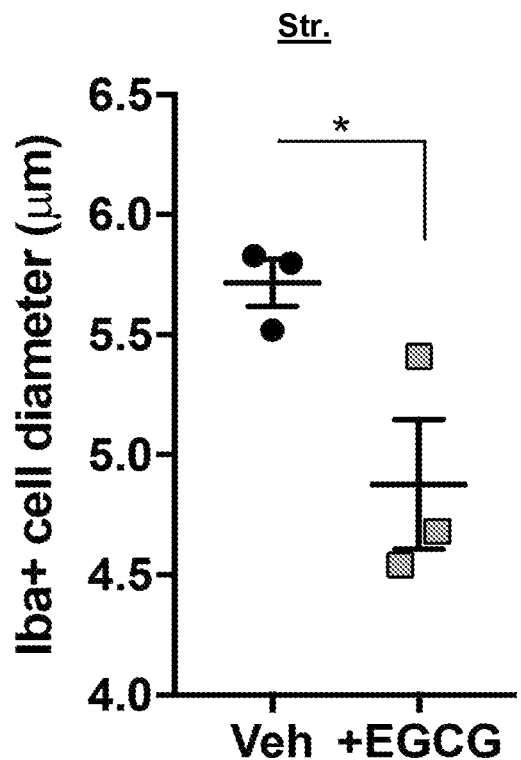
Figure 1O:
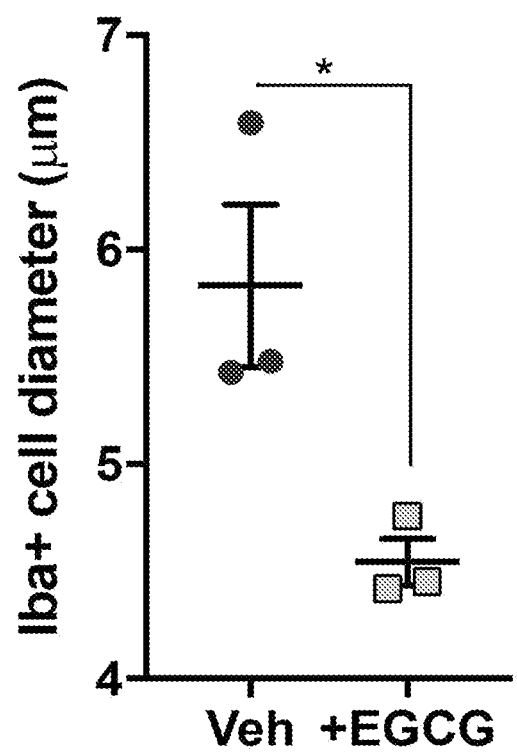

FIGS. 1L-M show quantification of insoluble αSyn fibrils in the striatum (FIG. 1L) and ventral midbrain (FIG. 1M) by dot blot assay. Thin sections of brain were stained for Iba1 (microglia), 3D cellular reconstructions generated, and morphological characteristics quantified from microglia resident in the striatum (FIG. 1N) and substania and nigra (FIG. 1O). n=3 (FIGS. 1A, 1B, 1N, 1O), n=8 (FIG. 1C), n=10-11 (FIGS. 1D-I), n=4 (FIGS. 1L-M). Points represent individuals, bars represent the mean and standard error. Data analyzed by one-way ANOVA with Tukey post-hoc test for FIG. 1A, two-tailed Mann-Whitney for FIGs. C-K, or two-tailed t-test for FIG. 1L. For FIGS. 1A-1L *p≤0.05; p≤0.01; *p≤0.001. Motor data are compiled from 2 independent cohorts.

Accordingly, it is shown that in vivo treatment with compounds in accordance with compositions and methods in accordance with some embodiments herein inhibit or reduce αSyn amyloid formation in vitro. Furthermore, these compounds improved motor scores, consistent with inhibition, amelioration, and alleviation of symptoms of aggregate-related diseases such as parkinsonism in accordance with some embodiments herein.

Example 7

Figure 2A:
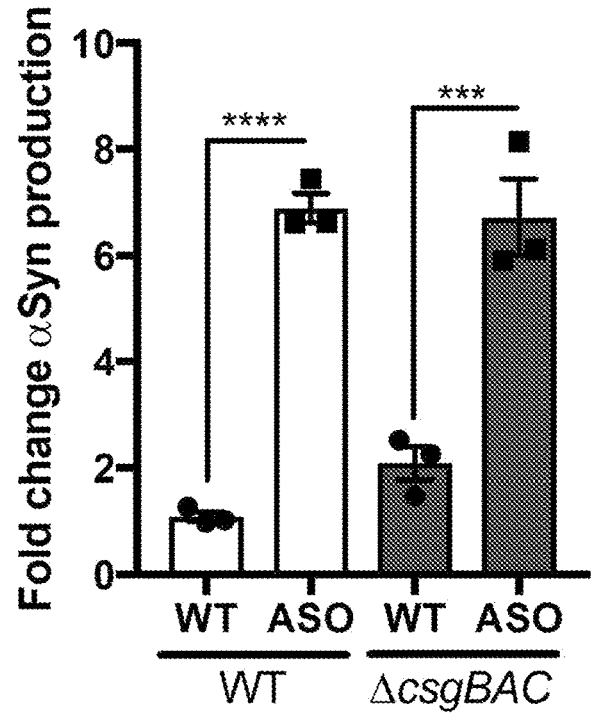
FIGS. 2A-G are a series of graphs and images depicting that mono-colonization with curli-sufficient bacteria induce increased αSyn-dependent pathology and inflammatory responses in the brain. Germ-free (GF) wild-type (WT) or Thy1-αSyn (ASO) animals were mono-colonized with either wild-type, curli-sufficient *E. coli* (WT) or curli-deficient *E. coli* (ΔcsgBAC).
Figure 2B:
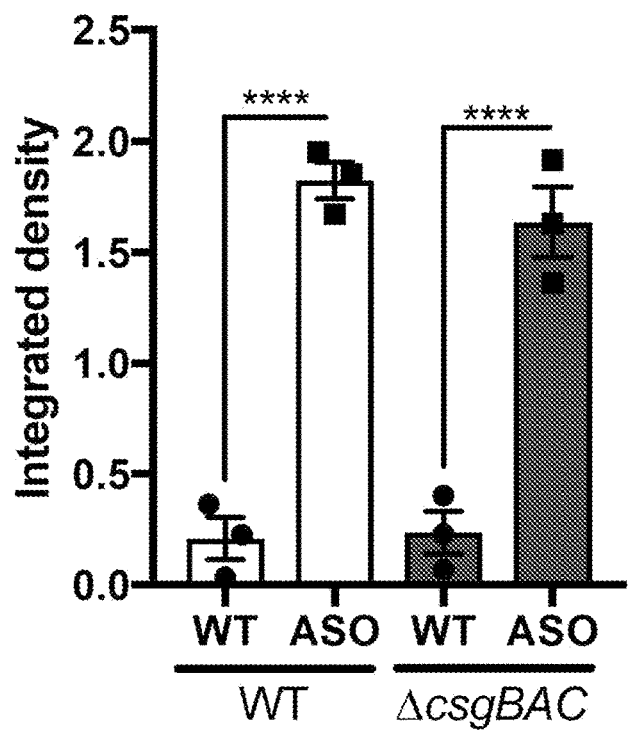
Figure 2C:
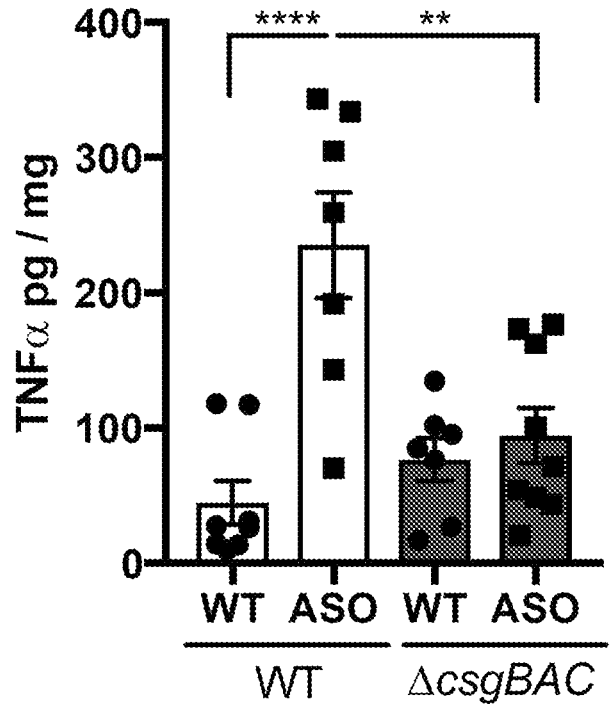
Figure 2D:
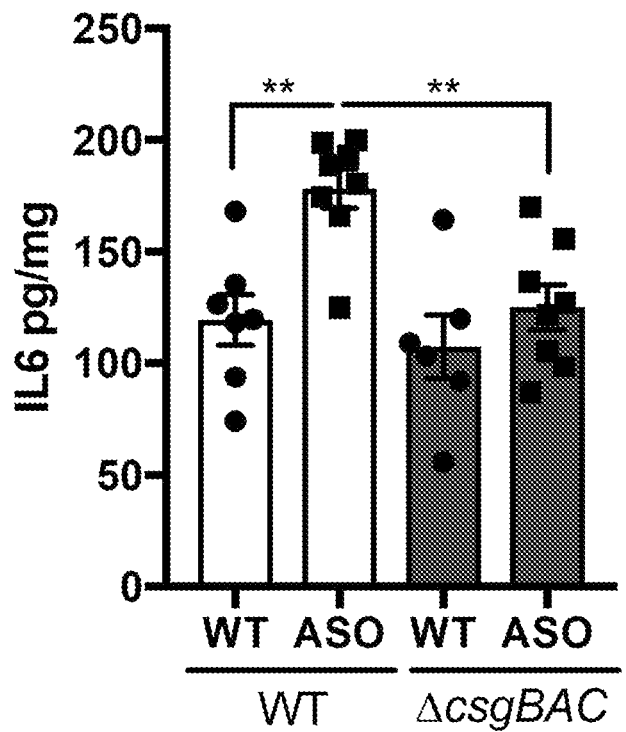
Figure 2E:
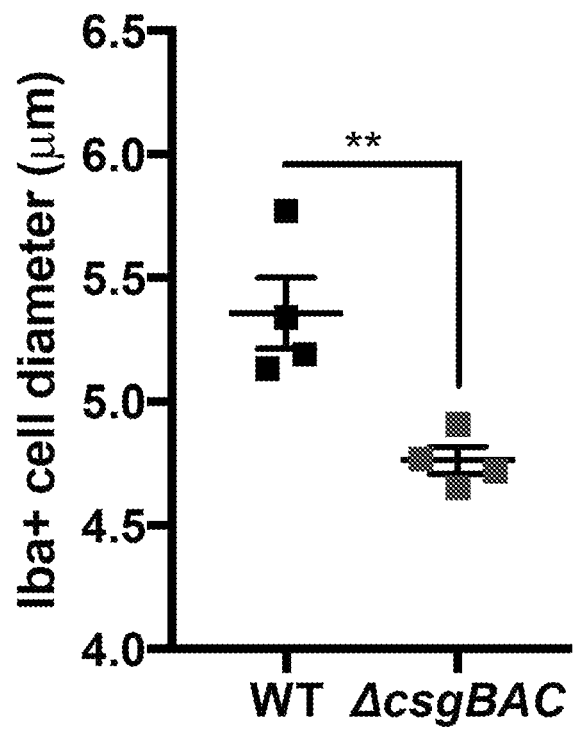
Figure 2F:
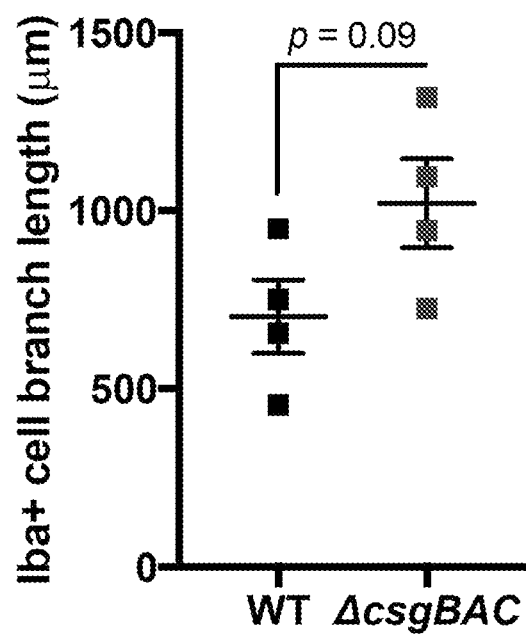
Figure 2G:
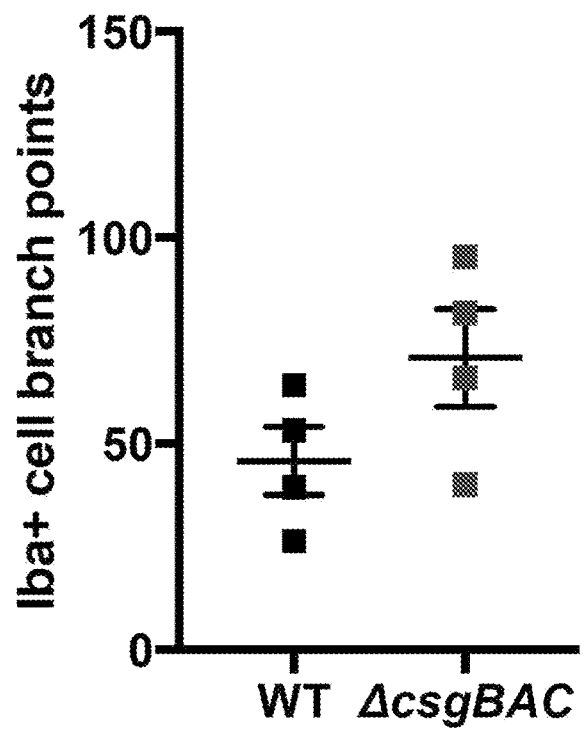
Figure 2H:
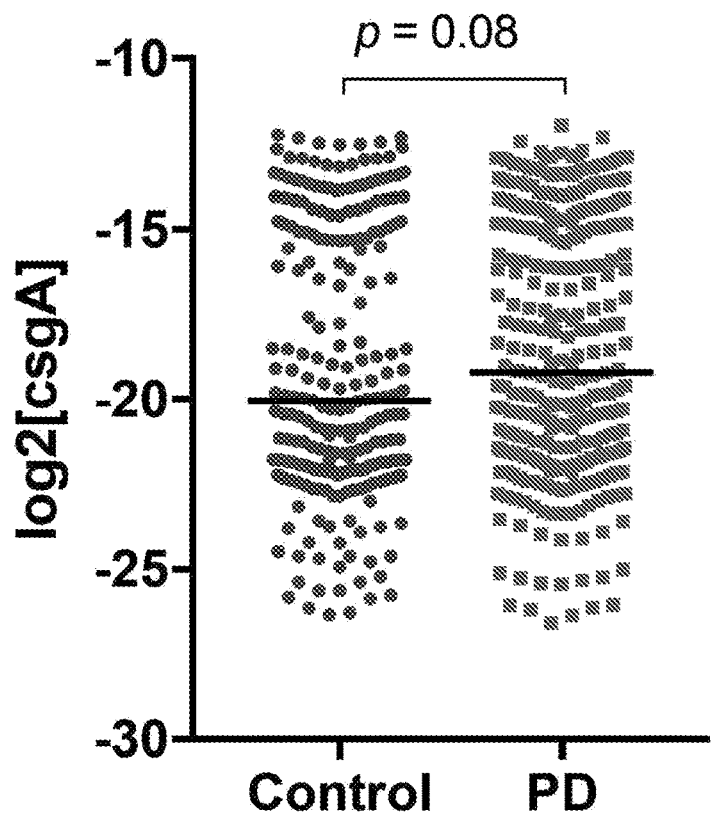
FIGS. 2H-J are a series of graphs showing levels of csgA in human fecal samples (FIG. 2H), in wild-type mice colonized with microbes derived from persons with PD or matched controls (FIG. 2I), or in Thy1-αSyn (ASO) mice colonized with microbes derived from persons with PD or matched controls (FIG. 2J).
Figure 2I:
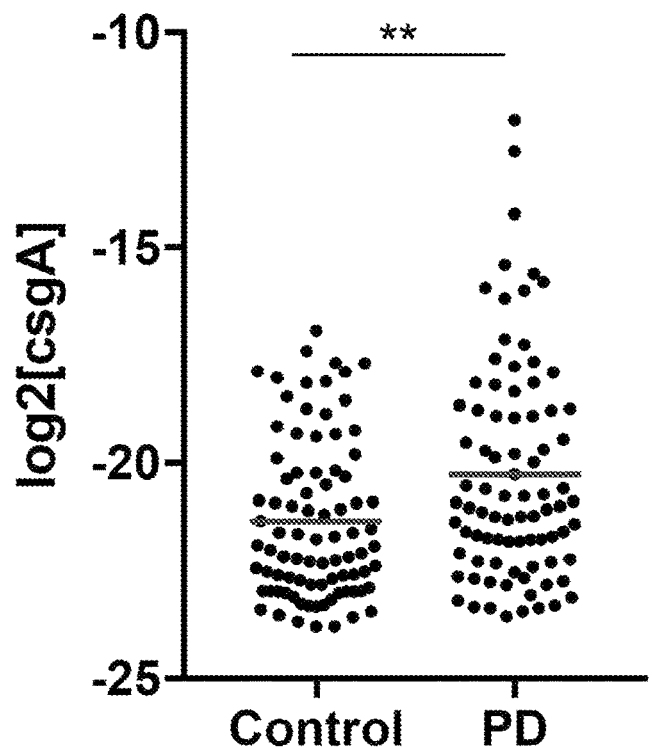
Figure 2J:
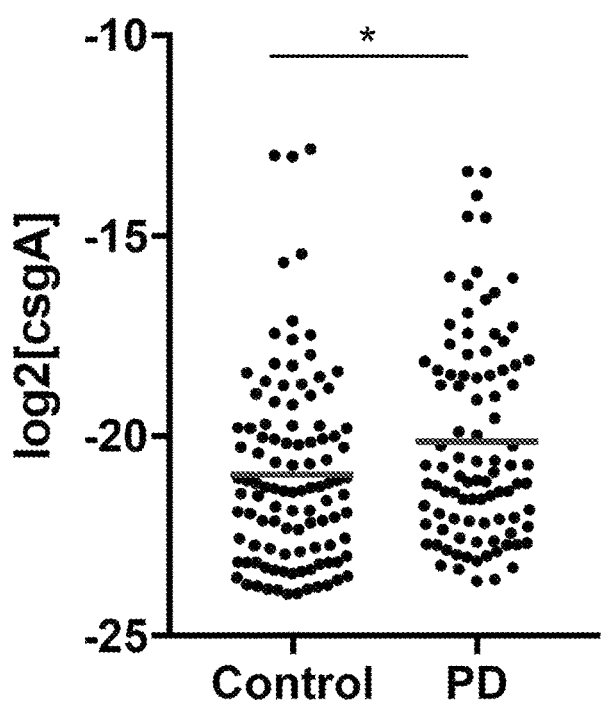

Additional experiments showed that mono-colonization with curli-sufficient bacteria induce increased αSyn-dependent pathology and inflammatory responses in the brain. Germ-free (GF) wild-type (WT) or Thy1-αSyn (ASO) mice were mono-colonized with either wild-type, curli-sufficient *E. coli* (WT) or curli-deficient *E. coli* (ΔcsgBAC). FIG. 2A is a graph showing total αSyn in whole brain lysates quantified by ELISA. FIG. 2B is a graph showing quantification of insoluble αSyn fibrils in the striatum by dot blot assay. FIGS. 2C-D show quantification of TNFα (FIG. 2C) and IL-6 (FIG. 2D) by ELISA from the striatum. FIGS. 2E-G show the results of staining thin sections of brains derived from ASO mice were stained for Iba1 (microglia), 3D cellular reconstructions generated, and morphological characteristics quantified of microglia resident in the striatum. n=3 (FIGS. 2A-B), n=6-7 (FIG. 2C, 2D), n=4 (FIGS. 2E-G) (averaged from 20-40 cells for diameters, or 5-7 cells for branching). Points represent individuals, bars represent the mean and standard error. Data analyzed by one-way ANOVA with Tukey post-hoc test for FIGS. 2A-D, or two-tailed t-test for FIGS. 2E and 2F *p≤0.05; p≤0.01; *p≤0.001; ****p≤0.0001. Consistent with this effect of curli-sufficient bacteria on mouse models, it is shown that the relative abundance of csgA is increased in the gut of human Parkinson's Disease (PD) patients. Relative abundance of csgA was determined by PICRUSt analysis of available 16S RNA data from human fecal samples (ENA Accessions: PRJNA268515, PRJEB4927, and PRJEB14674). Based on this analysis, it was observed that relative abundance of csgA was higher in the gut of the PD patients (FIG. 2H). Furthermore, wild-type (FIG. 2I) or Thy1-αSyn (ASO) (FIG. 2J) mice were colonized with microbes derived from persons with PD or matched controls (ENA Accession: PRJEB17694), and PICRUSt imputed analysis of 16s rRNA sequences indicated greater abundance in the PD-transplanted microbiomes compared to healthy controls (FIG. 2K). For FIGS. 2H-J, points represent individuals, bars represent the mean, data analyzed by two-tailed Mann-Whitney test. *p≤0.05; **p≤0.01. Thus, it is observed that the presence or elevated levels (compared to healthy controls) of bacterial proteins such as csgA in the gut correlates with amyloid disorders, including PD.

Example 8

Figure 3A:
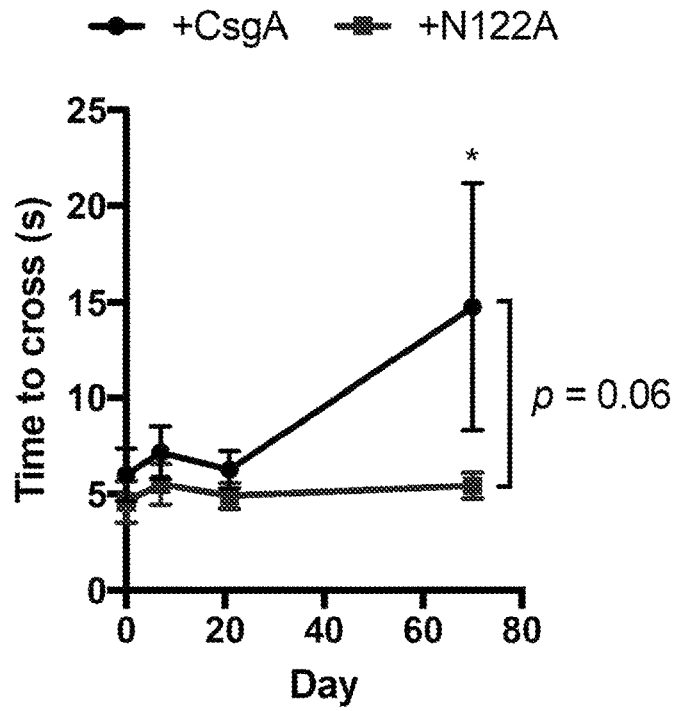
FIGS. 3A-I are a series of graphs depicting that intestinal curli promotes progressive synuclein-dependent pathophysiology. Conventionally-raised Thy1-αSyn (ASO) animals were injected intestinally with 30 μg of synthetic CsgA hexamer (CsgA; N-QYGGNN-C) or non-amyloidogenic peptide (N122A; N-QYGGNA-C). For FIGS. 3A-G, motor and GI function tested overtime at 0, 7, 21, and 70 days post-injection in the beam traversal (FIG. 3A), pole descent (FIG. 3B), adhesive removal (FIG. 3C), hindlimb clasping score (FIG. 3D), wirehang (FIG. 3E), fecal output (at day 70) (FIG. 3F).
Figure 3B:
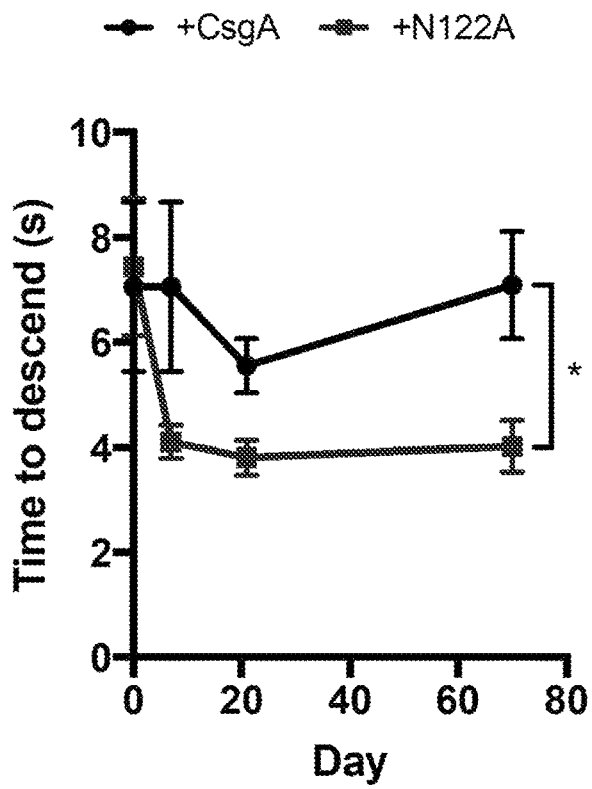
Figure 3C:
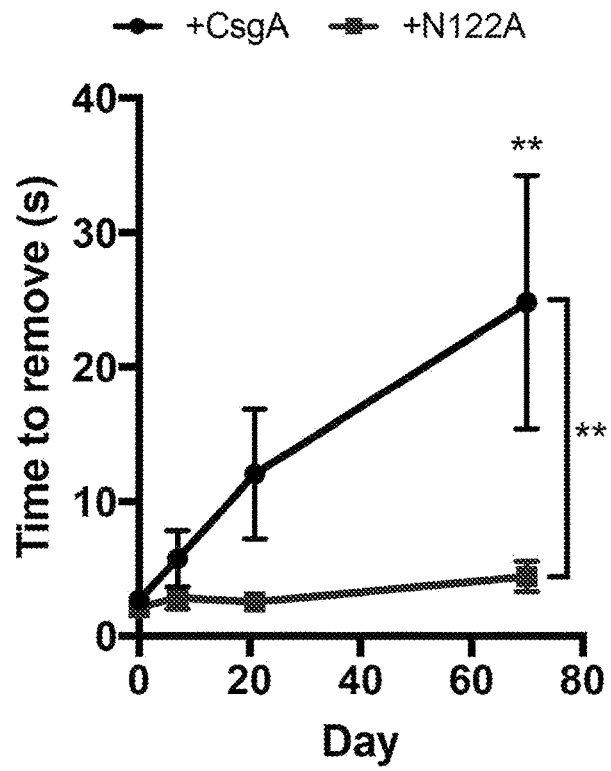
Figure 3D:
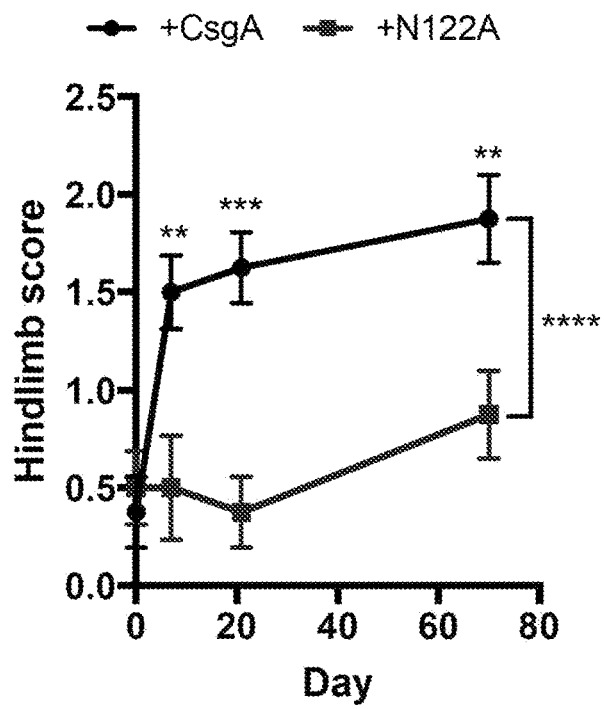
Figure 3E:
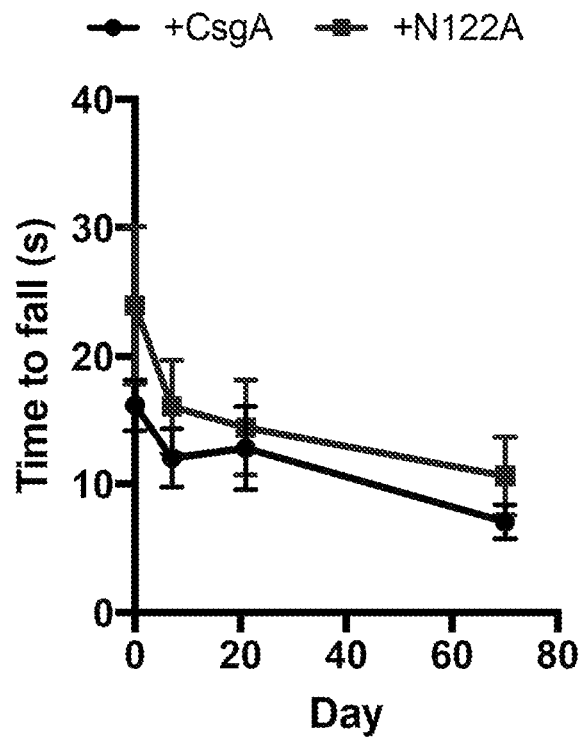
Figure 3F:
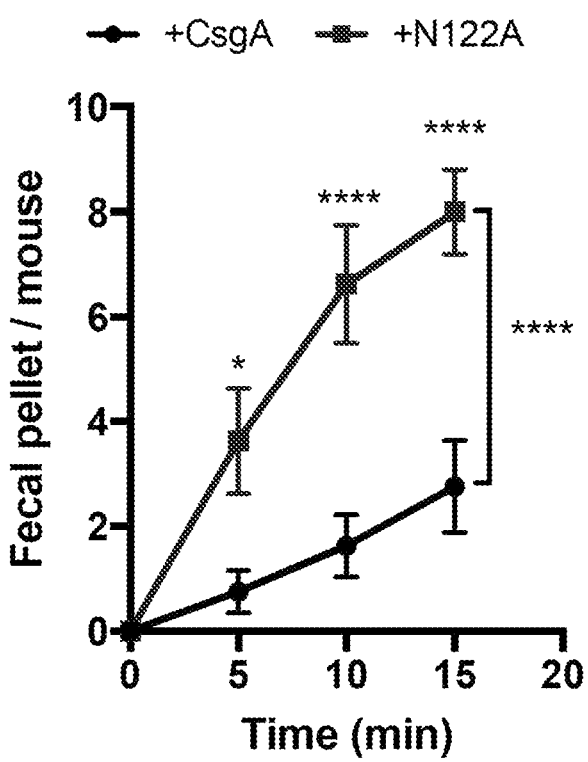
Figure 3G:
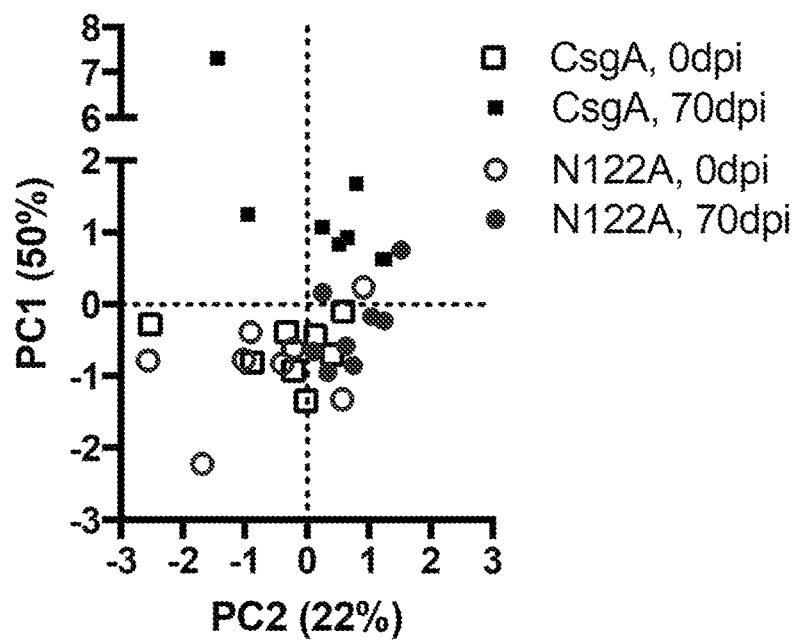
Figure 3H:
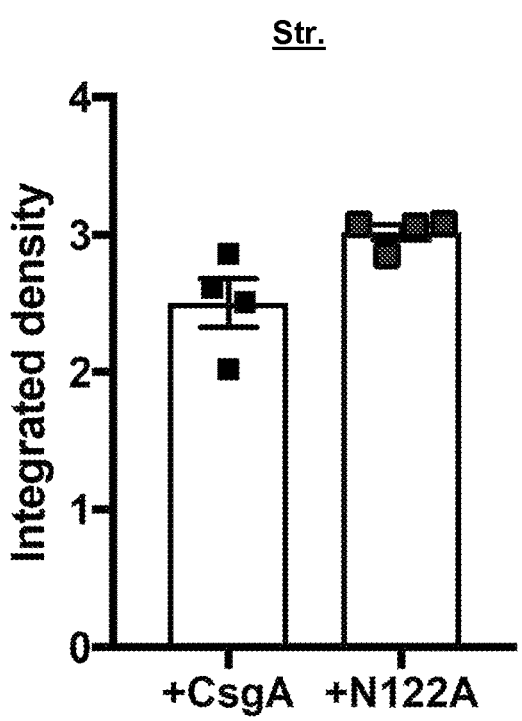
Figure 3I:
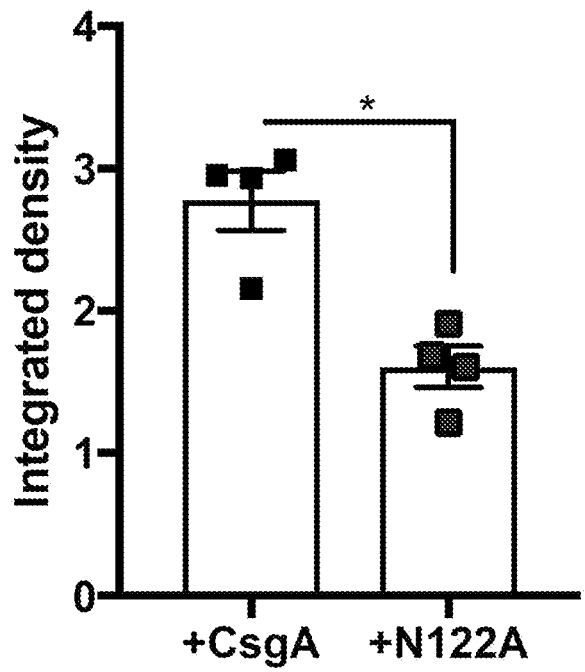

Additional experiments show that that intestinal curli promotes progressive synuclein-dependent pathophysiology. Conventionally-raised Thy1-αSyn (ASO) animals were injected intestinally with 30 g of synthetic CsgA hexamer (CsgA; N-QYGGNN-C) or non-amyloidogenic peptide (N122A; N-QYGGNA-C). Each peptide spanned the aggregation domain of CsgA. Motor and GI function tested over time at 0, 7, 21, and 70 days post-injection in the beam traversal (FIG. 3A), pole descent (FIG. 3B), adhesive removal (FIG. 3C), hindlimb clasping score (FIG. 3D), wire hang (FIG. 3E), fecal output (at day 70) (FIG. 3F). FIG. 3G is a graph depicting principal component analysis of compiled motor scores of FIGS. 3A-F. FIGS. 3H-I depict quantification of insoluble αSyn fibrils in the striatum (FIG. 3H) and ventral midbrain (FIG. 3I) by dot blot assay. n=8 (FIGS. 3A-G), n=4 (FIG. 3H). Points represent individuals, bars represent the mean and standard error. Time courses analyzed by two-way ANOVA, with Sidak post-hoc test for between group comparisons indicated above individual time points, and brackets indicating significance between treatments. Data in FIG. 3H were analyzed by two-tailed Mann-Whitney test. For FIGS. 3A-I, *p≤0.05; p≤0.01; *p≤0.001; ****p≤0.0001. Compilation of motor performance by PCA indicates a symptomatic shift in mice injected with the CsgA peptide compared to controls, demonstrating that the overall motor function of these animals has been impaired (FIG. 3G). Furthermore, increased αSyn fibrils are detected in the midbrains of amyloidogenic CsgA-injected animals (FIG. 3H), demonstrating alterations to central nervous system (CNS) pathology following amyloid administration directly to the GI tract. Thus, gut exposure to a CsgA peptide capable of forming amyloids is sufficient to exacerbate long-lasting motor deficits in αSyn over-expressing mice.

Thus, it was shown herein that intestinal curli increased time to cross, time to descend, time to remove, and hindlimb score, and decreased time to fall and fecal pellets per mouse. The increases in time to cross, time to descend, and hindlimb score, and decrease in fecal pellets per mouse were statistically significant at the noted levels (See FIGS. 3B-D and 3F). Accordingly, it is contemplated that intestinal curli can induce symptoms of amyloid disorders in vivo.

Example 9

Figure 4A:
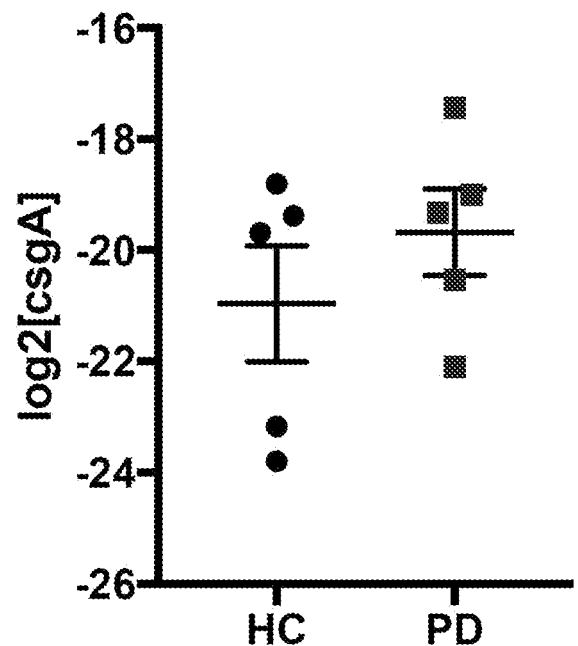
FIGS. 4A-C are a series of graphs depicting fecal abundance of amyloid-producing bacteria in humanized animals. Human samples from previous cohort (ENA Accession: PRJEB17694) were analyzed by PICRUSt to infer abundance of csgA encoded within each population, arrow indicates sample utilized for transplantation (FIG. 4A). Fecal pellets of Thy1-αSyn (ASO) mice receiving healthy-human derived fecal microbes enriched with either wild-type, curli-sufficient E. coli (WT) or curli-deficient E. coli (ΔcsgBAC) were analyzed by b, qPCR for rrsA abundance relative to 16s rRNA present in fecal bacterial DNA and by c, qPCR analysis for csgA expression relative to rrsA in fecal bacterial RNA. n=5 (FIG. 4A), n=8 (FIGS. 4B-C). Points represent individuals, bars represent the mean and standard error. Data were analyzed by two-tailed Mann-Whitney test. ***$p \leq 0.001$.
Figure 4B:
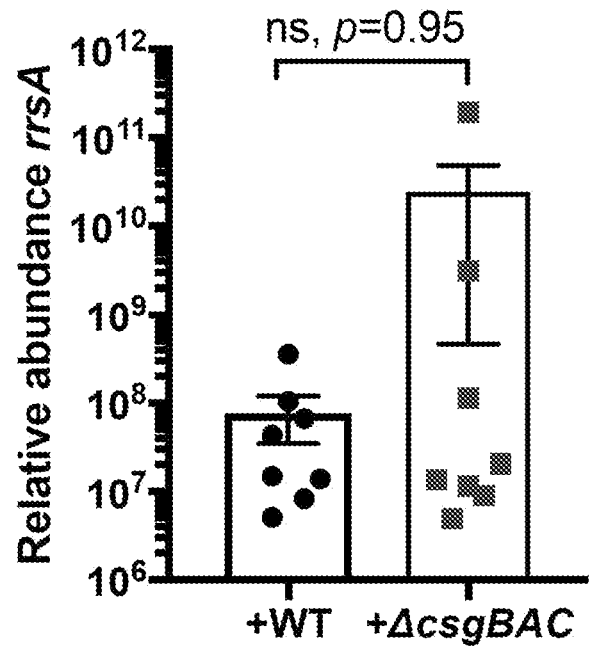
Figure 4C:
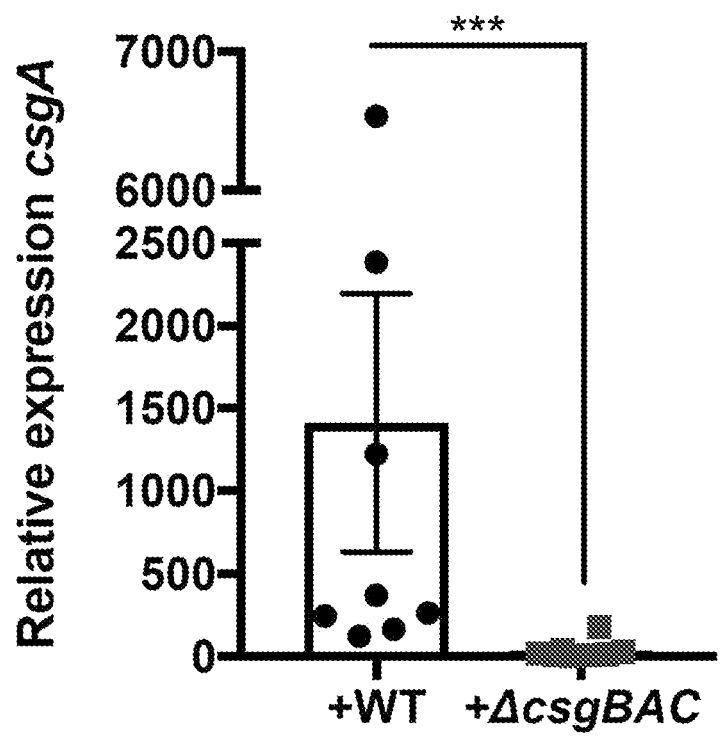

To further explore cause-and-effect relationships between the microbiome and PD, it was studied whether production of curli by an otherwise healthy human microbiome is sufficient to impair motor performance. GF ASO mice were transplanted with microbiota from a healthy human donor predicted to contain low levels of CsgA-producing bacteria, as indicated by PICRUSt analysis following 16S rRNA sequencing. Fecal abundance of amyloid-producing bacteria in these humanized animals was studied. Human samples from previous cohort (ENA Accession: PRJEB17694) were analyzed by PICRUSt to infer abundance of csgA encoded within each population, arrow indicates sample utilized for transplantation (FIG. 4A). Fecal pellets of Thy1-αSyn (ASO) mice receiving healthy-human derived fecal microbes enriched with either wild-type, curli-sufficient E. coli (WT) or curli-deficient E. coli (ΔcsgBAC) were analyzed by b, qPCR for rrsA abundance relative to 16s rRNA present in fecal bacterial DNA and by c, qPCR analysis for csgA expression relative to rrsA in fecal bacterial RNA. n=5 (FIG. 4A), n=8 (FIGS. 4B-C). Points represent individuals, bars represent the mean and standard error. Data were analyzed by two-tailed Mann-Whitney test. ***p≤0.001. Therefore, in the presence of a complex consortium of human microbes, curli-producing E. coli exacerbate pathophysiology in a mouse model of PD.

Thus, it is shown that intestinal levels of amyloid-producing microbial organisms can be detected in samples in accordance with some embodiments herein, and moreover, intestinal levels of amyloid-producing microbial organisms have been shown differ in subjects having amyloid aggregates that model an amyloid disorder (compared to healthy controls).

Example 10

Figure 5A:
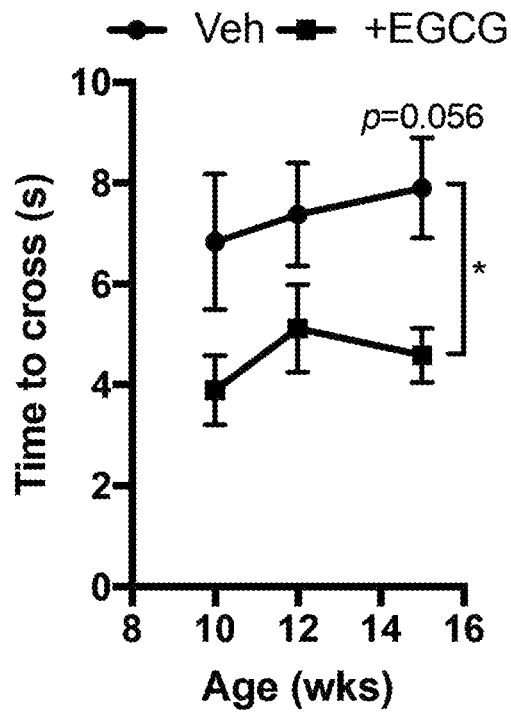
FIGS. 5A-J are a series of graphs depicting inhibition of functional amyloid formation in accordance with some embodiments herein dampens progressive motor deficits. Germ-free Thy1-αSyn mice (ASO) were monocolonized with wild-type E. coli and treated with water alone (Vehicle, Veh) or given EGCG ad lib in drinking water (+EGCG). Motor function was assessed at 10, 12, and 15 weeks of age by quantifying beam traversal time (FIG. 5A), pole descent time (FIG. 5B), nasal adhesive removal time (FIG. 5C), hindlimb clasping score (FIG. 5D), and wirehang tests (FIG. 5E).
Figure 5B:
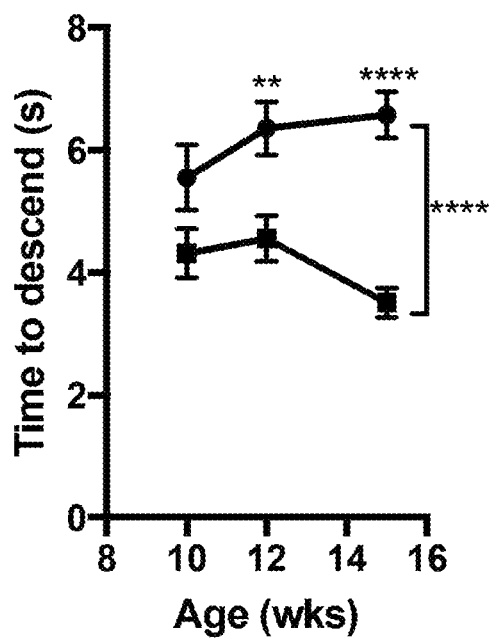
Figure 5C:
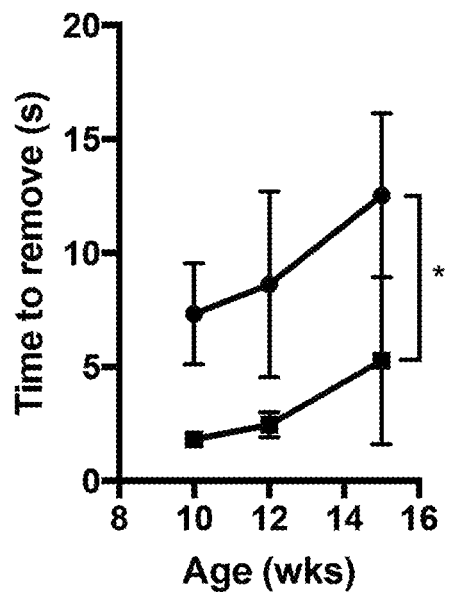
Figure 5D:
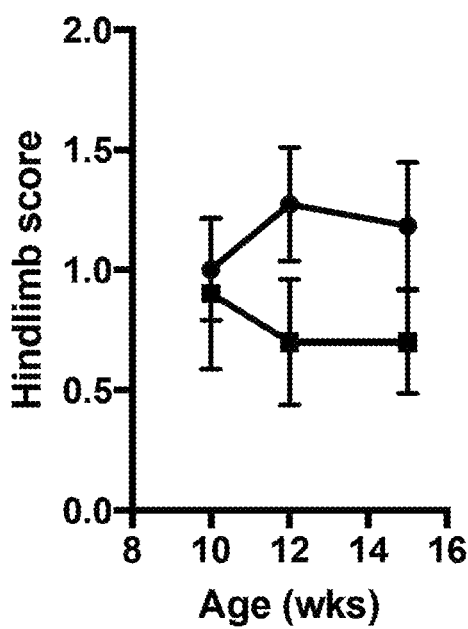
Figure 5E:
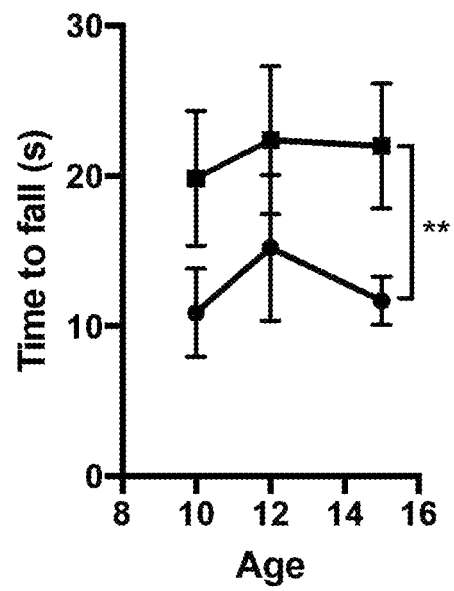
Figure 5F:
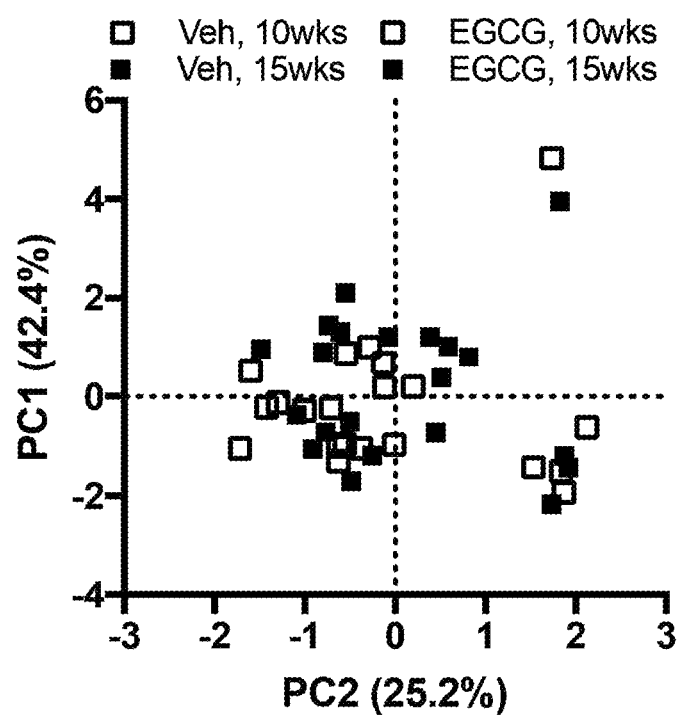
Figure 5G:
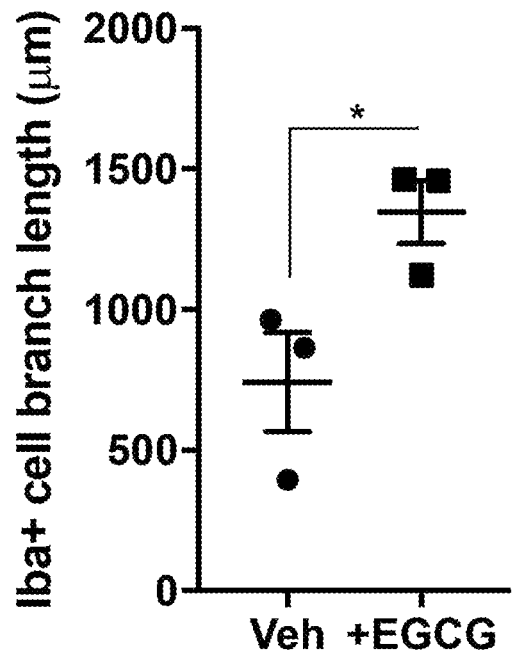
Figure 5H:
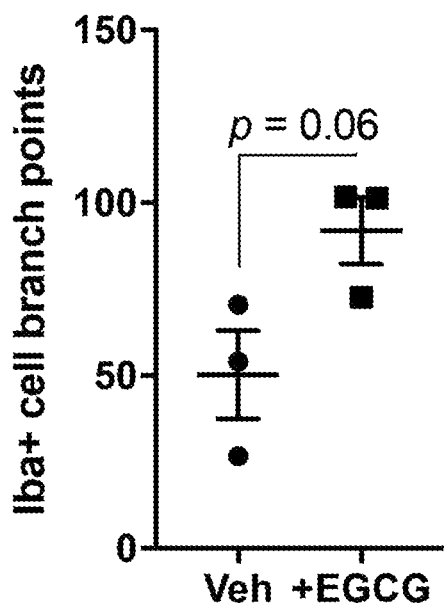
Figure 5I:
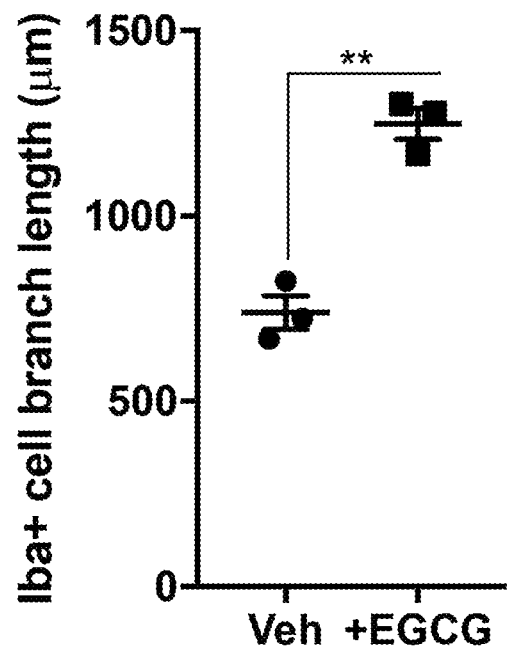
Figure 5J:
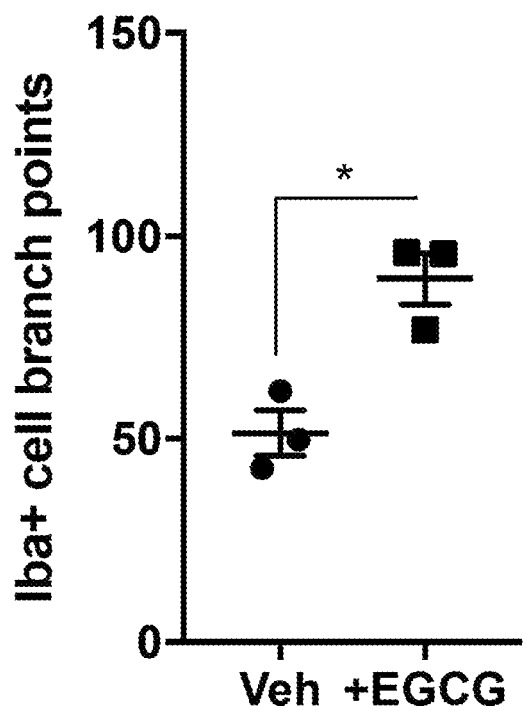

Inhibition of functional amyloid formation was studied. Germ-free Thy1-αSyn mice (ASO) were monocolonized with wild-type E. coli and treated with water alone (Vehicle, Veh) or given EGCG ad lib in drinking water (+EGCG). Motor function was assessed at 10, 12, and 15 weeks of age by quantifying beam traversal time (FIG. 5A), pole descent time (FIG. 5B), nasal adhesive removal time (FIG. 5C), hindlimb clasping score (FIG. 5D), and wire hang tests (FIG. 5E). FIG. 5F depicts principal component analysis of compiled motor scores from FIGS. 5A-D. Thin sections of brain were stained for Iba1 (microglia) and morphological characteristics quantified of microglia resident in the striatum (FIGS. 5G-H) and substantia nigra (FIGS. 5I-J). N=10-11 (FIGS. 5A-F), n=3 (FIGS. 5G-J) (averaged from 5-7 cells for branching). Bars represent the mean and standard error. Time courses analyzed by two-way ANOVA, with Sidak post-hoc test for between group comparisons indicated above individual time points, and brackets indicating significance between treatments. Data in (FIGS. 5G-J) analyzed by two-tailed t-test. *p≤0.05; p≤0.01; **p≤0.0001.

Accordingly, inhibition of functional amyloid formation in accordance with some embodiments herein dampens progressive motor deficits. Without being limited by theory, it is contemplated that curli produced by E. coli utilize an amyloid-dependent pathway to exacerbate hallmark motor deficits and pathologies of PD in this preclinical model. It is further contemplated that inhibition of bacterial amyloid production, formation and/or interaction with mammalian amyloids in accordance with some embodiments herein is a useful intervention of neurodegenerative conditions caused by protein aggregation, for example amyloid disorders as described herein.

Example 11

Figure 6A:
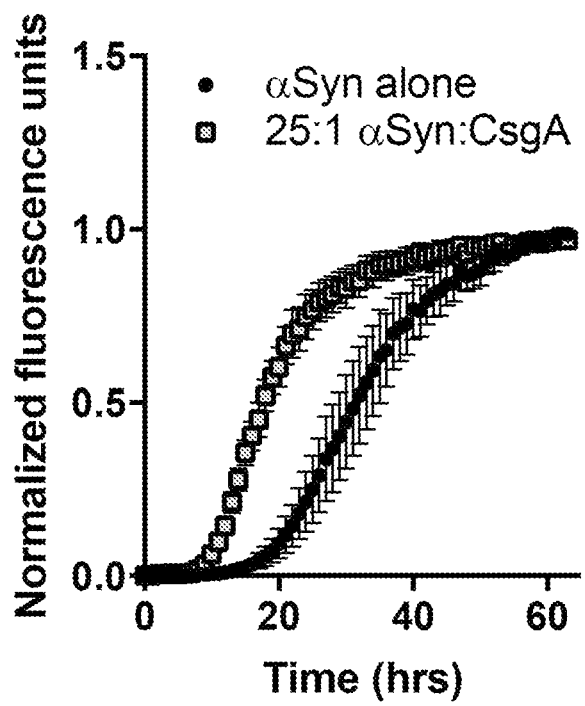
Figure 6B:
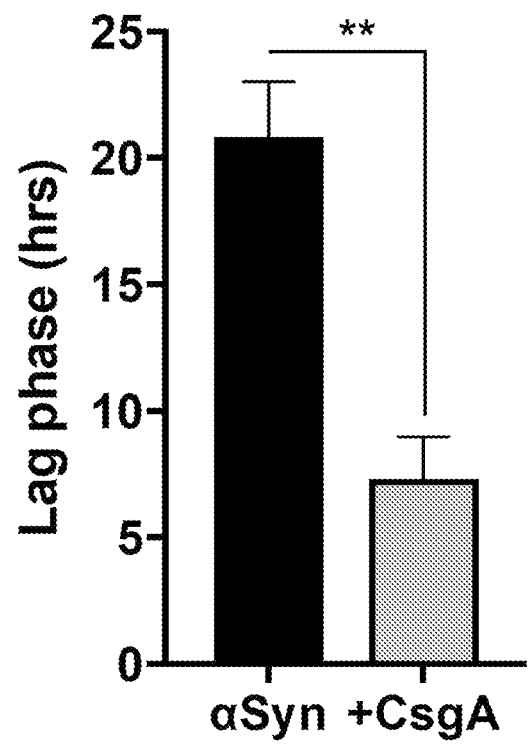
Figure 6I:
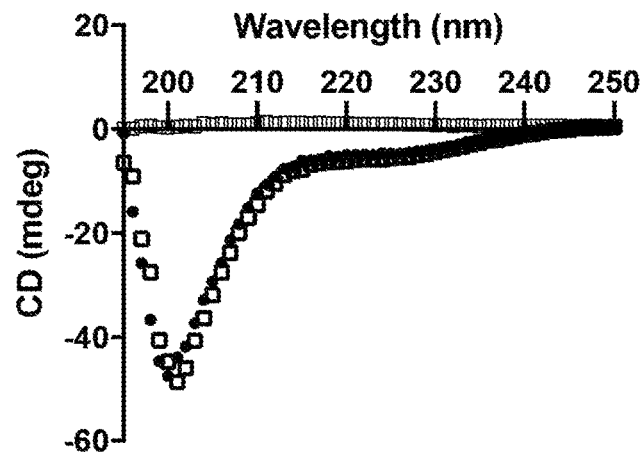
Figure 6J:
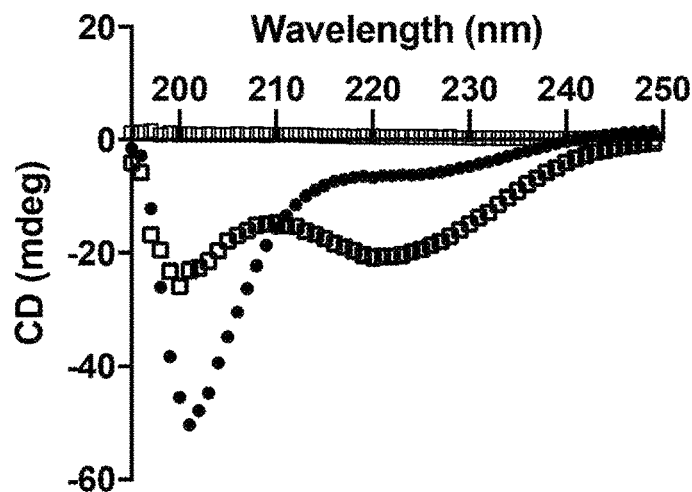
Figure 6K:
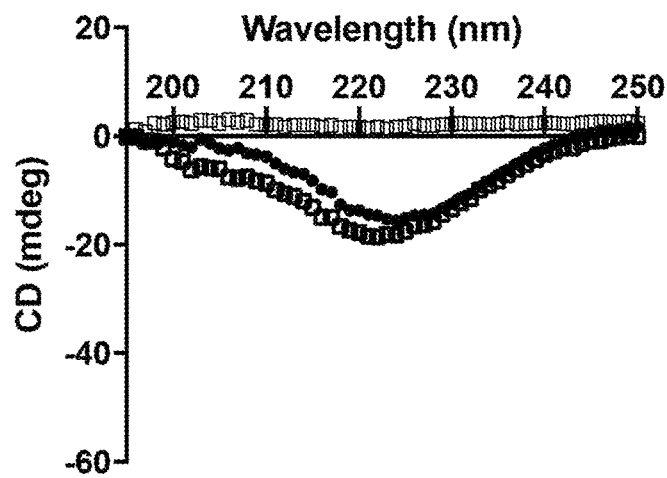

Effects of the bacterial amyloid protein, CsgA on the seeding of αSyn fibrilization were studied. In vitro biophysical analysis was conducted with purified αSyn and CsgA proteins. It was tested whether the major curli subunit, CsgA, is capable of cross-seeding the formation of αSyn aggregations. It was observed that addition of purified CsgA to monomeric αSyn in vitro results in significantly accelerated production of αSyn aggregates (FIGS. 6A-B). FIG. 6A shows aggregation as measured by Thioflavin T fluorescence over time during αSyn amyloid formation alone or in the presence of CsgA monomers (25:1 molar ratio, yellow). FIG. 6B shows time to reach exponential fibrilization, lag phase. FIGS. 6C-H are a series of representative transmission electron micrographs of αSyn alone (FIGS. 6C, 6F) or CsgA alone (FIGS. 6E, 6H), or in combination (FIGS. 6D, 6G), at 0 hours (FIGS. 6C-E) and 60 hours (FIGS. 6F-H) post-aggregation. FIGS. 6I-K are a series of graphs illustrating circular dichroism spectroscopic analysis of αSyn fibrilization alone or in the presence of CsgA at 0, 12.5, and 60 hours post-aggregation. For FIG. 6A and FIG. 6B, n=3. Bars represent the mean and standard error. Data are analyzed by two-tailed, t-test. **p≤0.01. Data are representative of 2 independent trials. Thus, the bacterial amyloid protein, CsgA, in accordance with some embodiments herein seeds aSyn fibrilization. Without being limited by theory, it is contemplated that CsgA not only accelerates the generation of αSyn aggregates in vitro, but these subsequent αSyn structures maintain pathogenic attributes, similar to observations with other amyloids that propagate in a prion-like manner.

Example 12

Effects of CsgA on seeding synuclein aggregation and propagation was studied through transient interactions.

Figure 7A:
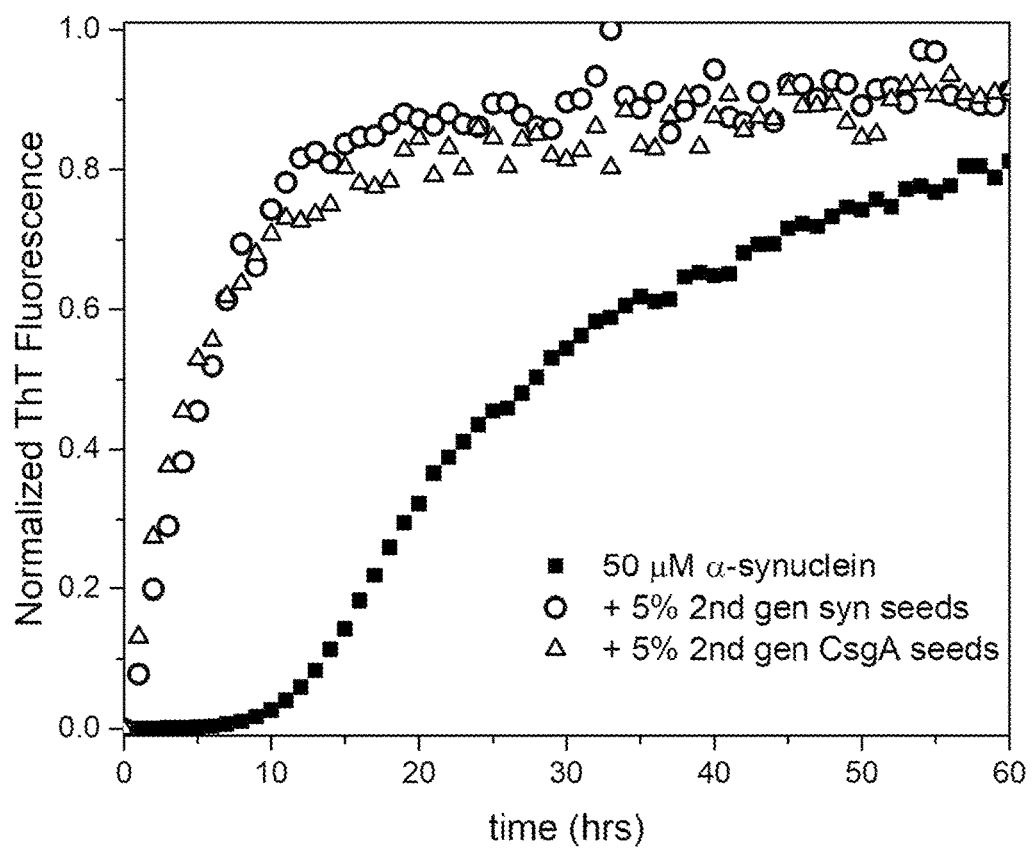
FIGS. 7A-F are a series of graphs and transmission electron microscope images illustrating that CsgA seeds synuclein aggregation and propagation through transient interactions.
Figure 7B:
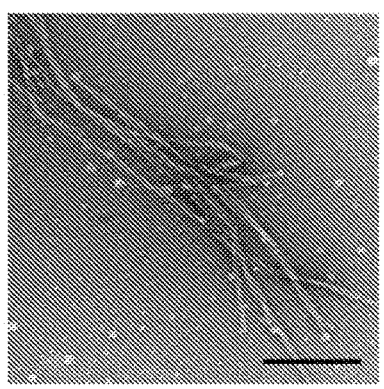
Figure 7C:
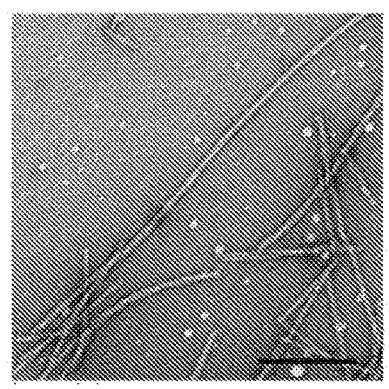
Figure 7D:
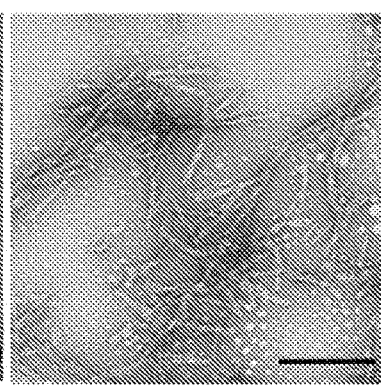
Figure 7E:
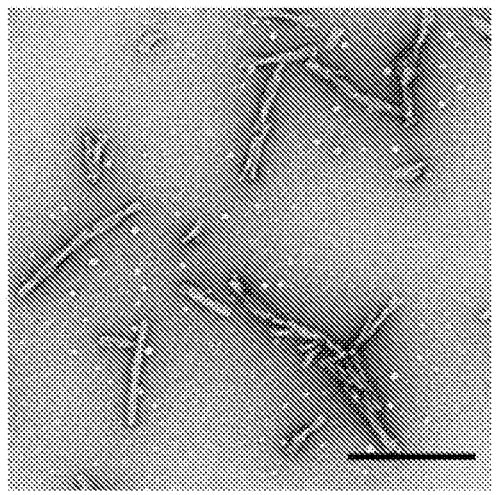
Figure 7F:
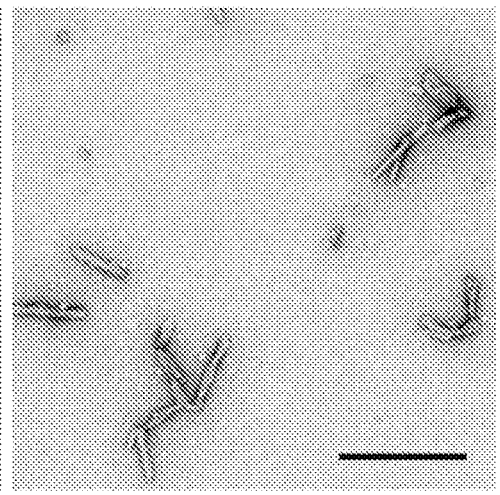
Figure 7G:
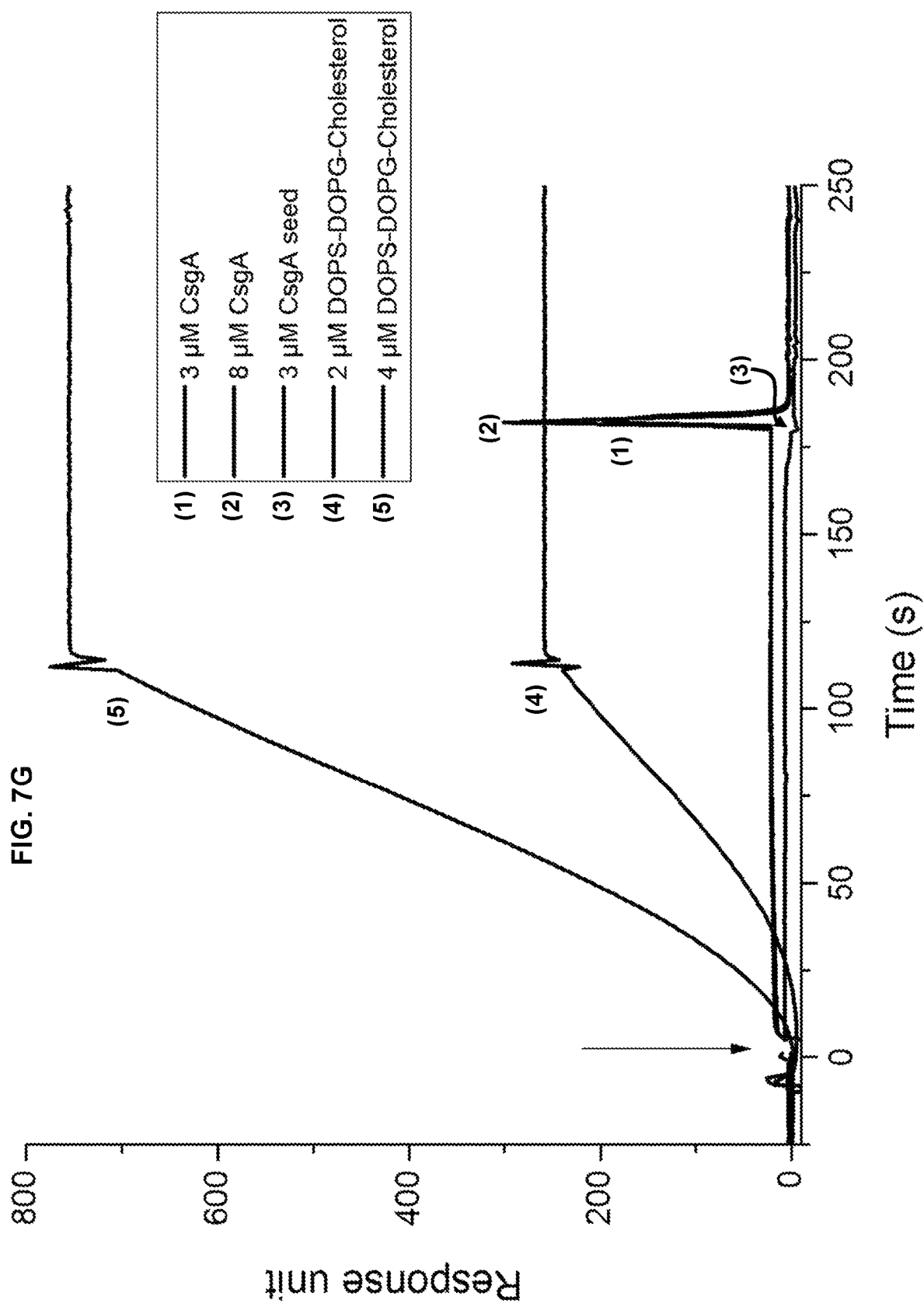
FIG. 7G is a graph showing surface plasmon resonance measurements of surface immobilized αSyn with additions of either CsgA monomer or seeds, or DOPS-DOPG cholesterol as positive control.
Figure 8:
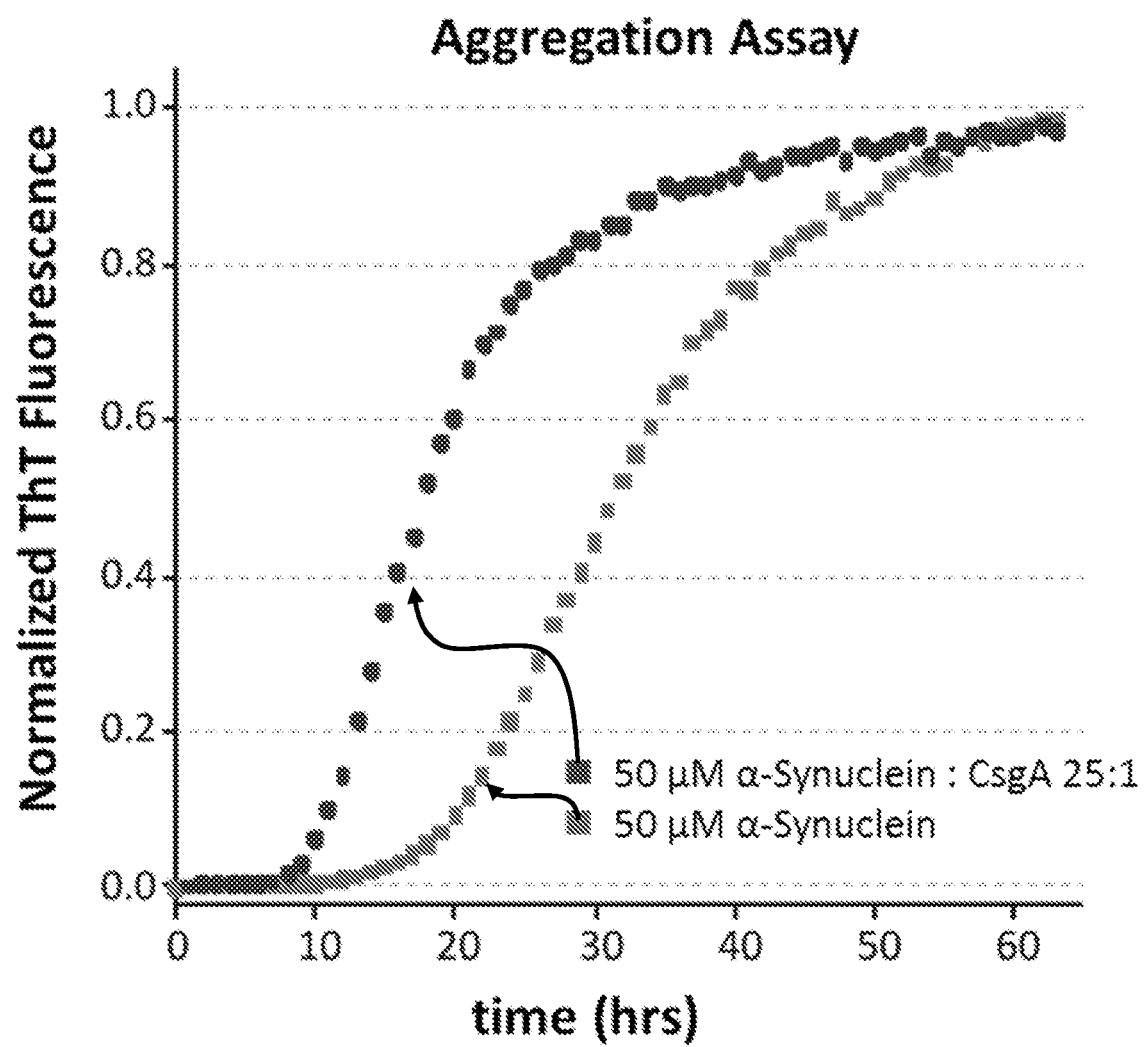
FIG. 8 is a graph illustrating an amyloid aggregation assay according to some embodiments. Shown is the aggregation of α-Synuclein over time is measured by Thioflavin T (ThT) fluorescence, in the presence and absence of CsgA.

FIG. 7A is a graph showing thioflavin T fluorescence during αSyn amyloid formation alone or in the presence of 5% seeds previously generated by addition of CsgA monomer to αSyn (as in FIG. 2A) or αSyn alone. FIGS. 7B-F are a series of transmission electron micrograph of fibril structures generated by the addition of above seeds and of seeds themselves. FIG. 7G is a graph showing surface plasmon resonance measurements of surface immobilized αSyn with additions of either CsgA monomer or seeds, or DOPS-DOPG cholesterol as positive control. Thus, it is shown that the final CsgA-induced synuclein fibrils purified from completed biochemical reactions maintain an ability to accelerate αSyn amyloid formation. This assay did not to detect direct interactions between CsgA and αSyn monomers. Without being limited by theory, these results are consistent with transient interactions or interactions between oligomeric forms of the proteins at later stages in amyloidogenesis (FIG. 7G).

Accordingly, CsgA was shown to seed synuclein propagation through transient interactions.

Example 13

A library of potential amyloidogenesis inhibitors is obtained. Such libraries may be found in preexisting repositories, or may be generated de novo by, for example, combinatorial synthesis or by solid phase peptide synthesis utilizing such methods as are well known in the art. See, for example, Jensen, K. J. et al., eds, *Peptide Synthesis and Applications*, $2^{nd}$ Edition, 2913, which is incorporated by reference herein for its teachings of solid phase peptide synthesis, combinatorial peptide synthesis, and the generation of peptide libraries. Natural product libraries may also be utilized. In a multi-well assay plate, a bacterial amyloid initiator, such as *E. coli* CsgA is placed in varying concentrations in one dimension, while a host-derived amyloidogenic protein, such as α-synuclein, is placed in varying amounts in the second dimension, such that each well contains a different ratio of amyloid initiator and amyloid precursor. To each well, a constant amount of an indicator of amyloid formation, such as thioflavin (ThT), is added, as well as a constant amount of an individual test compound. Each tray is agitated to initiate amyloid formation, and thioflavin fluorescence is monitored. Compounds that show deviations in the rate of fluorescence development over time will be identified as candidates that enhance or inhibit amyloid formation.

Example 14

A suspected amyloidogenesis inhibitor is combined with a bacterial amyloid initiator and an amyloid precursor in the presence of Thioflavin T (ThT). Separately, as a control, bacterial amyloid initiator, amyloid precursor, and Thioflavin T are combined in the absence of the suspected amyloidogenesis inhibitor. Thioflavin T fluorescence is monitored over time. A reduction in the rate of increase in ThioflavinT fluorescence, and/or a reduction in the maximum level of Thioflavin T fluorescence in the sample containing the suspected inhibitor, relative to the control sample, confirms that the suspected amyloidogenesis inhibitor is in fact functioning to inhibit amyloid formation.

Example 15

A sample of tissue, fluid, feces, or intestinal contents is collected from a subject. Said sample is combined with a bacterial amyloid initiator, such as *E. coli* CsgA, a host-derived amyloidogenic protein, such as α-synuclein and an indicator of amyloid formation, such as Thioflavin T (ThT). Thioflavin T fluorescence is monitored. An increase in fluorescence consistent with an increase in the rate of formation of amyloid in the presence of said sample, relative to the rate of amyloid formation in the absence of said sample, indicates an increase in the risk of α-synucleinopathy, including Parkinson's disease and/or Lewy body dementia. This increased risk is further correlated with results from conventional neurological examinations in order to calculate a defined risk of commencement and/or progression of an α-synucleinopathy or other neurodegenerative disorder implicating amyloid formation.

Example 16

In non-binding, black plastic, 96-well plates, 50-100 μM α-synuclein is incubated in 0.01M phosphate-buffered saline solution (pH 7.4) in the presence of 12 μM of Thioflavin T (prepared in 0.01M phosphate buffered saline). Purified CsgA monomer in phosphate buffered saline is added to each well at a molar ratio of 1:10, 1:25, 1:50, or 1:100. Inhibitory compounds are prepared in appropriate buffered solutions based on solubility, such as phosphate buffered saline or DMSO. Compounds and appropriate buffer controls are added to α-synuclein- and CsgA-containing wells, to a final volume of 150 μL per well. The concentration of each compound is dependent on the type of compound being screened but generally is expected to fall within the range of 1 μM to 200 μM in initial screens. Details regarding the addition of such compounds depend on the types of compounds available in the accessible small molecule libraries. Independent wells containing α-synuclein alone and CsgA alone serve as specificity controls, or in combination in the absence of potential inhibitors. A single, sterilized glass or Teflon bead with a ~2 mm diameter is added to each well. The plate is incubated within a fluorescent-capable microplate reader with continuous orbital shaking (~100-250 rpm) at 37° C. Fluorescence is measured every 1-2 hours with an excitation of 440±10 nm and emission of 490±10 nm. Measurements are taken over a 24-72 hour period. As α-synuclein amyloids form, emission spectra hit maximum intensity ~24-48 hours under these conditions following a sigmoidal curve. After this time, emission intensity can decrease as amyloids become insoluble and non-fluorescent.

Amyloid formation appears over 3 phases (See, e.g., FIG. 1B): (1) a lag phase whereby fluorescence intensity is low occurring over the first ~0-24 hrs; (2) A log phase whereby fluorescence intensity increases logarithmically from ~6-48 hrs; and (3) a plateau phase whereby fluorescence intensity hits a maximum and either remains unchanged for the remaining time period or begins to decrease due to insoluble α-synuclein precipitating out of solution. Maximum intensity occurs between 24-48 hours.

Aggregation kinetics, as measured by thioflavin fluorescence, in the presence of compounds can be normalized to the kinetics observed with α-synuclein and CsgA alone. Potential inhibitors may act to lengthen the lag phase, decrease the rate of change during the log phase, decrease the maximum intensity reached, or any combination thereof.

Once initial candidates are identified, dose responses over a wide-range of concentrations can be determined, as well as specificity against CsgA:synuclein aggregates, or CsgA and α-synuclein individually. In some variations of this screen, CsgA:synuclein aggregates can be monitored until the log phase, and potential inhibitory compounds introduced at this time. Subsequently, inhibitors which can act once amyloid formation is already in process can be identified (See, e.g., FIG. 1B).

Example 17

The assay is practiced as described in Example 16, in which full concentration curves are generated for each compound. This enables accurate determination of the EC50 for each compound and can expose certain compounds limitations (e.g., expose compounds that do not lead to complete inhibition of aggregation).

Example 18

The assay is practiced as described in Example 16, and is formatted for higher throughput screening in a variety of ways. For example, rather than a full concentration curve for each compound, a three-point concentration curve is used to distinguish compounds with a dose-response effect from those with a non-specific and concentration-independent effect. For even higher throughput screening, the assay is formatted in 96-well, 384-well or 1536-well plates and compounds are tested at a single concentration (e.g., 1 µM) and at a single timepoint (e.g., 24-72 hours). This enables the observer to distinguish potential candidates from compounds with no effect or with no effect at a relevant concentration.

Example 19

The assay is practiced as described in Example 16, in which full time course curves are generated for each compound. Time-course curves show whether a compound inhibits in a linear or sigmoidal fashion over time, and/or whether the complete inhibition can be achieved with a given compound.

Example 20

The assay is practiced as described in Example 16, and is further modified to assess mechanistic processes and compound activity in a more dynamic environment in which both α-synuclein (or other host amyloid protein) and curli (or other bacterial amyloid) are present in the assay. The observer then assesses the ability of compounds to inhibit aggregation of one or the other proteins in the presence of an aggregation template. For example, bacterial amyloid component CsgA is known to promote and/or accelerate α-synuclein aggregation. In an in vivo environment, a candidate compound with α-synuclein aggregation inhibition activity is exposed to an aggregation promoting or templating activity from bacterial amyloid. Thus, formatting the assay by inclusion of both monomeric α-synuclein (or other host amyloid) and aggregated bacterial amyloid allows assessment of drug candidates in a more physiologically relevant in vitro environment.

Example 21

The assay is practiced as described in Example 16, wherein the method further comprises combining a curli (bacterial amyloid) aggregation inhibitor with an α-synuclein aggregation inhibitor. This combination has the added benefit of blocking aggregation at two critical points simultaneously. The assay utilizes the monomeric forms of both α-synuclein and curli (CsgA), and measurements analogous to those shown in FIG. 1B are obtained.

Example 22

The assay is practiced as described in Example 16, wherein the method further comprises combining a curli (bacterial amyloid) dis-aggregation promoter with a promoter of α-synuclein dis-aggregation. This combination has the added advantage of effecting dis-aggregation at two critical points simultaneously. The assay utilizes the fully aggregated forms of both α-synuclein and curli, and measurements analogous to those shown in FIG. 1B are obtained.

Example 23

The assay is practiced as described in Example 16, wherein the method further comprises combining a curli (CsgA, bacterial amyloid) aggregation inhibitor with an α-synuclein dis-aggregation promoter. This combination has the added advantage of inhibiting the nucleation or origination of amyloid while simultaneously effecting dis-aggregation of an already initiated process. The assay utilizes the fully aggregated form of α-synuclein and the monomeric form of curli (CsgA), and measurements analogous to those shown in FIGS. 2A-3I are obtained.

Example 24

The assay is practiced as described in Example 16, wherein the method further comprises combining a curli (bacterial amyloid) dis-aggregation promoter with an α-synuclein aggregation inhibitor. This combination has the added advantage of destroying pathogenic bacterial amyloid while simultaneously inhibiting α-synuclein aggregation. The assay utilizes the monomeric form of α-synuclein and the fully aggregated form of curli, and measurements analogous to those shown in FIGS. 2A-3I are obtained.

Example 25

The assay is practiced as in any of Examples 16-24, except that a CsgA mutant that is incapable of aggregation is included. Compounds that rely on the presence of structured (aggregated) CsgA in these processes will show reduced effectiveness in this version of the assay.

Example 26

Full length, untagged, recombinant α-synuclein can be prepared as described from: Chorell et al. (2015). *PLoS ONE* 10(10). Briefly, a plasmid is derived from a pET-3a vector containing human α-synuclein, with an N-terminal His-tag and caspase 7 cleavage site. The plasmid is transformed into BL21 (DE3) competent cells and grown at 37° C. in rich media supplemented with 100 mg/L carbenicillin or ampicillin and grown until OD600~0.6, mid-log phase. α-synuclein production is induced with 0.5 mM isopropyl b-D-1-thiogalactopyranoside (IPTG) for 6 hours at 37° C.

The cells are pelleted and re-suspended in 8 M urea, 20 mM Tris, 20 mM imidazole, pH 8.0, sonicated on ice, followed by centrifugation at 20000 rpm for 30 minutes.

The supernatant is filtered and loaded on an affinity column (Ni Sepharose 6 Fast Flow, GE Healthcare), equilibrated with 20 mM Tris, 50 mM NaCl, 20 mM imidazole, 5% glycerol, pH 7.5, and eluted with the same buffer, but containing 250 mM imidazole.

For removal of the His-tag, the peptidase caspase 7 is added in a ratio of 1:100 (w/w), together with 20 mM 2-mercaptoethanol and is incubated overnight at 4° C. The sample is then loaded on an anion-exchange column (HiTrap Q FF, GE Healthcare) equilibrated with 20 mM Tris pH 8.0, and eluted with a linear NaCl gradient of 20 mM Tris, 1 M NaCl, pH 8.0. Finally, α-synuclein was run through a gel filtration column (HiLoad 16/60 Superdex 75, GE Healthcare), equilibrated with 50 mM ammonium carbonate. The α-synuclein concentration was determined using the absorption at 280 nm or BCA assay.

Example 27

Full length, recombinant CsgA monomers can be prepared as described from Zhou et al. (2012). *Journal of Biological Chemistry* 287(42). Briefly, CsgA is cloned into a pET11d vector containing a C-terminal 6×His tag. Following growth in rich media, CsgA production is induced at an OD600 of approximately 0.9 by 0.5 mM IPTG at 37° C. for 1 hr. Bacteria were lysed in 8M guanidine hydrochloride in 50 mM potassium phosphate buffer (Pi) overnight. After centrifugation at 10,000×g for 20 minutes, the supernatant was incubated with nickel-nitrilotriacetic acid resin (Sigma) at room temperature for 1 h and then loaded onto a disposable polypropylene column (Thermo). Proteins were eluted into 50 mM potassium Pi containing 125 mM imidazole. To get monomeric CsgA, fractions with the target protein were combined and loaded onto a 30-kDa centrifugal filter units (Thermo) to remove dimers and other oligomers.

Alternatively, synthetic hexapeptides of CsgA consisting of the sequence: Nterm-QYGGNN-Cterm, are commercially available from Bio-synthesis, Inc.

Example 28

Another alternative is to utilize pre-formed CsgA amyloid seeds, by preparing purified curli extracts from biofilms as described in Collinson et al. (1991). *Journal of Bacteriology*. 173(15).

Wild-type *Escherichia coli* is grown on YESCA media with or without Congo Red dye added, for 3-7 days at room temperature. The cultures are scraped into 10-30 mLs of 10 mM Tris, pH 8. Cells are lysed by sonication or by freeze-thaw. Cell lysates are treated with 0.1 mg RNase A, 0.1 mg DNase I and $MgCl_2$ added to 1 mM, and incubated for 20-30 min at 37 C. Lysozyme is added to 1 mg/mL and further incubated at 37° C. for 20-40 min. SDS is added to 1% and incubated at 37° C. for 20-40 min. Insoluble material is collected by centrifugation at 12,000×g for 15 min.

Samples are resuspended in 1-10 mL Tris buffer, boiled at 90° C. for 15 min, and the above processes are repeated (Digestion with RNase, DNase, Lysozyme, and SDS treatment).

Samples are washed twice with Tris buffer, resuspended in Laemli buffer, boiled, and loaded onto an SDS-PAGE gel (4-20%). Samples are electrophoresed at 20 mA for 5 hrs. The remaining insoluble material in the stacking gel is collected, washed three times with water, washed twice with 95% ethanol, and dried. The sample is resuspended in 0.2M glycine pH 1.5 and boiled for 10-15 min. Insoluble material is collected by centrifuging at 16 k×g for 10 min. The insoluble material is washed five times with water, and resuspended in PBS. Finally, the sample is sonicated by electrode or water bath for 1 hour before protein content determined by BCA or absorbance at 280 nm.

Such alterations may change the kinetics of aggregation, the concentrations of compounds needed to inhibit aggregation, the ratios required to display CsgA-mediated synuclein aggregation, or combinations of the above.

Example 29

In other iterations of the protein purifications used in the assays of Examples 27 and 28, CsgA may be produced without a histidine tag or with an alternate tag, and it may contain a sequence to promote its excretion from the cell. α-synuclein may be engineered to contain a histidine tag or other tag to promote purification by affinity for example to immobilized metals such as nickel. CsgA and α-synuclein may be purified using alternate methods familiar to one skilled in the art, such as ammonium sulfate precipitation with alternate concentrations of ammonium sulfate in a single step or in multiple steps with increasing concentrations of ammonium sulfate; alternately, ammonium sulfate precipitation may be omitted. Alternate resins or materials to separate CsgA or α-synuclein from other proteins based on protein affinity, cation exchange, anion exchange, hydrophobic interactions, multiple modes or mixed modes may be used, as are familiar to one skilled in the art. Protein separation may be performed using batch purification, pre-packed columns, gravity flow, low pressure, high pressure, and high pressure liquid chromatography, using methods familiar to one skilled in the art, and the methods may be used individually or in combination. CsgA or α-synuclein may be separated from other proteins on the basis of size using methods familiar to one skilled in the art, such as size exclusion chromatography or high pressure liquid chromatography. CsgA and α-synuclein may be purified under denaturing conditions for all or part of the assay purification process, with alternate concentrations of guanidinium hydrochloride or with alternate denaturants at various concentrations known to one skilled, such as urea. Alternately, CsgA and α-synuclein may be purified under native conditions familiar to one skilled in the art; CsgA is generally purified rapidly under native conditions or with steps using non-denaturing buffers to avoid aggregation during the purification process. His-tagged CsgA may be eluted from immobilized metal affinity materials such as Ni-NTA using alternate methods known to one skilled in the art, such as decreasing pH or addition of chelators such as ethylenediaminetetraacetic acid. In addition to or instead of immobilized metal affinity chromatography based on the affinity of histidine residues in the protein to immobilized nickel, alternate immobilized metal affinity chromatography or batch purification methods may be used, such as materials with immobilized copper, zinc, cobalt or nickel interacting with histidine or alternate amino acids in the protein, such as cysteine or tryptophan, as known to one skilled in the art. As known to one skilled in the art, alternate buffers may be used with Ni-NTA agarose, such as tris(hydroxymethyl)aminomethane, ("Tris"); 4-(2-hydroxyethyl)-1-piperazine ethanesulfonic acid, ("HEPES"); 3-(N-morpholino)propanesulfonic acid, ("MOPS"), optionally including sodium chloride, potassium chloride or other salts, and various detergents and reducing agents of compositions and concentrations compatible with Ni-NTA agarose chromatography or batch purification.

In the assays, alternate concentrations of dimethyl sulfoxide may be used, and concentrations of dimethyl sulfoxide significantly elevated above or decreased below 1% may affect the aggregation kinetics of CsgA and α-synuclein. Alternate concentrations of Thioflavin T may be used in the assay and may affect the fluorescent signal and sensitivity of the assay. Alternate concentrations of CsgA and α-synuclein may be used and such alterations may affect aggregation kinetics of α-synuclein and CsgA in the assay. Alternate concentrations of compounds may be tested in the assay, and dose-responses may be evaluated. Additional reagents may be added to the assay which may affect aggregation kinetics of α-synuclein and CsgA depending on their concentration, including detergents such as sodium dodecyl sulfate. Shaking may be included at alternate intervals in the assay and may affect CsgA and α-synuclein aggregation kinetics. 2 mm glass beads may be omitted from the assays including α-synuclein or may be included in the assays including CsgA, or other sizes or compositions of beads may be used, and these alterations may affect CsgA and α-synuclein aggregation kinetics. Alternate buffers, such as Tris, HEPES and MOPS, and alternate buffer concentrations may be used in the assay and may affect CsgA and α-synuclein aggregation kinetics. Any plate reader capable of fluorescent reads with excitation at 438 nM and emission at 495 nm with sufficiently narrow bandwidths, such as 10 nm, may be used. Alternate microplates may be used in the assay, such as black microplates with clear bottoms. Plates may be sealed with alternate coverings that do not absorb ThT fluorescence, or the coverings may be removed prior to reads. The fluorescence may be read at a single endpoint or at multiple points over various time intervals, and the time intervals at which the fluorescence is measured may be constant or may vary during the course of the assay. Other metrics may be used to determine the effects of the compounds on α-synuclein and CsgA expression, including examination of Thioflavin T signal over the course of a kinetic read to determine lag phase in Thioflavin T fluorescence, the shape of a curve produced by the fluorescent signal, and the slope of the curve.

Example 30

To assess the effects of compounds on aggregation of α-synuclein, a cell-free assay was performed using purified α-synuclein and Thioflavin T. In the assay, human α-synuclein was expressed in E. coli, cells were lysed by boiling for 20 minutes, cell debris was pelleted by centrifugation, clarified lysate was treated with 10% streptomycin sulfate at 136 μL/mL and glacial acetic acid at 228 μL/mL, lysate was centrifuged, supernatant was transferred to a fresh tube and protein was precipitated via addition of an equal volume of saturated (100%) ammonium sulfate. The ammonium sulfate pellet was washed with an equal volume of 100 mM ammonium acetate in ethanol, pelleted via centrifugation, washed twice with ethanol, dried overnight, resuspended in 50 mM potassium phosphate buffer pH 7.3, and passed through a 50 kDa cut-off column. The assay was conducted in 96-well black microplates with a single 2 mm bead in each well, 40 μM ThioflavinT, 1% DMSO, α-synuclein at 50 μM and compounds at 20-100 μM. Plates were sealed with sealing tape (ThermoFisher 232701), incubated at 37° C. in a Tecan Nano F200 plate reader with excitation at 438 nm using a 439 nm filter with a bandwidth of 8 nm, and emission at 495 nm with a 490 nm filter with a bandwidth of 10 nm, or in a SPECTRAMAX i3X device with excitation at 438 nM and emission at 495 nm. During the assay, plates were shaken continuously or were shaken for 999 seconds every 18 minutes. Readings were performed for up to 72 hours. The effect of compounds on α-synuclein aggregation in the assay was determined by comparing the average maximum fluorescence observed with a compound to the average maximum fluorescence in the no-compound control wells at a given timepoint, and the average maximum fluorescence with the compound was expressed as a percentage of the average fluorescence observed in untreated controls.

Example 31

To assess the effects of compounds on aggregation of E. coli CsgA, a cell-free assay was performed using purified CsgA and Thioflavin T. In the assay, histidine-tagged CsgA was over-expressed in E. coli, cells were lysed under denaturing conditions with 8 M guanidine hydrochloride in 200 mM potassium phosphate buffer pH 7.3-7.6, and CsgA was purified via immobilized-metal affinity chromatography by batch purification with Nickel-nitrilotriacetic acid ("NTA") agarose and gravity flow through a disposable polypropylene column, including washes with 50 mM potassium phosphate buffer pH 7.3 followed by 12.5 mM imidazole in 50 mM potassium phosphate buffer pH 7.3, and elution with 125 mM imidazole in 50 mM potassium phosphate buffer pH 7.3. In some iterations of the purification, a wash with 8 M guanidine hydrochloride in 200 mM potassium phosphate pH 7.6 was included prior to the wash with 50 mM potassium phosphate buffer pH 7.3. Buffers with imidazole were freshly prepared prior to the protein purification. Purified CsgA was passed through a 30 kDa cut-off filter, and in some iterations was passed through a desalting column. The assay was conducted in 96-well black microplates with 40 mM ThioflavinT, 1% DMSO, CsgA at 10-20 mM, and compounds at a molar concentration equivalent to the CsgA concentration. Plates were incubated at 25° C. in a Tecan Nano F200 plate reader with excitation at 438 nm using a 439 nm filter with a bandwidth of 8 nm, and emission at 495 nm with a 490 nm filter with a bandwidth of 10 nm, or in a SpectraMax® i3X with excitation at 438 nM and emission at 495 nm. During the assay, plates were shaken initially for 5 seconds and subsequently for 3 seconds prior to fluorescent readings, or plates were shaken continuously for 999 seconds every 18 minutes. Readings were performed for up to 24-72 hours. The effect of compounds on CsgA aggregation in the assay was determined by comparing the average maximum fluorescence observed with a compound to the average maximum fluorescence in the no-compound control wells at a given timepoint, and the average maximum fluorescence with the compound was expressed as a percentage of the average fluorescence observed in untreated controls.

Example 32

In Vitro ThioflavinT Assay to Determine Effects of Compounds on CsgA Aggregation.

To assess the effects of compounds on aggregation of E. coli CsgA, a cell-free assay was performed using purified CsgA and Thioflavin T. In the assay, histidine-tagged CsgA was over-expressed in *E. coli* NEB 3016 slyD::kan cells harboring a pET11d vector containing csgA with the sequence for 6 histidine residues added to the C-terminus and without the Sec signal (amino acid 1-22) sequence. To induce over-expression of CsgA, 0.5 mM isopropyl β-D-1-thiogalactopyranoside ("IPTG") was added to cultures with an optical density at 600 nm ($OD_{600}$) of 0.8-1, and induced cells were cultured at 37° C. for 1 hour prior to harvest via centrifugation. Cells were lysed under denaturing conditions with 8 M guanidine hydrochloride in 50 mM potassium phosphate buffer pH 7.3, and CsgA was purified via immobilized-metal affinity chromatography by batch purification with Nickel-NTA agarose and a combination of low pressure and gravity flow through a disposable polypropylene column, including washes under low pressure applied manually via application of a syringe plunger to the column with 50 mM potassium phosphate buffer pH 7.3 followed by 12.5 mM imidazole in 50 mM potassium phosphate buffer pH 7.3, and elution by gravity flow with 125 mM imidazole in 50 mM potassium phosphate buffer pH 7.3. Buffers with imidazole were freshly prepared prior to the protein purification. Purified CsgA was passed through a 30 kDa molecular weight cut-off filter and passed through a desalting column. All steps of the CsgA purification in the absence of guanidine hydrochloride were conducted in rapid succession with as little delay as possible. The assay was conducted in 96-well black microplates with 40 µM ThioflavinT, 1% DMSO, CsgA at 20 µM, and compounds at 20 µM. Plates were incubated at 25° C. in a Tecan Nano F200 plate reader with excitation at 438 nm using a 439 nm filter with a bandwidth of 8 nm, and emission at 495 nm with a 490 nm filter with a bandwidth of 10 nm. During the assay, plates were shaken initially for 5 seconds and subsequently for 3 seconds prior to fluorescent readings. Readings were performed every 20 minutes for up to 24 hours. The effect of compounds on CsgA aggregation in the assay was determined with data from 18 hours, following the plateau of the fluorescent signal in the untreated (no compound) control wells containing CsgA. Fluorescence values for each compound with CsgA were first adjusted by subtracting the average fluorescence of the compound in the absence of CsgA. These adjusted values were normalized by dividing them by the average fluorescence in the no-compound (i.e., untreated) control wells containing CsgA and α-synuclein, and the average normalized fluorescence with the compound was expressed as a percentage of the average fluorescence observed in untreated controls. Percent inhibition of CsgA aggregation by a compound was determined by subtracting the percent average fluorescence with the compound at 18 hours from 100%. Results are shown in Table 3 and discussed below.

In Vitro Thioflavin T Assay to Determine the Effects of Compounds on CsgA-Seeded α-Synuclein Aggregation.

To assess the effects of compounds on aggregation of α-synuclein seeded by *E. coli* CsgA, a cell-free assay was performed using purified α-synuclein, purified CsgA and Thioflavin T. In the assay, histidine-tagged CsgA was over-expressed in *E. coli* NEB 3016 slyD::kan cells harboring a pET11d vector containing csgA with the sequence for 6 histidine residues added to the C-terminus and without the Sec signal (amino acid 1-22) sequence. To induce over-expression of CsgA, 0.5 mM IPTG was added to cultures with an optical density at 600 nm ($OD_{600}$) of 0.8-1, and induced cells were cultured at 37° C. for 1 hour prior to harvest via centrifugation. Cells were lysed under denaturing conditions with 8 M guanidine hydrochloride in 50 mM potassium phosphate buffer pH 7.3, and CsgA was purified via immobilized-metal affinity chromatography by batch purification with Nickel-NTA agarose and a combination of low pressure and gravity flow through a disposable polypropylene column, including washes under low pressure applied manually via application of a syringe plunger to the column with 50 mM potassium phosphate buffer pH 7.3 followed by 12.5 mM imidazole in 50 mM potassium phosphate buffer pH 7.3, and elution with 125 mM imidazole in 50 mM potassium phosphate buffer pH 7.3. Buffers with imidazole were freshly prepared prior to the protein purification. Purified CsgA was passed through a 30 kDa molecular weight cut-off filter and through a desalting column. All steps of the CsgA purification in the absence of guanidine hydrochloride were conducted in rapid succession with as little delay as possible. Human α-synuclein was expressed in *E. coli*, cells were lysed by boiling for 20 minutes, cell debris was pelleted by centrifugation, clarified lysate was treated with 10% streptomycin sulfate at 136 µL/mL and glacial acetic acid at 228 µL/mL, lysate was centrifuged, supernatant was transferred to a fresh tube and protein was precipitated via addition of an equal volume of saturated (100%) ammonium sulfate. The ammonium sulfate pellet was washed with an equal volume of 100 mM ammonium acetate in ethanol, pelleted via centrifugation, washed twice with ethanol, dried overnight, resuspended in 10 mM Tris pH 7.4, and passed through a 50 kDa cut-off column. The assay was conducted in 96-well black microplates with a single glass 2 mm bead per well, 40 µM ThioflavinT, 1% DMSO, 2 µM CsgA, 50 µM α-synuclein, 100 mM sodium chloride, 9.3 mM potassium phosphate pH 7.3, and compounds at 50 µM. Plates were sealed with sealing tape (ThermoFisher 232701), incubated with continuous shaking at 37° C. in a Tecan Nano F200 plate reader, with excitation at 438 nm using a 439 nm filter with a bandwidth of 8 nm, and emission at 495 nm with a 490 nm filter with a bandwidth of 10 nm, and readings were performed hourly for up to 73 hours. The effect of compounds on CsgA-seeded α-synuclein aggregation in the assay was determined with data from 40 hours, following the plateau of the fluorescent signal in the untreated (no compound) control wells containing CsgA and α-synuclein. Fluorescence values for each compound with CsgA and α-synuclein were first adjusted by subtracting the average fluorescence of the compound in the absence of CsgA and α-synuclein. These adjusted values were normalized by dividing them by the average fluorescence in the no-compound (i.e., untreated) control wells containing CsgA and α-synuclein, and the average normalized fluorescence with the compound was expressed as a percentage of the average fluorescence observed in untreated controls. Percent inhibition of CsgA-seeded α-synuclein aggregation by a compound was determined by subtracting the percent average fluorescence with the compound at 40 hours from 100%. Results are shown in Table 3 and discussed below.

In Vitro Thioflavin T Assay to Determine the Effects of Compounds on α-Synuclein Aggregation.

To assess the effects of compounds on aggregation of α-synuclein, a cell-free assay was performed using purified α-synuclein and Thioflavin T. In the assay, human α-synuclein was expressed in *E. coli*, cells were lysed by boiling for 20 minutes, cell debris was pelleted by centrifugation, clarified lysate was treated with 10% streptomycin sulfate at 136 µL/mL and glacial acetic acid at 228 µL/mL, lysate was centrifuged, supernatant was transferred to a fresh tube and protein was precipitated via addition of an equal volume of saturated (100%) ammonium sulfate. The ammonium sulfate pellet was washed with an equal volume of 100 mM ammonium acetate in ethanol, pelleted via centrifugation, washed twice with ethanol, dried overnight, resuspended in 10 mM Tris pH 7.4, and passed through a 50 kDa cut-off column. The assay was conducted in 96-well black microplates with a single 2 mm bead in each well, 40 μM ThioflavinT, 1% DMSO, 50 μM α-synuclein, 100 mM sodium chloride, 9.3 mM potassium phosphate pH 7.3, 4.6 mM Tris pH 7.4 (added as the solvent for α-synuclein or independently for controls lacking α-synuclein), and compounds at 1 μM or 50 μM. Plates were sealed with sealing tape (ThermoFisher 232701) and incubated with continuous shaking at 37° C. in a Tecan Nano F200 plate reader, with excitation at 438 nm using a 439 nm filter with a bandwidth of 8 nm, and emission at 495 nm with a 490 nm filter with a bandwidth of 10 nm. Readings were performed hourly for up to 73 hours. The effect of compounds on α-synuclein aggregation in the assay was determined with data from 40 hours, following the plateau of the fluorescent signal in the untreated (no compound) control wells containing α-synuclein. Fluorescence values for each compound with α-synuclein were first adjusted by subtracting the average fluorescence of the compound in the absence of α-synuclein. These adjusted values were normalized by dividing them by the average fluorescence in the no-compound (i.e., untreated) control wells containing α-synuclein, and the average normalized fluorescence with the compound was expressed as a percentage of the average fluorescence observed in untreated controls. Percent inhibition of α-synuclein aggregation by a compound was determined by subtracting the percent average fluorescence with the compound at 40 hours from 100%. Results are shown in Table 3 and discussed below.

TABLE 3

Effects of Compounds Tested

| Compound | Structure | Inhibition of Aggregation | | |
|---|---|---|---|---|
| | | αSyn | CsgA-seeded αSyn | CsgA |
| EGCG | 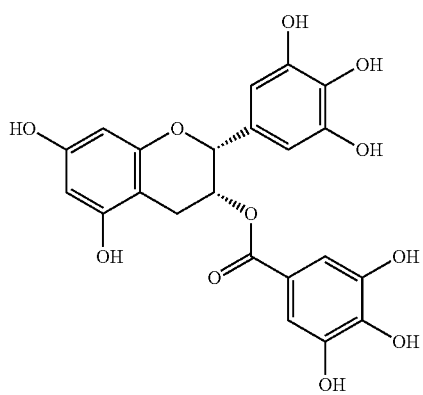 [SMILES: O=C(O[C@@H]1Cc2c(O)cc(O)cc2O[C@@H]1c1cc(O)c(O)c(O)c1)c1cc(O)c(O)c(O)c1] | 99% (+++) | 77% (+++) | 56% (++) |
| quercetin | 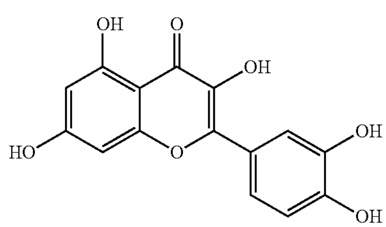 [SMILES: O=c1c(O)c(-c2ccc(O)c(O)c2)oc2cc(O)cc(O)c12] | 99% (+++) | | 33% (++) |
| morin | 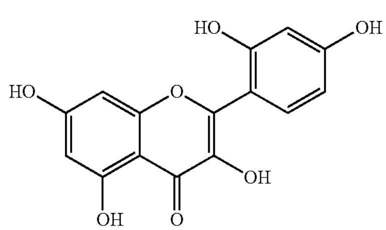 [SMILES: O=c1c(O)c(-c2ccc(O)cc2O)oc2cc(O)cc(O)c12] | 88% (+++) | 70% (+++) | 69% (+++) |

TABLE 3-continued

Effects of Compounds Tested

| Compound | Structure | Inhibition of Aggregation | | |
| --- | --- | --- | --- | --- |
| | | αSyn | CsgA-seeded αSyn | CsgA |
| rosmarinic acid | 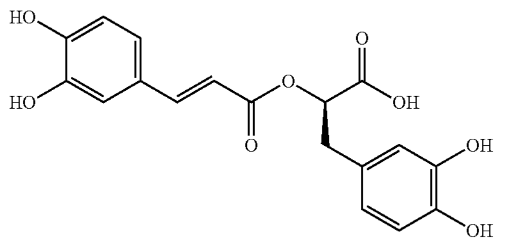 [SMILES: O=C(/C=C/c1ccc(O)c(O)c1)O[C@H](Cc1ccc(O)c(O)c1)C(=O)O] | 99% (+++) | | 48% (++) |
| gallic acid | 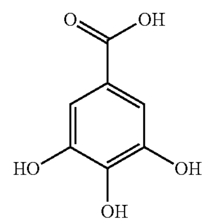 [SMILES: O=C(O)c1cc(O)c(O)c(O)c1] | 99% (+++) | 63% (+++) | 82% (+++) |
| methoxy-hydroquinone | 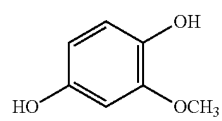 | 100% (+++) | 80% (+++) | 50% (++) |
| curcumin | 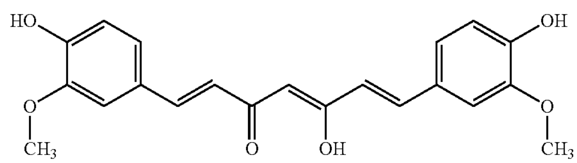 [SMILES: COc1cc(/C=C/C(=O)/C=C(O)/C=C/c2ccc(O)c(OC)c2)ccc1O] | 89% (+++) | 86% (+++) | |
| resveratrol | 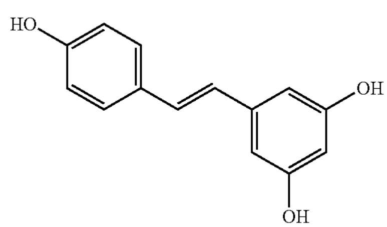 [SMILES: Oc1ccc(/C=C/c2cc(O)cc(O)c2)cc1] | 86% (+++) | | 62% (+++) |
| apigenin | 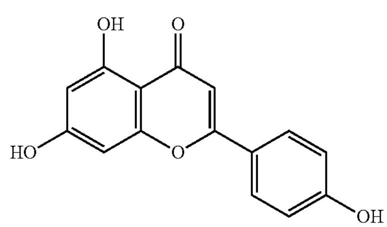 [SMILES: O=c1cc(-c2ccc(O)cc2)oc2cc(O)cc(O)c12] | 56% (++) | | |
| NDGA | 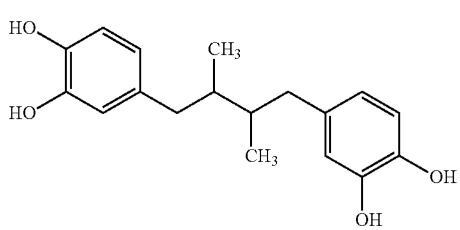 [SMILES: CC(Cc1ccc(O)c(O)c1)C(C)Cc1ccc(O)c(O)c1] | 54% (++) | 39% (++) | 23% (+) |

TABLE 3-continued

Effects of Compounds Tested

| Compound | Structure | Inhibition of Aggregation | | |
|---|---|---|---|---|
| | | αSyn | CsgA-seeded αSyn | CsgA |
| phloretin | | 46% (++) | 21% (+) | 18% (+) |
| genistein | | 40% (++) | | |
| lauryl gallate | | 33% (++) | 24% (+) | 1% (−) |
| isoeugenol | | 9% (−) | 35% (++) | −4% (−) |
| 4-allyl-1,2-dimethoxy-benzene | | 5% (−) | 36% (++) | −18% (−−) |
| eugenol | | −1% (−) | 42% (++) | −10% (−) |
| 4-ethyl guaiacol | | −2% (−) | −10% (++) | −82% (+++) |
| guaiacol | | −2% (−) | 40% (++) | −5% (−) |

TABLE 3-continued

Effects of Compounds Tested

| Compound | Structure | Inhibition of Aggregation | | |
| --- | --- | --- | --- | --- |
| | | αSyn | CsgA-seeded αSyn | CsgA |
| Anle 138b | | 1% (−) | 6% (−) | 9% (−) |
| carvacrol | | 2% (−) | −2% (−) | −20% (−) |
| thymol | | −21% (−−) | 9% (−) | −4% (−) |

Compound activity ranges presented are defined as follows: (−−) is less than −10% inhibition; (−) is between −10% to 10% inhibition; (+) is between 10% to 30% inhibition; (++) is between 30% to 60% inhibition; and (+++) is greater than 60% inhibition.

Results of Thioflavin T Assays of Compound Effects on Aggregation.

Compound activity ranges are defined below Table 3, above. Tested compounds demonstrated a variety of effects in the Thioflavin T assays of aggregation of α-synuclein, CsgA-seeded α-synuclein, and CsgA. Gallic acid, morin, EGCG and methoxyhydroquinone demonstrated relatively stronger inhibition of all three types of aggregation in the assay, with (+++) inhibition of α-synuclein aggregation, (+++) inhibition of CsgA-seeded α-synuclein aggregation, and (++) to (+++) inhibition of CsgA aggregation. NDGA and phloretin demonstrated relatively weak to moderate inhibition of all three types of aggregation in the assay, within a range of (++) to (+) inhibition of α-synuclein aggregation, within a range of (++) to (+) inhibition of CsgA-seeded α-synuclein aggregation, within a range of (+) inhibition of CsgA aggregation, respectively. The inhibition of all three types of aggregation in the assay suggests that gallic acid, morin, EGCG, methoxyhydroquinone, NDGA and phloretin may be useful in preventing α-synuclein aggregation, the seeding of α-synuclein aggregation by CsgA or other microbial amyloids, and the formation of microbial amyloids that may seed α-synuclein aggregation in vivo, and these compounds may thereby be useful in preventing or treating Parkinson's Disease and other α-synucleinopathies. Oral administration of these compounds may allow relatively high concentrations to be achieved in the gut, where microbes producing amyloids may be abundant, and the compounds could inhibit their seeding of α-synuclein aggregation. Inhibition by these compounds of aggregation of α-synuclein on its own could be independently beneficial or may be synergistic with their inhibition of microbial amyloid-seeded α-synuclein aggregation. In keeping with Braak's hypothesis of prion-like propagation of α-synuclein from the enteric nervous system to the central nervous system (see, e.g., Rietdijk et al., "Exploring Braak's Hypothesis of Parkinson's Disease," *Front. Neurol.*, 13 Feb. 2017), these inhibitory effects could be beneficial in preventing propagation of α-synuclein aggregates in both the enteric and central nervous systems; furthermore, if orally administered compounds alleviate a continual seeding of α-synuclein aggregation by microbial amyloids or independent formation of α-synuclein aggregates, the processes by which subjects may clear α-synuclein aggregates may be able to have a greater net effect (i.e., the processed may be able to keep pace with the aggregates formed), and the compounds may thereby be efficacious in preventing or treating Parkinson's Disease and other microbial amyloid-seeded α-synucleinopathies. Without being limited by theory, oral administration may provide particular benefit in the gastrointestinal tract, potentially restoring gastrointestinal function in those patients in whom it is compromised or in preventing or slowing additional loss of gastrointestinal function and/or improving one or more symptoms of, e.g., dysphagia, reduced gut motility, gastroparesis, constipation (including chronic constipation and chronic idiopathic constipation), small intestine bacterial overgrowth (SIBO), diarrhea, abdominal pain and/or cramping, bloating, flatulence, nausea, or any other symptoms of irritable bowel syndrome (IBS), inflammatory bowel disease (IBD), ulcerative colitis, Crohn's disease, intestinal hyperpermeability, or any combinations thereof, in patients with α-synucleinopathies or in subjects at risk for developing α-synucleinopathies.

As shown in Table 3, some compounds demonstrated inhibition of only one or two types of aggregation in the assays, while other compounds appeared inactive or enhanced one or more types of aggregation. Lauryl gallate demonstrated relatively moderate inhibition of α-synuclein aggregation (++) and CsgA-seeded α-synuclein aggregation (+%) in the assay but did not appear to inhibit CsgA aggregation; these results suggest that lauryl gallate may be useful in preventing α-synuclein aggregation with or without seeding by microbial amyloids and thereby may have benefit in preventing or treating α-synucleinopathies independent of microbial amyloids. Guaiacol, 4-allyl-1,2-dimethoxybenzene, isoeugenol and eugenol all demonstrated inhibition of CsgA-seeded α-synuclein aggregation in the assay without notable inhibition of aggregation of either α-synuclein or CsgA on their own. These compounds may thus be useful in preventing α-synuclein aggregation seeded by microbial amyloids and thereby have therapeutic benefit, particularly if dosed at sites where microbial amyloids may be abundant, such as the gastrointestinal tract. Carvacrol, 4-allyl-1,2-dimethoxybenzene and eugenol enhanced CsgA aggregation relatively weakly in the assay, as shown by their negative CsgA aggregation inhibition values of (--) respectively. 4-ethyl guaiacol demonstrated relatively strong enhancement of CsgA aggregation in the assay, with a negative CsgA inhibition value of (--). Thymol demonstrated relatively weak enhancement of α-synuclein aggregation in the assay, with a negative α-synuclein inhibition value of (--), but appeared to have little to no effect on CsgA-seeded α-synuclein aggregation or CsgA aggregation. Anle138b demonstrated relatively little to no effect on any types of aggregation in the assay.

Whereas the compounds discussed above were tested at 50 μM in the α-synuclein assay, resveratrol, rosmarinic acid, genistein, apigenin and quercetin were tested at 1 μM in the α-synuclein assay, and they demonstrated relatively moderate to strong inhibition of α-synuclein aggregation, ranging from (+++) to (++) inhibition. Resveratrol, rosmarinic acid and quercetin were assessed at concentrations of 20 μM for inhibition of CsgA, and they demonstrated relatively moderate to strong inhibition of CsgA aggregation, with a range from (+++) to (++)% inhibition of CsgA. Thus, these compounds may have therapeutic benefit in Parkinson's Disease and other α-synucleinopathies due to their inhibition of aggregation of α-synuclein and/or microbial amyloids, and in compounds where more than one type of aggregation is inhibited, these inhibitory effects may be additive or synergistic. Additionally, compounds which inhibit some but not all types of inhibition may have therapeutic benefit when used in combination with compounds which inhibit other forms of aggregation, and the effects of these combinations may be additive or synergistic.

Example 33

Figure 9:
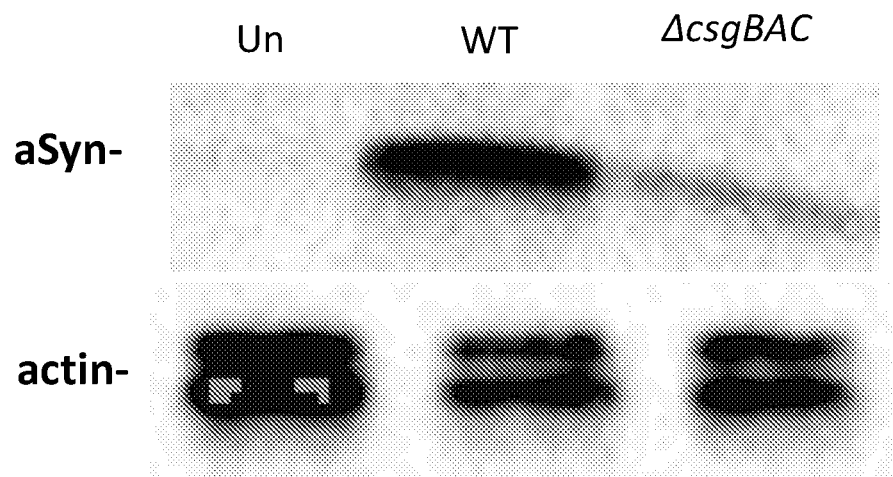
FIG. 9 is a western blot for α-Synuclein in enteroendocrine (STC-1 cell line) cells treated with E. coli K12 or the ΔcsgBAC, curli-deficient strain at an MOI of 10:1 for 4 hours.

Enteroendocrine cells (STC1 cell line cells) were treated with E. coli K12 or the ΔcsgBAC, curli-deficient strain at an MOI of 10:1 for 4 hours. Cells were lysed, and protein samples assessed by SDS-PAGE and western blot for alpha-synuclein (aSyn) and actin, as loading control. The western blot is shown in FIG. 9. These results indicate that CsgA affects aSyn aggregation in the gut, for example in enteroendocrine cells.

With respect to the use of substantially any plural and/or singular terms herein, those having skill in the art can translate from the plural to the singular and/or from the singular to plural as is appropriate to the context and/or application. The various singular/plural permutations can be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Wherever a method of using a composition (e.g., a method comprising administering a composition to a subject having an amyloid disorder) is disclosed herein, the corresponding composition for use is also expressly contemplated. For example, for the disclosure of a method of inhibiting, ameliorating, reducing the likelihood, delaying the onset of, treating, or preventing an amyloid disorder administering a composition to a subject, the corresponding composition for use in inhibiting, ameliorating, reducing the likelihood, delaying the onset of, treating, or preventing the amyloid disorder is also expressly contemplated.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of inhibiting, ameliorating, reducing the likelihood, delaying the onset of, or treating a microbially induced amyloid disorder, the method comprising administering to a subject in need thereof a composition comprising a compound selected from the group consisting of: epigallocatechin gallate, quercetin, morin, rosmarinic acid, gallic acid, lauryl gallate, methoxyhydroquinone, curcumin, resveratrol, apigenin, nordihydroguaiaretic acid, phloretin and genistein; or pharmaceutically acceptable salts thereof,
    wherein the subject in need has intestinal bacterial amyloid aggregates.

2. The method of claim 1, wherein the microbially induced amyloid disorder is selected from the group consisting of: α-synucleinopathy, Parkinson's Disease, Lewy Body Dementia, incidental Lewy body disease, Lewy body variant of Alzheimer's disease, multiple system atrophy, or pure autonomic failure, or any combination thereof.

3. The method of claim 1, wherein the microbially induced amyloid disorder is intestinal dysbiosis, intestinal hyperpermeability, irritable bowel syndrome (IBS), inflammatory bowel disease (IBD), ulcerative colitis and Crohn's disease.

4. The method of claim 1, wherein the subject suffers from gastrointestinal symptoms comprising one or more of dysphagia, reduced gut motility, gastroparesis, constipation, small intestine bacterial overgrowth (SIBO), diarrhea, abdominal pain and/or cramping, bloating, flatulence and nausea.

5. The method of claim 4, wherein the gastrointestinal symptoms are associated with Parkinson's Disease or Parkinsonism.

6. The method of claim 1, wherein the microbially induced amyloid disorder can be diagnosed by detecting the presence or level of the intestinal bacterial amyloid aggregates.

7. The method of claim 6, wherein the aggregates comprise a bacterial CsgA protein.

8. The method of claim 1, further comprising detecting a presence or level of a bacterial protein or a microorganism that produces the bacterial protein in an intestinal sample of the subject.

9. The method of claim 8, wherein the subject is selected as in need of the composition if a presence of the bacterial protein or the microorganism that produces the bacterial protein is detected in the intestinal sample, or if a level of the bacterial protein or the microorganism that produces the bacterial protein in the intestinal sample is greater than a predetermined level or control.

10. The method of claim 1, further comprising determining a decrease or absence of the intestinal amyloid aggregates following the administration.

11. The method of claim 1, further comprising identifying the subject as displaying a gastrointestinal symptom.

12. The method of claim 1, wherein said microbially induced amyloid aggregates comprise one or more of α-synuclein, tau, Beta amyloid from Amyloid precursor protein, Medin, Apolipoprotein AI, Atrial natriuretic factor, Beta amyloid, Cystatin, IAPP (Amylin), Beta-2 microglobulin, Transthyretin, PrP, Gelsolin, Lysozyme, Huntingtin, Keratoepithelin, Calcitonin, Prolactin, Serum amyloid A, and/or Immunoglobulin light chain AL.

13. The method of claim 6, wherein said microbially induced amyloid aggregates are present within the gastrointestinal tract, cranial sinus, or nasal cavity.

14. The method of claim 6, wherein said microbially induced amyloid aggregates are present within enteric nervous tissue or the olfactory bulb.

15. The method of claim 1, further comprising measuring or evaluating enteric amyloid levels and/or amyloid aggregation during the course of administration.

16. The method of claim 1, further comprising measuring or evaluating enteric amyloid levels and/or amyloid aggregation following the course of administration.

17. The method of claim 1, further comprising measuring or evaluating a change in the nervous system.

18. The method of claim 1, further comprising measuring or evaluating a change in the gastrointestinal system.

19. The method of claim 18, wherein said gastrointestinal symptom comprises constipation.

20. The method of claim 1, wherein the composition is administered following the appearance of a neurological symptom or condition.

21. The method of claim 20, wherein said neurological symptom or condition comprises one or more of anosmia, hyposmia, bradykinesia, ataxia, tremor, muscle rigidity, impaired posture and balance, loss of automatic movements, dysarthria or other speech changes, handwriting changes, orthostatic hypotension, memory deficit, dysphagia, incontinence, sleep disruption, cardiac arrhythmia, visual disturbance, psychiatric problems including depression and visual, auditory, olfactory, or tactile hallucinations, vertigo, cognitive dysfunction, altered dopamine levels, altered serotonin levels, altered kynurenine levels, and/or any combination thereof.

22. The method of claim 1, wherein the composition is administered prior to the appearance of a neurological symptom or condition.

23. The method of claim 1, wherein the composition is coadministered with a caffeine, nicotine, theophylline, theobromine, xanthine, or methylxanthine.

24. The method of claim 1, further comprising administering to said subject an inhibitor of α-synuclein aggregation.

25. The method claim 1, wherein said subject is one that has been identified or selected as having Parkinson's disease.

* * * * *

UNITED STATES PATENT AND TRADEMARK OFFICE
CERTIFICATE OF CORRECTION

PATENT NO. : 11,147,792 B2
APPLICATION NO. : 16/611406
DATED : October 19, 2021
INVENTOR(S) : Sampson et al.

It is certified that error appears in the above-identified patent and that said Letters Patent is hereby corrected as shown below:

On the Title Page

Column 1, Line 1, item (71), under Applicants, delete "Inc," and insert --Inc.,--.

On Page 3, Column 1, Line 67, item (56), under Other Publications, delete "Synthenase" and insert --Synthase--.

On Page 4, Column 1, Line 10, item (56), under Other Publications, delete "challege" and insert --challenge--.

On Page 4, Column 1, Line 15, item (56), under Other Publications, delete "etal" and insert --et al.--.

On Page 4, Column 1, Line 46, item (56), under Other Publications, delete "Pathogents" and insert --Pathogens--.

On Page 4, Column 2, Line 40, item (56), under Other Publications, delete "fibril0destabilizing" and insert --fibril-destabilizing--.

On Page 4, Column 2, Line 61, item (56), under Other Publications, delete "mircrobiota" and insert --microbiota--.

On Page 5, Column 2, Line 24, item (56), under Other Publications, delete "Biomarkerfor" and insert --Biomarker for--.

On Page 5, Column 2, Line 49, item (56), under Other Publications, delete "Target |" and insert --Target in--.

Signed and Sealed this
Third Day of May, 2022

Katherine Kelly Vidal
*Director of the United States Patent and Trademark Office*

In the Specification

In Column 2, Lines 41-56, delete " 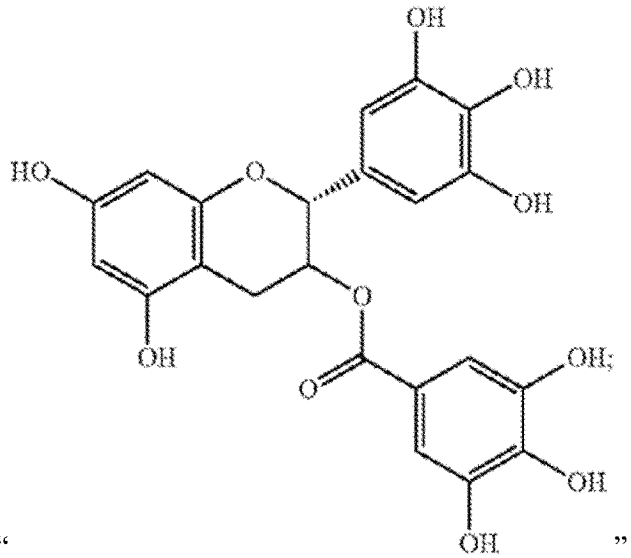 "

and insert -- 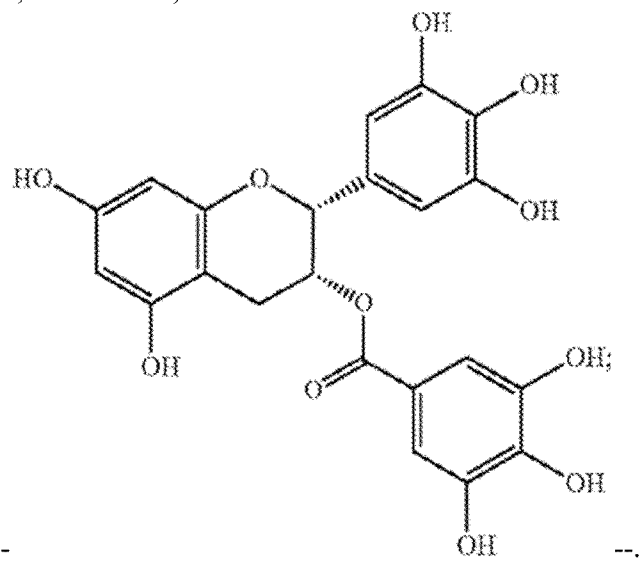 --.

In Column 4, Line 41, delete "herein." and insert --herein,--.

In Column 5, Line 47, delete "pyrollyl," and insert --pyrrolyl,--.

In Column 5, Line 51, delete "herein." and insert --herein,--.

In Column 6, Line 23 (Approx.), delete "O." and insert --O,--.

In Column 6, Lines 45-46, delete "—$C_6H_4C(O)CH_3$, —$C_6H_4C(O)CH_3$," and insert -- —$C_6H_4C(O)CH_3$,--.

In Column 6, Lines 50-51, delete "—$C_6H_4C(O)CH_3$, —$C_6H_4C(O)CH_3$," and insert -- —$C_6H_4C(O)CH_3$,--.

CERTIFICATE OF CORRECTION (continued)
U.S. Pat. No. 11,147,792 B2

In Column 6, Line 58, delete "—$C_6H_4C(O)CH_3$, —$C_6H_4C(O)CH_3$," and insert -- —$C_6H_4C(O)CH_3$,--.

In Column 6, Lines 66-67, delete "—$C_6H_4C(O)CH_3$, —$C_6H_4C(O)CH_3$," and insert -- —$C_6H_4C(O)CH_3$,--.

In Column 7, Lines 4-5, delete "—$C_6H_4C(O)CH_3$, —$C_6H_4C(O)CH_3$," and insert -- —$C_6H_4C(O)CH_3$,--.

In Column 7, Line 11, delete "—$C_6H_4C(O)CH_3$, —$C_6H_4C(O)CH_3$," and insert -- —$C_6H_4C(O)CH_3$,--.

In Column 7, Line 24, delete "3-(3,4-dihydroxyphenyl) propanoic acid)," and insert --3-(3,4-dihydroxyphenyl)propanoic acid),--.

In Column 8, Line 1, delete "quercertin," and insert --quercetin,--.

In Column 8, Line 12, delete "quercertin," and insert --quercetin,--.

In Column 10, Line 49, delete "carbodopa," and insert --carbidopa,--.

In Column 10, Line 51, delete "Benzotropine," and insert --Benzatropine,--.

In Column 10, Line 53, delete "Pimavanersin," and insert --Pimavanserin,--.

In Column 10, Line 57, delete "carbodopa," and insert --carbidopa,--.

In Column 10, Line 59, delete "Benzotropine," and insert --Benzatropine,--.

In Column 10, Line 61, delete "Pimavanersin," and insert --Pimavanserin,--.

In Column 10, Line 63, delete "carbodopa," and insert --carbidopa,--.

In Column 10, Line 66, delete "Benzotropine," and insert --Benzatropine,--.

In Column 10, Line 67, delete "Pimavanersin," and insert --Pimavanserin,--.

In Column 11, Line 3, delete "carbodopa," and insert --carbidopa,--.

In Column 11, Line 5, delete "Benzotropine," and insert --Benzatropine,--.

In Column 11, Lines 6-7, delete "Pimavanersin," and insert --Pimavanserin,--.

In Column 15, Line 13, delete "*Bifiobacterium*," and insert --*Bifidobacterium*,--.

In Column 16, Line 12, delete "FIGs. C-K" and insert --FIGS. 1C-1K--.

In Column 16, Line 32, delete "(FIG." and insert --(FIGS.--.

CERTIFICATE OF CORRECTION (continued)
U.S. Pat. No. 11,147,792 B2

In Column 17, Line 41, delete "aSyn" and insert --αSyn--.

In Column 19, Line 37, after "3" insert --.--.

In Column 19, Line 50, after "3" insert --.--.

In Column 19, Line 63, after "3" insert --.--.

In Column 20, Line 9, after "3" insert --.--.

In Column 20, Line 39, delete "Enterobacteraceae" and insert --Enterobacteriaceae--.

In Column 20, Line 50, delete "Chain.)." and insert --Cham.).--.

In Column 23, Line 57 (Approx.), delete "(S-IBM)" and insert --(SIBM)--.

In Column 29, Lines 49-50, delete "—$C_6H_4C(O)CH_3$, —$C_6H_4C(O)CH_3$," and insert -- —$C_6H_4C(O)CH_3$,--.

In Column 30, Lines 3-4, delete "—$C_6H_4C(O)CH_3$, —$C_6H_4C(O)CH_3$," and insert -- —$C_6H_4C(O)CH_3$,--.

In Column 30, Line 10, delete "—$C_6H_4C(O)CH_3$, —$C_6H_4C(O)CH_3$," and insert -- —$C_6H_4C(O)CH_3$,--.

In Column 30, Lines 19-20, delete "—$C_6H_4C(O)CH_3$, —$C_6H_4C(O)CH_3$," and insert -- —$C_6H_4C(O)CH_3$,--.

In Column 30, Lines 24-25, delete "—$C_6H_4C(O)CH_3$, —$C_6H_4C(O)CH_3$," and insert -- —$C_6H_4C(O)CH_3$,--.

In Column 30, Line 31, delete "—$C_6H_4C(O)CH_3$, —$C_6H_4C(O)CH_3$," and insert -- —$C_6H_4C(O)CH_3$,--.

In Column 46, Line 31, delete "*Bifiobacterium*," and insert --*Bifidobacterium*,--.

In Column 47, Line 43, delete "*Bifiobacterium*," and insert --*Bifidobacterium*,--.

In Column 50, Line 62, delete "*Bifiobacterium*," and insert --*Bifidobacterium*,--.

In Column 52, Lines 47-48, delete "—$C_6H_4C(O)CH_3$, —$C_6H_4C(O)CH_3$," and insert -- —$C_6H_4C(O)CH_3$,--.

In Column 52, Lines 52-53, delete "—$C_6H_4C(O)CH_3$, —$C_6H_4C(O)CH_3$," and insert -- —$C_6H_4C(O)CH_3$,--.

In Column 52, Line 59, delete "—$C_6H_4C(O)CH_3$, —$C_6H_4C(O)CH_3$," and insert -- —$C_6H_4C(O)CH_3$,--.

CERTIFICATE OF CORRECTION (continued)
U.S. Pat. No. 11,147,792 B2

In Column 53, Lines 10-11, delete "—$C_6H_4C(O)CH_3$, —$C_6H_4C(O)CH_3$," and insert -- —$C_6H_4C(O)CH_3$,--.

In Column 53, Lines 15-16, delete "—$C_6H_4C(O)CH_3$, —$C_6H_4C(O)CH_3$," and insert -- —$C_6H_4C(O)CH_3$,--.

In Column 53, Line 22, delete "—$C_6H_4C(O)CH_3$, —$C_6H_4C(O)CH_3$," and insert -- —$C_6H_4C(O)CH_3$,--.

In Column 53, Line 33, delete "Guiacol," and insert --Guaiacol,--.

In Column 53, Line 36, delete "quercertin," and insert --quercetin,--.

In Column 53, Line 48 (Approx.), delete "quercertin," and insert --quercetin,--.

In Column 53, Line 57, delete "Guiacol," and insert --Guaiacol,--.

In Column 54, Lines 29-30, delete "quercertin," and insert --quercetin,--.

In Column 63, Line 11 (Approx.), delete "Guiacol," and insert --Guaiacol,--.

In Column 69, Line 42, delete "croscarmelose;" and insert --croscarmellose;--.

In Column 76, Line 3, delete "FIGs. C-K" and insert --FIGS. 1C-1K--.

In Column 76, Line 33, delete "(FIG." and insert --(FIGS.--.

In Column 76, Line 63, delete "that that" and insert --that--.

In Column 76, Line 66, delete "30 g" and insert --30 µg--.

In Column 79, Line 1, delete "aSyn" and insert --αSyn--.

In Column 84, Line 2, delete "Laemli" and insert --Laemmli--.

In Column 98, Line 3, delete "(aSyn)" and insert --(αSyn)--.

In Column 98, Line 5, delete "aSyn" and insert --αSyn--.

In the Claims

In Column 101, Claim 25, Line 13, after "method" insert --of--.